(12) United States Patent
Watterson et al.

(10) Patent No.: US 8,158,627 B2
(45) Date of Patent: Apr. 17, 2012

(54) COMPOSITIONS AND TREATMENTS USING PYRIDAZINE COMPOUNDS AND CHOLINESTERASE INHIBITORS

(75) Inventors: D. Martin Watterson, Chicago, IL (US); Linda Van Eldik, Chicago, IL (US); Wenhui Hu, Guangzhou (CN)

(73) Assignee: Northwestern University, Evanston, IL (US)

( * ) Notice: Subject to any disclaimer, the term of this patent is extended or adjusted under 35 U.S.C. 154(b) by 152 days.

(21) Appl. No.: 12/298,623

(22) PCT Filed: Apr. 27, 2007

(86) PCT No.: PCT/US2007/010463
§ 371 (c)(1),
(2), (4) Date: Dec. 11, 2008

(87) PCT Pub. No.: WO2007/127474
PCT Pub. Date: Nov. 8, 2007

(65) Prior Publication Data
US 2009/0197885 A1    Aug. 6, 2009

Related U.S. Application Data

(60) Provisional application No. 60/796,348, filed on Apr. 28, 2006.

(51) Int. Cl.
*A61K 31/535* (2006.01)
*A61K 31/50* (2006.01)
*A61K 31/501* (2006.01)

(52) U.S. Cl. ............ 514/236.5; 514/252.02; 514/252.03

(58) Field of Classification Search ................. 514/63
See application file for complete search history.

(56) References Cited

U.S. PATENT DOCUMENTS

| | | |
|---|---|---|
| 2,857,384 A | 10/1958 | Druey et al. |
| 3,464,988 A | 9/1969 | Holava et al. |
| 4,169,158 A | 9/1979 | Laborit |
| 4,508,720 A | 4/1985 | Kan et al. |
| 4,562,196 A | 12/1985 | Horn et al. |
| 4,631,286 A | 12/1986 | Shutske et al. |
| 4,654,343 A | 3/1987 | Albright et al. |
| 4,710,499 A | 12/1987 | Wermuth et al. |
| 4,721,711 A | 1/1988 | Chambon et al. |
| 4,754,050 A | 6/1988 | Shutske et al. |
| 4,755,511 A | 7/1988 | Warrington |
| 4,816,456 A | 3/1989 | Summers et al. |
| 4,835,275 A | 5/1989 | Shutske et al. |
| 4,839,364 A | 6/1989 | Shutske et al. |
| 4,895,841 A | 1/1990 | Sugimoto et al. |
| 4,948,807 A | 8/1990 | Rosin et al. |
| 4,977,152 A | 12/1990 | Biziere et al. |
| 5,045,541 A | 9/1991 | Nakao et al. |
| 5,100,901 A | 3/1992 | Sugimoto et al. |
| 5,104,880 A | 4/1992 | Kozikowski et al. |
| 5,484,490 A | 1/1996 | Tokita et al. |
| 5,554,780 A | 9/1996 | Wolf |
| 5,693,668 A | 12/1997 | Schirlin et al. |
| 5,760,267 A | 6/1998 | Gandolfi et al. |
| 5,929,084 A | 7/1999 | Zhu et al. |
| 6,194,403 B1 | 2/2001 | Hu et al. |
| 6,403,586 B1 | 6/2002 | Ohkuchi et al. |
| 2003/0176437 A1 | 9/2003 | Watterson et al. |
| 2004/0078413 A1 | 4/2004 | Yoshimoto et al. |
| 2004/0235822 A1* | 11/2004 | Shiraishi et al. ......... 514/217.01 |
| 2005/0137397 A1 | 6/2005 | Nelson et al. |
| 2005/0143381 A1 | 6/2005 | Yu et al. |
| 2005/0192278 A1 | 9/2005 | Ewing et al. |
| 2006/0073472 A1 | 4/2006 | Watterson et al. |
| 2008/0021035 A1 | 1/2008 | Watterson et al. |
| 2008/0318899 A1 | 12/2008 | Watterson et al. |
| 2009/0029985 A1 | 1/2009 | Watterson et al. |

FOREIGN PATENT DOCUMENTS

| | | |
|---|---|---|
| EP | 0072726 A2 | 2/1983 |
| EP | 0 094 038 | 11/1983 |
| EP | 0 211 437 | 2/1987 |
| EP | 0211457 A2 | 2/1987 |
| EP | 0382634 A1 | 8/1990 |
| EP | 0628550 A2 | 12/1994 |
| EP | 1 061 077 A1 | 12/2000 |
| EP | 1061077 A1 | 12/2000 |
| FR | 2141697 A1 | 1/1973 |
| FR | 2 847 253 A1 | 5/2004 |
| JP | 63295577 | 12/1988 |
| JP | 04021670 | 1/1992 |
| JP | 04187674 | 7/1992 |
| WO | 9839000 | 9/1998 |
| WO | 1998046574 A1 | 10/1998 |
| WO | 0142241 A1 | 6/2001 |
| WO | WO-02 22605 | 3/2002 |
| WO | 03018563 A1 | 3/2003 |

(Continued)

OTHER PUBLICATIONS

J. M. Contreras et al., "Aminopyridazines as Acetylcholinesterase Inhibitors", J. Med. Chem., vol. 42 (1999) pp. 730-741.

J. M. Contreras et al., "Design, Synthesis, and Structure-Activity Relationships of a Series of 3-[2-(1-Benzylpiperidin-4-yl)ethylamino]pyridazine Derivatives as Acetylcholinesterase Inhibitors", J. Med. Chem., vol. 44 (2001) pp. 2707-2718.

Morris, R.G.M., "Spatial Localization Does Not Require the Presence of Local Cues," Learning and Motivation 12, 239-260 (1981).

Morris, R., "Developments of a Water-Maze Procedure for Studying Spatial Learning in the Rat," Journal of Neuroscience Methods, 11 (1984) 47-60.

(Continued)

*Primary Examiner* — Sreeni Padmanabhan
*Assistant Examiner* — Timothy E Betton
(74) *Attorney, Agent, or Firm* — Millen, White, Zelano & Branigan, P.C.

(57) ABSTRACT

The invention relates to compositions, conjugates and methods comprising pyridazine compounds and cholinesterase inhibitors for modulation of cellular pathways (e.g., signal transduction pathways), for treatment or prevention of inflammatory diseases (e.g., Alzheimer's disease), for research, drug screening, and therapeutic applications.

4 Claims, 13 Drawing Sheets

FOREIGN PATENT DOCUMENTS

| WO | 03047577 A3 | 6/2003 |
|---|---|---|
| WO | 2004046117 A1 | 6/2004 |
| WO | 2004052348 | 6/2004 |
| WO | 2004062652 | 7/2004 |
| WO | 2005009976 A1 | 2/2005 |
| WO | WO 2005/009976 A1 | 2/2005 |
| WO | 2005061509 A1 | 7/2005 |
| WO | 2005063761 A1 | 7/2005 |
| WO | WO 2005/061509 A1 | 7/2005 |
| WO | WO 2005/063761 A1 | 7/2005 |
| WO | 2006026135 A2 | 3/2006 |
| WO | 2006050359 A2 | 5/2006 |
| WO | 2006050389 A2 | 5/2006 |
| WO | WO 2006/050389 A2 | 5/2006 |
| WO | 2007127375 A1 | 4/2007 |
| WO | 2007127475 | 4/2007 |
| WO | 2007130383 | 4/2007 |
| WO | WO-2007-130383 | 4/2007 |
| WO | 2007127448 | 11/2007 |
| WO | 2007127474 | 11/2007 |
| WO | WO-2007-127488 | 11/2007 |
| WO | 2008109437 | 9/2008 |

OTHER PUBLICATIONS

Akiyama, et al., "Inflammation and Alzheimer's Disease," Neurobiol. Aging, 21:383-421 (2002).
Allen and Van Allen, "Some 3,4-Diphenylcinnolines and Related Compounds," J. Amer. Chem. Soc., 73:5854 (1951).
Apter, et al., "Buspirone: Future Directions," J. Clin. Psychopharmacol. 19:86-93 (1999).
Watterson, D.M., et al., "Discovery of New Chemical Classes of Synthetic Ligands that Suppress Neuroinflammatory Responses," Jrnl of Molecular Neuroscience, vol. 19, 89-93, 2002.
Chayer, S., et al., "(3-Pyridazinamin-3-yl) Alpha-Aminoacids: A Facilitated Method of Preparation of Phenylalanine and Proline Representatives," Tetrahedron Letters, 39:841-844, 1998.
Cignarella, G., et al., "Synthesis and biological evaluation of substituted benzo[A]cinnolinones and 3H-benzo[6,7] cyclohepta[1,2-c]pyridazinones: higher homologues of the antihypertensive and antithrombotic 5H-indeno[1,2-c] pyridazinones," J. Med. Chem. 32:2277-2282 (1989).
Contreras, et al., "Aminopyridazines as Acetylcholinesterase Inhibitors," J. of Med. Chem., 42(4):730-741 (1999).
Contreras, et al., "Design, Synthesis, and Structure—Activity Relationships of a Series of 3-[2-(1-Benzylpiperidin-4-yl) ethylamino]pyridazine Derivatives as Acetylcholinesterase Inhibitors," Journ. of Med. Chem., 44(17):2707-2718 (2001).
Constantino, et al., "Synthesis, activity, and molecular modeling of a new series of tricyclic pyridazinones as selective aldose reductase inhibitors," Jrnl. of Med. Chem., 39:4396-4405 (1996).
Constantino, et al., "Synthesis and aldose reductase inhibitory activity of a new series of benzo[h]cinnolinone derivatives," Il farmaco 55:544-552 (2000).
Coudert, et al., "A new synthetic route to 4,6-diarylpyridazinones and some of their derivatives," Jrnl. of Hetero. Chem., 25(3):799-802 (1988).
Craft, J.M., et al., "Human amyloid beta-induced neuroinflammation is an early event in neurodegeneration," Glia 53:484-490 (2006).
Craft, J.M., et al., "Aminopyridazines attenuate hippocampus dependent behavioral deficits induced by human (J-amyloid in a murine model of neuroinflammation," J. Mol. Neurosci., 24:115-122 (2004).
Craft, J.M., et al., "Aminopyridazines inhibit B-amyloid induced glial activation and neuronal damage in vivo," Neurobiol. Aging, 25:1283-1292 (2004).
Craft, J.M., et al., "Neuroinflammation: a potential therapeutic target," Expert. Opin. Ther. Targets, 9:887-900 (2005).
Csende, F., et al., "Copper(II) Chloride as an Efficient Reagent for the Dehydrogenation of Pyridazinone Derivatives," Synthesis, 1240-1242 (1995).
Database—Caplus—XP-002515676, AN:2003:775838 (2003).
Database—Beilstein—XP-002515678, RN:4403492 (Apr. 2008).
Database—Caplus—XP-002515675, AN:1989:423528 (1989).
Database—Capkus—XP-002515677, AN:1973:537067 (1973).
Database—Medline—XP-00253989, AN: NLM3950916 (1986).
Database—Medline—XP-00253989, AN: NLM2989499 (1985).
Du, Y., et al., "Association of an interleukin 1 [alpha] polymorphism with Alzheimer's disease," Neurology 55:480-484 (2000).
Eddy, S., et al., "Efficient Aromatization of 4,5-Dihydro-3(2H)-Pyridazinones Substituted at 5 Position by Using Anhydrous Copper(II) Chloride," Synthetic Communications 30(1):1-7 (2000).
Enyedy, I.J. et al., "Pharmacophore-based discovery of substituted pyridines as novel dopamine transporter inhibitors," Bioorganic & Medicinal Chemistry Letters 13(3) 513-517 (2003).
Farlow, M.R., "Utilizing combination therapy in the treatment of Alzheimer's disease," Expert review of Neurotherapeutics 4(5) 799-808 (2004).
Wermuth, C.-G., "Search for New Lead Compounds: The Example of the Chemical and Pharmacological Dissection of Aminopyridazines," Heterocyclic Chem., 35, 1091-1100 (1998).
Garattini, et al., "Notes on Buspirone's Mechanisms of Action," J. Clin. Psych, 43:19-24 (1982).
Griffin, et al., "Glial-Neuronal Interactions in Alzheimer's Disease: The Potential Role of a 'Cytokin cycle' in Disease Progression," Brain Pathol. 8:65-72 (1998).
Wermuth, C.-G., et al., "3-Aminopyridazine Derivatives with Atypical Antidepressant, Serotonergic, and Dipaminergic Activities," J. Med. Chem., 1989, 32, 528-537.
Hansen, K.B., et al., "First Generation Process for the Preparation of the DDP-IV Inhibitor Sitagliptin," Organic process research & development, 9:634-639 (2005).
Wermuth, C.-G., et al., "Synthesis and Structure-Activity Relationships of a Series of Aminopyridazine Derivatives of Y-Aminobutyric Acid Acting as Selective GABA-A Antagonists," J. Med. Chem., 1987, 30, 239-249.
Heinisch, G., et al., "Pharmacologically active pyridazine derivatives, Part I," Prog. Med. Chem. 27:1-49 (1990).
Heinisch, G., et al., "Pharmacologically active pyridazine derivatives, Part II," Prog. Med. Chem. 29:141-183 (1992).
Wing, L.K., et al., "De Novo and Molecular Target-Independent Discovery of Orally Bioavailable Lead Compounds for Neurological Disorders," Current Alzheimer Research, 2006, 3, 205-214.
Hu, W., et al., "Validation of the Neuroinflammation Cycle as a Drug Discovery Target Using Integrative Chemical Biology and Lead Compound Development with an Alzheimer's Disease-Related Mouse Model," Current Alzheimer's Research, 2:197-205 (2005).
Hu, W., et al., "Development of a novel therapeutic suppressor of brain pro-inflammatory cytokine up-regulation that attenuates synaptic dysfunction and behavioral deficits," Bioorgan. Med. Chem. Lett. 17:414-418 (Watterson) (1996).
Hu, et al., "Apolipoprotein E Attenuates beta-amyloid-induced Astrocyte Activation," J. Nuerochem. 7:1626-1634 (1998).
Hu, et al., "S100-beta Stimulates Inducible Nitric Oxide Synthase Activity and mRNA Levels in Rat Cortical Astrocytes," J. Biol. Chem. 271:2543-2547, 1996.
Hu, et al., "Amyloid-B peptide activates cultured astrocytes: morphological alterations, cytokine induction and nitric oxide release," Brain Res. 785-195-206 (1998).
Hu, W., et al., "Pyridazines as a New Chemotype for Alzheimer's Disease Drug Discovery that Targets Disease Progression," 29th National Medicinal Chemistry Symposium, University of Wisconsin—Madison, Jun. 27-Jul. 1, 2004, Abstract and Poster.
Jones, R.G., "Pyrazines and Related Compounds. I. A New Synthesis of Nydroxypyrazines," J. Amer. Chem. Soc. 71: 78-81 (1949).
Karpus, W.J., et al., "Inhibition of experimental autoimmune encaphalomyelitis by a novel small molecular weight proinflammatory cytokine suppressing drug," J. Neuroimmunology 203(1): 73-78 (2008).
LaDu, et al., "Apolipoprotein E receptors Mediate the Effects of beta-Amyloid on Astrocyte Vultures," J. Biol. Chem. 275:33974-33980 (2000).
LaDu, et al., "Apolipoprotein E and apolipoprotein E Receptors Modulate a beta-induced gilal neuroinflammatory responses," Nuerochem Intl. 39:427-434 (2001).
Lam, et al., "Mechanism of glial activation by S100B: involvement of the transcription factor NFxB," Nuerobiol. Aging 22:765-772 (2001).

Melikian, et al., "Condensation of Muscimol or Thiomuscimol with Aminopyridazines Yields GABA-A antagonists," J. Med. Chem. 35, 4092-4097 (1992).

Merck: "The Merck Manual," Merck & Co., U.S.A., p. 1398, col. 2, "prognosis and treatment of Alzheimer's disease," (1999).

Mirzoeva, et al., "Screening in a cell-based assay for inhibitors of microglial nitric oxide production reveals calmodulin-regulated protein kinases as potential drug discovery targets," Brain Res. 844:126-134 (1999).

Mirzoeva, et al., "Discovery of a 3-amino-6-phenyl-pyridazine Derivative as a New Synthetic Antineuroinflammatory Compound," J. of Medicinal Chem. 45(3):563-566 (Watterson) (2002).

Munoz, L., et al., "A novel p38 alpha MAPK inhibitor suppresses btain proinflammatory cytokine up-regulation and attenuates synaptic dysfunction and behavioral deficits in an Alzheimer's disease mouse model," J. Neuroinflammation 4:21 (Sep. 2007).

"Compound holds promise for neurodegenerative diseases," Nelson Lancet Neurology 5(3) 210 (2006).

Ohno, et al., "Differential effects of Alpha-CaMKII mutation on hippocampal learning and changes in intrinsic neuronal excitability," Eur. J. Neurosci. 23(8) 2235-2240 (2006).

Prusiner, S.B., et al. "Shattuck Lecture—Neurodegenerative Diseases and Prions," New Engl. J. Med. 344:1516-1526 (2001).

Ranaivo, H.R., et al., "Glia as a therapeutic target: selective suppression of human amyloid-beta-induced upregulation of brain proinflammatory cytokine production attenuates neurodegeneration," Jrnl. of Neurosc. 26(2) 662-670 (2006).

Ranaivo, H.R., et al., "Development of Orally Bioavailable Pyridazines that Suppress Neuroinflammation," 9th International Symposium on the Chemistry and Pharmacology of Pyridazines, Antwerp, Belgium, Jul. 2004, Abstract & Power.

Saturnino, C., et al., "Heterocyclic Amidines: I. A One-Step Synthesis of New alpha-substituted Imidazolyphenylacetic acids," Heterocycles 41(7):1491-1501 (1995).

Sheng, J., et al., "In vivo and in vitro evidence supporting a role for the inflammatory cytokine interleukin-1 as a driving force in Alzheimer pathogenesis," Neurobiol. Aging 17:761-766 (1996).

Somera-Molena K.C., et al., "Glial activation links early-life seizures and long-term neurologic dysfunction: evidence using a small molecule inhibitor of pro-inflammatory cytokine upregulation," Epilepsia 48: 1785-1800 (2007).

Sotelo, E., et al., "Efficient aromatization of 4,5-dihydro-3-(2H)-pyridazinones substituted at 5 position by using anhydrous copper (II) chloride," Synthetic Communications 30:1-7 (2000).

Sotelo, E., et al., "Pyridazines. Part 26, Efficient and regioselective Pd-catalyzed arylation of 4-bromo-6-chloro-3-phenylpyridazine," Synless (2) 223-226 (2002).

Sridhar, et al., "Protein Kinases as Therapeutics Targets," Pharm. Res. 17:1345-1353 (2000).

Stahl, P.H., et al., "Handbook of Pharmaceutical Salts, Properties, Selection, and Use," Verlag Helvetica Chimica Acta & Wiley-Vch, Weinheim, International Union of Pure and Applied Chemistry, XP-002459552 (2002).

Toma, L, et al., "6-Chloropyridazin-3-yl Derivatives Active as Nicotinic Agents: Synthesis Binding and Modeling Studies," Jrnl. of Med. Chem. 45(8):4011-4017 (2002).

Van Eldik, et al., "Glia proinflammatory cytokine upregulation as a therapeutic target for neurodegenerative diseases: function-based and target-based discovery approaches," Int. Rev. Neurobiol. 82:277-296 (2007).

Van Eldik, et al., "S100 beta expression in Alzheimer's disease: relation to neuropathology in brain regions," Biochem. Biophys. Acta 1223: 398-403 (1994).

Van Eldik, et al., "Attenuation of Human Abeta-induced Neuroinflammation, Neuronal Death, and Hippocampus-Dependent Behavioral Deficits by a New Class of Bioavailable Small Molecules," Presentation, CNS Diseases Congress: Advances in Therapeutics, Tools and Trails, Philadelphia, Jun. 28-29, 2004.

Van Niel, M.B., et al., "A New Phridazine Series of GABAA alpha-5 Ligands," J. Med. Chem., 48(19):6004-6011 (Merck) (2005).

Velentza, et al., "A protein kinase associated with apoptosis and tumor suppression: Structure, Activity and Discovery of Peptide Substrates," Jrnl. of Biol. Chem. 276(42):38956-38965 (2001).

Velentza, et al., "Structure, Activity, Regulation and Inhibitor Discovery for a Protein Kinase Associated with Apoptosis and Neuronal Death," Pharmacology & Therapeutics 93:217-224 (Feb. Mar. 2002).

Veleltza, et al., "An aminopyridazine-based inhibitor of a pro-apoptotic protein kinase attenuates hypoxia-ischermia induced acute brain injury," Bioorganic & Medicinal Chem. Ltrs. 13:3465-3470 (Watterson) (2003).

Velentza, et al., "Discovery of Substrates and Small Molecule Inhibitors for a Death Associated Protein Kinase," Cell. Biol. Mol. Lett. 6(2B):484-485 (2001).

Wainwright, M., et al., "Protein kinase involved in lung injury susceptibility: evidence from enzyme isoform genetic knockout and in vivo inhibitor treatment," Proc. Nat. Acad. Sci. USA (May 13, 2003) 100(10):6233-6238, Epub. May 2, 2003.

Watterson, et al., "Ligand modulation of glial activation: cell permeable, small molecule inhibitors of serine-threonine protein kinases can block induction of interleukin 1 beta and nitric oxide synthase II," Neurochem. Intl. 39:459-468 (2001).

Watterson, et al., "Discovery of New Chemical Classes of Synthetic Ligands that Suppress Neuroinflammatory Responses," J. Mol. Neuroscience 19:89-93 (2002).

Watterson, D.M., "Development of orally bioavailable small molecule modulators of disease progression in new Alzheimer's Disease related mouse models," Institute for the Study of Aging, Investigator's Meeting, New York, Oct. 7, 2004.

Watterson, D.M., "Discovery of new small molecule modulators of disease progression in an Alzheimer's Disease related mouse model," 12th Mainzer Forum in Medicinal Chemistry, Mainz, Germany, Oct. 2004, Presentation.

Abdel, M et al., "Synthesis of 3-heterocyclic-5,6-diphenylpyridazines," Egyptian Journal of Pharmaceuticals Sciences, 1998, vol. 38, No. 1-3, pp. 87-93.

Adams et al., "Concise Synthesis of 1 H-pyrazin-2-ones and 2-Aminopyrazines," Synlett., 2004, vol. 11, pp. 2031-2033.

Akama et al., "Amyloid Beta-peptide stimulates nitric oxide production in astrocytes through an NFxB-dependent mechanism," PNAS, 1998, vol. 95, pp. 5795-5800.

Badger et al., "Pharmacological Profile of SB 203580, a Selective Inhibitor of Cytokine Suppressive Binding Protein/ p38 Kinase, in Animal Models of Arthritis, Bone Resorption, Endotoxin Shock and Immune Funtion," J. Pharmacol Exp. Ther., vol. 279, pp. 1453-1461, 1996.

Bhagwat et al., "Gene-regulation protein kinases as important anti-inflammatory targets," Drug Disc. Today, 1999, vol. 4, pp. 472-479.

Bhat et al., "Extracellular Signal-regulated Kinase and p38 Subgroups of Mitogen-Activated Protein Kinases Regulate Nitric Oxide Synthase and Tumor Necrosis Factor-alpha Gene Expression in Endotoxin-Stimulated Primary Gilial Cultures," J. Neurosci., vol. 18, pp. 1633-1641, 1998.

Bhattacherjee et al., Zeitschrift fur Kristallographie, 1958, vol. 110, No. 1-6, pp. 472-474.

Blasi et al., "Immortalization of murine microglial cells by a v-raf/v-myc carrying retrovirus," J. Neuroimmunol. vol. 27, pp. 229-237, 1990.

Bluhm, J. Het. Chem., 1981, vol. 18, pp. 189-190.

Borsche et al., Justus Liebigs Annalen der Chemie, 1943, vol. 555, pp. 70-77.

Brott et al., "Treatment of acute ischemic stroke," N Engl J Med., Sep. 7, 2000, vol. 343, No. 10, pp. 710-722.

Cardona et al., "Control of microglial neurotoxicity by the fractalkine receptor, " Nature Neurosci., 2006, vol. 9, pp. 917-924.

Chen et al., "An Experimental Model of Closed Head Injury in Mice: Pathophysiology, Histopathology, and Cognitive Deficits," J. Neurotrauma, 1996, vol. 13, pp. 557-568.

Chitaley, K. et al., "Antagonism of Rho-Kinase Stimulates Rat Penile Erection Via a Nitric Oxide-Independent Pathway," Nature Medicine, Jan. 2001, vol. 7, No. 1, pp. 119-122.

Communication pursuant to Article 94(3) EPC for EP 02796459 dated Sep. 30, 2010.

Communication pursuant to Article 94(3) EPC for EP 07776351 dated Oct. 9, 2010.

Communication pursuant to Article 94(3) EPC for EP05823123 dated Dec. 17, 2009.

Communication pursuant to Article 94(3) EPC for EP07756162 dated Feb. 11, 2009.
Communication pursuant to Article 94(3) EPC for EP07756162 dated Feb. 5, 2010.
Communication regarding the European Search Report for EP 02796459 dated Oct. 29, 2004.
Communication regarding the Extended European Search Report for EP 05823123 dated Mar. 2, 2009.
Craft, J. et al., "Enhanced susceptibility of S-100B transgenic mice to neuroinflammation and neuronal dysfunction induced by intracerebroventricular infusion of human Beta-amyloid," GLIA, 2005, vol. 51, pp. 209-216.
D'Ambrosio, R. et al., "Epilepsy after head injury," Curr. Opin. Neurol., 2004, vol. 17, pp. 7431-7735.
De Silva et al., "Blockade of p38 Mitogen-activated Protein Kinases Pathway Inhibits Inducibel Nitric-oxide Synthase Expression in Mouse Astrocytes," J. Biol Chem., vol. 272, pp. 28373-28380, 1997.
Dogan et al., "Effects of MDL 72527, a Specific Inhibitor of Polyamine Oxidase, on Brain Edema, Ischemic Injury Volume, and Tissue Polyamine Levels in Rats After Temporary Middle Cerebral Artery Occlusion," J. Neurochem., 1999, vol. 72, pp. 765.
Donato, R. et al., "Functional roles of S100 proteins, calcium-binding proteins of the EF-hand type," Biochem Biophys Acta, vol. 1450, pp. 191-231, 1999.
Dos Santos, "Invited review: mechanisms of ventilator-induced lung injury: a perspective," Appl. Physiol, Oct. 2000, vol. 89, No. 4, pp. 1645-1655.
Dragunow M. et al., "Clusterin accumulates in dying neurons following status epilepticus," Mol. Brain. Res., 1005, vol. 32, pp. 279-290, 1995.
Du, Y. et al., "Association of an interleukin 1 [alpha] with Alzheimer's disease," Neurology, vol. 55, pp. 480-484, 2000.
Dube, C. et al., "Prolonged Febrile Seizures in the immature rat model enhance hippocampal excitability long term," Ann Neurol., 2000, vol. 47, pp. 336-344.
Finlayson et al., "Acquired QT interval prolongation and HERG: implications for drug discovery and development," Eur J. Pharmacol., Oct. 2004, vol. 500, No. 1-3, pp. 129-142.
Frautschy, S. A. et al., "Rodent models of Alzheimer's disease: rat A Beta infusion approaches to amyloid deposits," Neurobiol. Aging., 1996, vol. 17, pp. 311-321.
French, J. et al., "Characteristics of medial temporal lobe epilepsy. I. Results of history and physical examination," Ann Neurol., 1993, vol. 34, pp. 774-780.
Garcia Mera et al., Anales de Quimica, Serie C: Quimica Organica y Bioquimica, 1985, vol. 81, No. 3, pp. 280-283.
Garcia, "Regulation of Endothelial Cell Gap Formation and Barrier Dysfunction: Role of Myosin Light Chain Phosphorylation," J. Cell Physiol, 1995, vol. 163, pp. 510-522.
Ghajar et al., "Traumatic Brain Injury," Lancet, Sep. 9, 2000, 356(9233), pp. 923-929.
Gibbs, J. et al., "Mechanism-based target identification and drug discovery in cancer research," Science, 2000, vol. 287, pp. 1969-1973.
Giorgi, F et al., "Effects of status epilepticus early in life on susceptibility to ischemic injury in adulthood," Epilepsia, 2005, vol. 46, pp. 490-498.
Griesser, in Chapter 8, The Importance of Solvates (pp. 211-230), in the text, Polymorphism: In the Pharmaceutical Industry Hilfker, 2006.
Guo, L. et al., "Similar activation of glial cultures from different rat brain regions by neuroinflammatory stimuli and downregulation of the activation by a new class of small molecule ligands," Neurobiol. Aging. 2001, vol. 22, No. 6, pp. 975-981.
Guo, Z. et al., "Head Injury and the risk of AD in the Mirage study," Neurology, 2000, vol. 54, pp. 1316-1323.
Hagberg, H. et al., "Effect of inflammation on central nervous system development and vulnerability," Curr. Opin. Neurol., 2005, vol. 18, pp. 117-123.
Han, B. et al., "Clusterin contributes to caspase-3-independent brain injury following neonatal hypoxia-ischemia," Nature Med., 2001, vol. 7, pp. 338-343.

Hargreaves et al., "A new and sensitive method for measuring thermal nociception in cutaneous hyperalgesia," Pain, 1988, vol. 32, pp. 72-78.
Haut, S. et al., "Susceptibility of immature and adult brains to seizure effects," Lancet Neurol., 2004, vol. 3, pp. 608-617.
Heinisch, G. et al., Prog. Med. Chem. 1992, vol. 29, pp. 141-183.
Hirohashi et al., "Pharmacological Studies with the Alpha2-Adrenoceptor Antagonist Midaglizole," Arzneim-Forsch./ Drug Res., 1991, vol. 41, pp. 9-18.
Holmes, G. et al., "Effects of seizures on brain development: lessons from the laboratory," Pediatr Neurol., 2005, vol. 33, pp. 1-11.
Holmes, G. et al., "Seizures in the developing brain: perhaps not so benign after all," Neuron, 1998, vol. 21, pp. 1231-1234.
Huang, Y et al., "Glutamate transporters bring competition to the synapse," Curr. Opin. Neurobiol., 2004, vol. 14, pp. 346-352.
Igarashi et al., "Exogenous Tumor Necrosis Factor-Alpha Mimics Nucleus Pulposus-Induced Neuropathology," Spine, 2000, vol. 25, pp. 2975-2980.
Jensen, F. et al., "NBQX blocks acute and late epileptogenic effects of perinatal hypoxia," Epilepsia, 1995, vol. 36, pp. 966-972.
Koh, S. et al., "Early-life seizures increase susceptibility to seizure-induced brain injury in adulthood," Neurology, 1999, vol. 53, pp. 915-921.
Kulkarni, V., "Structure-activity relationship in pyridazine and phathalazine series of antihypertensive agents by molecular orbital calculations," Indian Juran of Biochemistry & Biophysics, 1975, vol. 12, No. 4, pp. 367-369.
Kumar et al., "Drugs Targeted Against Protein Kinase," Expert Opinion, 2001, vol. 6, No. 2, pp. 303-315.
Laskowitz et al., "Downregulation of Microglial Activation by Apolopoprotein E and ApoE-Mimetic Peptides," Exp. Neurol. 2001, vol. 167, pp. 74-85.
Letty, S. et al., "Differential impairments of spatial memory and social behavior in two models of limbic epilepsy," Epilepsia, 1995, vol. 36, pp. 973-982.
Levition, A. et al., "Brain damage markers in children. Neurobiological and clinical aspects," Acta Paediatrica, 2002, vol. 91, pp. 9-13.
Longa et al., "Reversible Middle Cerebral Artery Occlusion Without Craniectomy in Rats," Stroke, 1989, vol. 30, pp. 84-91.
Loscher, W. et al., "New Horizons in the development of antiepileptic drugs," Epilepsy Res., 2002, vol. 50, pp. 3-16.
Maragakis, N. et al., "Glutamate transporters: animal models t neurologic disease," Neurobiol Dis. 2004, vol. 15, pp. 461-473.
Maroney et al., "CEP-1347 (KT7515), a semisynthetic inhibitor of the mixed lineage kinase family," J. Biol Chem., 2001, vol. 276, No. 27, pp. 25302-25308.
Maroney et al., "CEP-1347 (KT7515), an inhibitor of JNK Activation, Rescues Sympathetic Neurons and Neuronally Differentiated PC 12 Cells from Death Evoked by Three Distinct Insults," J. Neurochem., 2001, vol. 73, pp. 1901-1912.
Minghetti, L. et al., "Role of Inflammation in neurodegenerative diseases," Curr. Opin. Neurol., 2005, vol. 18, pp. 315-321.
Mrak, R. et al., "Glia and cytoknes in progression of neurodogeneration," Neurobiol Aging, 2005, Volo. 26, pp. 349-354.
Nakao, Tatsu et al., "Preparation of triazolopyridazine-containing polyheterocycles as pharmaceuticals," Database Caplus XP-002515675, 1989.
Namura et al., "Intravenous administration of MEK inhibitor U00126 affords brain protection against forebrain Ischemia and focal cerebral ischemia," Proc Natl Acad Sci USA, Sep. 25, 2001, vol. 98, No. 20, pp. 11569-11574, Epub Aug. 14, 2001.
Office Action for CN 200580037702 dated Sep. 4, 2009 with translation.
Office Action for MX/a/2007/005247 dated Aug. 25, 2009 with translation.
Office Action regarding POA documents for MX/a/2007/005247 dated Nov. 2, 2005.
Ohno et al., "Trace eyeblink conditioning requires the hippocampus but not autophosphorylation of Alpha-CaMKII in mice," Learning & Memory, 2005, vol. 12, No. 3, pp. 211-215.
Parker, J. et al., "Inhibitors of myosin light chain kinase and phosphodiesterase reduce ventilator-induced lung injury," J. Appl. Physiol, Dec. 2000, vol. 89, No. 6, pp. 2241-2248.

Partyka et al., J. Med. Chem., 1971, vol. 14, No. 3, pp. 262-264.
Perry, V et al., "Systemic infections and inflammation affect chronic neurodegeneration," Nat Rev Immunol., 2007, doi: 10.1038/nri 2015.
Petrova et al., "Cyclopentenone prostaglandins suppress activation of microglia: Down-regulation of inducible nitric-oxide synthase by 15-deoxy-Δ 12, 14-prostaglandin J2," PNAS, 1999, vol. 96, pp. 4668-4673.
Pirvola, U. et al., "Rescue of Hearing Auditory Hair Cells, and Neurons by CEP-1347/KT7515, an inhibitor of c-Jun N-Terminal Kinase Activation," J. Neurosci., 2000, vol. 20, pp. 43-50.
Rao, V. et al., "Antisense Knockdown of the glial glutamate transporter GLT-1 exacerbates hippocampal damage following traumatic injury to rat brain," Eur. J. Neurosci., 2001, vol. 13, pp. 119-128.
Ravizza et al., "Inflammatory response and glia activation in developing rat hippocampus after status epilepticus," Epilepsia, 2005, vol. 46, pp. S113-S117.
Recanatini et al., "QT prolongation through hERG K (+) channel blockade: current knowledge and strategies for the early prediction during drug development," Med Res Rev, Mar. 2005, vol. 25, No. 2, pp. 133-166.
Reply to Communication pursuant to Article 94(3) EPC for EP 02796459 of Sep. 30, 2010 dated Apr. 8, 2009.
Reply to Communication pursuant to Article 94(3) EPC for EP07756162 of Feb. 11, 2009 dated Nov. 19, 2009.
Reply to Office Action for MX/a/2007/005247 of Aug. 25, 2009 dated Mar. 1, 2010.
Rizzi et al., "Glia activation and cytokine increase in rat hippocampus by kainic acid-induced status epilepticus during postnatal development," Neurobiol. Dis., 2003, vol. 14, pp. 494-503.
Roden, "Drug-induced prolongation of the QT interval," N. Engl. J. Med., Mar. 4, 2004, vol. 350, No. 10, pp. 1013-1022.
Rothermundt, M. et al., "S100B in brain damage and neurodegeneration," Mircoscopy Research & Technique, 2003, vol. 60, pp. 614-632.
Sanchez et al., "Decreased glutamate receptor 2 expression and enchanced epileptogenesis in immature rat hippocampus after perinatal hypoxia-induced seizures," J. Neurosci., 2001, vol. 21, pp. 8154-8563.
Sayin, U., et al., "Seizures in the developing brain cause adverse long-term effects o spatial learning and anxiety," Epilepsia, 2004, vol. 45, pp. 1539-1548.
Schmid, R. et al., "Effects of neonatal seizures on subsequent seizure-induced brain injury," Neurology, 1999, vol. 53, pp. 1754-1761.
Schmued, L. et al., "Fluoro-Jade B: a high affinity fluorescent marker for the localization of neuronal degeneration," Brain Res., 2000, vol. 874, pp. 123-130.
Schumacher et al., "Death Associated Protein Kinase as a Potential Therapeutic Target," Expert Opin. Ther. Targets, Aug. 2002, vol. 6, No. 4, pp. 497-506.
Selkoe, D. J. et al., "Alzheimer's Disease: Genes, Proteins, and Therapy," Physiol. Rev., 2001, vol. 81, pp. 741-766.
Stevens et al., "NHLBI workshop report: endothelial cell phenotypes in heart, lung, and blood diseases," Am J Physiol Cell Physiol, Nov. 2001, vol. 281, No. 5, pp. 1422-1433.
Strohmeyer, R. et al., "Association of factor H of the alternative pathway of complement with agrin and complement receptor 3 in Alzheimer's disease brain," J. Neuroimmunol., 2002, vol. 131, pp. 135-146.
Strohmeyer, R. et al., "Molecular and cellular mediators of Alzheimer's disease inflammation," J. Alz. Dis., 2001, vol. 3, pp. 131-157.
Supplementary European Search Report for EP 02796459 dated Oct. 7, 2004.
Supplementary European Search Report for EP05823123 dated Feb. 18, 2009.
Suzuki et al., Heterocycles (2002), 57(4), pp. 723-731.
Tereshko et al., "Crystal structures of the catalytic domain of human protein kinase associated with apoptosis and tumor suppression," Nat Struct Biol., Oct. 2001, vol. 8, No. 10, pp. 899-907.
Thomson Innovation Record View, "New triazole: pyridazine derives. have anti-anxiety drug neutralizing activity and analgesic anti-inflammatory action," Retrieved Nov. 3, 2010; English Abstract of JP63295577.
Thomson Innovation, "3-amino-6-aryl-1,2,4-triazolo(4,3-b) pyridazines, their preparation and use," Retrieved from Patent Record View on Sep. 1, 2010; English Abstracts of EP0094038.
Tinsley et al., "Myosin light chain kinase transference induces myosin light chain activation and endothelial hyperpermeability," Am J Physiol Cell Physiol, Oct. 2000, vol. 279, No. 4, pp. 1285-1289.
Troy et al., "Beta-amyloid-induced neuronal apoptosis required c-Jun N-terminal kinase activation," J. Neurochem., 2001, vol. 77, pp. 157-164.
Van Eldik et al., "Synthesis and Expression of a Gene Coding for the Calrium-modulated Protein S100B and designed for cassette-based, Site-directed Mutagenesis," J. Biol. Chem., 1988, vol. 263, pp. 7830-7837.
Van Eldik et al., "The Janus face of glial-derived S100B: beneficial and detrimental functions in the brain," Restorative Neurol Neurosci., 2003, vol. 21, pp. 97-108.
Veber et al., "Molecular 30 properties that influence the oral bioavailability of drug candidates," J. Med. Chem, 2002, vol. 45, pp. 2615-2623.
Verbitsky, M. et al., "Altered hippocampal transcript profile accompanies an age-related spatial memory deficit in mice," 2004, Learning and Memory, vol. 11, pp. 253-260.
Vezzani et al., "Functional role of inflammatory cytokines and anti-inflammatory molecules in seizures and epileptogenesis," Epilepsia, 2002, vol. 43, pp. S30-S35.
Vezzani, A Epilepsy Currents, vol. 4, No. 2, Feb. 26, 2004, pp. 73-75.
Vezzani, A. et al., "Brain Inflammation in epilepsy: Experimental and clinical evidence," Epilepsia, 2005, vol. 46, pp. 1724-1743.
Vieth et al., "Characteristics physical properties and structural fragments of marketed oral drugs," J. Med. Chem., 2004, vol. 47, pp. 224-232.
Villa et al., J. Het. Chem., 1999, vol. 36(2), pp. 485-492.
Wainwright, M et al., "Carnitine treatment inhibits increases in cerebral carnitine esters and glutamate detected by mass spectrometry following hypoxiaischemia in newborn rats," Stroke 37,2005, pp. 524-530.
Wainwright, M. et al., "Increased susceptibility of S100B transgenic mice to perinatal hypoxia-ischemia," Annals of Neurol., 2004, vol. 56, pp. 61-67.
Watterson, D. M. et al., "Discovery of a new class of synthetic protein kinase inhibitors that suppress selective aspects of glial activation and protect against [J-amyloid induced injury. A foundation for future medicinal chemistry efforts focused on target Alzheimer's Disease progression," J. Mol. Neurosci., vol. 20, pp. 411-424, 2003.
Watterson, D. M. et al., "Discovery of a new class of synthetic protein kinase inhibitors that suppress selective aspects of glial activation and protect against [J-amyloid induced injury. A foundation for future medicinal chemistry efforts focused on target Alzheimer's Disease progression," Database Caplus XP-002515676, 2003.
Weiss, C. et al., "Spatial learning and memory in aging C57BL/b mice," Neurosci. Res. Comm., 1998, vol. 23, No. 2, pp. 77-92.
Weiss, S. et al., "Anatomic studies of DNA fragmentation in rat brain after systemic kainic acid administration," Neuroscience, vol. 74, No. 2, pp. 541-551, 1996.
Wermuth, C. G. et al., Selected Procedures for the Preparation of Pharmaceutically acceptable salts, in Stahl. P.H., Wermuth, C.G. (Ed.) Handbook of Pharmaceutical Salts, Wiley-VCH, pp. 249-264, 2002.
Wikipedia, Isomers, last modified Aug. 16, 2010, http://en.wikipedia.org/wiki/Isomer, downloaded Aug. 24, 2010.
Yamamoto et al., "Development changes in distribution of death-associated protein kinase mRNAs," J Neurosci Res., 1999, vol. 58, pp. 674-683.
Yoshinari et al., "Effects of a dual inhibitor of tumor necrosis factor-alpha and interleukin-1 on lipopolysaccharide-induced lung injury in rats: involvement of the p38 mitogen-activated protein kinase pathway," Crit. Care Med., Mar 2001, vol. 29, No. 3, pp. 628-634.
Zhang, G. et al., "Long-term alterations in glutamate receptor and transporter expression following early-life seizures are associated with increased seizure susceptibility," J. Neurochem., 2004, vol. 88, pp. 91-101.
Zhou et al., "Herg-like K+ Channels in Microglia," J. Gen Physiol, 1998, vol. 111, No. 6, pp. 781-794.

* cited by examiner

MW01-5-188WH

MW01-6-189WH

MW01-7-076WH          MW01-7-085WH and CHOLINESTERASE INHIBITORS

This application claims the benefit of the filing date of U.S. Provisional Application Ser. No. 60/796,348 filed Apr. 28, 2006.

This invention was made with government support under Grant Numbers NS047586 and AG013939 awarded by the National Institutes of Health. The government has certain rights in the invention.

FIELD OF INVENTION

The invention relates to novel compositions, conjugates and methods using pyridazine compounds and cholinesterase inhibitors.

BACKGROUND OF INVENTION

Actylcholinesterase inhibitors or cholinesterase inhibitors reduce the degradation of acetylcholine thereby enhancing cholinergic transmission. A number of cholinesterase inhibitors, including tacrine (COGNEX®), galantamine (RAZADYNE®), rivastigmine (EXELON®), and donepezil (ARICEPT®) are approved for administration to Alzheimer's disease (AD) patients. Other compounds including physostigmine are under investigation as potential therapy for Alzheimer's disease. These compounds offer relatively similar mean gains in cognitive abilities to patients with AD in controlled clinical trials, and they have similar side effects—nausea, vomiting or diarrhea.

SUMMARY OF INVENTION

The present invention relates to compositions, conjugates, and methods (e.g. combination therapies) comprising one or more pyridazine compound and one or more cholinesterase inhibitor. The compositions, conjugates and methods may be used for the prevention, intervention, and/or treatment of a disease disclosed herein, and they may comprise a therapeutically effective amount of a pyridazine compound and a therapeutically effective amount of a cholinesterase inhibitor.

A composition, conjugate, or method (e.g. combination therapy) comprising one or more pyridazine compound and one or more cholinesterase inhibitor may employ different mechanisms to achieve maximum therapeutic efficacy, and they may improve tolerance to the therapy with a reduced risk of side effects that may result from higher doses or longer term monotherapies (i.e., therapies with each compound alone). Therefore, a treatment of the invention may permit the use of lower doses of each compound (e.g., lower doses of a cholinesterase inhibitor) with reduced adverse effects of each compound (e.g., reduced side effects of cholinesterase inhibitors). Suboptimal dosages may provide increased safety margins, and may also reduce the costs of drug(s) necessary to achieve prophylaxis and therapy. A treatment utilizing a single combination dosage unit may also provide increased convenience and may result in enhanced compliance. Advantages of a composition, conjugate, or combination therapy may additionally include higher stability towards degradation and metabolism, longer duration of action, and/or longer duration of action or effectiveness at particularly low doses.

The invention relates to a composition, in particular a pharmaceutical composition, comprising one or more pyridazine compound and one or more cholinesterase inhibitor optionally in pharmaceutically acceptable carriers, excipients, or vehicles. The invention also relates to a pharmaceutical composition comprising one or more pyridazine compound and one or more cholinesterase inhibitor that provide one or more beneficial effects relative to each compound alone. A beneficial effect may include enhanced therapeutic effects.

The invention in aspects contemplates a pharmaceutical composition for the treatment of a disease comprising therapeutically effective amounts of one or more pyridazine compound and one or more cholinesterase inhibitor to provide beneficial effects, in particular sustained beneficial effects relative to each compound alone. The beneficial effects provided by a composition of the invention can include enhanced therapeutic effects, in particular sustained therapeutic effects. In an embodiment, the composition is in a form or the components are in effective dosages such that administration to a subject modulates and in particular provides a reduction or reversal, in particular selective reduction or reversal, of one or more of the following: inflammation (e.g. neuroinflammation), activation of signaling pathways involved in inflammation (e.g., neuroinflammation), cell signaling molecule production, activation of glia or glial activation pathways and responses, proinflammatory cytokines or chemokines (e.g., interleukin (IL), in particular IL-1β) or tumor necrosis factor (TNF, in particular TNFα), activation of astrocytes or astrocyte activation pathways and responses, activation of microglia or microglial activation pathways and responses, oxidative stress-related responses such as nitric oxide synthase production and nitric oxide accumulation, acute phase proteins, loss of synaptophysin and PSD-95, components of the complement cascade, loss or reduction of synaptic function, protein kinase activity (e.g., death associated protein kinase activity), behavioral deficits, cell damage (e.g., neuronal cell damage), cell death (e.g., neuronal cell death), and/or amyloid β deposition of amyloid plaques, in the subject, in particular for a sustained period of time after cessation of treatment. A composition can have increased bioavailability (absorbed more rapidly and to a higher degree) or provide enhanced therapeutic effects.

The invention also provides a pharmaceutical composition for the treatment of a disease comprising a therapeutically effective amount of a pyridazine compound and a cholinesterase inhibitor, to provide a sustained beneficial effect following treatment in a pharmaceutically acceptable carrier, excipient, or vehicle. In an aspect, a pharmaceutical composition comprising a pyridazine compound and a cholinesterase inhibitor is provided which has been adapted for administration to a subject to provide beneficial effects to treat a disease. In an embodiment, the composition is in a form such that administration to a subject results in therapeutic effects in the subject for a sustained period of time after cessation of treatment.

In an aspect, the invention features a composition comprising one or more pyridazine compound and one or more cholinesterase inhibitor in dosages effective for modulation of, in particular reducing inflammation, activation of signaling pathways involved in inflammation, cell signaling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses, acute phase proteins, loss of synaptophysin and PSD-95, components of the complement cascade, loss or reduction of synaptic function, protein kinase activity, behavioral deficits, neuronal cell damage, neuronal cell death, and/or amyloid β deposition of amyloid plaques, in particular for a sustained period following administration of the pyridazine compound and cholinesterase inhibitor.

In another aspect, the invention features a composition comprising a pyridazine compound and a cholinesterase inhibitor in a dosage effective for reducing glial activity, microglial activity and/or astrocyte activity, inflammation, and/or cognitive decline in the subject, in particular for a sustained period following administration of the composition.

The invention provides a composition, in particular a pharmaceutical composition, comprising a pyridazine compound and a cholinesterase inhibitor that provides beneficial effects in the treatment of a disease disclosed herein, in particular diseases involving neuroinflammation.

In an aspect the invention provides a combination of a pyridazine compound and a cholinesterase inhibitor that provides beneficial effects in the treatment of conditions for which either a pyridazine compound or a cholinesterase inhibitor have been demonstrated to have a therapeutic effect, including but not limited to Alzheimer's disease, and similar diseases.

The invention also provides a pharmaceutical composition in separate containers and intended for simultaneous or sequential administration to a subject especially to provide beneficial effects, comprising one or more pyridazine compound and one or more cholinesterase inhibitor both optionally together with pharmaceutically acceptable carriers, excipients, or vehicles.

The invention further provides a conjugate comprising a pyridazine compound interacting with or linked to a cholinesterase inhibitor.

The invention still further provides methods for preparing compositions and conjugates of the invention. In an aspect, the invention provides a method of preparing a stable pharmaceutical composition comprising one or more pyridazine compound and one or more cholinesterase inhibitor adapted to provide beneficial effects, in particular sustained beneficial effects, following treatment. A method can comprise mixing one or more pyridazine compound and one or more cholinesterase inhibitor, and optionally pharmaceutically acceptable carriers, excipients, or vehicles. A pharmaceutically acceptable carrier, excipient, or vehicle may be selected that is effective to physically stabilize the pyridazine compound(s) and/or cholinesterase inhibitor(s). After compositions or conjugates have been prepared, they can be placed in an appropriate container and labeled for treatment of an indicated disease or condition. For administration of a composition or conjugate of the invention, such labeling would include amount, frequency, and method of administration.

In some aspects the invention provides methods to make commercially available pills, tablets, caplets, soft and hard gelatin capsules, lozenges, sachets, cachets, vegicaps, liquid drops, elixirs, suspensions, emulsions, solutions, syrups, aerosols (as a solid or in a liquid medium) suppositories, sterile injectable solutions, and/or sterile packaged powders, which contain a pyridazine compound and a cholinesterase inhibitor.

The invention also contemplates the use of one or more pyridazine compound and one or more cholinesterase inhibitor, a composition, conjugate, or method of the invention for therapeutic applications (e.g., preventing, and/or ameliorating disease severity, disease symptoms, and/or periodicity of recurrence of a disease disclosed herein), or for research, drug screening, and therapeutic applications.

Therefore, the invention contemplates the prevention and treatment, in a subject, of diseases using a pyridazine compound and a cholinesterase inhibitor, a composition, combination treatment, and/or conjugate of the invention. In particular, the invention provides a method for treating and/or preventing a disease in a subject comprising administering to the subject therapeutically effective amounts of one or more pyridazine compound and one or more cholinesterase inhibitor, in particular to provide beneficial effects. In an aspect the invention provides a treatment which results in sustained beneficial effects following treatment. A method of the invention can be used therapeutically or prophylactically in a subject susceptible to, or having a predisposition to a disease disclosed herein.

In an aspect, the invention provides a method for the prevention and/or intervention of a disease disclosed herein in a subject comprising administration of at least one pyridazine compound and at least one cholinesterase inhibitor or a composition or conjugate of the invention to the subject.

The invention provides a method of treating a disease comprising administering therapeutically effective amounts of at least one pyridazine compound and at least one cholinesterase inhibitor, a composition, combination treatment or conjugate of the invention to a subject in need thereof to thereby produce beneficial effects. In an embodiment, the compounds, composition, and/or conjugate are administered orally or systemically.

In an embodiment, the invention provides a method for the prevention and/or intervention of a disease discussed herein in a subject comprising co-administering at least one pyridazine compound and at least one cholinesterase inhibitor or a composition or conjugate of the invention to a subject in need thereof.

In a further aspect, the invention provides a method for amelioriating progression of a disease or obtaining a less severe stage of a disease in a subject suffering from such disease comprising administering therapeutically effective amounts of at least one pyridazine compound and at least one cholinesterase inhibitor, or a composition or conjugate of the invention.

The invention relates to a method of delaying the progression of a disease comprising administering therapeutically effective amounts at least one pyridazine compound and at least one cholinesterase inhibitor, or a composition or conjugate of the invention.

The invention also relates to a method of increasing survival of a subject suffering from a disease comprising administering therapeutically effective amounts of at least one pyridazine compound and at least one cholinesterase inhibitor, or a composition or conjugate of the invention.

In an embodiment, the invention relates to a method of improving the lifespan of a subject suffering from a disease comprising administering therapeutically effective amounts of at least one pyridazine compound and at least one cholinesterase inhibitor, or a composition or conjugate of the invention.

A treatment method of the invention may be sustained over several days, weeks, months or years thereby having a major beneficial impact on the severity of a disease and its complications.

In methods of the invention, a pyridazine compound and a cholinesterase inhibitor are administered simultaneously or sequentially. In methods using simultaneous administration, the agents can be present in a combined composition or can be administered separately. In combinations and methods of the invention, each active ingredient can be administered either in accordance with their usual dosage range or a dose below their usual dosage range.

A pyridazine compound and a cholinesterase inhibitor in a composition, conjugate or method of the invention may be in a ratio selected to augment the activity of the pyridazine compound and/or a cholinesterase inhibitor to provide one or more beneficial effects.

Combinations of a pyridazine compound and a cholinesterase inhibitor in compositions, conjugates and methods of the invention may be selected to provide unexpectedly additive effects or greater than additive effects i.e. synergistic effects.

The invention also contemplates the use of at least one pyridazine compound and at least one cholinesterase inhibitor for the preparation of a medicament for preventing and/or treating a disease. In an embodiment, the invention relates to the use of additive or synergistically effective amounts of at least one pyridazine compound and at least one cholinesterase inhibitor for the preparation of a medicament for preventing and/or treating a disease disclosed herein. The invention additionally provides uses of a pharmaceutical composition and a conjugate of the invention in the preparation of medicaments for the prevention and/or treatment of diseases disclosed herein. In aspects of the invention, the medicaments provide beneficial effects, preferably sustained beneficial effects following treatment. A medicament may be in a form suitable for consumption by a subject, for example, a pill, tablet, caplet, soft and hard gelatin capsule, lozenge, sachet, cachet, vegicap, liquid drop, elixir, suspension, emulsion, solution, syrup, aerosol (as a solid or in a liquid medium) suppository, sterile injectable solution, and/or sterile packaged powder.

A composition, conjugate, or method (e.g. combination therapy) of the invention comprising a pyridazine compound and a cholinesterase inhibitor may be used to modulate, in particular, reduce or inhibit activation of signaling pathways involved in inflammation (e.g., neuroinflammation), cell signaling molecule production, activation of glia or glial activation pathways and responses, activation of astrocytes or astrocyte activation pathways and responses, activation of microglia or microglial activation pathways and responses, proinflammatory cytokines or chemokines [e.g., interleukin (IL) or tumor necrosis factor (TNF)], oxidative stress-related responses such as nitric oxide synthase production and nitric oxide accumulation, acute phase proteins, loss or reduction of synaptic function, components of the complement cascade, protein kinase activity (e.g., death associated protein kinase activity), behavioral deficits, neuronal cell damage, and/or neuronal cell death.

A composition, conjugate, or method (e.g. combination therapy) comprising a pyridazine compound and a cholinesterase inhibitor may also be used to reverse or inhibit neuroinflammation and/or reduce beta amyloid deposits in the brain (beta-amyloid plaques).

Further, a composition, conjugate, or method (e.g. combination therapy) comprising a pyridazine compound and a cholinesterase inhibitor may also be used to amelioriate progression of a disease or obtain a less severe stage of a disease in a subject suffering from such disease; delay the progression of a disease; increase survival of a subject suffering from a disease; treat or prevent a neurodegenerative disease; and/or treat memory or cognitive impairment, in particular mild cognitive impairment (MCI).

In an aspect, the invention provides a method for treating in a subject a neuroinflammatory disease comprising administering to the subject therapeutically effective amounts of a pyridazine compound and a cholinesterase inhibitor in pharmaceutically acceptable carriers, excipients, or vehicles.

In an aspect, the invention provides a method of treating memory and/or cognitive impairment comprising administering to a subject (e.g., a human) simultaneously or sequentially, a pyridazine compound and a cholinesterase inhibitor, a composition or conjugate of the invention. In another aspect, the invention provides a method for preventing and/or treating memory and/or cognitive impairment associated with dementia comprising administering a therapeutically effective amount of at least one pyridazine compound and at least one cholinesterase inhibitor, or a composition or conjugate of the invention.

The invention has particular applications in preventing and/or treating Alzheimer's disease and other similar diseases. In an aspect, the invention provides a method for preventing and/or treating Alzheimer's disease comprising administering therapeutically effective amounts of at least one pyridazine compound and at least one cholinesterase inhibitor, or a composition or conjugate of the invention. In an embodiment, the invention relates to a method of treating Alzheimer's disease comprising administering therapeutically effective amounts of one or more pyridazine compound and one or more cholinesterase inhibitor which upon administration to a subject with symptoms of Alzheimer's disease produces beneficial effects, in particular sustained beneficial effects. In an aspect, the invention provides a method of treating memory and/or cognitive impairment associated with Alzheimer's disease comprising administering to a subject (e.g., a human) simultaneously or sequentially, a pyridazine compound and a cholinesterase inhibitor.

An embodiment of the invention provides a method for preventing and/or treating Alzheimer's disease, the method comprising administering to a mammal in need thereof a combination of a pyridazine compound and cholinesterase inhibitor in an amount sufficient to inhibit, reduce, or reverse neuroflammation, activation of glia, activation of microglia, activation of astrocytes, proinflammatory cytokines, loss of synaptic function, oxidative stress-related enzymes, acute phase proteins, components of the complement cascade, amyloid β deposition or aggregation, behaviorial deficits, and/or deposition of cerebral amyloid plaques, thereby preventing and/or treating the disease.

In an embodiment, the invention provides a method of reversing or reducing neuroflammation, activation of glia, activation of microglia, activation of astrocytes, proinflammatory cytokines, loss of synaptic function, oxidative stress-related enzymes, acute phase proteins, components of the complement cascade, behavioral deficits, amyloid β deposition or aggregation, and/or deposition of cerebral amyloid after the onset of cognitive deficits and amyloid plaque neuropathology in a subject comprising administering to the subject a therapeutically effective amount of a pyridazine compound and a cholinesterase inhibitor, composition, or conjugate of the invention.

In aspects of the invention, a composition, conjugate, or method (e.g. combination therapy) comprising a pyridazine compound and a cholinesterase inhibitor may be used to improve memory of a healthy subject or the memory of a subject with age impaired memory; improve memory, especially short-term memory and other mental dysfunction associated with the aging process; treat a mammal in need of improved memory, wherein the mammal has no diagnosed disease, disorder, infirmity or ailment known to impair or otherwise diminish memory; and/or improve the lifespan of a subject suffering from Alzheimer's disease.

A composition, conjugate or method of the invention may be administered to a healthy subject or a subject suffering from a disease disclosed herein. Accordingly, in an embodiment, a composition, conjugate or method is administered before or after the onset of cognitive deficits and Alzheimer's disease neuropathology in a subject.

Since the present invention in part relates to a method of treatment comprising a combination of active agents which may be administered separately or as conjugates, the invention also provides a kit comprising a pyridazine compound and a cholinesterase inhibitor, a pharmaceutical composition, or conjugate of the invention in kit form. In an aspect, the invention provides a kit comprising one or more pyridazine compound and one or more cholinesterase inhibitor, composition, or conjugate of the invention. In particular, the invention provides a kit for preventing and/or treating a disease, containing a composition comprising one or more pyridazine compound and one or more cholinesterase inhibitor, a container, and instructions for use. The composition of the kit can further comprise a pharmaceutically acceptable carrier, excipient, or vehicle.

In an embodiment, the invention provides a kit for preventing and/or treating Alzheimer's disease and similar diseases, containing a pyridazine compound and a cholinesterase inhibitor, a composition, or conjugate of the invention a container, and instructions for use. The composition of the kit can further comprise a pharmaceutically acceptable carrier.

These and other aspects, features, and advantages of the present invention should be apparent to those skilled in the art from the following detailed description.

DETAILED DESCRIPTION

Figure 1:
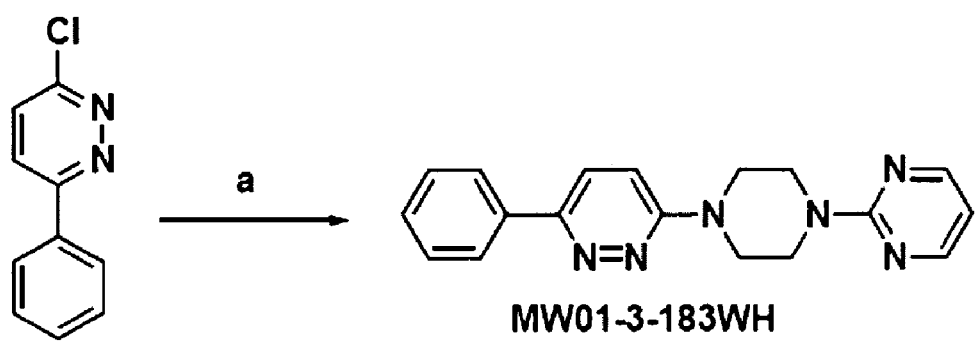
FIG. 1 depicts a synthetic scheme for MW01-3-183WH.

For convenience, certain terms employed in the specification, examples, and appended claims are collected here.

Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." The term "about" means plus or minus 0.1 to 50%, 5-50%, or 10-40%, preferably 10-20%, more preferably 10% or 15%, of the number to which reference is being made. Further, it is to be understood that "a," "an," and "the" include plural referents unless the content clearly dictates otherwise. Thus, for example, reference to a composition comprising "a compound" includes a mixture of two or more compounds.

As used herein the terms "administering" and "administration" refer to a process by which a therapeutically effective amount of a compound or composition contemplated herein is delivered to a subject for prevention and/or treatment purposes. Compositions are administered in accordance with good medical practices taking into account the subject's clinical condition, the site and method of administration, dosage, patient age, sex, body weight, and other factors known to physicians.

The term "treating" refers to reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a compound or composition of the present invention to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above. The purpose of prevention and intervention is to combat the disease, condition, or disorder and includes the administration of the active compounds to prevent or delay the onset of the symptoms or complications, or alleviating the symptoms or complications, or eliminating the disease, condition, or disorder.

The terms "subject", "individual", or "patient" are used interchangeably herein and refer to an animal preferably a warm-blooded animal such as a mammal. Mammal includes without limitation any members of the Mammalia. A mammal, as a subject or patient in the present disclosure, can be from the family of Primates, Carnivora, Proboscidea, Perissodactyla, Artiodactyla, Rodentia, and Lagomorpha. Among other specific embodiments a mammal of the present invention can be *Canis familiaris* (dog), *Felis catus* (cat), *Elephas maximus* (elephant), *Equus caballus* (horse), *Sus domesticus* (pig), *Camelus dromedarious* (camel), *Cervus axis* (deer), *Giraffa camelopardalis* (giraffe), *Bos taurus* (cattle/cows), *Capra hircus* (goat), *Ovis* aries (sheep), *Mus musculus* (mouse), *Lepus brachyurus* (rabbit), *Mesocricetus auratus* (hamster), *Cavia porcellus* (guinea pig), *Meriones unguiculatus* (gerbil), or *Homo sapiens* (human). In a particular embodiment, the mammal is a human. In other embodiments, animals can be treated; the animals can be vertebrates, including both birds and mammals. In aspects of the invention, the terms include domestic animals bred for food or as pets, including equines, bovines, sheep, poultry, fish, porcines, canines, felines, and zoo animals, goats, apes (e.g. gorilla or chimpanzee), and rodents such as rats and mice.

In aspects of the invention, the terms refer to organisms to be treated by the methods of the present invention. Such organisms preferably include, but are not limited to, mammals (e.g., murines, simians, equines, bovines, porcines, canines, felines, and the like), and most preferably include humans. In the context of particular aspects of the invention, the term "subject" generally refers to an individual who will receive or who has received treatment [e.g., administration of a pyridazine compound(s) and a cholinesterase inhibitor(s)] for a disease disclosed herein, in particular a disease characterized by inflammation (more particularly neuroinflammation), memory and/or cognitive impairment, dementia, the dysregulation of protein kinase activity, and/or dysregulation of apotic processes.

Typical subjects for treatment include persons afflicted with or suspected of having or being pre-disposed to a disease disclosed herein, or persons susceptible to, suffering from or that have suffered a disease disclosed herein. A subject may or may not have a genetic predisposition for a disease disclosed herein such as Alzheimer's disease. In particular aspects, a subject shows signs of cognitive deficits and Alzheimer's disease neuropathology. In embodiments of the invention the subjects are susceptible to, or suffer from Alzheimer's disease.

As utilized herein, the term "healthy subject" means a subject, in particular a mammal, having no diagnosed disease, disorder, infirmity, or ailment, more particularly a disease, disorder, infirmity or ailment known to impair or otherwise diminish memory and/or cognitive function.

As used herein, the term "modulate" refers to the activity of compounds or therapies (e.g., comprising a pyridazine compound and a cholinesterase inhibitor) to affect (e.g., to promote or retard) an aspect of cellular function.

As used herein, the terms "co-administration", "combination treatment", and "administering in combination" refer to the administration of one or more pyridazine compound and one or more cholinesterase inhibitor, or therapies to a subject. In aspects, the administration of two or more agents/therapies is concurrent. In other aspects, a first agent/therapy is administered prior to a second agent/therapy. In this aspect, each component may be administered separately, but sufficiently close in time to provide the desired effect, in particular a beneficial, additive, or synergistic effect. Thus, the terms refer to the administration of a pyridazine compound and a cholinesterase inhibitor, including separate administration of medicaments each containing one of the compounds as well as simultaneous administration whether or not the compounds are combined in one formulation or whether they are in separate formulations. The formulations, routes of administration and the appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of an agent that has an undesirable side effect at higher dosages.

An "additive effect" of a pyridazine compound and a cholinesterase inhibitor refers to an effect that is equal to the sum of the effects of the two individual compounds.

A "synergistic effect" of a pyridazine compound and a cholinesterase inhibitor refers to an effect that is greater than the additive effect that results from the sum of the effects of the two individual compounds.

The terms "associated", "linked", "interact", "interaction", or "interacting" refer to any physical association between molecules. The terms preferably refer to a stable association between two molecules due to, for example, electrostatic, hydrophobic, ionic, hydrogen-bond interactions, or covalent interactions.

A "beneficial effect" refers to an effect of a pyridazine compound and cholinesterase inhibitor or a composition or conjugate of the invention, including favorable pharmacological and/or therapeutic effects, and improved biological activity. In aspects of the invention, the beneficial effects include without limitation prevention, reduction, reversal, or inhibition of one or more of the following: inflammation (e.g. neuroinflammation); activation of signaling pathways involved in inflammation (e.g., neuroinflammation); cell signaling molecule production; activation of glia or glial activation pathways and responses; proinflammatory cytokines or chemokines (e.g., interleukin (IL), in particular IL-1β) or tumor necrosis factor (TNF, in particular TNFα); activation of astrocytes or astrocyte activation pathways and responses; activation of microglia or microglial activation pathways and responses; oxidative stress-related responses such as nitric oxide synthase production and nitric oxide accumulation; acute phase proteins; loss of synaptophysin and/or PSD-95; components of the complement cascade; loss or reduction of synaptic function; protein kinase activity (e.g., death associated protein kinase activity); cell damage (e.g., neuronal cell damage); cell death (e.g., neuronal cell death); amyloid β deposition of amyloid plaques; and behavioral deficits.

In some aspects, a beneficial effect is a favourable characteristic of a composition, conjugate or treatment method comprising a pyridazine compound and a cholinesterase inhibitor, including without limitation enhanced stability, a longer half life, reduced risk of side effects of a compound alone, and/or enhanced uptake and transport across the blood brain barrier.

The beneficial effect can be a statistically significant effect in terms of statistical analysis of an effect of a pyridazine compound and a cholinesterase inhibitor versus the effects without the compound. "Statistically significant" or "significantly different" effects or levels may represent levels that are higher or lower than a standard. In aspects of the invention, the difference may be 1.5, 2, 3, 4, 5, 6, 7, 8, 9, 10, 15, 20, 25 or 50 times higher or lower compared with the effect obtained without a pyridazine compound and a cholinesterase inhibitor.

In aspects, the beneficial effect is a "sustained beneficial effect" where the beneficial effect is sustained for a prolonged period of time after termination of treatment. A beneficial effect can be sustained over several days, weeks, months or years thereby having a major beneficial impact on the severity of the disease and its complications. In aspects of the invention, a beneficial effect may be sustained for a prolonged period of at least about 1 to 3, 2 to 4 weeks, 2 to 5 weeks, 3 to 5 weeks, 2 to 6 weeks, 2 to 8 weeks, 2 to 10 weeks, 2 to 12 weeks, 2 to 14 weeks, 2 to 16 weeks, 2 to 20 weeks, 2 to 24 weeks, 2 weeks to 12 months, 2 weeks to 18 months, 2 weeks to 24 months, or several years following treatment. The period of time a beneficial effect is sustained may correlate with the duration and timing of the treatment. A subject may be treated continuously for about or at least about 1 to 3 days, 1 week, 2 to 4 weeks, 2 to 6 weeks, 2 to 8 weeks, 2 to 10 weeks, 2 to 12 weeks, 2 to 14 weeks, 2 to 16 weeks, 2 weeks to 6 months, 2 weeks to 12 months, 2 weeks to 18 months, or several years, periodically or continuously.

The term "pharmaceutically acceptable carrier, excipient, or vehicle" refers to a medium which does not interfere with the effectiveness or activity of an active ingredient and which is not toxic to the hosts to which it is administered. A carrier, excipient, or vehicle includes diluents, binders, adhesives, lubricants, disintegrates, bulking agents, wetting or emulsifying agents, pH buffering agents, and miscellaneous materials such as absorbants that may be needed in order to prepare a particular composition. Examples of carriers etc. include but are not limited to saline, buffered saline, dextrose, water, glycerol, ethanol, and combinations thereof. The use of such media and agents for an active substance is well known in the art.

"Therapeutically effective amount" relates to the amount or dose of an active pyridazine compound and a cholinesterase inhibitor or composition or conjugate of the invention that will lead to one or more desired effects, in particular, one or more therapeutic effects or beneficial effects. A therapeutically effective amount of a substance can vary according to factors such as the disease state, age, sex, and weight of the subject, and the ability of the substance to elicit a desired response in the subject. A dosage regimen may be adjusted to provide the optimum therapeutic response (e.g. sustained beneficial effects). For example, several divided doses may be administered daily or the dose may be proportionally reduced as indicated by the exigencies of the therapeutic situation.

"Suboptimal dose" or "suboptimal dosage" refers to a dose or dosage of an active compound in a combination therapy which is less than the optimal dose or dosage for that compound when used in monotherapy.

A "pyridazine compound" refers to a compound of the formula I, II, III, IV, or V, or a compound depicted in Table 1, 2, 3, 4, or 5, in particular Table 2, 3, 4, or 5. In aspects of the invention a pyridazine compound refers to a pyridazinyl radical pendant with an aryl or substituted aryl, a heteroaryl or substituted heteroaryl. In some aspects the term includes the structures disclosed in US Patent Application Serial Numbers 20030176437 and 20060073472.

In aspects, a pyridazine compound that demonstrates beneficial effects, in particular statistically significant beneficial effects is selected for use in the present invention.

In aspects of the invention, a compound of the following formula I is employed.

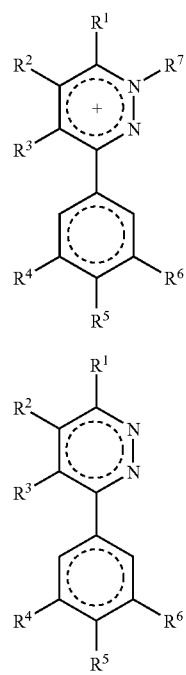

wherein $R^1$, $R^2$, and $R^3$ are independently substituted or unsubstituted hydrogen, hydroxyl, alkyl, alkenyl, alkynyl, alkylene, alkenylene, alkoxy, alkenyloxy, cycloalkyl, cycloalkenyl, cycloalkynyl, cycloalkoxy, aryl, aryloxy, arylalkoxy, aroyl, heteroaryl, heterocyclic, acyl, acyloxy, sulfonyl, sulfinyl, sulfenyl, sulfoxide, sulfate, sulfonate, amino, imino, azido, thiol, thioalkyl, thioalkoxy, thioaryl, nitro, ureido, cyano, halo, silyl, silyloxy, silylalkyl, silylthio, $=O$, $=S$, phosphonate, carboxyl, carbonyl, carbamoyl, or carboxamide; $R^7$ is substituted or unsubstituted hydrogen, hydroxyl, alkyl, alkenyl, alkynyl, alkylene, alkenylene, alkoxy, alkenyloxy, cycloalkyl, cycloalkenyl, cycloalkynyl, cycloalkoxy, aryl, aryloxy, arylalkoxy, aroyl, heteroaryl, heterocyclic, acyl, acyloxy, sulfonyl, sulfinyl, sulfenyl, sulfoxide, sulfate, sulfonate, amino, imino, azido, thiol, thioalkyl, thioalkoxy, thioaryl, nitro, ureido, cyano, halo, silyl, silyloxy, silylalkyl, silylthio, $=O$, $=S$, phosphonate, carboxyl, carbonyl, carbamoyl, or carboxamide or $R^7$ may be absent and there is a double bond between N at position 1 and C at position 6; $R^4$, $R^5$, and $R^6$ are independently hydrogen, alkyl, alkoxy, halo, or nitro; or $R^1$ and $R^2$, $R^1$ and $R^7$, or $R^2$ and $R^3$ may form a heteroaryl or heterocyclic ring; or an isomer or a pharmaceutically acceptable salt thereof.

In an aspect, a compound of the Formula Ia or Ib is employed wherein: (a) $R^1$ is optionally substituted halo, hydroxyl, alkyl, alkenyl, alkoxy, cyano, amino, cycloalkyl, sulfonyl, sulfinyl, sulfenyl, thioaryl, thioalkyl, carbonyl, silyl, piperazinyl, piperidinyl, pyrrolidinyl, morpholinyl, —$SR^{20}$ wherein $R^{20}$ is optionally substituted alkyl, carbonyl, carboxyl, carbamoyl, aryl, heterocylic, or heteroaryl; (b) $R^2$ is optionally substituted halo, hydroxyl, alkyl, alkenyl, alkoxy, carbonyl, carboxyl, phenyl, benzyl, amino, aryl, cyano, —COH, piperazinyl, alcohol, piperidinyl, morpholinyl, or naphthyl; (c) $R^3$ is optionally substituted hydrogen, halo, hydroxyl, alkyl, alkenyl, alkoxy, phenyl, piperazinyl, piperidinyl, pyrrolidinyl, morpholinyl, thiol, sulfenyl, sulfonyl, sulfinyl, or nitro; (d) $R^4$ is hydrogen, halo, or nitro; (e) $R^5$ is optionally substituted hydrogen, halo, alkoxy, or amido; (f) $R^7$ is substituted or unsubstituted hydrogen halo, hydroxyl, alkyl, alkenyl, alkoxy, carboxy, morpholino, imidazolyl, piperazinyl, piperidinyl, pyrrolidinyl, morpholinyl or $R^7$ is absent and there is a double bond between N at position 1 and C at position 6; and/or (g) $R^1$ and $R^2$, $R^1$ and $R^7$ or $R^2$ and $R^3$ may form a substituted or unsubstituted heteroaryl or heterocyclic ring.

In another aspect of the invention a compound of the Formula Ia or Ib is employed wherein $R^1$ is Cl or Br, —$NH_2$, alkyl, —CN, $=S$, silyl, sulfonyl, thioalkyl, thioaryl, piperazinyl, piperidinyl, morpholinyl, pyrrolyl, or pyrrolidinyl, which may be optionally substituted with halo, $=O$, alkoxy, alkenyl, alkyl, substituted alkyl, —CN, —$SR^{21}$ wherein $R^{21}$ is optionally substituted methyl, ethyl, phenyl, heterocyclic, or heteroaryl, or —CO substituted with phenyl or substituted phenyl.

In another aspect of the invention a compound of the Formula Ia or Ib is employed wherein $R^2$ is carbonyl, piperazinyl, morpholinyl, sulfonyl, sulfinyl, sulfenyl, or phenyl, —CN, —COH, —$CH_2OH$, —$OCH_2CH_3$, or alkyl which may be optionally substituted with alkyl, alkoxy, amino, halo, phenyl, substituted phenyl, benzyl, hydroxyl, amino, piperidinyl, or morpholinyl.

In another aspect of the invention a compound of the Formula Ia or Ib is employed wherein $R^3$ is piperazinyl; substituted piperzinyl; alkyl which may optionally be substituted with amino; phenyl; substituted phenyl; amino which may be optionally substituted with alkyl or alkylamine (e.g., $NHCOOC(CH_3)_3$), carboxyl, or substituted carboxyl; hydroxyl; or nitro.

In another aspect of the invention a compound of the Formula Ia or Ib is employed wherein $R^4$ is nitro or hydrogen.

In another aspect of the invention a compound of the Formula Ia or Ib is employed wherein $R^5$ is hydrogen, halo, —$OCH_2CH_2CH_2NHCOOC(CH_3)_3$, or —$OCH_3$.

In another aspect of the invention a compound of the Formula Ia or Ib is employed wherein $R^7$ is alkyl, morpholinyl, benzyl, imidazolyl, —$CH_2COOCH_2CH_3$, $CH_2C$=$COOCH_2CH_3$, $CH_2CH_2CH_2SO_2OH$, $CH_2CH_2CH_2SO_3$—, $CH_2CH_2CH_2CH_2PO(OH)_2$, or $CH_2CH_2CH_2PO(OH)_2$.

In another aspect of the invention a compound of the Formula Ia or Ib is employed wherein $R^7$ is absent and there is a double bond between N at position 1 and C at position 6.

In a further aspect, a compound of the Formula Ia is employed wherein $R^1$, $R^2$, $R^3$, and $R^7$ are independently substituted aliphatic, lower alkyl substituted amino, lower alkyl substituted halogen, cycloaliphatic, or substituted cycloaliphatic.

In a still further aspect of the invention a compound of the Formula Ia or Ib is employed wherein $R^1$ is a piperazinyl which may be substituted (e.g., with a pyrimidinyl moiety); halo; amino which may be substituted; cyano; —$SR^{22}$ wherein $R^{22}$ is alkyl or aryl (e.g. phenyl) which may be substituted (e.g., halo); substituted alkyl [e.g., alkyl substituted with halogen, such as $CH(Br)_2$]; morpholinyl; pyrrolyl which may be substituted; hydroxyl; —$OR^{28}$ wherein $R^{28}$ is alkyl; —C=$CHR^{30}$ wherein $R^{30}$ is alkyl; or pyrrolidinyl.

In a still further aspect of the invention a compound of the Formula Ia or Ib is employed wherein $R^2$ is hydrogen; morpholinyl; piperazinyl which may be substituted (e.g., with a pyrimidinyl moiety); phenyl; alkyl; alkoxy (e.g. CH$(OCH_3)_2$); substituted alkyl; substituted aryl (e.g., phenyl); cyano; or hydroxyl.

In another aspect of the invention a compound of the Formula Ib is employed wherein $R^1$ is pyridinyl, and $R^2$ is an N-substituted piperzinyl.

In another embodiment a compound of the Formula Ib is employed wherein $R^1$ is amino substituted with alkyl or cycloalkyl and $R^2$ is pyridinyl.

In a still further aspect of the invention a compound of the Formula Ia or Ib is employed wherein $R^3$ is hydrogen; hydroxyl; alkyl which may be substituted (e.g., halo); amino which may be substituted; —$COR^{31}$ wherein $R^{31}$ is hydrogen, hydroxyl, alkoxy (e.g. —$OCH_3$); or, aryl (e.g. phenyl) which may be substituted (e.g., alkyl).

In a still further aspect of the invention a compound of the Formula Ia or Ib is employed wherein $R^4$ is hydrogen or halo; $R^5$ is hydrogen or halo; $R^6$ is hydrogen or halo.

In a still further aspect of the invention a compound of the Formula Ia is employed wherein $R^7$ is hydrogen; alkyl which may be substituted (e.g. with phenyl); —$CH_2CH_2COOR^{32}$ wherein $R^{32}$ is alkyl, —$CH_2C$=$COOR^{33}$ wherein $R^{33}$ is alkyl, $CH_2CH_2CH_2S(O)_2OH$, morpholinyl, benzyl, imidazolyl, or $[CH_2]_nPO(OH)_2$ wherein n is 1 to 6, in particular 3 or 4.

In a still further aspect of the invention a compound of the Formula Ia or Ib is employed wherein $R^1$ and $R^2$ form a piperidinyl ring which may optionally be substituted with a carboxyl.

In a still further aspect of the invention a compound of the Formula Ia is employed wherein $R^1$ and $R^7$ form a pyrimidinyl ring which may optionally be substituted with alkyl, aryl, halo, or hydroxyl.

In a particular aspect, a compound of the formula Ia or Ib is employed wherein $R^1$ is —$NR^{34}R^{35}$ wherein $R^{34}$ is hydrogen or alkyl, and $R^{35}$ is hydrogen, alkyl, carbonyl, aryl, amino, cycloalkane, heterocylic, or heteroaryl which may be substituted. In embodiments $R^{35}$ may comprise or be selected from the group consisting of hydrogen, $C_1$-$C_6$ alkyl (e.g. methyl or ethyl) which may be substituted with optionally substituted hydroxyl, alkyl, amino, carbonyl, carboxyl, morpholinyl, isoquinolinyl, or an amino which may be substituted with one or more of optionally substituted alkyl, benzyl, carboxyl, alcohol group, heteroaryl or heterocyclic, a propanol group, phenyl which may be optionally substituted with halo, benzyl which may be substituted with alkoxy, cyclohexyl, piperidinyl which may be substituted with optionally substituted phenyl, pyrrolidinyl or pyrrolidinylalkyl which may be substituted with alkyl, —$COOR^8$ wherein $R^8$ is alkyl which may be substituted, or $[CH_2]_m$-piperidinyl wherein m is 1 to 4, in particular 1 to 3 and the piperidinyl is optionally substituted with optionally substituted alkyl, phenyl, or benzyl.

In embodiments, $R^{35}$ is —$R^{44}R^{45}$ wherein $R^{44}$ is —NH$[CH_2]_w$NH wherein w is 1 to 4, in particular 2 or 3, and $R^{45}$ is piperazinyl substituted with pyrimidinyl which may be substituted, in particular substituted with alkyl.

In embodiments, $R^{35}$ is —$R^{46}R^{47}$ wherein $R^{46}$ is —$[CH_2]_w$N(CH$_3$) wherein w is 1 to 4, in particular 2 or 3, and $R^{47}$ is piperazinyl substituted with pyrimidinyl which may be substituted, in particular substituted with alkyl.

In an aspect of the invention, a compound of the Formula Ia or Ib is employed wherein $R^1$ is halo especially chloro or bromo, $R^2$ is alkyl which may be substituted, in particular substituted with alkoxy (e.g., methoxy, dimethoxy), substituted aryl which may be substituted with alkyl, alkoxy, (e.g., benzyl, methoxy phenyl), halo (e.g. bromo or chloro), or carbonyl, a substituted or unsubstituted saturated 3 to 6-membered heteromonocylic group containing 1 to 4 nitrogen atoms [e.g., piperidinyl, and piperazinyl] or a saturated 3 to 6-membered heteromonocyclic group containing 1 to 2 oxygen atoms and 1 to 3 nitrogen atoms [e.g. morpholinyl; sydnonyl], in particular a substituted morpholinyl, piperazinyl, or piperazinyl substituted with a heteroaryl in particular an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, or pyridazinyl, especially pyrimidinyl, and optionally $R^3$, $R^4$, $R^5$, $R^6$, and $R^7$ are hydrogen.

In another aspect of the invention, a compound of the Formula Ia is employed wherein $R^1$ is halo especially chloro or bromo, and $R^3$ is a substituted or unsubstituted saturated 3 to 6-membered heteromonocylic group containing 1 to 4 nitrogen atoms [e.g., piperidinyl, and piperazinyl] or a saturated 3 to 6-membered heteromonocyclic group containing 1 to 2 oxygen atoms and 1 to 3 nitrogen atoms [e.g. morpholinyl; sydnonyl], in particular a substituted morpholinyl, piperazinyl, or piperazinyl substituted with alkyl or a heteroaryl in particular an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, or pyridazinyl, especially pyrimidinyl, or $R^2$ is a substituted amino, in particular amino substituted with alkyl or substituted alkyl, in particular alkyl substituted with alkoxy carbonyl, and optionally $R^2$, $R^4$, $R^5$, $R^6$, and $R^7$ are hydrogen.

In further aspect $R^1$ is halo, especially bromo or chloro, and $R^2$ and $R^3$ form an unsaturated ring, in particular phenyl, $R^5$ is a heteroaryl, in particular a substituted or unsubstituted unsaturated 5 to 6 membered heteromonocyclyl group containing 1 to 4 nitrogen atoms, in particular, pyrrolyl, pyrrolinyl, imidazolyl, pyrazolyl, especially imidazolyl, and optionally $R^4$, $R^6$ and $R^7$ are hydrogen.

In a further aspect, $R^1$ is halo, especially bromo or chloro, and $R^4$ is nitro, and optionally $R^2$, $R^3$, $R^5$, $R^6$, and $R^7$ are hydrogen.

In a further aspect, the invention employs a compound of the Formula Ia wherein $R^1$ is a thiol substituted with alkyl (thioalkyl); substituted alkyl, in particular alkyl substituted with a substituted or unsubstituted saturated 3 to 6-membered heteromonocylic group containing 1 to 4 nitrogen atoms [e.g. pyrrolidinyl, imidazolidinyl, piperidinyl, and piperazinyl] or a saturated 3 to 6-membered heteromonocyclic group containing 1 to 2 oxygen atoms and 1 to 3 nitrogen atoms [e.g. morpholinyl; sydnonyl], especially a substituted morpholinyl or piperidinyl; aryl; substituted aryl; carboxyl which may be substituted with substituted or unsubstituted aryl; optionally $R^2$ is alkyl, in particular lower alkyl; optionally $R^3$ is alkyl, in particular lower alkyl or nitro; optionally $R^5$ is alkoxy; optionally $R^7$ is alkyl; and optionally $R^4$, $R^5$, and $R^6$, are hydrogen.

In a further aspect of the invention, a compound of the Formula Ia is employed wherein $R^1$ is =S, and optionally $R^2$ is alkyl, in particular lower alkyl, $R^5$ is alkoxy, and $R^3$, $R^4$, $R^6$ and $R^7$ are hydrogen.

In a further aspect of the invention, a compound of the Formula Ia is employed wherein $R^1$ is sulfonyl which may be substituted with substituted or unsubstituted aryl, in particular substituted phenyl, and optionally $R^2$ is alkyl and $R^3$, $R^4$, $R^5$, $R^6$, and $R^7$ are hydrogen.

In a further aspect of the invention, a compound of the Formula Ia is employed wherein $R^1$ is substituted or unsubstituted alkyl or alkynyl, in particular alkyl substituted with aryl, substituted aryl, halo, cyano, or alkynyl substituted with alkyl; and optionally $R^2$ is alkyl, $R^7$ is alkyl, and $R^3$, $R^4$, $R^5$, and $R^6$ are hydrogen.

In a further aspect of the invention, a compound of the Formula Ia is employed wherein $R^1$ is cyano and $R^2$ is aryl or alkyl, and optionally $R^3$, $R^4$, $R^5$, $R^6$, and $R^7$ are hydrogen.

In a further aspect of the invention, a compound of the Formula Ia is employed wherein one or both of $R^1$ and $R^2$ are a saturated 3 to 6-membered heteromonocyclic group containing 1 to 2 oxygen atoms and 1 to 3 nitrogen atoms [e.g. morpholinyl; sydnonyl], especially a substituted morpholinyl, and optionally $R^3$, $R^4$, $R^5$, $R^6$, and $R^7$ are hydrogen.

In a further aspect of the invention, a compound of the Formula Ia is employed wherein $R^1$ is a saturated 3 to 6-membered heteromonocylic group containing 1 to 4 nitrogen atoms [e.g. pyrrolidinyl], which may be substituted with substituted or unsubstituted carboxyl; $R^2$ is alkyl or halo, and optionally $R^3$, $R^4$, $R^5$, $R^6$, and $R^7$ are hydrogen.

In a further aspect of the invention, a compound of the Formula Ia is employed wherein $R^1$ is hydroxyl; $R^2$ is alkyl or substituted alkyl or $R^3$ is a saturated 3 to 6-membered heteromonocylic group containing 1 to 4 nitrogen atoms [e.g. piperidinyl, and piperazinyl] which may optionally be substituted with a heteroaryl [e.g., pyrimidinyl], and the other of $R^2$ or $R^3$ is hydrogen, and optionally $R^4$, $R^5$, $R^6$, and $R^7$ are hydrogen.

In a further aspect of the invention, a compound of the Formula Ia is employed wherein $R^1$ is a saturated 3 to 6-membered heteromonocylic group containing 1 to 4 nitrogen atoms [e.g., piperidinyl and piperazinyl] which may be substituted with carboxyl or carboxyl substituted with alkyl or alkoxy or with purinyl or substituted purinyl; $R^2$ is alkyl or substituted alkyl, in particular alkylaryl, and optionally $R^3$, $R^4$, $R^5$, $R^6$, and $R^7$ are hydrogen.

In a further aspect of the invention, a compound of the Formula Ia is employed wherein $R^1$ is =O, and $R^2$ is alkyl, alkylaryl, cyano, alkoxy, or substituted alkoxy, and optionally $R^3$, $R^4$, $R^5$, $R^6$, and $R^7$ are hydrogen.

In a further aspect of the invention, a compound of the Formula Ia is employed wherein $R^1$ is alkoxy, $R^2$ is alkyl, substituted alkyl, or alkoxy, and optionally $R^3$, $R^4$, $R^5$, $R^6$, and $R^7$ are hydrogen.

In a further aspect of the invention, a compound of the Formula Ia is employed wherein $R^1$ and $R^2$ form a heterocyclic, in particular a saturated 3 to 6-membered heteromonocylic group containing 1 to 4 nitrogen atoms, in particular a 6-membered ring comprising 1 or 2 nitrogen atoms [e.g., piperidinyl and piperazinyl] which may be substituted for example with alkyl, halo, carboxyl, or alkoxy carbonyl, and optionally $R^3$, $R^4$, $R^5$, $R^6$, and $R^7$ are hydrogen.

In a further aspect of the invention, a compound of the Formula Ia is employed wherein $R^1$ and $R^7$ form a heteroaryl, in particular an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, or pyridazinyl, $R^2$ is hydrogen or alkyl, and $R^3$, $R^4$, $R^5$, $R^6$, and $R^7$ are hydrogen.

In a further aspect of the invention, a compound of the Formula Ia is employed wherein $R^1$ is silyl which may be substituted, in particular substituted with alkyl, $R^2$ is alkyl, and $R^3$, $R^4$, $R^5$, $R^6$, and $R^7$ are hydrogen.

In some aspects, one or more of the following compounds are not within the scope of a pyridazine compound of the formula Ia or Ib employed in the present invention:

a) a compound wherein when $R^1$ is =O, $R^3$ is —COOCH$_3$, CH=CHCOOCH$_3$, —CH=CHC(=O)-phenyl, —CH=CH(C(=O)OCH$_3$)$_2$, —S-phenyl, —CH=CH(COCH$_3$)(COOCH$_3$), CH=CH(COOCH$_2$CH$_3$)$_2$, -phenyl-COOCH$_3$, —CH=CHCO-phenyl, —CH$_2$CH(Cl)(CH$_2$OH), -methylphenyl, $R^7$ is hydrogen or —CH$_2$OCH$_3$, and $R^1$, $R^2$, $R^4$, $R^5$ and $R^6$ are hydrogen;

b) a compound wherein when $R^1$ is =O, $R^2$ is cyano, $R^3$ is —C(=O)OCH$_3$, and $R^3$, $R^4$, $R^5$, and $R^6$ are hydrogen;

c) a compound wherein when $R^1$ is =O, $R^2$ is -methylthiophene or benzyl, $R^3$, $R^4$, $R^5$, $R^6$, and $R^7$ are hydrogen;

d) a compound wherein when $R^1$ is =O, $R^2$ is methyl, $R^5$ is hydrogen, hydroxyl, chloro, or bromo, $R^7$ is hydrogen or ethylmorpholinyl, and $R^3$, $R^4$, and $R^6$ are hydrogen;

e) a compound wherein when $R^2$ is methyl, $R^5$ is chloro, bromo, or hydrogen, $R^7$ is hydrogen or —CH$_2$CH$_2$-morpholinyl, and $R^1$, $R^3$, $R^4$, and $R^6$ are hydrogen;

f) a compound wherein when $R^1$ is piperazinyl, piperazinyl substituted with pyridinyl, phenyl, or methyl, $R^2$ is hydrogen or methyl, and $R^3$, $R^4$, $R^5$, and $R^6$ are hydrogen;

g) a compound wherein when $R^1$ is chloro or bromo, $R^2$ is C$_1$-C$_3$ alkyl, phenyl, amino, benzyl, morpholinyl, chloro, —C(=O)NH$_2$, —NH$_2$, C$_1$-C$_3$ alkylphenyl, —CH(CH$_3$)$_2$, —CH$_2$CH(CH$_3$)$_2$, -benzylchloro, and $R^3$, $R^4$, $R^5$ and $R^6$ are hydrogen;

h) a compound wherein when $R^1$ is chloro or bromo, $R^3$ is hydroxyl, chloro, bromo, C$_1$-C$_3$ alkyl, phenyl, or —N(CH$_3$)$_2$, and $R^2$, $R^4$, $R^5$ and $R^6$ are hydrogen;

i) a compound wherein when $R^1$ is chloro, $R^2$ is methyl, $R^5$ is hydroxyl, and $R^3$, $R^4$, and $R^6$ are hydrogen;

j) a compound wherein when $R^1$ is chloro, $R^2$, $R^3$, $R^4$, $R^5$ and $R^6$ are hydrogen;

k) a compound wherein when $R^1$ is hydroxyl, $R^2$ is C$_1$-C$_4$ alkyl, and $R^3$, $R^4$, $R^5$ and $R^6$ are hydrogen;

l) a compound wherein when $R^1$ is —C$_1$-C$_4$ alkoxy, or C$_1$-C$_4$ alkoxy substituted with —N(CH$_3$)$_2$, morpholinyl, or piperidinyl substituted with benzyl, $R^2$ is hydrogen or methyl, $R^3$, $R^4$, $R^5$ and $R^6$ are hydrogen, $R^7$ is absent, hydrogen, or methyl;

m) a compound wherein when $R^1$ is —SH, —SCH$_3$, or —SCH$_2$C(=O)CH$_3$, $R^2$ is hydrogen or methyl, and $R^3$, $R^4$, $R^5$ and $R^6$ are hydrogen;

n) a compound wherein when $R^1$ is =S, $R^2$ is hydrogen or methyl, $R^7$ is methyl or benzyl, and $R^3$, $R^4$, and $R^6$ are hydrogen;

o) a compound wherein when $R^1$ is =S, $R^2$ is methyl and $R^7$ is chloro or $R^7$ is methyl, and $R^3$, $R^4$, and $R^6$ are hydrogen;

p) a compound wherein when $R^1$ is hydroxyl, $R^2$ is hydrogen, methyl, or butyl, and $R^3$, $R^4$, $R^5$ and $R^6$ are hydrogen;

q) a compound wherein when $R^1$ is methoxy, $R^2$, $R^3$, $R^4$, $R^5$ and $R^6$ are hydrogen;

r) a compound wherein when $R^1$ is $C_1$-$C_2$ alkoxy or $C_1$-$C_4$ alkoxy substituted with morpholinyl, —N(CH$_3$)$_2$, or piperidinyl substituted with benzyl, $R^2$ is methyl, and $R^3$, $R^4$, $R^5$ and $R^6$ are hydrogen;

s) a compound wherein $R^2$, $R^3$, $R^4$, $R^5$ and $R^6$ are hydrogen;

t) a compound wherein $R^1$ is cyano or cyano substituted with —C(OCH$_2$CH$_3$)$_2$, —CH(OH)(CH$_3$), —Si(CH$_2$CH$_3$)$_2$, cyclohexyl, —CH$_2$O-trimethyldiphenylsilyl or cyclohexyl substituted with hydroxyl, and $R^3$, $R^4$, $R^5$ and $R^6$ are hydrogen;

u) a compound wherein $R^1$ is cyano substituted with —CH(OH)(CH$_3$)$_2$, —Si(CH$_2$CH$_3$)$_2$, morpholinyl, trimethyldiphenylsilyl, or —CH(OCH$_2$CH$_3$)$_2$, $R^2$ is methyl, and $R^3$, $R^4$, $R^5$ and $R^6$ are hydrogen;

v) a compound wherein $R^7$ is oxy, and $R^2$ is hydrogen or methyl, and $R^3$, $R^4$, $R^5$ and $R^6$ are hydrogen;

w) a compound wherein $R^1$ is methyl, and $R^2$, $R^3$, $R^4$, $R^5$ and $R^6$ are hydrogen;

x) a compound wherein $R^2$ is methyl, and $R^1$, $R^3$, $R^4$, $R^5$ and $R^6$ are hydrogen;

y) a compound wherein $R^1$ is methoxycarbonyl, $R^3$ is hydrogen, and $R^2$, $R^4$, $R^5$ and $R^6$ are hydrogen;

z) a compound wherein $R^1$ is —NH$_2$, $R^2$ is methyl, chlorophenyl, methoxyphenyl, ethylphenyl, ethylmethoxyphenyl, propylphenyl, or —CH(CH$_3$)$_2$, $R^4$, $R^5$ and $R^6$ are hydrogen, and $R^7$ is absent or —CH$_2$CH$_2$CH$_2$COOH;

aa) a compound wherein $R^1$ is —OR$^{29}$ wherein $R^{29}$ is ethylmorpholinyl or —CH$_2$CH$_2$N(CH$_3$)$_2$ and $R^2$, $R^3$, $R^4$, $R^5$ and $R^6$ are hydrogen;

bb) a compound wherein $R^1$ is —NH$_2$, $R^3$ is —NH$_2$, and $R^3$, $R^4$, $R^5$ and $R^6$ are hydrogen;

cc) a compound wherein $R^1$ is —NH$_2$, $R^5$ and $R^6$ are methoxy, and $R^3$ and $R^4$ are hydrogen;

dd) a compound wherein $R^1$ is —NH$_2$, $R^3$ is methyl and $R^4$, $R^5$ and $R^6$ are hydrogen;

ee) a compound wherein $R^1$ is —NH$_2$, $R^5$ is chloro, and $R^3$, $R^4$ and $R^6$ are hydrogen;

ff) a compound wherein $R^1$ is —NH-chlorophenyl, and $R^2$ and $R^3$ form a phenyl group, and $R^4$, $R^5$ and $R^6$ are hydrogen;

gg) a compound wherein $R^1$ is —NH$_2$, $R^4$ and $R^5$ is methoxy, and $R^2$, $R^3$ and $R^6$ are hydrogen;

hh) a compound wherein $R^1$ is —NH$_2$, $R^2$ is ethylmethoxyphenyl, $R^7$ is carboxyethyl or carboxypropyl, and $R^3$, $R^4$ and $R^6$ are hydrogen;

ii) a compound wherein $R^1$ is —NHR$^{48}$ wherein $R^{48}$ is ethylmorpholinyl, ethylmorpholinyl substituted with =O, —CH$_2$CH$_2$OCH$_3$, —CH$_2$CH$_2$CH$_2$CH$_2$CH$_2$CH$_2$CH$_3$, —CH$_2$CH$_2$CH$_2$CH$_2$OH, —CH$_2$CH$_2$OH, or —CH$_2$CH$_2$OCH$_3$, $R^2$ is hydrogen, methyl, ethyl, —CHO, —CH$_2$OH, —COOH, chloro, —CH$_2$CH$_2$NH$_2$, —NO$_2$, —C≡N, —C(=O)OCH$_2$CH$_3$, or —C(=O)NH$_2$, and $R^3$, $R^4$, $R^5$ and $R^6$ are hydrogen;

jj) a compound wherein $R^1$ is —NHR$^{49}$ wherein $R^{49}$ is ethanol, methylpiperidinylbenzyl, ethylpiperidinyl, ethylpiperidinylbenzyl, or butylpiperidinylbenzyl, $R^2$ is hydrogen, methyl, or —C(CH$_3$)$_2$, and $R^3$, $R^4$, $R^5$ and $R^6$ are hydrogen;

kk) a compound wherein $R^1$ is —NHR$^{55}$ wherein $R^{55}$ is hydrogen, and $R^3$, $R^4$, $R^5$ and $R^6$ are hydrogen;

ll) a compound wherein $R^1$ is —NHR$^{56}$ wherein $R^{56}$ is —CH$_2$CH$_2$N(CH$_2$CH$_3$)$_2$ or ethylmorpholinyl, $R^3$ is ethyl, and $R^4$, $R^5$ and $R^6$ are hydrogen;

mm) a compound wherein $R^1$ is —NHNH$_2$, $R^3$ is hydrogen, alkyl, or phenyl, and $R^3$, $R^4$, $R^5$ and $R^6$ are hydrogen;

nn) a compound wherein $R^1$ is —NHR$^{57}$ wherein $R^{57}$ is NH$_2$, —CH$_2$CH$_2$OH, CH$_2$CH(OH)(CH$_3$), ethylmorpholinyl, ethylmorpholinyl substituted with =O, ethylphenyl, —CH$_2$CH$_2$NHCH$_3$, —CH$_2$CH$_2$N(—CH$_2$CH$_2$CH$_3$)$_2$, ethylpiperidinyl, or ethylpiperidinylbenzyl, $R^2$ is methyl, and $R^3$, $R^4$, $R^5$ and $R^6$ are hydrogen;

oo) a compound wherein $R^1$ is morpholinyl, $R^2$ is —C(F)$_3$, —C(=O), —CH$_2$OH, —C(=O)H, —COOH, chloro, —NO$_2$, or cyano, and $R^3$, $R^4$, $R^5$ and $R^6$ are hydrogen;

pp) a compound wherein $R^1$ is —NHR$^{58}$ wherein $R^{58}$ is heptyl, phenyl, benzyl, or ethylphenyl, $R^2$ is hydrogen, methyl, or chlorophenyl, $R^4$, $R^5$ and $R^6$ are hydrogen;

qq) a compound wherein $R^1$ is —NR$^9$ wherein $R^9$ is phenyl and $R^2$, $R^3$, $R^4$, $R^5$ and $R^6$ are hydrogen;

rr) a compound wherein $R^1$ is morpholinyl and $R^2$, $R^3$, $R^4$, $R^5$ and $R^6$ are hydrogen;

ss) a compound wherein $R^1$ is methylpiperazinyl and $R^2$, $R^3$, $R^4$, $R^5$ and $R^6$ are hydrogen;

tt) a compound wherein $R^1$ is —NHCH$_2$CH$_2$OH or NHCH$_2$CH$_2$OCH$_3$, $R^2$ is phenyl and $R^3$, $R^4$, $R^5$ and $R^6$ are hydrogen;

uu) a compound wherein $R^1$ is —NHR$^{59}$ wherein $R^{59}$ is ethylamino, butylamino, ethylaminomethyl, and $R^2$ is hydrogen, methyl, or —C(=O)NH$_2$, and $R^3$, $R^4$, $R^5$ and $R^6$ are hydrogen;

vv) a compound wherein $R^1$ is —NHR$^{60}$ wherein $R^{60}$ is ethylpiperidinyl, methylpiperidinylbenzyl, piperidinylbenzyl, ethylpiperidinylbenzyl, methylpyrrolidinylmethyl, ethylpiperazinylbenzyl, —CH$_2$C(=O)-piperazinylbenzyl, —C(=O)-methylnaphthyl, —CH$_2$CH$_2$CH$_2$CH$_2$CH$_2$N(CH$_3$)(C$_7$H$_7$), —CH$_2$C(=O)-piperidinylbenzyl, —C(=O)-methylpiperidinylbenzyl, or —CH(CH$_3$)$_2$, and $R^3$, $R^4$, $R^5$ and $R^6$ are hydrogen;

ww) a compound wherein $R^1$ is —CHCH$_2$CH$_2$-isoquinolinyl, —NHCH$_2$CH$_2$N(CH$_2$CH$_2$CH$_3$)$_2$, propyl substituted with piperidinyl fused to phenyl, —NHCH$_2$CH$_2$, or —NHCH$_2$CH$_2$CH$_2$CH$_2$CH$_2$ substituted with a piperidinyl fused to two adjacent carbon atoms of a phenyl moiety;

xx) a compound wherein $R^1$ is —NH substituted with two pyrrolidinyl groups; $R^3$ is methyl, and $R^2$, $R^4$, $R^5$ and $R^6$ are hydrogen;

yy) a compound wherein $R^1$ is —COOCH$_3$, $R^3$ is methyl, and $R^2$, $R^4$, $R^5$ and $R^6$ are hydrogen;

zz) a compound wherein $R^1$ is hydrogen, $R^2$ is methyl, $R^7$ is oxygen;

aaa) a compound wherein $R^7$ is methyl or oxygen, and $R^1$, $R^2$, $R^4$, $R^5$ and $R^6$ are hydrogen;

bbb) a compound wherein $R^1$ is —NHCH$_2$CH$_2$N(CH$_2$CH$_3$)$_2$, $R^3$ is ethyl, and $R^2$, $R^4$, $R^5$ and $R^6$ are hydrogen; and ccc) a compound wherein $R^1$ is —NHCH$_2$CH(OH)(CH$_3$) or —NHCH$_2$CH$_2$NHCH$_2$CH$_2$OH, $R^2$ is methyl, and $R^3$, $R^4$, $R^5$ and $R^6$ are hydrogen.

In aspects of the invention a compound of the formula Ia or Ib is employed wherein $R^1$ is a piperazinyl or substituted piperazinyl, in particular a piperazinyl substituted with a pyrimidinyl of Formula A below.

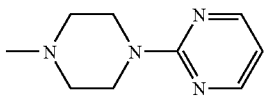

A

Thus, a pyridazine compound for use in the present invention includes compounds of the Formula II:

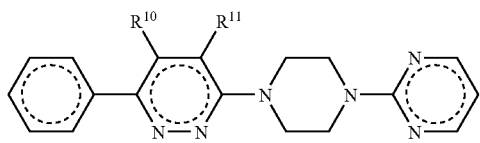

II wherein $R^{10}$ and $R^{11}$ are independently substituted or unsubstituted hydrogen, hydroxyl, alkyl, alkenyl, alkynyl, alkylene, alkenylene, alkoxy, alkenyloxy, cycloalkyl, cycloalkenyl, cycloalkynyl, cycloalkoxy, aryl, aryloxy, arylalkoxy, aroyl, heteroaryl, heterocyclic, acyl, acyloxy, sulfonyl, sulfinyl, sulfenyl, sulfoxide, sulfate, sulfonate, amino, imino, azido, thiol, thioalkyl, thioalkoxy, thioaryl, nitro, ureido, phosphonate, cyano, halo, silyl, silyloxy, silylalkyl, silylthio, =O, =S, carboxyl, carbonyl, carbamoyl, or carboxamide; or an isomer or a pharmaceutically acceptable salt thereof.

In an aspect of the invention, a compound of the Formula II is employed wherein $R^{10}$ is hydrogen; hydroxyl; alkyl; aryl [e.g. phenyl which is optionally substituted (e.g., halide)]; piperazinyl which may be substituted (e.g. substituted with a pyrimidinyl); —$NR^{36}R^{37}$ wherein $R^{36}$ is hydrogen or alkyl, and $R^{37}$ is phenyl which may be substituted or alkyl which may be substituted (e.g. amino, in particular —$CH_2CH_2NH_2$; $CH_2CH_2NHCOOC(CH_3)_3$); morpholinyl which may be substituted; or —$SR^{23}$ wherein $R^{23}$ is phenyl which may be substituted; and $R^{11}$ is hydrogen, or aryl (e.g. phenyl) which may be substituted.

In a particular aspect of the invention a compound of the Formula II is employed wherein $R^{10}$ is hydrogen, halo, optionally substituted hydroxyl, alkyl, pyridinyl, phenyl, benzyl, piperazinyl, amino, morpholinyl, or —$SR^{24}$ wherein $R^{24}$ is alkyl or aryl. In an embodiment, $R^{10}$ is —$NH[CH_2]_m NR^{61}R^{62}$ wherein m is 1 to 6, in particular 2 to 4, $R^{61}$ is hydrogen, $R^{62}$ is a carboxyl, in particular —$COOC(CH_3)_3$.

In an aspect of the invention, a compound of the Formula II is employed wherein $R^{11}$ is hydrogen, halo, optionally substituted alkyl, pyridinyl, piperidinyl, morpholinyl, piperazinyl, or phenyl.

In another aspect of the invention, a compound of the Formula II is employed wherein both of $R^{10}$ and $R^{11}$ are not hydrogen.

In particular embodiments of the invention, one or more of $R^{10}$ and $R^{11}$ are alkyl, in particular $C_1$-$C_6$ alkyl and the other of $R^{10}$ and $R^{11}$ is hydrogen.

In particular embodiments of the invention, one or more of $R^{10}$ and $R^{11}$ are aryl in particular phenyl or benzyl and the other of $R^{10}$ and $R^{11}$ is hydrogen.

In particular embodiments of the invention, a compound of the Formula II is a compound in Table 3, more particularly a compound designated MW01-2-065LKM, MW01-2-069SRM, MW01-2-151SRM, MW01-5-188WH, MW01-6-127WH, MW01-6-189WH, or MW01-7-107WH, and pharmaceutically acceptable salts, and derivatives thereof.

In aspects, the invention employs a compound of the Formula III:

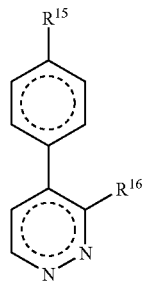

III wherein $R^{15}$ and $R^{16}$ are independently substituted or unsubstituted hydrogen, hydroxyl, alkyl, alkenyl, alkynyl, alkylene, alkenylene, alkoxy, alkenyloxy, cycloalkyl, cycloalkenyl, cycloalkynyl, cycloalkoxy, aryl, aryloxy, arylalkoxy, aroyl, heteroaryl, heterocyclic, acyl, acyloxy, sulfonyl, sulfinyl, sulfenyl, sulfoxide, sulfate, sulfonate, amino, imino, azido, thiol, thioalkyl, thioalkoxy, thioaryl, nitro, ureido, cyano, halo, silyl, silyloxy, silylalkyl, silylthio, =O, =S, phosphonate, carboxyl, carbonyl, carbamoyl, or carboxamide; or an isomer or a pharmaceutically acceptable salt thereof.

In other aspects, the invention employs a compound of the Formula IV:

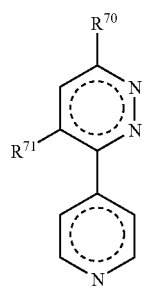

IV wherein $R^{70}$ and $R^{71}$ are independently substituted or unsubstituted hydrogen, hydroxyl, alkyl, alkenyl, alkynyl, alkylene, alkenylene, alkoxy, alkenyloxy, cycloalkyl, cycloalkenyl, cycloalkynyl, cycloalkoxy, aryl, aryloxy, arylalkoxy, aroyl, heteroaryl, heterocyclic, acyl, acyloxy, sulfonyl, sulfinyl, sulfenyl, sulfoxide, sulfate, sulfonate, amino, imino, azido, thiol, thioalkyl, thioalkoxy, thioaryl, nitro, ureido, cyano, halo, silyl, silyloxy, silylalkyl, silylthio, =O, =S, phosphonate, carboxyl, carbonyl, carbamoyl, or an isomer or pharmaceutically acceptable salt thereof.

In other aspects, a compound of the formula IV is employed wherein $R^{70}$ is substituted or unsubstituted hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, or carboxamide, especially heterocyclic, heteroaryl, amino, and substituted amino and $R^{71}$ is aryl or substituted aryl; or an isomer or a pharmaceutically acceptable salt thereof.

In another aspect, a compound of the Formula IV is employed wherein $R^{70}$ is a heterocylic, in particular a saturated 3 to 6-membered heteromonocylic group containing 1 to 4 nitrogen atoms more particularly, pyrrolidinyl, imidazolidinyl, piperidinyl, and piperazinyl, especially piperazinyl or piperidinyl, which may be substituted with alkyl especially methyl, dimethyl, cycloalkyl especially cyclohexyl, aryl especially phenyl, a substituted or unsubstituted unsaturated condensed heterocyclic group containing 1 to 5 nitrogen atoms, in particular, indolyl, isoindolyl, indolizinyl, indazolyl, quinazolinyl, pteridinyl, quinolizidinyl, phthalazinyl, naphthyridinyl, quinoxalinyl, cinnolinyl, phenanthridinyl, acridinyl, phenanthrolinyl, phenazinyl, carbazolyl, purinyl, benzimidazolyl, quinolyl, isoquinolyl, quinolinyl, isoquinolinyl, or indazolyl, especially benzimidazolyl substituted with oxy.

In other aspects, a compound of the Formula IV is employed wherein $R^{70}$ is amino or substituted amino, and optionally $R^{71}$ is aryl, in particular phenyl. In an aspect $R^{70}$ is —N—$R^{63}$ wherein $R^{63}$ is hydrogen or alkyl, in particular $C_1$-$C_6$ alkyl, more particularly methyl or dimethyl, or —N—$R^{40}R^{41}$ wherein $R^{40}$ is hydrogen or alkyl, in particular $C_1$-$C_6$ alkyl, more particularly methyl and $R^{41}$ is alkyl substituted with amino or substituted amino, heterocyclic, substituted heterocyclic, or cycloalkyl. In an embodiment, $R^{70}$ is —N—$R^{42}R^{43}$ wherein $R^{42}$ is hydrogen or alkyl, in particular $C_1$-$C_6$ alkyl, more particularly methyl and $R^{43}$ is $C_1$-$C_6$ alkyl, especially methyl or ethyl substituted with a cycloalkyl especially cyclopropyl, a heterocyclic especially piperidinyl, pyrrolidinyl, or morpholinyl which may be substituted in particular substituted with aryl, especially benzyl.

A compound of the Formula IV may comprise a structure designated as compound 124, 125, 126, 127, 128, 129, 130, 131, 132, 133, 134, 135, 136, 137, 138, or 139 in Table 5 or pharmaceutically acceptable salts, isomers, or derivatives thereof.

In further aspects, the invention employs a compound of the Formula V:

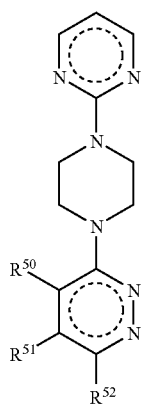

V wherein $R^{50}$, $R^{51}$, and $R^{52}$ are independently substituted or unsubstituted hydrogen, hydroxyl, alkyl, alkenyl, alkynyl, alkylene, alkenylene, alkoxy, alkenyloxy, cycloalkyl, cycloalkenyl, cycloalkynyl, cycloalkoxy, aryl, aryloxy, arylalkoxy, aroyl, heteroaryl, heterocyclic, acyl, acyloxy, sulfonyl, sulfinyl, sulfenyl, sulfoxide, sulfate, sulfonate, amino, imino, azido, thiol, thioalkyl, thioalkoxy, thioaryl, nitro, ureido, cyano, halo, silyl, silyloxy, silylalkyl, silylthio, =O, =S, phosphonate, carboxyl, carbonyl, carbamoyl, or carboxamide; or an isomer or a pharmaceutically acceptable salt thereof.

In aspects of the invention a compound of the Formula V is employed wherein $R^{50}$ is substituted or unsubstituted hydrogen, alkyl, aryl, or heterocyclic; $R^{51}$ is substituted or unsubstituted hydrogen or alkyl, and $R^{52}$ is substituted or unsubstituted hydrogen, alkyl, cycloalkyl, heteroaryl or halo. In an aspect, a compound of the Formula V is employed wherein $R^{50}$ is hydrogen, $C_1$-$C_6$ alkyl which may be substituted with alkyl, especially methyl or trimethyl, phenyl, or a 3 to 6-membered heteromonocylic group containing 1 to 4 nitrogen atoms more particularly, piperidinyl or morpholinyl, $R^{51}$ is hydrogen or alkyl especially methyl, and $R^{52}$ is hydrogen, alkyl especially methyl, dimethyl, ethyl, or propyl, cyclohexyl, chloro, or an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, or pyridazinyl, especially pyridinyl. In an embodiment, $R^{50}$ is aryl, $R^{51}$ is hydrogen, and $R^{52}$ is $C_1$-$C_6$ alkyl.

A compound of the Formula V may comprise compound MW01-7-057WH, or structure 32, 34, 36, 38, 39, 40, 41, 42, 43, 44, 46, 47, 48, 49, 63, 69, 70, 71, 75, 76, 77, 78, 79, 80, 81, or 82 in Table 5 or pharmaceutically acceptable salts, isomers or derivatives thereof.

In aspects of the invention the pyridazine compound is an isolated and pure, in particular, substantially pure, compound of the Formula I, II, III, IV, or V, or an isomer or a pharmaceutically acceptable salt thereof. As used herein, the term "pure" in general means better than 90%, 92%, 93%, 94%, 95%, 96%, 97%, 98%, or 99% pure, and "substantially pure" means a compound synthesized such that the compound, as made or as available for consideration into a composition or dosage form described herein, has only those impurities that can not readily nor reasonably be removed by conventional purification processes.

A pyridazine compound employed in the invention includes derivatives, in particular derivatives of a compound of the Formula I, II, III, IV, or V. The term "derivative" of a compound, as used herein, refers to a chemically modified compound wherein the chemical modification takes place either at a functional group of the compound or on the aromatic ring. Non-limiting examples of derivatives of compounds of the Formula I, II, III, IV, or V (e.g., pyridazine derivatives of the present invention) may include N-acetyl, N-methyl, N-hydroxy groups at any of the available nitrogens in the compound. Derivative groups that may be used to modify the compounds of the Formula I, II, III, IV, or V can be found in U.S. Patent Application No. 20030176437 (herein incorporated by reference in its entirety for all purposes).

In some embodiments, the organic compounds, and/or heterocyclic derivatives thereof depicted in Tables 1, 2, 3, 4 or 5 are employed, in particular Tables 2, 3, 4, or 5.

In particular aspects the invention employs a compound of the Formula I, II, III, IV, or V as defined herein, with the proviso that compounds depicted in Table 1 are excluded.

In other particular aspects the invention employs a compound of the Formula II with the proviso that the compounds depicted in Table 1 are excluded.

In further particular aspects the invention employs a compound of the Formula III with the proviso that compounds depicted in Table 1 are excluded.

In further particular aspects the invention employs compounds of the Formula IV with the proviso that compounds depicted in Table 1 are excluded.

In still further particular aspects the invention employs compounds of the Formula V with the proviso that compounds depicted in Table 1 are excluded.

In accordance with aspects of the invention pyridazine compounds and/or related heterocyclic derivatives thereof (see, for example, the Figures and Tables herein, in particular Table 2, 3, 4 and/or 5 or heterocyclic derivatives thereof), are employed in the treatment or prevention of diseases disclosed herein. In some embodiments, the compounds employed are those depicted in the Figures and Table 2, 3, 4, and/or 5 or derivatives thereof. In some embodiments, the invention employs one or more of the compounds designated herein as MW01-3-183WH, MW01-5-188WH, MW01-2-065LKM, MW01-2-184WH, MW01-2-189WH and MW01-2-151SRM, or isomers or pharmaceutically acceptable salts thereof.

In some embodiments, the invention employs one or more of the compounds designated herein as MW01-3-183WH, MW01-5-188WH, MW01-2-065LKM, MW01-2-184WH, MW01-2-189WH and MW01-2-151SRM, or isomers or pharmaceutically acceptable salts thereof.

In some embodiments, the invention employs one or more of the compounds designated MW01-3-183WH, MW01-5-188WH, MW01-2-065LKM, MW01-2-184WH, MW01-2-151SRM, MW01-2-189WH, and MW01-1-01-L-D07, and/or related derivatives, in particular, heterocyclic derivatives, of these compounds. In another particular embodiment of the invention, MW01-2-151SRM, an isomer, a pharmaceutically acceptable salt, or derivative thereof is employed in the invention. In a particular embodiment of the invention, MW01-5-188WH, an isomer, a pharmaceutically acceptable salt, or derivative thereof is employed in the invention.

A pyridazine compound also includes "pharmaceutically acceptable salt(s)". By pharmaceutically acceptable salts is meant those salts which are suitable for use in contact with the tissues of a subject or patient without undue toxicity, irritation, allergic response and the like, and are commensurate with a reasonable benefit/risk ratio. Pharmaceutically acceptable salts are described for example, in S. M. Berge, et al., J. Pharmaceutical Sciences, 1977, 66:1. Examples of salts include the compounds designated herein as MW01-1-01-L-D10, MW01-1-01-L-E02, MW01-1-01-L-E08, MW01-1-03-L-A05, MW01-1-16-L-D09, and MW01-1-17-L-G04.

In aspects of the invention, an acid addition salt, in particular a halide salt, more particularly a chloride salt, most particularly a hydrochloride salt of a compound of the formula II is employed. In a particular embodiment, a pharmaceutically acceptable halide salt of the pyridazine compound 4-methyl-6-phenyl-3-(4-pyrimidin-2-ylpiperazin-1-yl)pyridazine(5) shown in FIG. 1 is employed.

In an embodiment, a pharmaceutically acceptable salt employed in the invention is a chloride salt of 4-methyl-6-phenyl-3-(4-pyrimidin-2-ylpiperazin-1-yl)pyridazine(5) shown in FIG. 1. In a particular embodiment, a pharmaceutically acceptable salt is a hydrochloride salt of 4-methyl-6-phenyl-3-(4-pyrimidin-2-ylpiperazin-1-yl)pyridazine    (5)

shown in FIG. 1, more particularly the di-hydrochloride hydrate salt shown below (i.e., MW01-9-034WH) (6).

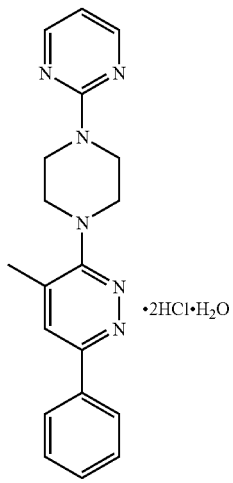

A pyridazine compound, in particular a compound of the Formula I, II, III, IV, or V, may contain one or more asymmetric centers and may give rise to enantiomers, diasteriomers, and other stereoisomeric forms which may be defined in terms of absolute stereochemistry as (R)- or (S)-. Thus, pyridazine compounds include all possible diasteriomers and enantiomers as well as their racemic and optically pure forms. Optically active (R)- and (S)-isomers may be prepared using chiral synthons or chiral reagents, or resolved using conventional techniques. When a pyridazine compound contains centers of geometric asymmetry, and unless specified otherwise, it is intended that the compounds include both E and A geometric isomers. All tautomeric forms are also included within the scope of a pyridazine compound employed in the present invention.

A compound of the formula I, II, III, IV or V includes crystalline forms which may exist as polymorphs. Solvates of the compounds formed with water or common organic solvents are also intended to be encompassed within the term. Thus, a pyridazine compound, in particular a compound of the Formula I, II, III, IV, or V, can exist in unsolvated as well as solvated forms with pharmaceutically acceptable solvents such as water, ethanol, and the like. The solvated forms may be considered equivalent to the unsolvated forms for the purposes of the present invention. In addition, hydrate forms of the compounds and their salts are encompassed within this invention. Further prodrugs of compounds of the formula I, II, III, IV or V are encompassed within the term.

The term "solvate" means a physical association of a compound with one or more solvent molecules or a complex of variable stoichiometry formed by a solute (for example, a compound of the invention) and a solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological activity of the solute. Solvates encompass both solution-phase and isolatable solvates. Representative solvates include hydrates, ethanolates, methanolates, and the like.

Dehydrate, co-crystals, anhydrous, or amorphous forms of the compounds of the invention are also included. The term "hydrate" means a solvate wherein the solvent molecule(s) is/are $H_2O$, including, mono-, di-, and various poly-hydrates thereof. Solvates can be formed using various methods known in the art.

Crystalline compounds of the formula I, II, III, IV or V can be in the form of a free base, a salt, or a co-crystal. Free base compounds can be crystallized in the presence of an appropriate solvent in order to form a solvate. Acid salt compounds of the formula I, II, III, IV or V (e.g. HCl, HBr, benzoic acid) can also be used in the preparation of solvates. For example, solvates can be formed by the use of acetic acid or ethyl acetate. The solvate molecules can form crystal structures via hydrogen bonding, van der Waals forces, or dispersion forces, or a combination of any two or all three forces.

The amount of solvent used to make solvates can be determined by routine testing. For example, a monohydrate of a compound of the formula I, II, III, IV or V would have about 1 equivalent of solvent ($H_2O$) for each equivalent of a compound of the invention. However, more or less solvent may be used depending on the choice of solvate desired.

Compounds of the formula I, II, III, IV or V may be amorphous or may have different crystalline polymorphs, possibly existing in different solvation or hydration states. By varying the form of a drug, it is possible to vary the physical properties thereof. For example, crystalline polymorphs typically have different solubilities from one another, such that a more thermodynamically stable polymorph is less soluble than a less thermodynamically stable polymorph. Pharmaceutical polymorphs can also differ in properties such as shelf-life, bioavailability, morphology, vapor pressure, density, color, and compressibility.

A compound of the Formula I, II, III, IV, or V may be in the form of a prodrug that is converted in vivo to an active compound. In a compound of the Formula I one or more of $R^1$, $R^2$, $R^3$, $R^4$, $R^5$, $R^6$, and $R^7$ may comprise a cleavable group that is cleaved after administration to a subject to provide an active (e.g., therapeutically active) compound, or an intermediate compound that subsequently yields the active compound. A cleavable group can be an ester that is removed either enzymatically or non-enzymatically.

The term "prodrug" means a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309 396; Burger's Medicinal Chemistry and Drug Discovery, 5th Ed., M. Wolff (ed.), John Wiley & Sons, 1995, particularly Vol. 1 and pp. 172 178 and pp. 949 982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Examples of prodrugs include, but are not limited to esters (e.g., acetate, formate, and benzoate derivatives), carbamates (e.g. N,N-dimethylaminocarbonyl) of hydroxy functional groups on compounds of the formula I, II, III, IV or V, and the like.

A compound of the formula I, II, III, IV or V can include a pharmaceutically acceptable co-crystal or a co-crystal salt. A pharmaceutically acceptable co-crystal includes a co-crystal that is suitable for use in contact with the tissues of a subject or patient without undue toxicity, irritation, allergic response and has the desired pharmacokinetic properties.

The term "co-crystal" as used herein means a crystalline material comprised of two or more unique solids at room temperature, each containing distinctive physical characteristics, such as structure, melting point, and heats of fusion. Co-crystals can be formed by an active pharmaceutical ingredient (API) and a co-crystal former either by hydrogen bonding or other non-covalent interactions, such as pi stacking and van der Waals interactions. An aspect of the invention provides for a co-crystal wherein the co-crystal former is a second API. In another aspect, the co-crystal former is not an API. In another aspect, the co-crystal comprises more than one co-crystal former. For example, two, three, four, five, or more co-crystal formers can be incorporated in a co-crystal with an API. Pharmaceutically acceptable co-crystals are described, for example, in "Pharmaceutical co-crystals," Journal of Pharmaceutical Sciences, Volume 95 (3) Pages 499-516, 2006. The methods producing co-crystals are discussed in the United States Patent Application 20070026078.

A co-crystal former which is generally a pharmaceutically acceptable compound, may be, for example, benzoquinone, terephthalaldehyde, saccharin, nicotinamide, acetic acid, formic acid, butyric acid, trimesic acid, 5-nitroisophthalic acid, adamantane-1,3,5,7-tetracarboxylic acid, formamide, succinic acid, fumaric acid, tartaric acid, malic acid, malonic acid, benzamide, mandelic acid, glycolic acid, fumaric acid, maleic acid, urea, nicotinic acid, piperazine, p-phthalaldehyde, 2,6-pyridinecarboxylic acid, 5-nitroisophthalic acid, citric acid, and the alkane- and arene-sulfonic acids such as methanesulfonic acid and benzenesulfonic acid.

In general, all physical forms of compounds of the formula I, II, III, IV or V are intended to be within the scope of the present invention.

A pyridazine compound, in particular a compound of the Formula I, II, III, IV, or V, may optionally comprise a carrier interacting with one or more radicals in the compound, for example $R^1$, $R^2$, $R^3$, $R^4$, $R^5$, $R^6$ or $R^7$ in Formula I. A carrier may be a polymer, carbohydrate, or peptide, or derivatives or combinations thereof, and it may be optionally substituted, for example, with one or more alkyl, halo, hydroxyl, halo, or amino. A carrier may be directly or indirectly covalently attached to a pyridazine compound. A carrier may be substituted with substituents described herein including without limitation one or more alkyl, amino, nitro, halogen, thiol, thioalkyl, sulfate, sulfonyl, sulfinyl, sulfoxide and hydroxyl groups. In aspects of the invention the carrier is an amino acid including alanine, glycine, praline, methionine, serine, threonine, asparagine, alanyl-alanyl, prolyl-methionyl, or glycylglycyl. A carrier can also include a molecule that targets a pyridazine compound, in particular a compound of the Formula I, II, III, IV, or V, to a particular tissue or organ. Thus, a carrier may facilitate or enhance transport of a pyridazine compound, in particular a compound of the Formula I, II, III, IV or V to a target therapeutic site, for example the brain.

A "polymer" refers to molecules comprising two or more monomer subunits that may be identical repeating subunits or different repeating subunits. A monomer generally comprises a simple structure, low-molecular weight molecule containing carbon. Polymers may optionally be substituted. Polymers that can be used in the present invention include without limitation vinyl, acryl, styrene, carbohydrate derived polymers, polyethylene glycol (PEG), polyoxyethylene, polymethylene glycol, poly-trimethylene glycols, polyvinylpyrrolidone, polyoxyethylene-polyoxypropylene block polymers, and copolymers, salts, and derivatives thereof. In aspects of the invention, the polymer is poly(2-acrylamido-2-methyl-1-propanesulfonic acid); poly(2-acrylamido-2-methyl,-1-propanesulfonic acid-coacrylonitrile, poly(2-acrylamido-2-methyl-1-propanesulfonic acid-co-styrene), poly(vinylsulfonic acid); poly(sodium 4-styrenesulfonic acid); and sulfates and sulfonates derived therefrom; poly(acrylic acid), poly(methylacrylate), poly(methyl methacrylate), and poly(vinyl alcohol).

A "carbohydrate" as used herein refers to a polyhydroxyaldehyde, or polyhydroxyketone and derivatives thereof. The term includes monosaccharides such as erythrose, arabinose, allose, altrose, glucose, mannose, threose, xylose, gulose, idose, galactose, talose, aldohexose, fructose, ketohexose, ribose, and aldopentose. The term also includes carbohydrates composed of monosaccharide units, including disaccharides, oligosaccharides, or polysaccharides. Examples of disaccharides are sucrose, lactose, and maltose. Oligosaccharides generally contain between 3 and 9 monosaccharide units and polysaccharides contain greater than 10 monosaccharide units. A carbohydrate group may be substituted at one two, three or four positions, other than the position of linkage to a pyridazine compound. For example, a carbohydrate may be substituted with one or more alkyl, amino, nitro, halo, thiol, carboxyl, or hydroxyl groups, which are optionally substituted. Illustrative substituted carbohydrates are glucosamine, or galactosamine. In aspects of the invention, the carbohydrate is a sugar, in particular a hexose or pentose and may be an aldose or a ketose. A sugar may be a member of the D or L series and can include amino sugars, deoxy sugars, and their uronic acid derivatives. In embodiments of the invention where the carbohydrate is a hexose, the hexose is glucose, galactose, or mannose, or substituted hexose sugar residues such as an amino sugar residue such as hexosamine, galactosamine, glucosamine, in particular D-glucosamine (2-amino-2-doexy-D-glucose) or D-galactosamine (2-amino-2-deoxy-D-galactose). Illustrative pentose sugars include arabinose, fucose, and ribose.

A sugar residue may be linked to a pyridazine compound from a 1,1 linkage, 1,2 linkage, 1,3 linkage, 1,4 linkage, 1,5 linkage, or 1,6 linkage. A linkage may be via an oxygen atom of a pyridazine compound. An oxygen atom can be replaced one or more times by —CH$_2$— or —S— groups.

The term "carbohydrate" also includes glycoproteins such as lectins (e.g. concanavalin A, wheat germ agglutinin, peanutagglutinin, seromucoid, and orosomucoid) and glycolipids such as cerebroside and ganglioside.

A "peptide" carrier includes one, two, three, four, or five or more amino acids covalently linked through a peptide bond. A peptide can comprise one or more naturally occurring amino acids, and analogs, derivatives, and congeners thereof. A peptide can be modified to increase its stability, bioavailability, solubility, etc. "Peptide analogue" and "peptide derivative" as used herein include molecules which mimic the chemical structure of a peptide and retain the functional properties of the peptide. A carrier can be an amino acid such as alanine, glycine, proline, methionine, serine, threonine, histidine, asparagine, alanyl-alanyl, prolyl-methionyl, or glycyl-glycyl. A carrier can be a polypeptide such as albumin, antitrypsin, macroglobulin, haptoglobin, caeruloplasm, transferring, α- or β-lipoprotein, β- or γ-globulin or fibrinogen. A peptide can be attached to a pyridazine compound through a functional group on the side chain of certain amino acids (e.g. serine) or other suitable functional groups. A carrier may comprise four or more amino acids with groups attached to three or more of the amino acids through functional groups on side chains. In an aspect, the carrier is one amino acid, in particular a sulfonate derivative of an amino acid, for example cysteic acid.

Approaches to designing peptide analogues, derivatives and mimetics are known in the art. For example, see Farmer, P. S. in Drug Design (E. J. Ariens, ed.) Academic Press, New York, 1980, vol. 10, pp. 119-143; Ball. J. B. and Alewood, P. F. (1990) J Mol. Recognition 3:55; Morgan, B. A. and Gainor, J. A. (1989) Ann. Rep. Med. Chem. 24:243; and Freidinger, R. M. (1989) Trends Pharmacol. Sci. 10:270. See also Sawyer, T. K. (1995) "Peptidomimetic Design and Chemical Approaches to Peptide Metabolism" in Taylor, M. D. and Amidon, G. L. (eds.) Peptide-Based Drug Design: Controlling Transport and Metabolism, Chapter 17; Smith, A. B. 3rd, et al. (1995) J. Am. Chem. Soc. 117:11113-11123; Smith, A. B. 3rd, et al. (1994) J. Am. Chem. Soc. 116:9947-9962; and Hirschman, R., et al. (1993) J. Am. Chem. Soc. 115:12550-12568.

The term "alkyl", either alone or within other terms such as "thioalkyl" and "arylalkyl", means a monovalent, saturated hydrocarbon radical which may be a straight chain (i.e. linear) or a branched chain. An alkyl radical for use in the present invention generally comprises from about 1 to 20 carbon atoms, particularly from about 1 to 10, 1 to 8 or 1 to 7, more particularly about 1 to 6 carbon atoms, or 3 to 6 carbon atoms. Illustrative alkyl radicals include methyl, ethyl, n-propyl, n-butyl, n-pentyl, n-hexyl, isopropyl, isobutyl, isopentyl, amyl, sec-butyl, tert-butyl, tert-pentyl, n-heptyl, n-octyl, n-nonyl, n-decyl, undecyl, n-dodecyl, n-tetradecyl, pentadecyl, n-hexadecyl, heptadecyl, n-octadecyl, nonadecyl, eicosyl, dosyl, n-tetracosyl, and the like, along with branched variations thereof. In certain aspects of the invention an alkyl radical is a $C_1$-$C_6$ lower alkyl comprising or selected from the group consisting of methyl, ethyl, n-propyl, n-butyl, n-pentyl, n-hexyl, isopropyl, isobutyl, isopentyl, amyl, tributyl, sec-butyl, tert-butyl, tert-pentyl, and n-hexyl. An alkyl radical may be optionally substituted with substituents as defined herein at positions that do not significantly interfere with the preparation of compounds of the Formula I, II, III, IV, or V and do not significantly reduce the efficacy of the compounds. In certain aspects of the invention, an alkyl radical is substituted with substituents, in particular one to five substituents, including halo, lower alkoxy, lower aliphatic, a substituted lower aliphatic, hydroxy, cyano, nitro, thio, amino, keto, aldehyde, ester, amide, substituted amino, carboxyl, sulfonyl, sulfinyl, sulfenyl, sulfate, sulfoxide, substituted carboxyl, halogenated lower alkyl (e.g. $CF_3$), halogenated lower alkoxy, hydroxycarbonyl, lower alkoxycarbonyl, lower alkylcarbonyloxy, lower alkylcarbonylamino, cycloaliphatic, substituted cycloaliphatic, or aryl (e.g., phenylmethyl (i.e. benzyl)). Substituents on an alkyl group may themselves be substituted.

As used herein in respect to certain aspects of the invention, the term "substituted aliphatic" refers to an alkyl or an alkane possessing less than 10 carbons where at least one of the aliphatic hydrogen atoms has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such groups include, but are not limited to, 1-chloroethyl and the like.

As used herein in respect to certain aspects of the invention, the term "lower-alkyl-substituted-amino" refers to any alkyl unit containing up to and including eight carbon atoms where one of the aliphatic hydrogen atoms is replaced by an amino group. Examples of such groups include, but are not limited to, ethylamino and the like.

As used herein in respect to certain aspects of the invention, the term "lower-alkyl-substituted-halogen" refers to any alkyl chain containing up to and including eight carbon atoms where one of the aliphatic hydrogen atoms is replaced by a halogen. Examples of such groups include, but are not limited to, chlorethyl and the like.

As used herein, the term "acetylamino" shall mean any primary or secondary amino that is acetylated. Examples of such groups include, but are not limited to, acetamide and the like.

As used herein the term "alkenyl" refers to an unsaturated, acyclic branched or straight-chain hydrocarbon radical comprising at least one double bond. An alkenyl radical may contain from about 2 to 24, 2 to 15, or 2 to 10 carbon atoms, in particular from about 3 to 8 carbon atoms and more particularly about 3 to 6 or 2 to 6 carbon atoms. Suitable alkenyl radicals include without limitation ethenyl, propenyl (e.g., prop-1-en-1-yl, prop-1-en-2-yl, prop-2-en-1-yl (allyl), and prop-2-en-2-yl), buten-1-yl, but-1-en-2-yl, 2-methyl-prop-1-en-1-yl, but-2-en-1-yl, but-2-en-2-yl, buta-1,3-dien-1-yl, buta-1,3-dien-2-yl, hexen-1-yl, 3-hydroxyhexen-1-yl, hepten-1-yl, and octen-1-yl, and the like. An alkenyl radical may be optionally substituted similar to alkyl.

In aspects of the invention, "substituted alkenyl" includes an alkenyl group substituted by, for example, one to three substituents, preferably one to two substituents, such as alkyl, alkoxy, haloalkoxy, alkylalkoxy, haloalkoxyalkyl, alkanoyl, alkanoyloxy, cycloalkyl, cycloalkoxy, acyl, acylamino, acyloxy, amino, alkylamino, alkanoylamino, aminoacyl, aminoacyloxy, cyano, halogen, hydroxyl, carboxyl, carboxylalkyl, carbamyl, keto, thioketo, thiol, alkylthio, sulfonyl, sulfonamido, thioalkoxy, aryl, nitro, and the like.

As used herein, the term "alkynyl" refers to an unsaturated, branched or straight-chain hydrocarbon radical comprising one or more triple bonds. An alkynyl radical may contain about 1 to 20, 1 to 15, or 2-10 carbon atoms, particularly about 3 to 8 carbon atoms and more particularly about 3 to 6 carbon atoms. Suitable alkynyl radicals include without limitation ethynyl, such as prop-1-yn-1-yl and prop-2-yn-1-yl, butynyls such as but-1-yn-1-yl, but-1-yn-3-yl, and but-3-yn-1-yl, pentynyls such as pentyn-1-yl, pentyn-2-yl, 4-methoxypentyn-2-yl, and 3-methylbutyn-1-yl, hexynyls such as hexyn-1-yl, hexyn-2-yl, hexyn-3-yl, and 3,3-dimethylbutyn-1-yl radicals and the like. An alkynyl may be optionally substituted similar to alkyl. The term "cycloalkynyl" refers to cyclic alkynyl groups.

In aspects of the invention, "substituted alkynyl" includes an alkynyl group substituted by, for example, a substituent, such as, alkyl, alkoxy, alkanoyl, alkanoyloxy, cycloalkyl, cycloalkoxy, acyl, acylamino, acyloxy, amino, alkylamino, alkanoylamino, aminoacyl, aminoacyloxy, cyano, halogen, hydroxyl, carboxyl, carboxylalkyl, carbamyl, keto, thioketo, thiol, alkylthio, sulfonyl, sulfonamido, thioalkoxy, aryl, nitro, and the like.

As used herein the term "alkylene" refers to a linear or branched radical having from about 1 to 10, 1 to 8, 1 to 6, or 2 to 6 carbon atoms and having attachment points for two or more covalent bonds. Examples of such radicals are methylene, ethylene, propylene, butylene, pentylene, hexylene, ethylidene, methylethylene, and isopropylidene. When an alkenylene radical is present as a substituent on another radical it is typically considered to be a single substituent rather than a radical formed by two substituents.

As used herein the term "alkenylene" refers to a linear or branched radical having from about 2 to 10, 2 to 8, or 2 to 6 carbon atoms, at least one double bond, and having attachment points for two or more covalent bonds. Examples of alkenylene radicals include 1,1-vinylidene (—CH$_2$=C—), 1,2-vinylidene (—CH=CH—), and 1,4-butadienyl (—CH=CH—CH=CH—).

As used herein the term "halo" refers to a halogen such as fluorine, chlorine, bromine or iodine atoms.

As used herein the term "hydroxyl" or "hydroxy" refers to an —OH group.

As used herein the term "cyano" refers to a carbon radical having three of four covalent bonds shared by a nitrogen atom, in particular —C≡N. A cyano group may be substituted with substituents described herein.

As used herein the term "alkoxy" refers to a linear or branched oxy-containing radical having an alkyl portion of one to about ten carbon atoms, such as a methoxy radical, which may be substituted. In aspects of the invention an alkoxy radical may comprise about 1-10, 1-8, 1-6, or 1-3 carbon atoms. In embodiments of the invention, an alkoxy radical comprises about 1-6 carbon atoms and includes a $C_1$-$C_6$ alkyl-O-radical wherein $C_1$-$C_6$ alkyl has the meaning set out herein. Examples of alkoxy radicals include without limitation methoxy, ethoxy, propoxy, butoxy, isopropoxy and tert-butoxy alkyls. An "alkoxy" radical may optionally be substituted with one or more substituents disclosed herein including alkyl atoms to provide "alkylalkoxy" radicals; halo atoms, such as fluoro, chloro or bromo, to provide "haloalkoxy" radicals (e.g. fluoromethoxy, chloromethoxy, trifluoromethoxy, difluoromethoxy, trifluoroethoxy, fluoroethoxy, tetrafluoroethoxy, pentafluoroethoxy, and fluoropropox) and "haloalkoxyalkyl" radicals (e.g. fluoromethoxymethyl, chloromethoxyethyl, trifluoromethoxymethyl, difluoromethoxyethyl, and trifluoroethoxymethyl).

As used herein the term "alkenyloxy" refers to linear or branched oxy-containing radicals having an alkenyl portion of about 2 to 10 carbon atoms, such as an ethenyloxy or propenyloxy radical. An alkenyloxy radical may be a "lower alkenyloxy" radical having about 2 to 6 carbon atoms. Examples of alkenyloxy radicals include without limitation ethenyloxy, propenyloxy, butenyloxy, and isopropenyloxy alkyls. An "alkenyloxy" radical may be substituted with one or more substitutents disclosed herein including halo atoms, such as fluoro, chloro or bromo, to provide "haloalkenyloxy" radicals (e.g. trifluoroethenyloxy, fluoroethenyloxy, difluoroethenyloxy, and fluoropropenyloxy).

A "carbocylic" includes radicals derived from a saturated or unstaturated, substituted or unsubstituted 5 to 14, 5 to 12, or 5 to 10 member organic nucleus whose ring forming atoms (other than hydrogen) are solely carbon. Examples of carbocyclic radicals are cycloalkyl, cycloalkenyl, aryl, in particular phenyl, naphthyl, norbornanyl, bicycloheptadienyl, toluoyl, xylenyl, indenyl, stilbenzyl, terphenylyl, diphenylethylenyl, phenylcyclohexyl, acenapthtylenyl, anthracenyl, biphenyl, bibenzylyl, and related bibenzylyl homologs, octahydronaphthyl, tetrahydronaphthyl, octahydroquinolinyl, dimethoxytetrahydronaphthyl and the like.

As used herein, the term "cycloalkyl" refers to radicals having from about 3 to 15, 3 to 10, 3 to 8, or 3 to 6 carbon atoms and containing one, two, three, or four rings wherein such rings may be attached in a pendant manner or may be fused. In aspects of the invention, "cycloalkyl" refers to an optionally substituted, saturated hydrocarbon ring system containing 1 to 2 rings and 3 to 7 carbons per ring which may be further fused with an unsaturated $C_3$-$C_7$ carbocyclic ring. Examples of cycloalkyl groups include single ring structures such as cyclopropyl, cyclobutyl, cyclopentyl, cyclohexyl, cycloheptyl, cyclooctyl, cyclononyl, cyclodecyl, cyclododecyl, and the like, or multiple ring structures such as adamantanyl, and the like. In certain aspects of the invention the cycloalkyl radicals are "lower cycloalkyl" radicals having from about 3 to 10, 3 to 8, 3 to 6, or 3 to 4 carbon atoms, in particular cyclopropyl, cyclobutyl, cyclopentyl, cyclohexyl and cycloheptyl. The term "cycloalkyl" also embraces radicals where cycloalkyl radicals are fused with aryl radicals or heterocyclyl radicals. A cycloalkyl radical may be optionally substituted with groups as disclosed herein.

In aspects of the invention, "substituted cycloalkyl" includes cycloalkyl groups having from 1 to 5 (in particular 1 to 3) substituents including without limitation alkyl, alkenyl, alkoxy, cycloalkyl, substituted cycloalkyl, acyl, acylamino, acyloxy, amino, aminoacyl, aminoacyloxy, oxyacylamino, cyano, halogen, hydroxyl, carboxyl, carboxylalkyl, keto, thioketo, thiol, thioalkoxy, aryl, aryloxy, heteroaryl, heteroaryloxy, hydroxyamino, alkoxyamino, and nitro.

As used herein in respect to certain aspects of the invention, the term "cycloaliphatic" refers to a cycloalkane possessing less than 8 carbons or a fused ring system consisting of no more than three fused cycloaliphatic rings. Examples of such groups include, but are not limited to, decalin and the like.

As used herein in respect to certain aspects of the invention, the term "substituted cycloaliphatic" refers to a cycloalkane possessing less than 8 carbons or a fused ring system consisting of no more than three fused rings, and where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such groups include, but are not limited to, 1-chlorodecalyl and the like.

A used herein, the term "cycloalkenyl" refers to radicals comprising about 4 to 16, 2 to 15, 2 to 10, 2 to 8, 4 to 10, 3 to 8, 3 to 7, 3 to 6, or 4 to 6 carbon atoms, one or more carbon-carbon double bonds, and one, two, three, or four rings wherein such rings may be attached in a pendant manner or may be fused. In certain aspects of the invention the cycloalkenyl radicals are "lower cycloalkenyl" radicals having three to seven carbon atoms. Examples of cycloalkenyl radicals include without limitation cyclobutenyl, cyclopentenyl, cyclohexenyl and cycloheptenyl. A cycloalkenyl radical may be optionally substituted with groups as disclosed herein, in particular 1, 2, or 3 substituents which may be the same or different.

As used herein the term "cycloalkoxy" refers to cycloalkyl radicals (in particular, cycloalkyl radicals having 3 to 15, 3 to 8 or 3 to 6 carbon atoms) attached to an oxy radical. Examples of cycloalkoxy radicals include cyclohexoxy and cyclopentoxy. A cycloalkoxy radical may be optionally substituted with groups as disclosed herein.

As used herein, the term "aryl", alone or in combination, refers to a carbocyclic aromatic system containing one, two or three rings wherein such rings may be attached together in a pendant manner or may be fused. In aspects of the invention an aryl radical comprises 4 to 24 carbon atoms, in particular 4 to 10, 4 to 8, or 4 to 6 carbon atoms. Illustrative "aryl" radicals includes without limitation aromatic radicals such as phenyl, benzyl, naphthyl, indenyl, benzocyclooctenyl, benzocycloheptenyl, pentalenyl, azulenyl, tetrahydronaphthyl, indanyl, biphenyl, acephthylenyl, fluorenyl, phenalenyl, phenanthrenyl, and anthracenyl. An aryl radical may be optionally subsitituted with groups as disclosed herein, in particular hydroxyl, alkyl ("arylalkyl"), carbonyl, carboxyl, thiol ("thioalkyl"), amino, and/or halo, in particular a substituted aryl includes without limitation arylamine and arylalkylamine.

As used herein in respect to certain aspects of the invention, the term "substituted aryl" includes an aromatic ring, or fused aromatic ring system consisting of no more than three fused rings at least one of which is aromatic, and where at least one of the hydrogen atoms on a ring carbon has been replaced by a halogen, an amino, a hydroxy, a nitro, a thio, an alkyl, a ketone, an aldehyde, an ester, an amide, a lower aliphatic, a substituted lower aliphatic, or a ring (aryl, substituted aryl, cycloaliphatic, or substituted cycloaliphatic). Examples of such groups include, but are not limited to, hydroxyphenyl, chlorophenyl and the like.

In aspects of the invention, an aryl radical may be optionally subsitituted with one to four substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, arylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. A substituent may be further substituted by hydroxy, halo, alkyl, alkoxy, alkenyl, alkynyl, aryl or aralkyl. In aspects of the invention an aryl radical is substituted with hydroxyl, alkyl, carbonyl, carboxyl, thiol, amino, and/or halo. The term "aralkyl" refers to an aryl or a substituted aryl group bonded directly through an alkyl group, such as benzyl. Other particular examples of substituted aryl radicals include chlorobenyzl, and amino benzyl.

As used herein, the term "aryloxy" refers to aryl radicals, as defined above, attached to an oxygen atom. Exemplary aryloxy groups include napthyloxy, quinolyloxy, isoquinoliziny-loxy, and the like.

As used herein the term "arylalkoxy," refers to an aryl group attached to an alkoxy group. Representative examples of arylalkoxy groups include, but are not limited to, 2-phenylethoxy, 3-naphth-2-ylpropoxy, and 5-phenylpentyloxy.

As used herein, the term "aroyl" refers to aryl radicals, as defined above, attached to a carbonyl radical as defined herein, including without limitation benzoyl and toluoyl. An aroyl radical may be optionally substituted with groups as disclosed herein.

As used herein the term "heteroaryl" refers to fully unsaturated heteroatom-containing ring-shaped aromatic radicals having at least one heteroatom selected from carbon, nitrogen, sulfur and oxygen. A heteroaryl radical may contain one, two or three rings and the rings may be attached in a pendant manner or may be fused. In aspects of the invention the term refers to fully unsaturated heteroatom-containing ring-shaped aromatic radicals having from 3 to 15, 3 to 10, 3 to 8, 5 to 15, 5 to 10, or 5 to 8 ring members selected from carbon, nitrogen, sulfur and oxygen, wherein at least one ring atom is a heteroatom. Examples of "heteroaryl" radicals, include without limitation, an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, tetrazolyl and the like; an unsaturated condensed heterocyclic group containing 1 to 5 nitrogen atoms, in particular, indolyl, isoindolyl, indolizinyl, indazolyl, quinazolinyl, pteridinyl, quinolizidinyl, phthalazinyl, naphthyridinyl, quinoxalinyl, cinnolinyl, phenanthridinyl, acridinyl, phenanthrolinyl, phenazinyl, carbazolyl, purinyl, benzimidazolyl, quinolyl, isoquinolyl, quinolinyl, isoquinolinyl, indazolyl, benzotriazolyl, tetrazolopyridazinyl and the like; an unsaturated 3 to 6-membered heteromonocyclic group containing an oxygen atom, in particular, 2-furyl, 3-furyl, pyranyl, and the like; an unsaturated 5 to 6-membered heteromonocyclic group containing a sulfur atom, in particular, thienyl, 2-thienyl, 3-thienyl, and the like; unsaturated 5 to 6-membered heteromonocyclic group containing 1 to 2 oxygen atoms and 1 to 3 nitrogen atoms, in particular, furazanyl, benzofurazanyl, oxazolyl, isoxazolyl, and oxadiazolyl; an unsaturated condensed heterocyclic group containing 1 to 2 oxygen atoms and 1 to 3 nitrogen atoms, in particular benzoxazolyl, benzoxadiazolyl and the like; an unsaturated 5 to 6-membered heteromonocyclic group containing 1 to 2 sulfur atoms and 1 to 3 nitrogen atoms, for example, thiazolyl, isothiazolyl, thiadiazolyl and the like; an unsaturated condensed heterocyclic group containing 1 to 2 sulfur atoms and 1 to 3 nitrogen atoms such as benzothiazolyl, benzothiadiazolyl and the like. The term also includes radicals where heterocyclic radicals are fused with aryl radicals, in particular bicyclic radicals such as benzofuranyl, benzothiophenyl, phthalazinyl, chromenyl, xanthenyl, and the like. A heteroaryl radical may be optionally substituted with groups as disclosed herein, for example with an alkyl, amino, halogen, etc., in particular a heteroarylamine.

In aspects of the invention, the term refers to an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, tetrazolyl and the like.

A heteroaryl radical may be optionally substituted with groups disclosed herein, for example with an alkyl, amino, halogen, etc., in particular a substituted heteroaryl radical is a heteroarylamine.

The term "heterocyclic" refers to saturated and partially saturated heteroatom-containing ring-shaped radicals having at least one heteroatom selected from carbon, nitrogen, sulfur and oxygen. A heterocyclic radical may contain one, two or three rings wherein such rings may be attached in a pendant manner or may be fused. In an aspect, the term refers to a saturated and partially saturated heteroatom-containing ring-shaped radicals having from about 3 to 15, 3 to 10, 5 to 15, 5 to 10, or 3 to 8 ring members selected from carbon, nitrogen, sulfur and oxygen, wherein at least one ring atom is a heteroatom. Examplary saturated heterocyclic radicals include without limitiation a saturated 3 to 6-membered heteromonocylic group containing 1 to 4 nitrogen atoms [e.g. pyrrolidinyl, imidazolidinyl, piperidinyl, and piperazinyl]; a saturated 3 to 6-membered heteromonocyclic group containing 1 to 2 oxygen atoms and 1 to 3 nitrogen atoms [e.g. morpholinyl; sydnonyl]; and, a saturated 3 to 6-membered heteromonocyclic group containing 1 to 2 sulfur atoms and 1 to 3 nitrogen atoms [e.g., thiazolidinyl] etc. Examples of partially saturated heterocyclyl radicals include without limitation dihydrothiophene, dihydropyranyl, dihydrofuranyl and dihydrothiazolyl. Illustrative heterocyclic radicals include without limitation aziridinyl, azetidinyl, 2-pyrrolinyl, 3-pyrrolinyl, pyrrolidinyl, azepinyl, 1,3-dioxolanyl, 2H-pyranyl, 4H-pyranyl, piperidinyl, 1,4-dioxanyl, morpholinyl, pyrazolinyl, 1,4-dithianyl, thiomorpholinyl, 1,2,3,6-tetrahydropyridinyl, oxiranyl, oxetanyl, tetrahydrofuranyl, tetrahydropyranyl, tetrahydropyridinyl, tetrahydrothiopyranyl, thioxanyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3H-indolyl, quinuclidinyl, quinolizinyl, and the like.

As used herein in respect to certain aspects of the invention, the term "heterocyclic" refers to a cycloalkane and/or an aryl ring system, possessing less than 8 carbons, or a fused ring system consisting of no more than three fused rings, where at least one of the ring carbon atoms is replaced by oxygen, nitrogen or sulfur. Examples of such groups include, but are not limited to, morpholino and the like.

As used herein in respect to certain aspects of the invention, the term "substituted heterocyclic" refers to a cycloalkane and/or an aryl ring system, possessing less than 8 carbons, or a fused ring system consisting of no more than three fused rings, where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amide, a lower aliphatic, a substituted lower aliphatic, or a ring (aryl, substituted aryl, cycloaliphatic, or substituted cycloaliphatic). Examples of such groups include, but are not limited to 2-chloropyranyl.

The foregoing heteroaryl and heterocyclic groups may be C-attached or N-attached (where such is possible).

As used herein the term "sulfonyl", used alone or linked to other terms such as alkylsulfonyl or arylsulfonyl, refers to the divalent radicals —SO$_2$—. In aspects of the invention, the sulfonyl group may be attached to a substituted or unsubstituted hydroxyl, alkyl group, ether group, alkenyl group, alkynyl group, aryl group, cycloalkyl group, cycloalkenyl group, cycloalkynyl group, heterocyclic group, carbohydrate, peptide, or peptide derivative.

The term "sulfinyl", used alone or linked to other terms such as alkylsulfinyl (i.e. —S(O)-alkyl) or arylsulfinyl, refers to the divalent radicals —S(O)—.

The term "sulfonate" is art recognized and includes a group represented by the formula:

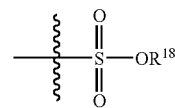

wherein R$^{18}$ is an electron pair, hydrogen, alkyl, cycloalkyl, aryl, alkenyl, alkynyl, cycloalkenyl, cycloalkynyl, heterocyclic, carbohydrate, peptide, or peptide derivative.

The term "sulfate", used alone or linked to other terms, is art recognized and includes a group that can be represented by the formula:

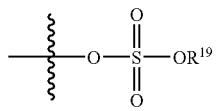

wherein R$^{19}$ is an electron pair, hydrogen, alkyl, alkenyl, alkynyl, cycloalkyl, cycloalkenyl, cycloalkynyl, aryl, heterocyclic, carbohydrate, peptide or peptide derivative.

The term "sulfoxide" refers to the radical —S=O.

As used herein the term "amino", alone or in combination, refers to a radical where a nitrogen atom (N) is bonded to three substituents being any combination of hydrogen, hydroxyl, alkyl, cycloalkyl, alkenyl, alkynyl, aryl, silyl, heterocyclic, or heteroaryl with the general chemical formula —NR$^{38}$R$^{39}$ where R$^{38}$ and R$^{39}$ can be any combination of hydrogen, hydroxyl, alkyl, cycloalkyl, alkoxy, alkenyl, alkynyl, aryl, carbonyl carboxyl, amino, silyl, heteroaryl, or heterocyclic which may or may not be substituted. Optionally one substituent on the nitrogen atom may be a hydroxyl group (—OH) to provide an amine known as a hydroxylamine. Illustrative examples of amino groups are amino (—NH$_2$), alkylamino, acylamino, cycloamino, acycloalkylamino, arylamino, arylalkylamino, and lower alkylsilylamino, in particular methylamino, ethylamino, dimethylamino, 2-propylamino, butylamino, isobutylamino, cyclopropylamino, benzylamino, allylamino, hydroxylamino, cyclohexylamino, piperidinyl, hydrazinyl, benzylamino, diphenylmethylamino, tritylamino, trimethylsilylamino, and dimethyl-tert.-butylsilylamino, which may or may not be substituted.

As used herein the term "thiol" means —SH. A thiol may be substituted with a substituent disclosed herein, in particular alkyl (thioalkyl), aryl (thioaryl), alkoxy (thioalkoxy) or carboxyl.

The term "sulfenyl" used alone or linked to other terms such as alkylsulfenyl, refers to the radical —SR$^{25}$ wherein R$^{25}$ is not hydrogen. In aspects of the invention R$^{25}$ is substituted or unsubstituted alkyl, cycloalkyl, alkenyl, alkynyl, aryl, silyl, silylalkyl, heterocyclic, heteroaryl, carbonyl, carbamoyl, alkoxy, or carboxyl.

As used herein, the term "thioalkyl", alone or in combination, refers to a chemical functional group where a sulfur atom (S) is bonded to an alkyl, which may be substituted. Examples of thioalkyl groups are thiomethyl, thioethyl, and thiopropyl. A thioalkyl may be substituted with a substituted or unsubstitute carboxyl, aryl, heterocylic, carbonyl, or heterocyclic.

As used herein the term "thioaryl", alone or in combination, refers to a chemical functional group where a sulfur atom (S) is bonded to an aryl group with the general chemical formula —SR$^{26}$ where R$^{26}$ is aryl which may be substituted. Illustrative examples of thioaryl groups and substituted thioaryl groups are thiophenyl, chlorothiophenyl, para-chlorothiophenyl, thiobenzyl, 4-methoxy-thiophenyl, 4-nitro-thiophenyl, and para-nitrothiobenzyl.

As used herein the term "thioalkoxy", alone or in combination, refers to a chemical functional group where a sulfur atom (S) is bonded to an alkoxy group with the general chemical formula —SR$^{27}$ where R$^{27}$ is an alkoxy group which may be substituted. A "thioalkoxy group" may have 1-6 carbon atoms i.e. a —S—(O)—C$_1$-C$_6$ alkyl group wherein C$_1$-C$_6$ alkyl have the meaning as defined above. Illustrative examples of a straight or branched thioalkoxy group or radical having from 1 to 6 carbon atoms, also known as a C$_1$-C$_6$ thioalkoxy, include thiomethoxy and thioethoxy.

A thiol may be substituted with a substituted or unsubstituted heteroaryl or heterocyclic, in particular a substituted or unsubstituted saturated 3 to 6-membered heteromonocylic group containing 1 to 4 nitrogen atoms [e.g. pyrrolidinyl, imidazolidinyl, piperidinyl, and piperazinyl] or a saturated 3 to 6-membered heteromonocyclic group containing 1 to 2 oxygen atoms and 1 to 3 nitrogen atoms [e.g. morpholinyl; sydnonyl], especially a substituted morpholinyl or piperidinyl.

As used herein, the term "carbonyl" refers to a carbon radical having two of the four covalent bonds shared with an oxygen atom.

As used herein, the term "carboxyl", alone or in combination, refers to —C(O)OR$^{14}$— or —C(=O)OR$^{14}$ wherein R$^{14}$ is hydrogen, alkyl, alkenyl, alkynyl, cycloalkyl, cycloalkenyl, amino, thiol, aryl, heteroaryl, thioalkyl, thioaryl, thioalkoxy, a heteroaryl, or a heterocyclic, which may optionally be substituted. In particular aspects of the invention, —C(O)OR$^{14}$ provides an ester or an amino acid derivative. An esterified form is also particularly referred to herein as a "carboxylic ester". In aspects of the invention a "carboxyl" may be substituted, in particular substituted with alkyl which is optionally substituted with one or more of amino, amino, halo, alkylamino, aryl, carboxyl or a heterocyclic. Examples of carboxyl groups are methoxycarbonyl, butoxycarbonyl, tert.alkoxycarbonyl such as tert.butoxycarbonyl, arylmethyoxycarbonyl having one or two aryl radicals including without limitation phenyl optionally substituted by for example lower alkyl, lower alkoxy, hydroxyl, halo, and/or nitro, such as benzyloxycarbonyl, methoxybenxyloxycarbonyl, diphenyl-methoxycarbonyl, 2-bromoethoxycarbonyl, 2-iodoethoxy-carbonyltert.butylcarbonyl, 4-nitrobenzyloxycarbonyl, diphenylmethoxy-carbonyl, benzhydroxycarbonyl, di-(4-methoxyphenyl-methoxycarbonyl, 2-bromoethoxycarbonyl, 2-iodoethoxycarbonyl, 2-trimethylsilylethoxycarbonyl, or 2-triphenylsilylethoxycarbonyl. Additional carboxyl groups in esterified form are silyloxycarbonyl groups including organic silyloxycarbonyl. The silicon substituent in such compounds may be substituted with lower alkyl (e.g. methyl), alkoxy (e.g. methoxy), and/or halo (e.g. chlorine). Examples of silicon substituents include trimethylsilyl and dimethylter-t.butylsilyl. In aspects of the invention, the carboxyl group may be an alkoxy carbonyl, in particular methoxy carbonyl, ethoxy carbonyl, isopropoxy carbonyl, t-butoxycarbonyl, t-pentyloxycarbonyl, or heptyloxy carbonyl, especially methoxy carbonyl or ethoxy carbonyl.

As used herein, the term "carbamoyl", alone or in combination, refers to amino, monoalkylamino, dialkylamino, monocycloalkylamino, alkylcycloalkylamino, and dicycloalkylamino radicals, attached to one of two unshared bonds in a carbonyl group.

As used herein, the term "carboxamide" refers to the group —CONH—.

As used herein, the term "nitro" means —NO$_2$—.

As used herein, the term "acyl", alone or in combination, means a carbonyl or thiocarbonyl group bonded to a radical selected from, for example, optionally substituted, hydrido, alkyl (e.g. haloalkyl), alkenyl, alkynyl, alkoxy ("acyloxy" including acetyloxy, butyryloxy, iso-valeryloxy, phenylacetyloxy, benzoyloxy, p-methoxybenzoyloxy, and substituted acyloxy such as alkoxyalkyl and haloalkoxy), aryl, halo, heterocyclyl, heteroaryl, sulfinyl (e.g. alkylsulfinylalkyl), sulfonyl (e.g. alkylsulfonylalkyl), cycloalkyl, cycloalkenyl, thioalkyl, thioaryl, amino (e.g alkylamino or dialkylamino), and aralkoxy. Illustrative examples of "acyl" radicals are formyl, acetyl, 2-chloroacetyl, 2-bromacetyl, benzoyl, trifluoroacetyl, phthaloyl, malonyl, nicotinyl, and the like.

In aspects of the invention, "acyl" refers to a group —C(O)R$^{64}$, where R$^{64}$ is hydrogen, alkyl, cycloalkyl, cycloheteroalkyl, aryl, arylalkyl, heteroalkyl, heteroaryl, and heteroarylalkyl. Examples include, but are not limited to formyl, acetyl, cyclohexylcarbonyl, cyclohexylmethylcarbonyl, benzoyl, benzylcarbonyl and the like.

As used herein the term "phosphonate" refers to a C—PO(OH)$_2$ or C—PO(OR$^{65}$)$_2$ group wherein R$^{65}$ is alkyl or aryl which may be substituted.

As used herein, "ureido" refers to the group "—NH-CONH—". A ureido radical includes an alkylureido comprising a ureido substituted with an alkyl, in particular a lower alkyl attached to the terminal nitrogen of the ureido group. Examples of an alkylureido include without limitation N'-methylureido, N'-ethylureido, N'-n-propylureido, N'-i-propylureido and the like. A ureido radical also includes a N',N'- dialkylureido group containing a radical —NHCON where the terminal nitrogen is attached to two optionally substituted radicals including alkyl, aryl, heterocylic, and heteroaryl.

The terms used herein for radicals including "alkyl", "alkoxy", "alkenyl", "alkynyl", "hydroxyl" etc. refer to both unsubstituted and substituted radicals. The term "substituted," as used herein, means that any one or more moiety on a designated atom (e.g., hydrogen) is replaced with a selection from a group disclosed herein, provided that the designated atom's normal valency is not exceeded, and that the substitution results in a stable compound. Combinations of substituents and/or radicals are permissible only if such combinations result in stable compounds. "Stable compound" refers to a compound that is sufficiently robust to survive isolation to a useful degree of purity from a reaction mixture, and formulation into an efficacious therapeutic agent.

A radical in a pyridazine compound may be substituted with one or more substituents apparent to a person skilled in the art including without limitation alkyl, alkoxy, alkenyl, alkynyl, alkanoyl, alkylene, alkenylene, hydroxyalkyl, haloalkyl, haloalkylene, haloalkenyl, alkoxy, alkenyloxy, alkenyloxyalkyl, alkoxyalkyl, aryl, alkylaryl, haloalkoxy, haloalkenyloxy, heterocyclic, heteroaryl, alkylsulfonyl, sulfinyl, sulfonyl, sulfenyl, alkylsulfinyl, aralkyl, heteroaralkyl, cycloalkyl, cycloalkenyl, cycloalkoxy, cycloalkenyloxy, amino, oxy, halo, azido, thio, =O, =S, cyano, hydroxyl, phosphonato, phosphinato, thioalkyl, alkylamino, arylamino, arylsulfonyl, alkylcarbonyl, arylcarbonyl, heteroarylcarbonyl, heteroarylsulfinyl, heteroarylsulfony, heteroarylamino, heteroaryloxy, heteroaryloxylalkyl, arylacetamidoyl, aryloxy, aroyl, aralkanoyl, aralkoxy, aryloxyalkyl, haloaryloxyalkyl, heteroaroyl, heteroaralkanoyl, heteroaralkoxy, heteroaralkoxyalkyl, thioaryl, arylthioalkyl, alkoxyalkyl, and acyl groups. These substitutents may themselves be substituted.

A chemical substituent is "pendant" from a radical if it is bound to an atom of the radical. In this context, the substituent can be pending from a carbon atom of a radical, a carbon atom connected to a carbon atom of the radical by a chain extender, or a heteroatom of the radical. The term "fused" means that a second ring is present (i.e, attached or formed) by having two adjacent atoms in common or shared with the first ring.

Pyridazine compounds, in particular compounds of the Formula I, II, III, IV, or V can be prepared using reactions and methods generally known to the person of ordinary skill in the art, having regard to that knowledge and the disclosure of this application including the Examples. The reactions are performed in a solvent appropriate to the reagents and materials used and suitable for the reactions being effected. It will be understood by those skilled in the art of organic synthesis that the functionality present on the compounds should be consistent with the proposed reaction steps. This will sometimes require modification of the order of the synthetic steps or selection of one particular process scheme over another in order to obtain a desired compound of the invention. It will also be recognized that another major consideration in the development of a synthetic route is the selection of the protecting group used for protection of the reactive functional groups present in the compounds. An authoritative account describing the many alternatives to the skilled artisan is Greene and Wuts (Protective Groups In Organic Synthesis, Wiley and Sons, 1991).

The starting materials and reagents used in preparing the pyridazine compounds are either available from commercial suppliers or are prepared by methods well known to a person of ordinary skill in the art, following procedures described in such references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

The starting materials, intermediates, and pyridazine compounds may be isolated and purified using conventional techniques, such as precipitation, filtration, distillation, crystallization, chromatography, and the like. The pyridazine compounds may be characterized using conventional methods, including physical constants and spectroscopic methods, in particular HPLC.

Pyridazine compounds which are basic in nature can form a wide variety of different salts with various inorganic and organic acids. In practice is it desirable to first isolate a pyridazine compound from the reaction mixture as a pharmaceutically unacceptable salt and then convert the latter to the free base compound by treatment with an alkaline reagent and subsequently convert the free base to a pharmaceutically acceptable acid addition salt. The acid addition salts of the base compounds of the pyridazine compounds are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

Pyridazine compounds which are acidic in nature are capable of forming base salts with various pharmacologically acceptable cations. These salts may be prepared by conventional techniques by treating the corresponding acidic compounds with an aqueous solution containing the desired pharmacologically acceptable cations and then evaporating the resulting solution to dryness, preferably under reduced pressure. Alternatively, they may be prepared by mixing lower alkanolic solutions of the acidic compounds and the desired alkali metal alkoxide together and then evaporating the resulting solution to dryness in the same manner as before. In either case, stoichiometric quantities of reagents are typically employed to ensure completeness of reaction and maximum product yields.

In particular aspects, a compound of the formula II wherein $R^{11}$ is hydrogen and $R^{10}$ is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl, may be prepared by reacting a compound with a structure of formula II wherein $R^{10}$ is halo, in particular chloro, and $R^{11}$ is hydrogen, with boronic acid substituted with an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl, under suitable conditions to prepare a compound of the formula II wherein $R^{11}$ is hydrogen and $R^{10}$ is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl. In an embodiment, $R^{10}$ is phenyl substituted with halo.

In another aspect, a compound of the formula II wherein $R^{11}$ is hydrogen and $R^{10}$ is a substituted aryl is prepared by reacting a compound with the structure of formula II wherein $R^{10}$ is halo, in particular chloro, and $R^{11}$ is hydrogen, with a substituted aryl boronic acid under suitable conditions.

In another aspect, a compound of the formula II wherein $R^{10}$ is hydrogen and $R^{11}$ is alkyl is prepared by reacting a compound with the structures of formula II wherein $R^{11}$ is halo, in particular chloro, and $R^{10}$ is hydrogen, with an alkyl boronic acid under suitable conditions. In an embodiment, $R^{11}$ is lower alkyl, in particular methyl or ethyl, and a compound of the formula II wherein $R^{11}$ is chloro is reacted with lower alkyl boronic acid, in particular methyl or ethyl boronic acid under suitable conditions.

In another aspect, a compound of the formula II is prepared wherein $R^{10}$ is hydrogen and $R^{11}$ is an alkyl by reacting a pyridazine substituted at the C3 position with halo (e.g., chloro), at the C4 position with alkyl, and at the 6 position with phenyl, with 2-(piperidin-4-yloxy)pyrimidine under suitable conditions to prepare a compound of the formula II wherein $R^{10}$ is hydrogen and $R^{11}$ is an alkyl. In an embodiment, $R^{11}$ is methyl or ethyl.

In another aspect, a compound of the formula II wherein $R^{10}$ is hydrogen and $R^{11}$ is aryl is prepared by reacting a compound with the structure of formula II wherein $R^{10}$ is hydrogen and $R^{11}$ is halo (e.g., chloro), with pyridazine substituted at the C3 position with halo (e.g., chloro), at the C4 position with aryl, and at the 6 position with phenyl, with 2-(piperidin-4-yloxy)pyrimidine under suitable conditions. In an embodiment, $R^{11}$ is phenyl.

In another aspect, a compound of the formula II is prepared wherein $R^{10}$ is hydrogen and $R^{11}$ is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl by reacting a compound of the formula II wherein $R^{11}$ is halo, in particular chloro, and $R^{10}$ is hydrogen, with a boronic acid substituted with an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl, under suitable conditions.

In an embodiment, a compound of the formula II is prepared wherein $R^{10}$ is hydrogen and $R^{11}$ is pyridinyl by reacting a compound of the formula II wherein $R^{11}$ is halo, in particular chloro, and $R^{10}$ is hydrogen, with a pyridinyl boronic acid under suitable conditions.

In another aspect, a compound of the formula II is prepared wherein $R^{10}$ is hydrogen and $R^{11}$ is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl by reacting a pyridazine substituted at the C3 position with halo, at the C4 position with an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl, and at the 6 position with phenyl, with 2-(piperidin-4-yloxy)pyrimidine under suitable conditions.

In an embodiment, a compound of the formula II is prepared wherein $R^{10}$ is hydrogen and $R^{11}$ is pyridinyl by reacting a pyridazine substituted at the C3 position with halo, at the C4 position with pyridinyl, and at the 6 position with phenyl, with 2-(piperidin-4-yloxy)pyrimidine under suitable conditions to prepare a compound of the formula II wherein $R^{10}$ is hydrogen and $R^{11}$ is pyridinyl.

In another aspect, a compound of the formula II is prepared wherein $R^{10}$ is hydrogen and $R^{11}$ is piperidinyl or substituted piperidinyl by reacting a compound of the formula II wherein $R^{11}$ is halo, in particular chloro, and $R^{10}$ is hydrogen with piperazinyl or substituted piperazinyl under suitable conditions.

In another aspect, a compound of the formula I is prepared wherein $R^1$ is piperazinyl or piperazinyl substituted with alkyl, aryl, or cycloalkyl, $R^2$ is aryl, $R^3$, $R^4$, $R^5$ and $R^6$ are hydrogen and $R^7$ is absent, by reacting a pyridazine substituted at the C3 position with halo and at the C4 position with aryl, with a piperazinyl or piperazinyl substituted with alkyl, aryl, or cycloalkyl under suitable conditions.

In another aspect, a compound of the formula I is prepared wherein $R^1$ is piperazinyl or piperazinyl substituted with alkyl, aryl, or cycloalkyl, $R^2$ is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl, $R^3$, $R^4$, $R^5$ and $R^6$ are hydrogen and $R^7$ is absent, by reacting a pyridazine substituted at the C3 position with halo and at the C4 position with an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl, with piperazinyl or piperazinyl substituted with alkyl, aryl, or cycloalkyl under suitable conditions.

In another aspect, a compound of the formula I is prepared wherein $R^1$ is substituted amino in particular amino substituted with substituted morpholinyl, in particular morpholinoethyl, $R^2$ is aryl or an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, in particular pyridinyl, $R^3$, $R^4$, $R^5$ and $R^6$ are hydrogen and $R^7$ is absent, by reacting a pyridazine substituted at the C3 position with halo, at the C4 position with aryl or an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, more particularly pyridinyl, with substituted amino in particular amino substituted with substituted morpholinyl, in particular morpholinoethyl, under suitable conditions.

In another aspect, a compound of the formula V is prepared wherein $R^{50}$ is aryl, $R^{51}$ is hydrogen, and $R^{52}$ is alkyl by reacting a pyridazine substituted at position C3 with halo, at position C4 with aryl and at position 6 with alkyl, with 1-(2-pyrimidyl)piperazine under suitable conditions.

In another aspect, a compound of the formula I is prepared wherein $R^1$ is substituted amino, $R^2$ is an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, in particular pyridinyl, $R^3$, $R^4$, $R^5$ and $R^6$ are hydrogen and $R^7$ is absent by reacting a pyridazine substituted at the C3 position with halo, at the C4 position with an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, or tetrazolyl, in particular pyridinyl, and at the C6 position with phenyl, and a substituted amino under suitable conditions.

In the preparation of compounds of the Formula II, a precursor (see, for example, FIG. 1) that may be utilized can be obtained commercially and used directly for the synthesis of the illustrated compound MW01-3-183WH without further purification. Compounds may be synthesized with yields of 81-96%. All purified compounds may be characterized by HPLC, mass spectrometry and NMR in order to confirm syntheses. In FIG. 1, a synthetic scheme is shown, for synthesis of MW01-3-183WH with unconstrained aromatic ring at position 6 and no modification at position 5.

Thus, in an aspect, a compound of the Formula II is prepared wherein a substituted 6-phenylpyridazine is reacted with 2-(piperazin-1yl)pyridmidine to produce a compound of the Formula II wherein $R^{10}$ and $R^{11}$ are hydrogen. A compound of the formula II wherein $R^{10}$ and $R^{11}$ are hydrogen can be reacted under suitable conditions and with suitable reagents to introduce the radicals $R^{10}$ and $R^{11}$ which are independently hydrogen, hydroxyl, alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, amino, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, or carboxamide.

The term "cholinesterase inhibitor" means a compound that inhibits or reduces the activity of acetylcholinesterase or butyrylcholinesterase. The activity of an esterase may be reduced by at least 25%, at least 30%, at least 40%, at least 50%, at least 60%, at least 75%, at least 80%, at least 85%, at least 90%, at least 95% or at least 99%. The activity of a cholinesterase is compared to cholinesterase activity in the absence of the compound. A "pharmaceutically acceptable" cholinesterase inhibitor is one that does not cause unacceptable side effects in the subject being treated when administered at a therapeutically effective amount. Inhibitors of acetylcholinesterase or butyrylcholinesterase or dual inhibitors can be used to practice the present invention. In aspects, of the invention acetylcholinesterase inhibitors are employed. Examples of cholinesterase inhibitors include without limitation tacrine or tacrine analogues (e.g., see, for example, U.S. Pat. Nos. 4,562,196, 4,754,050, 4,835,275, 4,839,364, 4,631,286, 4,816,456 and 6,194,403), huperzine A or its analogues (e.g., see, for example, U.S. Pat. Nos. 5,104,880 and 5,929,084), galantamine or its analogues, rivastigmine or its analogues (e.g., see, for example, U.S. Pat. No. 4,948,807), donepizil or its analogues (e.g., see, for example, U.S. Pat. Nos. 4,895,841 and 5,100,901), zifrosilone or its analogues (e.g., see, for example, U.S. Pat. Nos. 5,693,668, 5,554,780, 5,760,267), or pharmaceutically acceptable salts thereof. In addition, any of the following compounds as well as their analogs and pharmaceutically acceptable salts can be employed: Green mamba snake (*Dendroaspis angusticeps*) toxin fasciculin, metrifonate, heptyl-physostigmine, norpyridostigmine, nomeostigmine, physostigmine, velnacrine, citicoline, 7-methoxytacrine, eptastigmine, icopezil, ipidacrine, pyridostigmine, anseculin, suronacrine, linopiridine, edrophonium, neostigmine, edrophonium, phenserine, demacarium, ambenonium, arecoline, xanomeline, subcomeline, cevimeline, alvameline, milameline, talsaclidine, phenserine, tolserine, phenethylnorcymserine, ganstigmine, citicoline, velnacrine, heptastigmine, TAK-147 (i.e., 3-[1-(phenylmethyl)-4-piperidinyl]-1-(2,3,4,5-tetrahydro-1H-1-benzazepin-8-yl)-1-propanone fumarate or other salts thereof; Takeda), T-82, upreazine, CHF2819 (Chiesi Farma), and the like.

According to aspects of the invention, the cholinesterase inhibitor is donepezil, rivastigimine, galantamine, icopezil, pyridostigmine, edrophonium, neostigmine, physostigmine, Huperzine A, phenserine, or tracine. In particular embodiments, the cholinesterase inhibitor used is REMINYL® (galantamine, specifically galantamine hydrobromide), COGNEX® (tracine, specifically tracine hydrochloride), ARICEPT® (donepezil, specifically donepezil hydrochloride), and Exelon® (rivastigimine, specifically rivastigimine tartrate).

In particular aspects of the invention the cholinesterase inhibitors are those described in U.S. Pat. No. 4,895,841 and WO 98/39000, including donepezil hydrochloride or ARICEPT®.

Cholinesterase inhibitors can be prepared by processes known in the art and described, for example, in U.S. Pat. No. 4,895,841, WO 98/39000, and Japanese Patent Application Nos. 4-187674 and 4-21670. Cholinesterase inhibitors may also be obtained from commercial sources. For example, donepezil hydrochloride, is commercially available as ARICEPT® from Eisai Inc., Teaneck, N.J.

A cholinesterase inhibitor may be in the form of a pharmaceutical composition that comprises (or consists of) a cholinesterase inhibitor that is greater than 95% and particularly greater than 99% pure by weight and one or more excipients, diluents or other inert ingredients commonly found in pharmaceutical compositions. Thus, a cholinesterase inhibitor that is a natural product, i.e., produced in nature, can be isolated and purified or produced synthetically before being used in the present invention.

A "disease" that can be treated and/or prevented using a pyridazine compound and a cholinesterase inhibitor, a composition, conjugate, or method of the invention includes a condition where a cholinesterase inhibitor or a pyridazine compound are indicated or efficacious. A disease includes a condition associated with or requiring modulation of one or more of inflammation (e.g. neuroinflammation); activation of signaling pathways involved in inflammation (e.g., neuroinflammation); cell signaling molecule production; activation of glia or glial activation pathways and responses; proinflammatory cytokines or chemokines (e.g., interleukin (IL), in particular IL-1β) or tumor necrosis factor (TNF, in particular TNFα); activation of astrocytes or astrocyte activation pathways and responses; activation of microglia or microglia activation pathways and responses, oxidative stress-related responses such as nitric oxide synthase production and nitric oxide accumulation; acute phase proteins; loss of synaptophysin and/or PSD-95; components of the complement cascade; loss or reduction of synaptic function; protein kinase activity (e.g., death associated protein kinase activity); cell damage (e.g., neuronal cell damage); cell death (e.g., neuronal cell death); amyloid β deposition of amyloid plaques; and behavioral deficits. In particular a disease is a dementing disorder, a neurodegenerative disorder, a CNS demyelinating disorder, an autoimmune disorder, or a peripheral inflammatory disease.

A disease may be characterized by an inflammatory process due to the presence of macrophages activated by an amyloidogenic protein or peptide. Thus, a method of the invention may involve inhibiting macrophage activation and/or inhibiting an inflammatory process. A method may comprise decreasing, slowing, ameliorating, or reversing the course or degree of macrophage invasion or inflammation in a patient.

Examples of diseases that can be treated and/or prevented using the compositions, conjugates and methods of the invention include Alzheimer's disease and related disorders, presenile and senile forms; amyloid angiopathy; mild cognitive impairment; Alzheimer's disease-related dementia (e.g., vascular dementia or Alzheimer dementia); AIDS related dementia, tauopathies (e.g., argyrophilic grain dementia, corticobasal degeneration, dementia pugilistica, diffuse neurofibrillary tangles with calcification, frontotemporal dementia with parkinsonism, Prion-related disease, Hallervorden-Spatz disease, myotonic dystrophy, Niemann-Pick disease type C, non-Guamanian Motor Neuron disease with neurofibrillary tangles, Pick's disease, postencephalitic parkinsonism, cerebral amyloid angiopathy, progressive subcortical gliosis, progressive supranuclear palsy, subacute sclerosing panencephalitis, and tangle only dementia), alpha-synucleinopathy (e.g., dementia with Lewy bodies, multiple system atrophy with glial cytoplasmic inclusions), multiple system atrophies, Shy-Drager syndrome, spinocerebellar ataxia (e.g., DRPLA or Machado-Joseph Disease); striatonigral degeneration, olivopontocerebellar atrophy, neurodegeneration with brain iron accumulation type I, olfactory dysfunction, and amyotrophic lateral sclerosis); Parkinson's disease (e.g., familial or non-familial); Amyotrophic Lateral Sclerosis; Spastic paraplegia (e.g., associated with defective function of chaperones and/or triple A proteins); Huntington's Disease, spinocerebellar ataxia, Freidrich's Ataxia; cerebrovascular diseases including stroke, hypoxia, ischemia, infarction, intracerebral hemorrhage; traumatic brain injury; Down's syndrome; head trauma with post-traumatic accumulation of amyloid beta peptide; Familial British Dementia; Familial Danish Dementia; Presenile Dementia with Spastic Ataxia; Cerebral Amyloid Angiopathy, British Type; Presenile Dementia With Spastic Ataxia Cerebral Amyloid Angiopathy, Danish Type; Familial encephalopathy with neuroserpin inclusion bodies (FENIB); Amyloid Polyneuropathy (e.g., senile amyloid polyneuropathy or systemic Amyloidosis); Inclusion Body myositis due to amyloid beta peptide; Familial and Finnish Type Amyloidosis; Systemic amyloidosis associated with multiple myeloma; Familial Mediterranean Fever; multiple sclerosis, optic neuritis; Guillain-Barre Syndrome; chronic inflammatory demyelinating polyneuropathy; chronic infections and inflammations; acute disseminated encephalomyelitis (ADEM); autoimmune inner ear disease (AIED); diabetes; myocardial ischemia and other cardiovascular disorders; pancreatitis; gout; inflammatory bowel disease; ulcerative colitis, Crohn's disease, rheumatoid arthritis, osteoarthritis; artheriosclerosis, inflammatory aortic aneurysm; asthma; adult respiratory distress syndrome; restenosis; ischemia/reperfusion injury; glomerulonephritis; sacoidosis cancer; restenosis; rheumatic fever; systemic lupus erythematosus; Reiter's syndrome; psoriatic arthritis; ankylosing spondylitis; coxarthritis; pelvic inflammatory disease; osteomyelitis; adhesive capsulitis; oligoarthritis; periarthritis; polyarthritis; psoriasis; Still's disease; synovitis; inflammatory dermatosis; and, wound healing.

In aspects of the invention, the disease is Alzheimer's disease, vascular dementia, dementia associated with Parkinson's disease, visuospatial deficits, Williams syndrome, encephalitis, meningitis, fetal alcohol syndrome, Korsakoff's syndrome, anoxic brain injury, cardiopulmonary resuscitation injuries, diabetes, Sjogren's syndrome, strokes, ocular diseases such as cataracts and macular degeneration, sleep disorders, and cognitive impairments caused by high cholesterol levels.

In aspects of the invention, a pyridazine compound and a cholinesterase inhibitor, a composition, conjugate, or method disclosed herein may be utilized to prevent and/or treat a disease involving neuroinflammation (i.e., neuroinflammatory disease). Neuroinflammation is a characteristic feature of disease pathology and progression in a diverse array of neurodegenerative disorders that are increasing in their societal impact (for a recent review, see, e.g., Prusiner, S. B. (2001) New Engl. J. Med. 344, 1516-1526). These neuroinflammation-related disorders include Alzheimer's disease (AD), amyotrophic lateral sclerosis, autoimmune disorders, priori diseases, stroke and traumatic brain injury. Neuroinflammation is brought about by glial cell (e.g., astrocytes and microglia) activation, which normally serves a beneficial role as part of an organism's homeostatic response to injury or developmental change. However, disregulation of this process through chronic or excessive activation of glia contributes to the disease process through the increased production of proinflammatory cytokines and chemokines, oxidative stress-related enzymes, acute phase proteins, and various components of the complement cascades. (See, e.g., Akiyama et al., (2000) Neurobiol. Aging 21, 383-421).

In certain selected aspects of the invention, the disease is a neurodegenerative disease or neurodegenerative disorder including such diseases and impairments as Alzheimer's disease, dementia, MCI, Huntington's disease, Parkinson's disease, amyotrophic lateral sclerosis, and other similar diseases and disorders disclosed herein.

For Alzheimer's disease (AD) the deposition of β-amyloid (Aβ) and neurofibrillary tangles are associated with glial activation, neuronal loss and cognitive decline. On a molecular level, Alzheimer's disease is characterized by; increased expression of nitric oxide synthase (NOS) in glial cells surrounding amyloid plaques; neuropathological evidence of peroxynitrite-mediated neuronal damage; and nitric oxide (NO) overproduction involved in Aβ-induced brain dysfunction. NOSH (iNOS) is induced as part of the glial activation response and is an oxidative stress-related enzyme that generates NO. When NO is present in high levels along with superoxide, the highly reactive NO-derived molecule peroxynitrite is generated, leading to neuronal cell death. The proinflammatory cytokine IL-1β is also overexpressed in activated glia in AD brain and polymorphisms in IL-1β genes are associated with an increased risk of early onset sporadic AD (See, e.g., Du et al., (2000) Neurology 55, 480-483). IL-1β can also influence amyloid plaque development and is involved in additional glial inflammatory and neuronal dysfunction responses (See, e.g., Griffin, et al., (1998) Brain Pathol. 8, 65-72; and Sheng, et al., (1996) Neurobiol. Aging 17, 761-766). Therefore, because glial activation and specific glial products are associated with neurodegenerative disorders (e.g., Alzheimer's disease), a pyridazine compound and cholinesterase inhibitor, conjugates, and compositions disclosed herein that are capable of modulating cell signaling pathways (e.g., glial activation pathways) will have particular application in the treatment and prevention of inflammatory disease.

In aspects of the invention, a pyridazine compound and cholinesterase inhibitor, a composition, conjugate, or method disclosed herein may be utilized to prevent and/or treat a disease involving disregulation of protein kinase signaling. Disregulation of protein kinase signaling often accompanies disregulation of cell signaling pathways (e.g., glial cell activation pathways). Protein kinases are a large family of proteins that play a central role in regulating a number of cellular functions including cell growth, differentiation and death. There are thought to be more than 500 protein kinases and 130 protein phosphatases exerting tight control on protein phosphorylation. Each protein kinase transfers the γ-phosphate of ATP to a specific residue(s) of a protein substrate. Protein kinases can be further categorized as tyrosine, serine/threonine or dual specific based on acceptor residue. Examples of serine/threonine kinases include MAP kinase, MAPK kinase (MEK), Akt/PKB, Jun kinase (JNK), CDKs, protein kinase A (PRA), protein kinase C (PKC), and calmodulin (CaM)-dependent kinases (CaMKs). Disregulated protein kinase activity (e.g., hyper- or hypo-active) leads to abnormal protein phosphorylation, underlying a great number of diseases including diabetes, rheumatoid arthritis, inflammation, hypertension, and proliferative diseases such as cancer. Therefore, because aberrant kinase activity is associated with inflammatory disease (e.g., neurodegenerative disorders like Alzheimer's disease), a pyridazine compound and cholinesterase inhibitor, compositions and conjugates that are disclosed herein that are capable of modulating kinases involved in cell signaling pathways will have particular application for treatment and prevention of inflammatory disease.

Compositions and Kits

One or more pyridazine compound, in particular a compound of the Formula I, II, III, IV, or V, and one or more cholinesterase inhibitor may be formulated into a pharmaceutical composition for administration to a subject. Pharmaceutical compositions of the present invention or fractions thereof comprise suitable pharmaceutically acceptable carriers, excipients, and vehicles selected based on the intended form of administration, and consistent with conventional pharmaceutical practices. Particular compositions of the invention may contain a pyridazine compound and a cholinesterase inhibitor that are pure or substantially pure. Compositions of the invention preferably contain pharmaceutically acceptable pyridazine compounds and pharmaceutically acceptable cholinesterase inhibitors.

Suitable pharmaceutical carriers, excipients, and vehicles are described in the standard text, *Remington: The Science and Practice of Pharmacy* (21$^{st}$ Edition. 2005, University of the Sciences in Philadelphia (Editor), Mack Publishing Company), and in The United States Pharmacopeia: The National Formulary (USP 24 NF19) published in 1999. By way of example for oral administration in the form of a capsule or tablet, the active components can be combined with an oral, non-toxic pharmaceutically acceptable inert carrier such as lactose, starch, sucrose, methyl cellulose, magnesium stearate, glucose, calcium sulfate, dicalcium phosphate, mannitol, sorbital, and the like. For oral administration in a liquid form, the drug components may be combined with any oral, non-toxic, pharmaceutically acceptable inert carrier such as ethanol, glycerol, water, and the like. Suitable binders (e.g. gelatin, starch, corn sweeteners, natural sugars including glucose; natural and synthetic gums, and waxes), lubricants (e.g. sodium oleate, sodium stearate, magnesium stearate, sodium benzoate, sodium acetate, and sodium chloride), disintegrating agents (e.g. starch, methyl cellulose, agar, bentonite, and xanthan gum), flavoring agents, and coloring agents may also be combined in the compositions or components thereof. Compositions as described herein can further comprise wetting or emulsifying agents, or pH buffering agents.

The invention provides formulations including without limitation pills, tablets, caplets, soft and hard gelatin capsules, lozenges, sachets, cachets, vegicaps, liquid drops, elixirs, suspensions, emulsions, solutions, syrups, aerosols (as a solid or in a liquid medium) suppositories, sterile injectable solutions, and/or sterile packaged powders, which contain a pyridazine compound and a cholinesterase inhibitor in particular a pure or substantially pure pyridazine compound and a cholinesterase inhibitor.

A composition of the invention can be a liquid solution, suspension, emulsion, tablet, pill, capsule, sustained release formulation, or powder. The compositions can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Various delivery systems are known and can be used to administer a composition of the invention, e.g. encapsulation in liposomes, microparticles, microcapsules, and the like.

In aspects of the invention, a pharmaceutical composition is provided for oral administration of one or more pyridazine compound and one or more cholinesterase inhibitor for treatment of a disease. In a particular aspect, a stable oral pharmaceutical composition for treatment of Alzheimer's disease and related diseases is provided comprising a substantially pure pyridazine compound and a substantially pure cholinesterase inhibitor.

Formulations for parenteral administration may include aqueous solutions, syrups, aqueous or oil suspensions and emulsions with edible oil such as cottonseed oil, coconut oil or peanut oil. Dispersing or suspending agents that can be used for aqueous suspensions include synthetic or natural gums, such as tragacanth, alginate, acacia, dextran, sodium carboxymethylcellulose, gelatin, methylcellulose, and polyvinylpyrrolidone.

Compositions for parenteral administration may include sterile aqueous or non-aqueous solvents, such as water, isotonic saline, isotonic glucose solution, buffer solution, or other solvents conveniently used for parenteral administration of therapeutically active agents. A composition intended for parenteral administration may also include conventional additives such as stabilizers, buffers, or preservatives, e.g. antioxidants such as methylhydroxybenzoate or similar additives.

Compositions of the invention can be formulated as pharmaceutically acceptable salts as described herein.

A composition of the invention may include at least one buffering agent or solution. Suitable buffering agents include, but are not limited to hydrochloric, hydrobromic, hydroiodic, sulfuric, phosphoric, formic, acetic, propionic, succinic, glycolic, glucoronic, maleic, furoic, citric, glutamic, benzoic, anthranilic, salicylic, phenylacetic, mandelic, embonic, pamoic, methanesulfonic, ethanesulfonic, pantothenic, benzenesulfonic, stearic, sulfanilic, algenic, galacturonic acid and mixtures thereof. Additional agents that may be included are one or more of pregelatinized maize starch, polyvinyl pyrrolidone, hydroxypropyl methylcellulose, lactose, microcrystalline cellulose, calcium hydrogen phosphate, magnesium stearate, talc, silica, potato starch, sodium starch glycolate, sodium lauryl sulfate, sorbitol syrup, cellulose derivatives, hydrogenated edible fats, lecithin, acacia, almond oil, oily esters, ethyl alcohol, fractionated vegetable oils, methyl, propyl-p-hydroxybenzoates, sorbic acid and mixtures thereof. Buffering agents may additionally comprise one or more of dichlorodifluoromethane, trichloro fluoromethane, dichlorotetra fluoroethane, carbon dioxide, poly (N-vinyl pyrrolidone), poly (methylmethacrylate), polyactide, polyglycolide and mixtures thereof. In some aspects, a buffering agent may be formulated as at least one medium including without limitation a suspension, solution, or emulsion. In other aspects, a buffering agent may additionally comprise a formulatory agent including without limitation a pharmaceutically acceptable carrier, excipient, suspending agent, stabilizing agent or dispersing agent.

The ratio of a pyridazine compound to cholinesterase inhibitor in a composition of the invention may be selected to augment the activity of the pyridazine compound or cholinesterase inhibitor. In particular aspects of the compositions of the invention the ratio of a pyridazine compound and a cholinesterase inhibitor is from about 1:1 to 1:100 and within that range from about 1:1 to 1:75, 1:1 to 1:50, 1:1 to 1:25, 1:1 to 1:10, 1:1 to 1:5, and 1:1. In other aspects the ratio of cholinesterase inhibitor to a pyridazine compound is from about 1:1 to 1:100 and within that range from about 1:1 to 1:75, 1:1 to 1:50, 1:1 to 1:25, 1:1 to 1:10, and 1:1 to 1:5.

In particular aspects, the ratio of a cholinesterase inhibitor to a pyridazine is, for example, 5:1 to 30:1, more particularly 15:1 to 25:1, for example 10:1, 12:1, 14:1, 16:1, 17:1, 18:1, 19:1, 21:1, 22:1, 23:1, 24:1, 27:1 and 29:1.

This invention provides a conjugate comprising a pyridazine compound linked to a cholinesterase inhibitor. A pyridazine compound and a cholinesterase inhibitor may be conjugated or linked with an intermediate spacer or linker. A suitable spacer or linker may be a mono- or di-saccharide, an amino acid, a sulfate, a succinate, an acetate, or an oligomeric polymeric spacer or linker comprising one or more of such moieties.

The covalent conjugates may be prepared by incubating or reacting a pyridazine compound with a cholinesterase inhibitor under suitable conditions that allow formation of a covalent linkage between the two compounds. Thus, the invention contemplates a process for preparing a covalent conjugate comprising a pyridazine compound covalently bonded or linked to a cholinesterase inhibitor, the process comprising: incubating or reacting the pyridazine compound with a cholinesterase inhibitor in the presence of suitable reagents and at a pH and for a time sufficient for formation of a covalent bond or linkage between the pyridazine compound and cholinesterase inhibitor, and isolating the covalent conjugate.

The invention also relates to isolated covalent conjugates of the invention, and compositions comprising covalent conjugates of the invention. In an aspect, the invention provides a pharmaceutical formulation of a substantially pure covalent conjugate comprising a pyridazine compound covalently linked to a cholinesterase inhibitor which provides beneficial effects preferably sustained beneficial effects compared to the pyridazine compound compound or cholinesterase alone.

A pharmaceutical composition of the invention may consist essentially of covalent conjugates comprising a pyridazine compound covalently linked without an intermediate spacer or linker to a cholinesterase inhibitor, or covalent conjugates comprising a pyridazine compound covalently linked with an intermediate spacer or linker to a cholinesterase inhibitor.

After pharmaceutical compositions or conjugates have been prepared, they can be placed in an appropriate container and labeled for treatment of an indicated condition. For administration of a composition or conjugate of the invention, such labeling would include amount, frequency, and method of administration.

A pyridazine compound and cholinesterase inhibitor, composition or conjugate of the invention may be sterilized by, for example, filtration through a bacteria retaining filter, addition of sterilizing agents to the compounds, composition, or conjugate, irradiation of the compounds, composition or conjugate, or heating the compounds, composition or conjugate. Alternatively, the compounds, compositions or conjugates of the present invention may be provided as sterile solid preparations e.g. lyophilized powder, which are readily dissolved in sterile solvent immediately prior to use.

The invention also provides a kit comprising a pyridazine compound and a cholinesterase inhibitor, composition or conjugate of the invention. The kit can be a package which houses a container which contains a pyridazine compound and a cholinesterase inhibitor, composition or conjugate of the invention and also houses instructions for administering the compounds, composition or conjugate to a subject. In particular, a kit may comprise instructions for simultaneous, separate or sequential use. In particular a label may include amount, frequency, and method of administration. A kit may contain a single dosage form or it may contain two dosage forms i.e. one for each compound to be administered. In an aspect, the kit comprises a fixed ratio dosage of a pyridazine compound and a cholinesterase inhibitor.

A kit may additionally include other materials desirable from a commercial and user standpoint, including, without limitation, buffers, diluents, filters, needles, syringes, and package inserts with instructions for performing any methods disclosed herein (e.g., methods for treating a disease disclosed herein). A medicament or formulation in a kit of the invention may comprise any of the combinations, compositions or conjugates disclosed herein.

The invention also provides a pharmaceutical pack or kit comprising one or more containers filled with one or more of the ingredients of a composition of the invention or with a conjugate of the invention to provide a beneficial effect, in particular a sustained beneficial effect. Associated with such container(s) can be various written materials such as instructions for use, or a notice in the form prescribed by a governmental agency regulating the labeling, manufacture, use or sale of pharmaceuticals or biological products, which notice reflects approval by the agency of manufacture, use, or sale for human administration.

In aspects of the invention, the kits may be useful for any of the methods disclosed herein, including, without limitation treating a subject suffering from Alzheimer's disease. Kits of the invention may contain instructions for practicing any of the methods described herein.

Applications

The invention is related to compositions, conjugates, and methods that utilize one or more pyridazine compound and one or more cholinesterase inhibitor in particular to provide one or more beneficial effect. In particular, the invention contemplates the use of one or more pyridazine compound and one or more cholinesterase inhibitor a composition or conjugate of the invention for treating a disease, in particular preventing, and/or ameliorating disease severity, disease symptoms, and/or periodicity of recurrence of a disease disclosed herein. The invention also contemplates preventing and/or treating diseases in mammals using a combination of one or more pyridazine compound and one or more cholinesterase inhibitor compositions, conjugates or treatments of the invention. The present invention in embodiments may provide a composition comprising one or more pyridazine compound and one or more cholinesterase inhibitor that provides beneficial effects including greater solubility, stability, efficacy, potency, and/or utility, in particular greater solubility and stability.

In an aspect, the invention provides a method of improving memory of a healthy subject or the memory of a subject with age impaired memory by administering an effective amount of one or more pyridazine compound and one or more cholinesterase inhibitor or a composition comprising one or more pyridazine compound and one or more cholinesterase inhibitor and a pharmaceutically acceptable carrier, excipient, or vehicle.

In another aspect, the present invention further relates to a method for improving memory, especially short-term memory and other mental dysfunction associated with the aging process comprising administering an effective amount of one or more pyridazine compound and one or more cholinesterase inhibitor or pharmaceutically acceptable salts thereof, or a composition comprising one or more pyridazine compound, and one or more cholinesterase inhibitor and a pharmaceutically acceptable carrier, excipient, or vehicle.

In an embodiment, a method is provided for treating a mammal in need of improved memory, wherein said mammal has no diagnosed disease, disorder, infirmity or ailment known to impair or otherwise diminish memory, comprising the step of administering to the mammal an effective memory-improving amount of one or more pyridazine compound and one or more cholinesterase inhibitor, or pharmaceutically acceptable salts thereof.

In an aspect, the invention provides a method involving administering to a subject a therapeutic compound of one or more pyridazine compound and one or more cholinesterase inhibitor or pharmaceutically acceptable salts thereof, or a composition comprising one or more pyridazine compound and one or more cholinesterase inhibitor, and a pharmaceutically acceptable carrier, excipient, or vehicle, which inhibit amyloid formation, deposition, accumulation and/or persistence, and/or which cause dissolution/disruption of pre-existing amyloid.

In an aspect, the invention provides a method for preventing, reversing, reducing or inhibiting amyloid fibril formation, organ specific dysfunction (e.g., neurodegeneration), or cellular toxicity in a subject comprising administering to the subject a therapeutically effective amount of one or more pyridazine compound and one or more cholinesterase inhibitor, pharmaceutically acceptable salts thereof, or a composition comprising one or more pyridazine compound and one or more cholinesterase inhibitor and a pharmaceutically acceptable carrier, excipient, or vehicle.

In an aspect, the invention provides a method for increasing or maintaining synaptic function in a subject comprising administering a therapeutically effective amount of one or more pyridazine compound and one or more cholinesterase inhibitor pharmaceutically acceptable salts thereof, or a composition comprising one or more pyridazine compound and one or more cholinesterase inhibitor and a pharmaceutically acceptable carrier, excipient, or vehicle.

The invention has particular applications in treating a disease characterized by amyloid deposition, in particular Alzheimer's disease. Thus, the invention relates to a method of treatment comprising administering a therapeutically effective amount of one or more pyridazine compound and one or more cholinesterase inhibitor, pharmaceutically acceptable salts thereof, or a composition comprising one or more pyridazine compound one or more cholinesterase inhibitor and a pharmaceutically acceptable carrier, excipient, or vehicle, which upon administration to a subject with symptoms of a disease characterized by amyloid deposition, more particularly Alzheimer's disease, produces beneficial effects, preferably sustained beneficial effects. In an embodiment, beneficial effects are evidenced by one or more of the following: disruption of aggregated Aβ or Aβ oligomers, maintenance of or increased synaptic function, and reduced or reversed cerebral accumulation of Aβ, deposition of cerebral amyloid plaques, soluble Aβ oligomers in the brain, glial activity, inflammation, and/or cognitive decline.

In an aspect, the invention provides a method for ameliorating progression of a disease or obtaining a less severe stage of a disease in a subject suffering from such disease (e.g. Alzheimer's disease) comprising administering a therapeutically effective amount of one or more pyridazine compound and one or more cholinesterase inhibitor pharmaceutically acceptable salts thereof, or a composition comprising one or more pyridazine compound and one or more cholinesterase inhibitor and a pharmaceutically acceptable carrier, excipient, or vehicle.

In another aspect, the invention relates to a method of delaying the progression of a disease (e.g. Alzheimer's disease) comprising administering a therapeutically effective amount of one or more pyridazine compound and one or more cholinesterase inhibitor or pharmaceutically acceptable salts thereof, or a composition comprising one or more pyridazine compound and one or more cholinesterase inhibitor and a pharmaceutically acceptable carrier, excipient, or vehicle.

In a further aspect, the invention relates to a method of increasing survival of a subject suffering from a disease (e.g., Alzheimer's disease) comprising administering a therapeutically effective amount of one or more pyridazine compound and one or more cholinesterase inhibitor pharmaceutically acceptable salts thereof, or a composition comprising one or more pyridazine compound and one or more cholinesterase inhibitor and a pharmaceutically acceptable carrier, excipient, or vehicle.

In an embodiment, the invention relates to a method of improving the lifespan of a subject suffering from a disease (e.g., Alzheimer's disease) comprising administering a therapeutically effective amount of one or more pyridazine compound and one or more cholinesterase inhibitor pharmaceutically acceptable salts thereof, or a composition comprising one or more pyridazine compound and one or more cholinesterase inhibitor, and a pharmaceutically acceptable carrier, excipient, or vehicle.

In an aspect the invention provides a method for treating mild cognitive impairment (MC1) comprising administering a therapeutically effective amount of one or more pyridazine compound and one or more cholinesterase inhibitor, pharmaceutically acceptable salts thereof, or a composition comprising one or more pyridazine compound and one or more cholinesterase inhibitor, and a pharmaceutically acceptable carrier, excipient, or vehicle.

In an embodiment, the invention provides a method of reducing or reversing amyloid deposition and neuropathology after the onset of cognitive deficits and amyloid plaque neuropathology in a subject comprising administering to the subject a therapeutically effective amount of one or more pyridazine compound and one or more cholinesterase inhibitor, pharmaceutically acceptable salts thereof, or a composition comprising one or more pyridazine compound and one or more cholinesterase inhibitor, and a pharmaceutically acceptable carrier, excipient, or vehicle.

Aspects of the invention provide improved methods and compositions for use of one or more pyridazine compound and one or more cholinesterase inhibitor for sustained treatment of a disease (e.g., Alzheimer's disease). The present invention in an embodiment provides a composition comprising one or more pyridazine compound and one or more cholinesterase inhibitor, that achieve greater efficacy, potency, and utility. For example, the greater efficacy can be shown by improving or reversing cognitive decline and/or survival in Alzheimer's disease with treatment resulting in sustained improvement and/or increased survival after ceasing treatment.

In an aspect of the invention a pyridazine compound is utilized with a cholinesterase inhibitor or gamma-cholinesterase inhibitor in the treatment of Alzheimer's disease. Thus, Alzheimer's disease may be treated by administering therapeutically effective amounts of a pyridazine compound and a cholinesterase inhibitor. Such treatment may be effective for retarding the degenerative effects of Alzheimer's disease, including specifically, but not exclusively, deterioration of the central nervous system, loss of mental facilities, loss of short term memory, and disorientation.

In an embodiment, where the disease is Alzheimer's disease, beneficial effects of a composition, conjugate or treatment of the invention can manifest as one, two, three, four, five, six, seven, eight, or all of the following, in particular five or more, more particularly seven or more of the following:

a) A reduction in protein kinase activity (e.g. DAPK), in particular at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% decrease in protein kinase activity.

b) A reduction in glial activation response, in particular, at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in glial activation response.

c) A reduction in glial activity in the brain, relative to the levels determined in the absence of a pyridazine compound and a cholinesterase inhibitor in subjects with symptoms of a neuroinflammatory disease. In particular, the compounds induce at least about a 2%, 5%, 10%, 15%, 20%, 30%, 40%, 50%, 60%, 70%, 80%, or 90% decrease in glial activity.

d) A reduction in astrocyte activation response, in particular, at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in astrocyte activation response.

e) A reduction in astrocyte activity in the brain, relative to the levels determined in the absence of the compounds or a treatment according to the invention. In particular, the compounds induce at least about a 2%, 5%, 10%, 15%, 20%, 30%, 40%, 50%, 60%, 70%, 80%, or 90% decrease in astrocyte activity.

f) A reduction in microglial activation, in particular, at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in microglial activation.

g) A reduction in microglial activation response, in particular, at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in microglial activation response.

h) A reduction in loss of synaptophysin and/or PSD-95, in particular at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in loss of synaptophysin and/or PSD-95.

i) A reduction in oxidative stress-related responses (e.g., nitric oxide synthase production and/or nitric oxide accumulation), in particular at least about a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in oxidative stress-related responses such as nitric oxide synthase production and nitric oxide accumulation.

j) A reduction in cellular apoptosis and/or death associated protein kinase activity, in particular a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in cellular apoptosis and/or death associated protein kinase activity.

k) A reduction in proinflammatory cytokine responses in particular a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in proinflammatory cytokine responses.

l) A reduction in interleukin-1β and/or tumor necrosis factor α production in particular a 0.05%, 0.1%, 0.5%, 1%, 2%, 5%, 10%, 15%, 20%, 30%, 33%, 35%, 40%, 45%, 50%, 60%, 70%, 80%, 90%, 95%, or 99% reduction in interleukin-1β and/or tumor necrosis factor α production.

m) A slowing of the rate of disease progression.

n) Increase in survival in a subject with symptoms of disease.

In particular aspects of the invention therapeutic effects of compounds, compositions or treatments of the invention can manifest as (a) and (b); (a), (b) and (c); (a) through (d); (a) through (e); (a) through (f); (a) through (g); (a) through (h); (a) through (i), (a) through (j), (a) through (k), (a) through (l), (a) through (m), or (a) through (n).

A pyridazine compound and a cholinesterase inhibitor, pharmaceutical compositions, conjugates and methods of the invention can be selected that have statistically significant beneficial effects, in particular one or more statistically significant beneficial effects of (a) through (n) above. A pyridazine compound and a cholinesterase inhibitor, pharmaceutical compositions, conjugates and methods of the invention can also be selected that have sustained beneficial effects, in particular statistically significant sustained beneficial effects. In an embodiment, a combination treatment or a pharmaceutical composition is provided with statistically significant sustained beneficial effects, in particular sustained beneficial effects of one or more of (a) through (n) above, comprising therapeutically effective amounts of one or more pyridazine compound and a cholinesterase inhibitor. In aspects of the invention, one or more of the beneficial effects provide enhanced therapeutic effects compared with conventional therapies.

Greater efficacy and potency of a treatment of the invention in some aspects may improve the therapeutic ratio of treatment, reducing untoward side effects and toxicity. Selected methods of the invention may also improve long-standing disease even when treatment is begun long after the appearance of symptoms. Prolonged efficacious treatment can be achieved in accordance with the invention following administration of one or more pyridazine compound and one or more cholinesterase inhibitor, or composition of the invention.

In an aspect, the invention provides a method for treating Alzheimer's disease in a patient in need thereof which includes administering to the individual one or more pyridazine compound and one or more cholinesterase inhibitor, or a composition comprising one or more pyridazine compound and one or more cholinesterase inhibitor, in a dose(s) sufficient to increase or maintain synaptic function. In another aspect, the invention provides a method for treating Alzheimer's disease comprising administering, preferably orally or systemically, amounts of a pyridazine compound and a cholinesterase inhibitor, to a mammal, to reduce cerebral accumulation of Aβ, deposition of cerebral amyloid plaques, soluble Aβ oligomers in the brain, glial activity, and/or inflammation for a prolonged period following administration.

The invention in an embodiment provides a method for treating Alzheimer's disease, the method comprising administering to a mammal in need thereof one or more pyridazine compound and one or more cholinesterase inhibitor, or a composition comprising one or more pyridazine compound and one or more cholinesterase inhibitor, in an amount(s) sufficient to reduce cognitive decline, especially for a prolonged period following administration, thereby treating the Alzheimer's disease.

The invention in an embodiment provides a method for treating Alzheimer's disease, the method comprising administering to a mammal in need thereof one or more pyridazine compound and one or more cholinesterase inhibitor, or a composition comprising one or more pyridazine compound and one or more cholinesterase inhibitor, in an amount(s) sufficient to increase or maintain synaptic function, especially for a prolonged period following administration, thereby treating the Alzheimer's disease.

The present invention also includes methods of using one or more pyridazine compound and one or more cholinesterase inhibitor, or compositions of the invention in combination treatments with one or more additional therapeutic agents including without limitation other inhibitors of beta-sheet aggregation/fibrillogenesis/ADDL formation (e.g. Alzhemed), NMDA antagonists (e.g. memantine), anti-oxidants (e.g. Vitamin E), hormones (e.g. estrogens), nutrients and food supplements (e.g. Gingko biloba), statins and other cholesterol lowering drugs (e.g. Lovastatin and Simvastatin), acetylcholinesterase inhibitors (e.g. donezepil), muscarinic agonists (e.g. AF102B (Cevimeline, EVOXAC), AF150(S), and AF267B), anti-psychotics (e.g. haloperidol, clozapine, olanzapine), anti-depressants including tricyclics and serotonin reuptake inhibitors (e.g. Sertraline and Citalopram Hbr), immunotherapeutics and antibodies to A$\beta$ (e.g. ELAN AN-1792), vaccines, inhibitors of kinases (CDK5, GSK3$\alpha$, GSK3$\beta$) that phosphorylate TAU protein (e.g. Lithium chloride), inhibitors of kinases that modulate A$\beta$ production (GSK3$\alpha$, GSK3$\beta$, Rho/ROCK kinases) (e.g. lithium Chloride and Tbuprofen), drugs that upregulate neprilysin (an enzyme which degrades A$\beta$); drugs that upregulate insulin degrading enzyme (an enzyme which degrades A$\beta$), agents that are used for the treatment of complications resulting from or associated with a disease, or general medications that treat or prevent side effects. The present invention also includes methods of using the compositions of the invention in combination treatments with one or more additional treatments including without limitation gene therapy and/or drug based approaches to upregulate neprilysin (an enzyme which degrades A$\beta$), gene therapy and/or drug based approaches to upregulate insulin degrading enzyme (an enzyme which degrades A$\beta$), or stem cell and other cell-based therapies.

In an aspect, the invention contemplates the use of one or more pyridazine compound and one or more cholinesterase inhibitor, or a composition comprising one or more pyridazine compound and one or more cholinesterase inhibitor, for the preparation of a medicament in treating a disease. The invention also contemplates the use of one or more pyridazine compound and one or more cholinesterase inhibitor, or a composition comprising one or more pyridazine compound and one or more cholinesterase inhibitor, for the preparation of a medicament for preventing and/or treating diseases. The medicaments provide beneficial effects, preferably sustained beneficial effects following treatment. The medicament may be in a form for consumption by a subject such as a pill, tablet, caplet, soft and hard gelatin capsule, lozenge, sachet, cachet, vegicap, liquid drop, elixir, suspension, emulsion, solution, syrup, aerosol (as a solid or in a liquid medium) suppository, sterile injectable solution, and/or sterile packaged powder for inhibition of amyloid formation, deposition, accumulation, and/or persistence, regardless of its clinical setting.

In an embodiment, the invention relates to the use of a therapeutically effective amount of one or more pyridazine compound and one or more cholinesterase inhibitor, or a composition comprising one or more pyridazine compound and one or more cholinesterase inhibitor, for preparation of a medicament for providing therapeutic effects, in particular beneficial effects, preferably sustained beneficial effects, in treating a disease.

In another embodiment the invention provides the use of one or more pyridazine compound and one or more cholinesterase inhibitor, or a composition comprising one or more pyridazine compound and one or more cholinesterase inhibitor, for the preparation of a medicament for prolonged or sustained treatment of Alzheimer's disease.

In a further embodiment the invention provides the use of one or more pyridazine compound and one or more cholinesterase inhibitor, or a composition comprising one or more pyridazine compound and one or more cholinesterase inhibitor, for preparation of a pharmaceutical composition to be employed through oral administration for treatment of a disorder characterized by neuroinflammation.

Therapeutic efficacy and toxicity of compositions, conjugates, and methods of the invention may be determined by standard pharmaceutical procedures in cell cultures or with experimental animals such as by calculating a statistical parameter such as the $ED_{50}$ (the dose that is therapeutically effective in 50% of the population) or $LD_{50}$ (the dose lethal to 50% of the population) statistics. The therapeutic index is the dose ratio of therapeutic to toxic effects and it can be expressed as the $ED_{50}/LD_{50}$ ratio. Pharmaceutical compositions which exhibit large therapeutic indices are preferred. One or more of the therapeutic effects, in particular beneficial effects disclosed herein, can be demonstrated in a subject or disease model. For example, beneficial effects may be demonstrated in a model described in the Examples herein.

Administration

Pyridazine compounds, cholinesterase inhibitors, conjugates, and compositions of the present invention can be administered by any means that produce contact of the active agent(s) with the agent's sites of action in the body of a subject or patient to produce a therapeutic effect or a beneficial effect, in particular a sustained beneficial effect.

A pyridazine compound, cholinesterase inhibitor, and/or composition of the invention can be formulated for sustained release, for delivery locally or systemically. It lies within the capability of a skilled physician or veterinarian to select a form and route of administration that optimizes the effects of the compositions and treatments of the present invention to provide therapeutic effects or beneficial effects, in particular sustained beneficial effects. The methods of administration of the pyridazine compound(s), and cholinesterase inhibitor(s) may vary. Thus, any of the agents may be administered, without limitation, orally, rectally, topically, sublingually, or parenterally.

Pyridazine compounds, cholinesterase inhibitors, conjugates, and/or compositions may be administered in oral dosage forms such as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular forms, all utilizing dosage forms well known to those of ordinary skill in the pharmaceutical arts. Pyridazine compounds, cholinesterase inhibitors, conjugates, and/or compositions may be administered by intranasal route via topical use of suitable intranasal vehicles, or via a transdermal route, for example using conventional transdermal skin patches. A dosage protocol for administration using a transdermal delivery system may be continuous rather than intermittent throughout the dosage regimen. A sustained release formulation can also be used for the therapeutic agents.

In aspects of the invention the pyridazine compounds, cholinesterase inhibitors, conjugates, and/or compositions are administered by peripheral administration, in particular by intravenous administration, intraperitoneal administration, subcutaneous administration, intramuscular administration, oral administration, topical administration, transmucosal administration, or pulmonary administration.

The dosage regimen of the invention will vary depending upon known factors such as the pharmacodynamic characteristics of the agents and their mode and route of administration; the species, age, sex, health, medical condition, and weight of the patient, the nature and extent of the symptoms, the kind of concurrent treatment, the frequency of treatment, the route of administration, the renal and hepatic function of the patient, and the desired effect.

An amount of a pyridazine compound, cholinesterase inhibitor, conjugate, and/or composition which will be effective in the treatment of a particular disease to provide effects, in particular beneficial effects, more particularly sustained beneficial effects, will depend on the nature of the disease, and can be determined by standard clinical techniques. The precise dose to be employed in the formulation will also depend on the route of administration, and the seriousness of the disease, and should be decided according to the judgment of the practitioner and each patient's circumstances.

Suitable dosage ranges for administration are particularly selected to provide therapeutic effects, in particular beneficial effects, more particularly sustained beneficial effects. A dosage range is generally effective for triggering the desired biological responses. The dosage ranges for the pyridazine compound and cholinesterase inhibitor are generally about 0.01 to about 3 g per kg, about 0.01 to 2 g per kg, about 0.1 to 2 g per kg, about 0.1 to 1 g per kg, about 0.1 to 500 mg per kg, about 0.1 to 400 mg per kg, about 0.1 to 300 mg per kg, about 0.1 to 200 mg per kg, about 0.1 to 100 mg per kg, about 0.1 to 50 mg per kg, about 0.1 to 25 mg per kg, about 0.1 to 15 mg per kg, about 0.1 to 10 mg per kg, about 0.1 to 5 mg per kg, 0.5 mg to about 2 g per kg, about 0.5 to about 1 g per kg, about 1 mg to about 1 g per kg, about 1 to about 500 mg per kg, about 1 to about 400 mg per kg, about 1 to about 300 mg/kg, about 1 mg to about 200 mg per kg, about 1 mg to about 100 mg per kg, about 1 mg to about 50 mg per kg, about 1 mg to about 25 mg per kg, about 1 to about 20 mg per kg, about 1 mg to about 15 mg per kg, about 1 mg to about 10 mg per kg, about 1 to about 6 mg per kg, about 1 to about 5 mg per kg, about 1 to about 3 mg per kg, or about 1 to about 2.5 mg per kg, of the weight of a subject.

In aspects of the invention the dosages ranges are about 0.01 to 3000 mg/kg, 0.01 to 2000 mg/kg, 0.5 to 2000 mg/kg, about 0.5 to 1000 mg/kg, 0.1 to 1000 mg/kg, 0.1 to 500 mg/kg, 0.1 to 400 mg/kg, 0.1 to 300 mg/kg, 0.1 to 200 mg/kg, 0.1 to 100 mg/kg, 0.1 to 50 mg/kg, 0.1 to 20 mg/kg, 0.1 to 10 mg/kg, 0.1 to 6 mg/kg, 0.1 to 5 mg/kg, 0.1 to 3 mg/kg, 0.1 to 2 mg/kg, 0.1 to 1 mg/kg, 1 to 1000 mg/kg, 1 to 500 mg/kg, 1 to 400 mg/kg, 1 to 300 mg/kg, 1 to 200 mg/kg, 1 to 100 mg/kg, 1 to 50 mg/kg, 1 to 20 mg/kg, 1 to 10 mg/kg, 1 to 6 mg/kg, 1 to 5 mg/kg, or 1 to 3 mg/kg, or 1 to 2.5 mg/kg, or less than or about 10 mg/kg, 5 mg/kg, 2.5 mg/kg, 1 mg/kg, or 0.5 mg/kg twice daily or less.

In embodiments of the invention, the dosages ranges are about 0.1 to 1000 mg/kg, 0.1 to 500 mg/kg, 0.1 to 400 mg/kg, 0.1 to 300 mg/kg, 0.1 to 200 mg/kg, 0.1 to 100 mg/kg, 0.1 to 75 mg/kg, 0.1 to 50 mg/kg, 0.1 to 25 mg/kg, 0.1 to 20 mg/kg, 0.1 to 15 mg/kg, 0.1 to 10 mg/kg, 0.1 to 9 mg/kg, 0.1 to 8 mg/kg, 0.1 to 7 mg/kg, 0.1 to 6 mg/kg, 0.1 to 5 mg/kg, 0.1 to 4 mg/kg, 0.1 to 3 mg/kg, 0.1 to 2 mg/kg, or 0.1 to 1 mg/kg.

The combined administration of the pyridazine compound(s) and the cholinesterase inhibitor(s) may require less of the generally-prescribed dose for any of agents when used alone and or may result in less frequent administration of either, both or all agents. In aspects of the invention the pyridazine compound is administered in an amount of, for example, 0.1-50 mg/day, in particular 0.1-25 mg/kg, more particularly 0.1 to 10 mg/kg, and the cholinesterase inhibitor is administered in an amount of, for example, 5-20 mg/day. In synergistic aspects of the invention the amount of pyridazine compound or cholinesterase inhibitor can be lower than the mentioned amounts. Thus, the cholinesterase inhibitor may be administered in an amount below 25 mg/day, 20 mg/day, 15 mg/day, 10 mg/day, or 5 mg/day. The pyridazine compound may be administered at an amount below 25 mg/day, 20 mg/day, 15 mg/day, 10 mg/day, 5 mg/day, 1 mg/day, or 0.5 mg/day.

In aspects of the compositions of the invention a pyridazine compound is used in combination with the cholinesterase inhibitor at therapeutically effective weight ratios of between about 1:1.5 to 1:150, preferably 1:2 to 1:50. In other aspects of the compositions of the invention a pyridazine compound and a cholinesterase inhibitor are present in doses that are at least about 1.1 to 1.4, 1.5, 2, 3, 4, 5, 6, 7, 8, 9, or 10 fold lower than the doses of each compound alone required to treat a disease disclosed herein.

A composition or treatment of the invention may comprise a unit dosage of at least one pyridazine compound and at least one cholinesterase inhibitor to provide beneficial effects, in particular in the case of Alzheimer's disease one or more of the beneficial effects (a) to (n) set out herein. A "unit dosage" or "dosage unit" refers to a unitary i.e., a single dose which is capable of being administered to a patient, and which may be readily handled and packed, remaining as a physically and chemically stable unit dose comprising either the active agents as such or a mixture with one or more solid or liquid pharmaceutical excipients, carriers, or vehicles.

A subject may be treated with a pyridazine compound and cholinesterase inhibitor, or a conjugate or composition of the invention on substantially any desired schedule. A pyridazine compound, cholinesterase inhibitor, or a conjugate or composition of the invention may be administered one or more times per day, in particular 1 or 2 times per day, once per week, once a month or continuously. However, a subject may be treated less frequently, such as every other day or once a week, or more frequently.

A pyridazine compound, cholinesterase inhibitor, or a conjugate or composition of the invention may be administered to a subject for about or at least about 1-3 days, 1 week, 2 weeks to 4 weeks, 2 weeks to 6 weeks, 2 weeks to 8 weeks, 2 weeks to 10 weeks, 2 weeks to 12 weeks, 2 weeks to 14 weeks, 2 weeks to 16 weeks, 2 weeks to 6 months, 2 weeks to 12 months, 2 weeks to 18 months, or 2 weeks to 24 months, periodically or continuously.

The active ingredients can be administered simultaneously or sequentially and in any order at different points in time to provide the desired therapeutic or beneficial effects. When separately administered, therapeutically effective amounts of compositions containing a pyridazine compound, and a cholinesterase inhibitor(s) are administered on a different schedule. One may be administered before the other as long as the time between the administrations falls within a therapeutically effective interval. A therapeutically effective interval is a period of time beginning when one of either (a) the pyridazine compound, or (b) cholinesterase inhibitor(s) is (are) administered to a mammal and ending at the limit of the beneficial effect in the treatment of the disease to be treated from the combination of (a) and (b).

In a combination therapy to treat the diseases discussed herein, a pyridazine compound compound(s) and a cholinesterase inhibitor(s) can be administered simultaneously. When administered simultaneously the pyridazine compound(s) and the cholinesterase inhibitor(s) can be incorporated into a single pharmaceutical composition, e.g., a pharmaceutical combination therapy composition. Alternatively, two or more separate compositions, i.e., one containing the pyridazine compound(s) and the other(s) containing the cholinesterase inhibitor(s), can be administered simultaneously.

The invention will be described in greater detail by way of specific examples. The following examples are offered for illustrative purposes, and are not intended to limit the invention in any manner.

EXAMPLES

Example 1

Synthesis of Exemplary Pyridazine Compounds

A. Preparation of 2-(4-(6-phenylpyridazin-3-yl)piperazin-1-yl)pyrimidine (MW01-3-183WH)

FIG. 1 depicts a synthetic scheme for the preparation of 2-(4-(6-phenylpyridazin-3-yl)piperazin-1-yl)pyrimidine (MW01-3-183WH). Reagent and condition: (a) 1-BuOH, $NH_4Cl$, and 2-(piperazin-1-yl)pyrimidine. A typical reaction mixture of comprised about 0.01 mol of 3-chloro-6-phenylpyridazine by 2-(piperazin-1-yl)pyrimidine, about 0.05 mol of 2-(piperazin-1-yl)pyrimidine and about 0.01 mol of ammonium hydrochloride was prepared in about 15 ml of 1-BuOH. The mixture was stirred at about 130° C. for about 48 h, and then the solvent was removed under reduced pressure. The remaining residue was then extracted with ethyl acetate, washed with water and brine, dried over anhydrous $Na_2SO_4$. Removal of solvent followed by recrystallization from 95% ethanol yielded light yellow crystals, yield 96.4%; HPLC: 97.4% purity; HRMS calculated 318.1587, found 318.1579; $^1H$ NMR ($CDCl_3$): δ 8.356 (d, J=4.5, $^2H$), 8.011 (d, J=7.5, 11 $^2H$), 7.692 (d, J=9.5, $^1H$), 7.468 (t, J=6.0, $^2H$), 7.417 (d, J=7.5, $^1H$), 7.047 (d, J=9.5, $^1H$), 6.546 (t, J=4.5, $^1H$), 4.013 (t, J=5.0, $^4H$), 3.826 (t, J=5.0, $^4H$).

B. Preparation of 4-methyl-6-phenyl-3-(4-pyrimidin-2-ylpiperazin-1-yl)pyridazine (MW01-2-151SRM)

Figure 2:
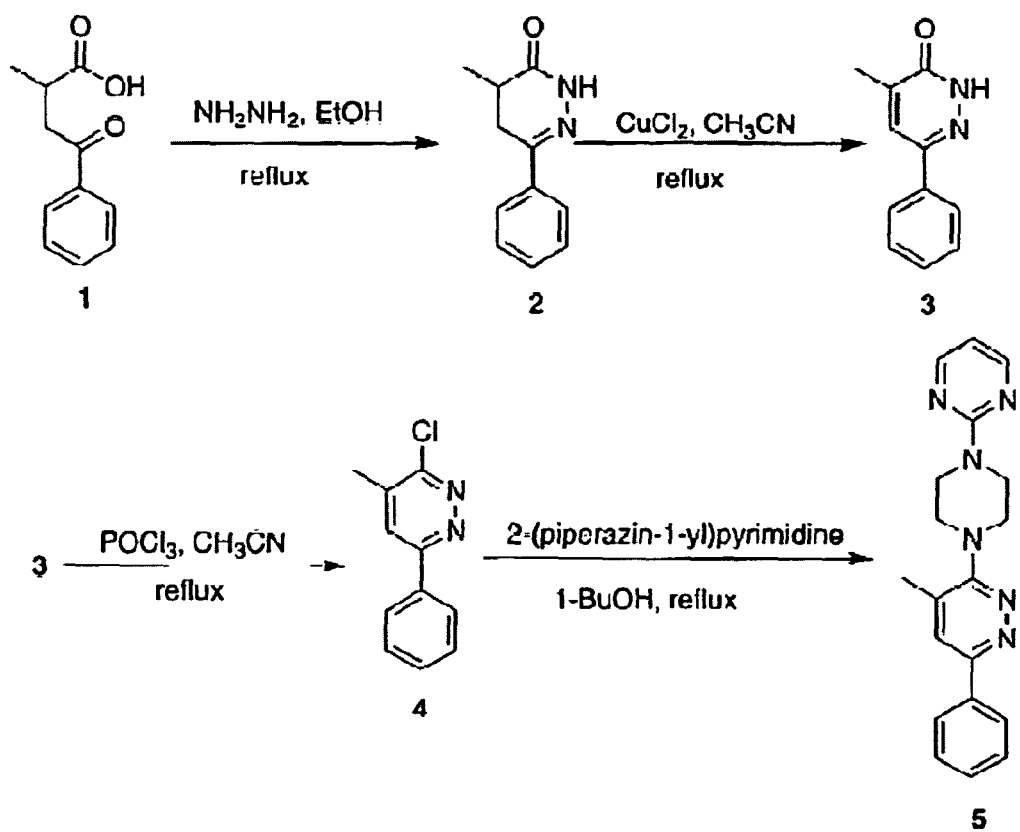
FIG. 2 depicts a synthetic scheme for MW01-2-151SRM.
Figure 3:
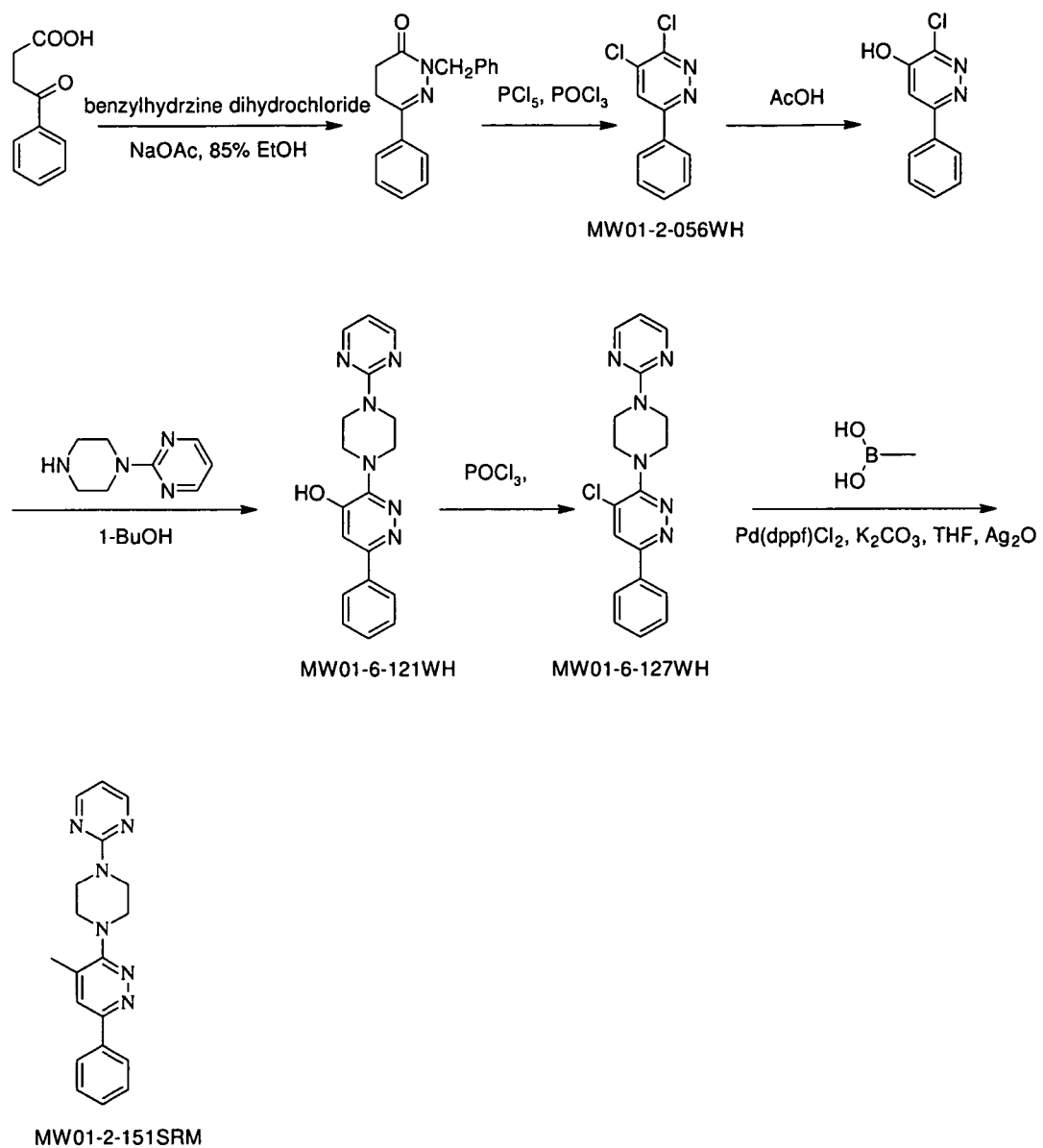
FIG. 3 depicts a synthetic scheme for MW01-2-151SRM.
Figure 4:
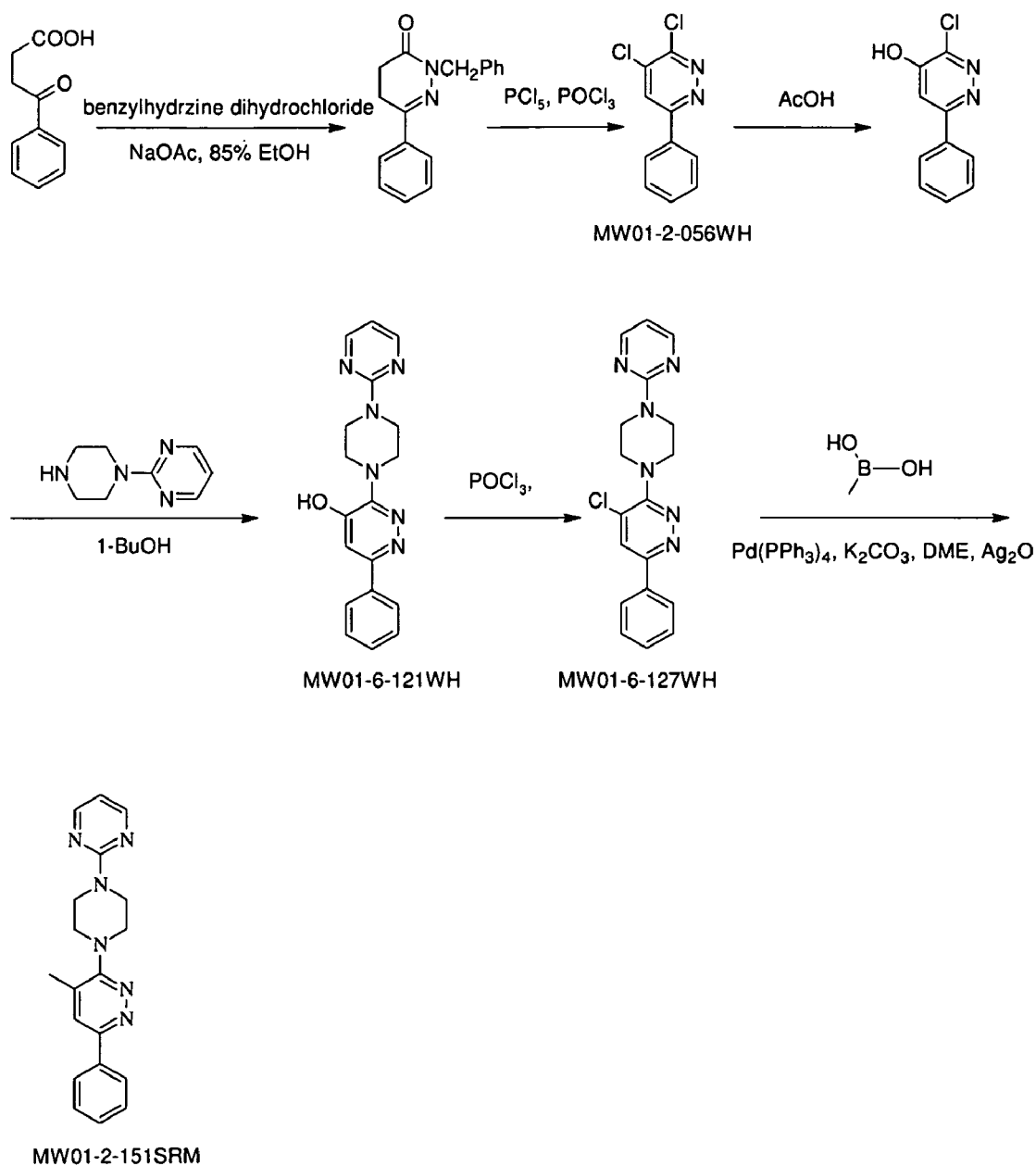
FIG. 4 depicts a synthetic scheme for MW01-2-151SRM.
Figure 5:
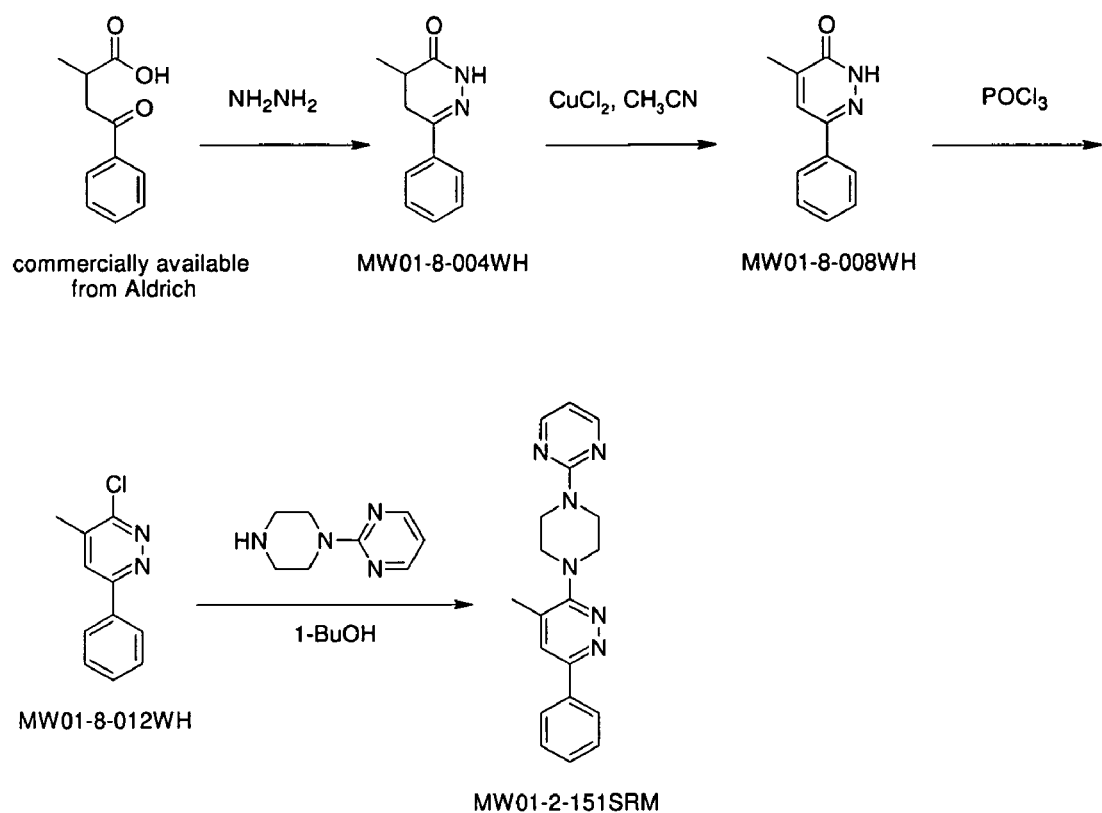
FIG. 5 depicts a synthetic scheme for MW01-2-151SRM.

4-methyl-6-phenyl-3-(4-pyrimidin-2-ylpiperazin-1-yl)pyridazine (MW01-2-151SRM) was prepared by several synthetic schemes as depicted in FIG. 2 (Scheme 1), FIG. 3 (Scheme 2), FIG. 4 (Scheme 3), and FIG. 5 (Scheme 4), which were carried out as described in detail herein. The various reaction schemes (Schemes 1, 2, and 3) are generally applicable to the compounds of the present invention and are not restricted in utility only to the preparation of MW01-2-151SRM.

Scheme 1 (FIG. 2)

4,5-dihydro-4-methyl-6-phenylpyridazin-3(2H)-one (2)

A 250 mL three-neck round bottom flask fit with a temperature probe and condenser is charged with 7.7 g (40 mmole) of 2-methyl-4-oxo-4-phenylbutanoic acid 1 and 20 ml of ethanol (95%). The suspension is cooled to below 10° C. and 2.2 ml (42 mmole, 1.05 equiv.) of hydrazine monohydrate in 10 mL of ethanol is added dropwise at a rate that maintains the solution temperature at below 20° C. Upon addition, the suspension changes to a pale yellow solution. After addition, the reaction mixture is heated to reflux and stirred for 2 h, and after 20 minutes of heating, a solid is seen in the mixture. Once the reaction is completed, the flask is removed from the oil bath and cooled to ambient temperature. Upon cooling, white crystals form in the flask, which are collected by filtration. The solid is washed first with 30 mL of 2N $NaHCO_3$, followed by 60 mL Milli-Q water three times, and dried over a medium frit sintered glass funnel in vacuo to give the desired product 2 in 96.1% yield. [See Hansen, K B et al. *Organic process research & development*, 2005, 9, 634-639; Nelson, D A. US 20050137397A1. Coudert, P et al. *Journal of Heterocyclic Chemistry*, 1988, 25(3), 799-802.]

4-methyl-6-phenylpyridazin-3(2H)-one (3)

7.0 g (35 mmole) of 2 is placed in a 250 ml single-necked round bottom flask followed by 30 mL of acetonitrile. The mixture is stirred to allow 2 to dissolve. 11.3 g (84 mmole, 2.4 equiv.) of anhydrous copper (II) chloride is added to the solution to give a green-yellow suspension. A reflux condenser is connected to the flask and a dry tube filled with anhydrous $CaCl_2$ is fitted to the top of the condenser. To control the HCl gas that forms during the course of the reaction, a NaOH solution is used to absorb the HCl that escapes from the dry tube. The reaction mixture is heated to reflux, and the color of the reaction suspension changes to dark green upon heating. When the reaction is complete (after refluxing for 2 h), the flask is removed from the oil bath and cooled to ambient temperature. The reaction is cooled in an ice-water bath and 150 mL of ice-water is added to quench the reaction. The mixture is stirred vigorously for 10 minutes to give a gray precipitate and blue liquid containing copper (I) chloride. The precipitate is collected by filtration (pH of the filtrate is 0-1) and washed with 100 mL of 1N HCl solution, then 100 mL of water 5 times. To remove remaining copper by-products that are trapped in the solid, the filter cake is stirred in 150 mL of 1N HCl solution for 0.5 h and filtered. The filter cake is subsequently washed with Milli-Q water until the filtrate is at pH 7 (approximately 7 washes). The solid is dried over a medium frit sintered glass funnel in vacuo to give 3 as a light gray powder in 93.8% yield. [See Eddy, S et al. *Synthetic Communications*, 2000, 30(1), 1-7. Csende, F et al. *Synthesis*, 1995, 1240-1242.]

3-chloro-4-methyl-6-phenylpyridazine (4)

6.0 g (32 mmole) of 3 is placed in a 250 mL single neck round bottom flask and 30 mL of acetonitrile is added to create a pale yellow slurry. 6.0 ml (64 mmole, 2 equiv.) of phosphorus oxychloride is added changing the slurry to a darker color. The flask is fitted with a reflux condenser and a dry tube filled with anhydrous $CaCl_2$ is fitted to the top of the condenser. The reaction mixture is heated at reflux and becomes a dark red liquid. After the reaction is completed (2.5 h), the mixture is cooled to ambient temperature and placed in an ice water bath. Ice water (150 mL) is slowly poured into the reaction mixture with stirring to decompose the phosphorus oxychloride into HCl and $H_3PO_4$, resulting in formation of a pink solid. The solid is collected by filtration and washed three times with 50 mL of Milli-Q water. The solid is transferred to a 250 mL beaker, followed by addition of 100 mL of water to form a suspension. Subsequently, 1N NaOH is added until the aqueous suspension is at pH=8, and the mixture is stirred for 5 minutes to remove all trace starting material contaminants. The solid is filtered and washed 3 times with 100 mL of water to wash out the excess base. The solid is dried over a medium frit sintered glass funnel in vacuo to provide 4 as a light pink powder in 96% yield. [See Contreras, J M et al. *Journal of Medicinal Chemistry*, 2001, 44(17), 2707-2718; Nelson, D A. US 20050137397A1.]

2-(4-(4-methyl-6-phenylpyridazin-3-yl)piperazin-1-yl)pyrimidine (5)

7.5 g (36.6 mmole) of 4 is placed in a 250 mL single neck round bottom flask and suspended in 125 mL of water. 60.17 g (366.0 mmole, 10 equiv.) of 2-(piperazine-1-yl)pyrimidine is added and the flask fit with a condenser. The reaction mixture is heated at reflux with rapid stirring for 60 h, with continuous amine addition possible to boost reaction rates. When complete, the reaction mixture is cooled to ambient temperature and two layers are observed in the flask consisting of an orange aqueous layer and a brown oil that settles to the bottom of the flask. The water is decanted off, leaving the oil, which is the product 5. The oil is then dissolved in minimal volume of isopropanol and heated to reflux. After 10 minutes of reflux, the solution is cooled to ambient temperature, and cooled to 0° C. to induce crystallization. Pale yellow crystals are filtered from isopropanol and rinsed with minimal cold ether to provide 5. Recovery of the crystals is 50%, but may be increased by recursive crystallization of compound. [Contreras, J M et al. *Journal of Medicinal Chemistry*, 1999, 42(4), 730-741. Chayer, S et al. *Tetrahedron Letters*, 1998, 39, 841-844.]

Scheme 2 (FIG. 3)

3-chloro-6-phenylpyridazin-4-ol was synthesized according to the procedure described by Coudert, P., et al., supra.

6-phenyl-3-(4-(pyrimidin-2-yl)piperazin-1-yl)pyridazin-4-ol (MW01-7-121WH)

This compound was prepared from 3-chloro-4-hydroxy-6-phenylpyridazine (14 g, 68 mmol) in the same manner as described below, yielding white solid (22.1 g, 66 mmol, 97.3%). ESI-MS: m/z 335.2 (M+H+). $^1$H NMR (DMSO): $^1$H NMR (DMSO): d 8.406 (d, J=6.5, $^2$H), 7.740 (d, J=4.0, $^2$H), 7.558 (s, $^3$H), 6.686 (t, J=4.8, J=4.4, $^1$H), 6.841 (s, $^1$H), 3.881 (s, $^4$H), 3.620 (s, $^4$H), 3.776 (s, $^4$H).

4-chloro-6-phenyl-3-(4-pyrimidin-2-ylpiperazin-1-yl)pyridazine (MW01-6-127WH)

6-phenyl-3-(4-pyrimidin-2-ylpiperazin-1-yl)pyridazin-4-ol (22.0 g, 66 mmol) was suspended in 75 ml phosphorus oxychloride and heated with stirring at 100° C. for 3 h. After cooling to room temperature the mixture was poured onto crushed ice. The mixture was then neutralized with NaOH solution to give white suspension. The precipitation was filtered off, washed with water, dried over filter funnel to provide white solid (21.3 g, 60.3 mmol, 91.4%). ESI-MS: m/z 353.4 (M+H+). $^1$H NMR (CDCl$_3$): d 8.377 (d, J=4.5, $^2$H), 8.036 (d, J=7.5, $^2$H), 7.833 (s, $^1$H), 7.508 (m, $^3$H), 6.564 (t, J=4.5, $^1$H), 4.073 (t, J=4.0, J=4.5, $^4$H), 3.672 (t, J=4.0, J=4.5, $^4$H).

4-methyl-6-phenyl-3-(4-pyrimidin-2-ylpiperazin-1-yl)pyridazine (MW01-2-151SRM)

Into a reaction tube were added MW01-6-127WH (1.4 g, 4.0 mmol), K$_2$CO$_3$ powder (1.7 g, 12.4 mmol), Pd(dppf)Cl2 (326 mg, 0.4 mmol), silver oxide (2.3 g, 10 mmol), methylboronic acid (324 mg, 5.4 mmol) and 20 ml of THF. Argon was then flushed through the tube for 3 min. The tube was then sealed tightly and heated with stirring at 80 degree for 12 h. After cooled down, the mixture was quenched with 10% NaOH solution and extracted with ethyl acetate. The organic phase was concentrated in vacuo and the residue was purified by column chromatography eluting with 1:4, Ethyl Acetate: Petroleum ether. White powder solid was obtained (0.60 g, 1.8 mmol, yield 45.2%). ESI-MS: m/z 333.4 (M+H+). $^1$H NMR (CDCl$_3$): d 8.380 (d, J=5.0, $^2$H), 7.065 (d, J=7.0, $^2$H), 7.626 (s, $^1$H), 7.473 (m, $^3$H), 6.567 (t, J=4.5, J=5.0, $^1$H), 4.056 (t, J=5.0, $^4$H), 3.475 (t, J=5.0, $^4$H), 2.456 (s, $^3$H).

Scheme 3 (FIG. 4)

Into a reaction tube were added MW01-6-127WH (1.4 g, 4.0 mmol), K$_2$CO$_3$ powder (1.7 g, 12.4 mmol), Pd(PPh$_3$)$_4$ (240 mg, 0.2 mmol), silver oxide (2.3 g, 10 mmol), methylboronic acid (324 mg, 5.4 mmol) and 20 ml of DME. Argon was then flushed through the tube for 3 min. The tube was then sealed tightly and heated with stirring at 120° C. for 24 h. After cooled down, the mixture was filter through acelite earth, the filtrate was then concentrated and the residue was purified by column chromatography eluting with 1:4, Ethyl Acetate: Petroleum ether. White powder solid was obtained (0.64 g, 1.93 mmol, yield 48.1%). ESI-MS: m/z 333.4 (M+H+). $^1$H NMR (CDCl$_3$): d 8.380 (d, J=5.0, $^2$H), 7.065 (d, J=7.0, $^2$H), 7.626 (s, $^1$H), 7.473 (m, $^3$H), 6.567 (t, J=4.5, J=5.0, $^1$H), 4.056 (t, J=5.0, $^4$H), 3.475 (t, J=5.0, $^4$H), 2.456 (s, $^3$H).

Scheme 4 (FIG. 5)

4,5-dihydro-4-methyl-6-phenylpyridazin-3(2H)-one (MW01-8-004WH)

7.7 g (40 mmole) of 2-methyl-4-oxo-4-phenylbutanoic acid was added to a 100 ml single-necked round bottom flask followed by 3.0 ml (60 mmole) of hydrazine monohydrate and then 20 ml of reagent grade ethanol (100%, 95% of ethanol should be fine also). The flask was fitted with a reflux condenser and the reaction mixture was heated to reflux in an oil bath at 110° C. (temperature of oil bath) and stirred for 2 h. The flask was then removed from the oil bath and the reaction mixture cooled to ambient temperature. The stir bar was removed and the solvent was evaporated in vacuo in a water bath at 45° C. The residue was then treated with 50 ml of Milli-Q water and stirred for 10 minutes to give a suspension. The precipitate was collected by filtering, washed with 100 ml of 2N NaHCO$_3$, then washed with 60 ml Milli-Q water three times, and dried over a medium frit sintered glass funnel in vacuo to give 7.15 g of white crystals (Syn. ID, WH-8-004). Yield, 95%, confirmed by ESI-MS. ESI-MS: m/z 189.2 (M+H+).

4-methyl-6-phenylpyridazin-3(2H)-one (MW01-8-008WH)

7.0 g (35 mmole) of MW01-8-004WH was placed in a 100 ml single-necked round bottom flask followed by 9.4 g (70 mmole) of anhydrous copper (II) chloride and then 30 ml of acetonitrile to give a brown yellow suspension. A reflux condenser was connected to the flask and a dry tube filled with CaCl$_2$ was fitted to the top of the condenser. The reaction mixture was heated to reflux in an oil bath (110° C.) for 3 h. The color of the reaction suspension changed to dark yellow once the reflux started. After the completion of the reaction (monitored by HPLC), the flask was removed from the oil bath and cooled to ambient temperature. The mixture was poured on to 300 g of crushed ice and stirred vigorously for 10 minutes to give a gray precipitate and blue liquid. The precipitate was then collected by filtering (pH of the filtrate was 1.5-2.0), and washed with 100 ml of a 1N HCl solution to rid the solid of any remaining copper byproducts. This is followed by washing with 100 ml of Milli-Q water to get rid of the acid in the solid, and is monitored by checking the pH value of the filtrate. The solid was washed until the filtrate shows a pH of 7, after approximately 5 washes. The solid was dried over a medium frit sintered glass funnel in vacuo to give 6.3 g of a blue gray solid. Yield was 96.7% and confirmed by ESI-MS. ESI-MS: m/z 187.3 (M+H+).

3-chloro-4-methyl-6-phenylpyridazine(MW01-8-012WH)

6.0 g (32 mmole) of MW01-8-008WH and 30 ml (320 mmole) of phosphorus oxychloride were placed in a 100 ml single-necked round bottom flask. The flask was connected with a reflux condenser and a dry tube filled with anhydrous $CaCl_2$ was fitted to the top of the condenser. (HCl gas is formed in the reaction so a basic solution such as NaOH may be needed to absorb HCl in a large-scale synthesis). The reaction mixture was stirred in an oil bath (90° C.) for 2 h, then cooled to ambient temperature and poured onto crushed ice (phosphorus oxychloride can be decomposed by water to give HCl and $H_3PO_4$). The mixture was then stirred vigorously for 10 minutes to give a white suspension. The suspension was neutralized with a 2N NaOH solution until the pH of the suspension was pH=7. The precipitate was filtered, washed three times with 100 ml of Milli-Q water and dried over a medium frit sintered glass funnel in vacuo to provide 5.9 g of a light pink powder (Syn. ID, WH-8-012). Yield was 89.4% and confirmed by ESI-MS. ESI-MS: m/z 205.4 (M+H+).

2-(4-(4-methyl-6-phenylpyridazin-3-yl)piperazin-1-yl)pyrimidine (MW01-2-151SRM)

0.82 g (4.0 mmole) of WH-8-012 was placed in a 30 ml pressure vessel followed by addition of 2.6 g (16.0 mmole) of 1-(2-pyrimidyl)piperazine and then 15 ml of 1-BuOH. The vessel was sealed tightly and placed into an oil bath and stirred at 130° C. (temperature of oil bath) for 2.5 days. The reaction mixture was then cooled to ambient temperature and transferred to a single-necked flask for evaporation under reduced pressure. Removal of solvent gave rise to a brown-red residue that was treated with 30 ml of water to give a brown sticky oil. The mixture was kept at ambient temperature overnight while the oil solidified gradually. The formed solid was then broken into small pieces with a steel spatula. The solid was collected by filtering and washed with 50 ml of Milli-Q water three times and dried over a filter funnel in vacuo to provide 1.25 g of light yellow solid (Syn. ID, WH-8-020). Yield was 94%. (Alternative separation is to use precipitation procedure instead of solidification process. Solidification is a simple and cheap operation, yet time-consuming. Precipitation is time efficient, yet more costly than the former one. So it is up to the process chemist to decide which procedure to pick for the manufacture. The precipitation process is below: The oil product was dissolved completely in 10 ml of reagent grade ethanol or acetone to form a solution. The solution was then added dropwise to 150 ml of ice water under vigorous stirring. Light yellow suspension was then formed gradually. The solid was collected by filtering, washed with Milli-Q water, dried over filter funnel in vacuo to give the desired product.) The final compound was confirmed by ESI-MS and NMR. ESI-MS: m/z 333.8 (M+H+). $^1$H NMR ($CDCl_3$): d 8.380 (d, J=5.0, $^2$H), 7.065 (d, J=7.0, $^2$H), 7.626 (s, $^1$H), 7.473 (m, $^3$H), 6.567 (t, J=4.5, J=5.0, $^1$H), 4.056 (t, J=5.0, $^4$H), 3.475 (t, J=5.0, $^4$H), 2.456 (s, $^3$H).

C. Preparation of 4,6-diphenyl-3-(4-pyrimidin-2-ylpiperazin-1-yl)pyridazine (MW01-5-188WH)

Figure 6:
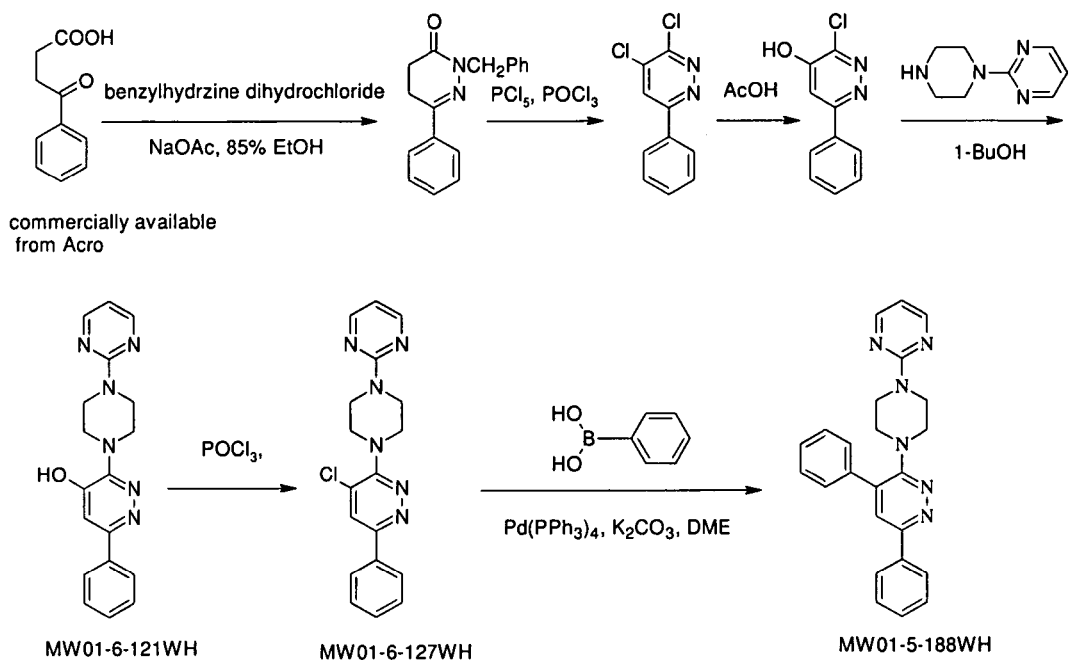
FIG. 6 depicts a synthetic scheme for MW01-5-188WH.
Figure 7:
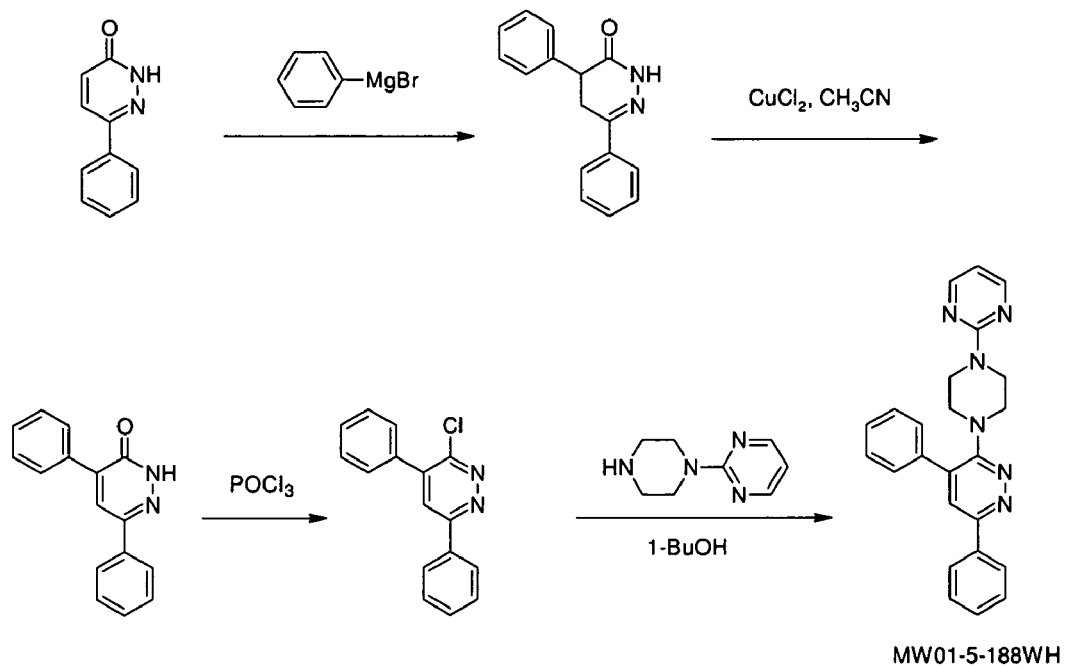
FIG. 7 depicts a synthetic scheme for MW01-5-188WH.
Figure 8:
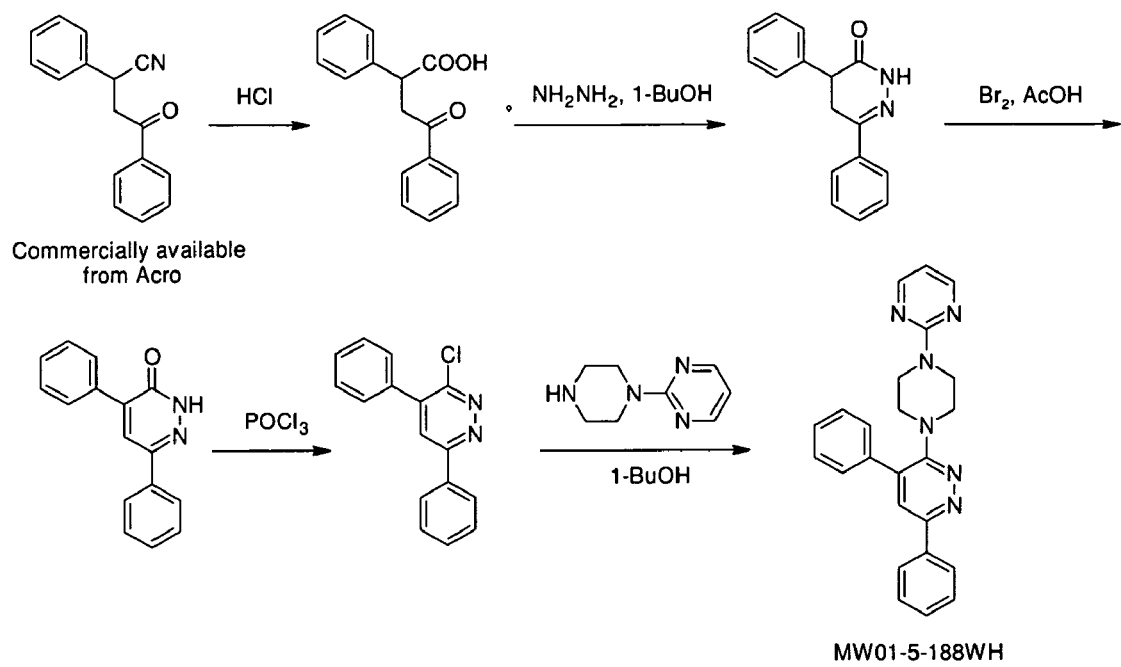
FIG. 8 depicts a synthetic scheme for MW01-5-188WH.

4,6-diphenyl-3-(4-pyrimidin-2-ylpiperazin-1-yl)pyridazine (MW01-5-188WH) was prepared by several synthetic schemes as depicted in FIG. 6 (Scheme 1), FIG. 7 (Scheme 2), and FIG. 8 (Scheme 3), which were carried out as described in detail herein. The various reaction schemes (Schemes 1, 2, and 3) are generally applicable to the compounds of the present invention and are not restricted in utility only to the preparation of MW01-2-188WH.
Scheme 1 (FIG. 6)
3-chloro-6-phenylpyridazin-4-ol was synthesized according to the procedure described by Coudert, P., et al. supra.

6-phenyl-3-(4-(pyrimidin-2-yl)piperazin-1-yl)pyridazin-4-ol (MW01-7-121WH)

The compound was prepared from 3-chloro-4-hydroxy-6-phenylpyridazine (14 g, 68 mmol). A mixture of 3-chloro-4,6-diphenylpyridazine (267 mg, 1.0 mmol), 1-(2-pyrimidyl)piperazine (656 mg, 4.0 mmol) in 3 ml of 1-BuOH was heated with stirring at 130° C. for 3 days. The solvent was removed by evaporation in vacuo the residue was treated with water to give a suspension. The solid was then filtered off, washed with water, dried over filter funnel in vacuo to give light pink solid yielding white solid (22.1 g, 66 mmol, 97.3%). ESI-MS: m/z 335.2 (M+H+). $^1$H NMR (DMSO): $^1$H NMR (DMSO): d 8.406 (d, J=6.5, $^2$H), 7.740 (d, J=4.0, $^2$H), 7.558 (s, $^3$H), 6.686 (t, J=4.8, J=4.4, $^1$H), 6.841 (s, $^1$H), 3.881 (s, $^4$H), 3.620 (s, $^4$H), 3.776 (s, $^4$H).

4-chloro-6-phenyl-3-(4-pyrimidin-2-ylpiperazin-1-yl)pyridazine (MW01-6-127WH)

6-phenyl-3-(4-pyrimidin-2-ylpiperazin-1-yl)pyridazin-4-ol (22.0 g, 66 mmol) was suspended in 75 ml phosphorus oxychloride and heated with stirring at 100° C. for 3 h. After cooling to room temperature the mixture was poured onto crushed ice. The mixture was then neutralized with NaOH solution to give white suspension. The precipitation was filtered off, washed with water, dried over filter funnel to provide white solid (21.3 g, 60.3 mmol, 91.4%). ESI-MS: m/z 353.4 (M+H+). $^1$H NMR ($CDCl_3$): d 8.377 (d, J=4.5, $^2$H), 8.036 (d, J=7.5, $^2$H), 7.833 (s, $^1$H), 7.508 (m, $^3$H), 6.564 (t, J=4.5, $^1$H), 4.073 (t, J=4.0, J=4.5, $^4$H), 3.672 (t, J=4.0, J=4.5, $^4$H).

4,6-diphenyl-3-(4-pyrimidin-2-ylpiperazin-1-yl)pyridazine (MW01-5-188WH)

A mixture of 3-chloro-4,6-diphenylpyridazine (267 mg, 1.0 mmol), 1-(2-pyrimidyl)piperazine (656 mg, 4.0 mmol) in 3 ml of 1-BuOH was heated with stirring at 130° C. for 3 days. The solvent was removed by evaporation in vacuo the residue was treated with water to give a suspension. The solid was then filtered off, washed with water, dried over filter funnel in vacuo to give light pink solid. (320 mg, 0.81 mmol, yield 81.1%). ESI-MS: m/z 395.5 (M+H+). HRMS calcd 395.1979, found 395.1973; $^1$H NMR (CDCl$_3$): d 8.329 (d, J=5.0, $^2$H), 8.101 (d, J=7.5, $^2$H), 7.734 (d, J=7.5, $^1$H), 7.655 (s, $^1$H), 7.509 (m, $^6$H), 6.530 (t, J=4.5, $^1$H), 3.836 (t, J=4.5, J=5.0, $^4$H), 3.394 (t, J=5.0, J=4.5, $^4$H).

Scheme 2 (FIG. 7)

4,5-dihydro-6-phenyl-4-phenylpyridazin-3(2H)-one 135 ml (135 mmole) of a solution of phenylmagnesium bromide (1M) in THF was added to a hot suspension of 6-phenylpyridazinone compound 7.8 g (45 mmole) in dry toluene (50 ml). The mixture was refluxed for 8 h, left overnight at ambient temperature, then decomposed with a saturated solution of ammonium chloride. The organic layer was separated, and the aqueous layer was extracted with 100 ml of ethyl acetate. The solvent was removed and the residue was crystallized from ethanol. The crystals were collected by filtering and dried over a medium frit sintered glass funnel in vacuo to give 5.6 g of white crystals. Yield was 50%, confirmed by ESI-MS. ESI-MS: m/z 250.1 (M+H+).

6-phenyl-4-phenylpyridazin-3(2H)-one 4.4 g (17.5 mmole) of 6-pyridazinone obtained above was placed in a 50 ml single-necked round bottom flask followed by 4.7 g (35 mmole) of anhydrous copper (II) chloride and then 20 ml of acetonitrile to give a brown yellow suspension. A reflux condenser was connected to the flask and a dry tube filled with CaCl$_2$ was fitted to the top of the condenser. The reaction mixture was heated to reflux in an oil bath (110° C.) for 3 h. The color of the reaction suspension changed to dark yellow once the reflux started. After the completion of the reaction (monitored by HPLC), the flask was removed from the oil bath and cooled to ambient temperature. The mixture was poured on to 200 g of crushed ice and stirred vigorously for 10 minutes to give a gray precipitate and blue liquid. The precipitate was then collected by filtering (pH of the filtrate was 1.5-2.0), and washed with 50 ml of a 1N HCl solution to rid the solid of any remaining copper byproducts. This is followed by washing with 100 ml of Milli-Q water to get rid of the acid in the solid, and is monitored by checking the pH value of the filtrate. The solid was washed until the filtrate shows a pH of 7, after approximately 5 washes. The solid was dried over a medium frit sintered glass funnel in vacuo to give 3.9 g of a blue gray solid. Yield was 90%, confirmed by ESI-MS. ESI-MS: m/z 248.1 (M+H+).

3-chloro-6-phenyl-4-phenylpyridazine 2.0 g (8 mmole) of 6-phenylpyridazinone obtained above and 10 ml (54 mmole) of phosphorus oxychloride (reagent grade, Aldrich) were placed in a 50 ml single-necked round bottom flask. The flask was connected with a reflux condenser and a dry tube filled with CaCl$_2$ was fitted to the top of the condenser. (HCl gas is formed in the reaction so a basic solution such as NaOH may be needed to absorb HCl in a large-scale synthesis). The reaction mixture was stirred in an oil bath (90° C.) for 2 h, then cooled to ambient temperature and poured onto crushed ice. (phosphorus oxychloride can be decomposed by water to give HCl and H$_3$PO$_4$). The mixture was then stirred vigorously for 10 minutes to give a white suspension. The suspension was neutralized with a 2N NaOH solution until the pH of the suspension was pH=7. The precipitate was filtered, washed three times with 100 ml of water and dried over a medium frit sintered glass funnel in vacuo to provide 1.8 g of a light pink powder. Yield was 85%, confirmed by ESI-MS. ESI-MS: m/z 266.4 (M+H+).

2-(4-(6-phenyl-4-phenylpyridazin-3-yl)piperazin-1-yl)pyrimidine 1.1 g (4.0 mmole) of 3-chloropyridazine obtained above was placed in a 30 ml pressure vessel followed by addition of 2.6 g (16.0 mmole) of 1-(2-pyrimidyl)piperazine and then 15 ml of 1-BuOH (reagent grade). The vessel was sealed tightly and placed into an oil bath and stirred at 130° C. (temperature of oil bath) for 3 days. The reaction mixture was then cooled to ambient temperature and transferred to a single-necked flask for evaporation under reduced pressure. Removal of solvent gave rise to a brown-red residue that was treated with 30 ml of water to give a brown suspension. The solid was collected by filtering and washed with 50 mL of water three times and dried over a filter funnel in vacuo to provide 0.96 g of light yellow solid. Yield was 90%, ESI-MS: m/z 395.5 (M+H+). HRMS calcd 395.1979, found 395.1973; $^1$H NMR (CDCl$_3$): d 8.329 (d, J=5.0, $^2$H), 8.101 (d, J=7.5, $^2$H), 7.734 (d, J=7.5, $^2$H), 7.655 (s, $^1$H), 7.509 (m, $^6$H), 6.530 (t, J=4.5, $^1$H), 3.836 (t, J=4.5, J=5.0, $^4$H), 3.394 (t, J=5.0, J=4.5, $^4$H).

Scheme 3 (FIG. 8)

3-chloro-6-phenylpyridazin-4-ol was synthesized according to the procedure described by Coudert, P., et al., supra.

4,6-diphenyl-3-(4-pyrimidin-2-ylpiperazin-1-yl)pyridazine (MW01-5-188WH)

A mixture of 3-chloro-4,6-diphenylpyridazine (267 mg, 1.0 mmol), 1-(2-pyrimidyl)piperazine (656 mg, 4.0 mmol) in 3 ml of 1-BuOH was heated with stirring at 130° C. for 3 days. The solvent was removed by evaporation in vacuo the residue was treated with water to give a suspension. The solid was then filtered off, washed with water, dried over filter funnel in vacuo to give light pink solid. (320 mg, 0.81 mmol, yield 81.1%). ESI-MS: m/z 395.5 (M+H+). HRMS calcd 395.1979, found 395.1973; $^1$H NMR (CDCl$_3$): d 8.329 (d, J=5.0, $^2$H), 8.101 (d, J=7.5, $^2$H), 7.734 (d, J=7.5, $^2$H), 7.655 (s, $^1$H), 7.509 (m, $^6$H), 6.530 (t, J=4.5, $^1$H), 3.836 (t, J=4.5, J=5.0, $^4$H), 3.394 (t, J=5.0, J=4.5, $^4$H).

D. Preparation of 4-pyridyl-6-phenyl-3-(4-pyrimidin-2-ylpiperazin-1-yl)pyridazine (MW01-6-189WH)

Figure 9A:
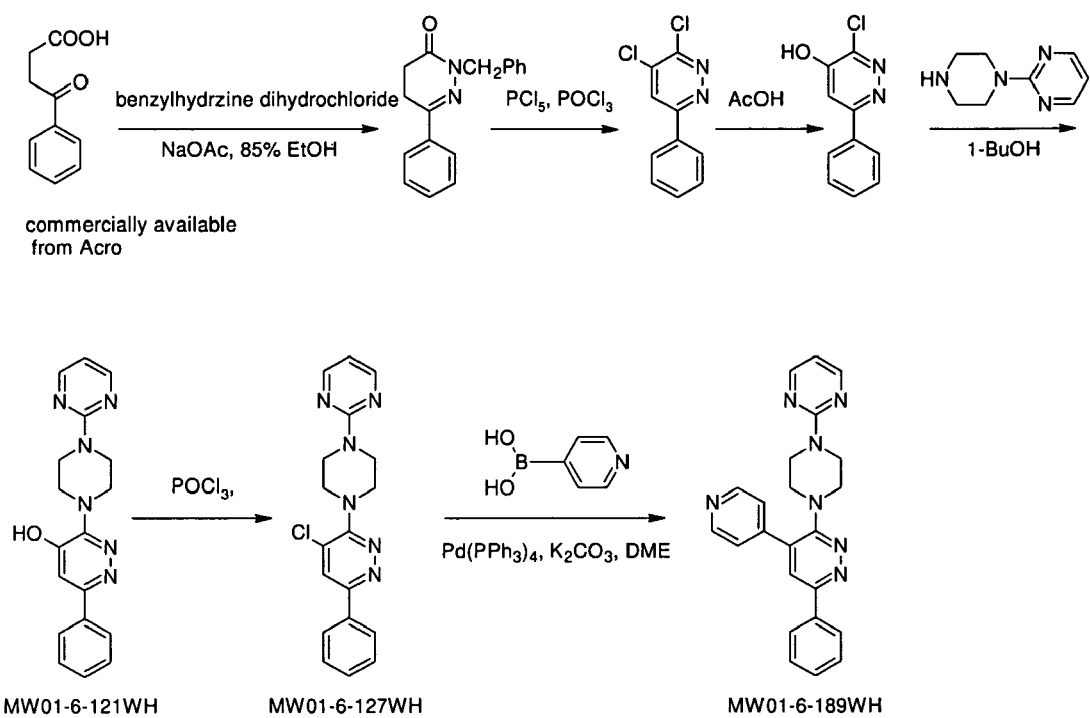
FIGS. 9A and 9B depict synthetic schemes for MW01-6-189WH.
Figure 9B:
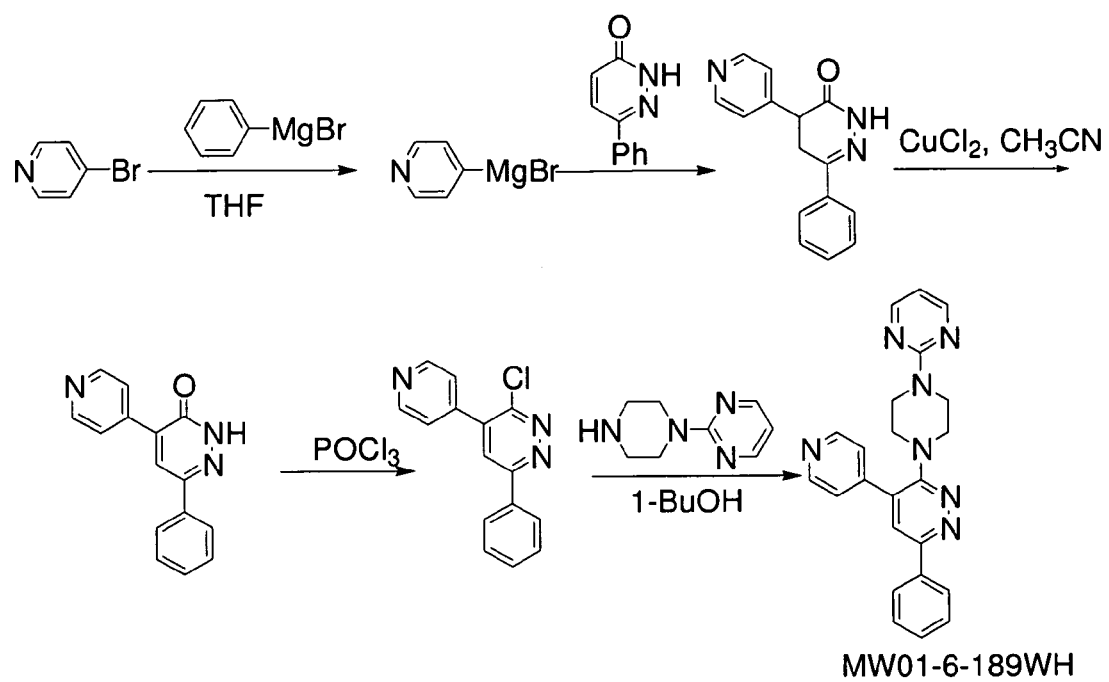

4-pyridyl-6-phenyl-3-(4-pyrimidin-2-ylpiperazin-1-yl)pyridazine (MW01-6-189WH) was prepared by two synthetic schemes as depicted in FIGS. 9A and 9B, which were carried out as described in detail herein. The various reaction schemes (Schemes 1 and 2) are generally applicable to the compounds of the present invention and are not restricted in utility only to the preparation of MW01-2-189WH.

Scheme 1

3-chloro-6-phenylpyridazin-4-ol was synthesized according to the procedure described by Coudert, P., et al., supra.

6-phenyl-3-(4-(pyrimidin-2-yl)piperazin-1-yl)pyridazin-4-ol (MW01-7-121WH)

This compound was prepared from 3-chloro-4-hydroxy-6-phenylpyridazine (14 g, 68 mmol) A mixture of 3-chloro-4,6-diphenylpyridazine (267 mg, 1.0 mmol), 1-(2-pyrimidyl)piperazine (656 mg, 4.0 mmol) in 3 ml of 1-BuOH was heated with stirring at 130° C. for 3 days. The solvent was removed by evaporation in vacuo the residue was treated with water to give a suspension. The solid was then filtered off, washed with water, dried over filter funnel in vacuo to give light pink solid. yielding white solid (22.1 g, 66 mmol, 97.3%). ESI-MS: m/z 335.2 (M+H+). $^1$H NMR (DMSO): $^1$H NMR (DMSO): d 8.406 (d, J=6.5, $^2$H), 7.740 (d, J=4.0, $^2$H), 7.558 (s, $^3$H), 6.686 (t, J=4.8, J=4.4, $^1$H), 6.841 (s, $^1$H), 3.881 (s, $^4$H), 3.620 (s, $^4$H), 3.776 (s, $^4$H).

4-chloro-6-phenyl-3-(4-pyrimidin-2-ylpiperazin-1-yl)pyridazine (MW01-6-127WH)

6-phenyl-3-(4-pyrimidin-2-ylpiperazin-1-yl)pyridazin-4-ol 1 h (22.0 g, 66 mmol) was suspended in 75 ml phosphorus oxychloride and heated with stirring at 100° C. for 3 h. After cooling to room temperature the mixture was poured onto crushed ice. The mixture was then neutralized with NaOH solution to give white suspension. The precipitation was filtered off, washed with water, dried over filter funnel to provide white solid (21.3 g, 60.3 mmol, 91.4%). ESI-MS: m/z 353.4 (M+H+). $^1$H NMR (CDCl$_3$): d 8.377 (d, J=4.5, $^2$H), 8.036 (d, J=7.5, $^2$H), 7.833 (s, $^1$H), 7.508 (m, $^3$H), 6.564 (t, J=4.5, $^1$H), 4.073 (t, J=4.0, J=4.5, $^4$H), 3.672 (t, J=4.0, J=4.5, $^4$H).

4-pyridyl-6-phenyl-3-(4-pyrimidin-2-ylpiperazin-1-yl)pyridazine (MW01-6-189WH)

Into a reaction tube were added WH-6-127 (1.4 g, 4.0 mmol), K2CO3 powder (1.7 g, 12.4 mmol), Pd(PPh$_3$)4 (240 mg, 0.2 mmol), 4-pyridineboronic acid (664 mg, 5.4 mmol) and 20 ml of DME. Argon was then flushed through the tube for 3 min. The tube was then sealed tightly and heated with stirring at 120 degree for 24 h. After cooled down, the mixture was filter through a celite earth, the filtrate was then concentrated and the residue was purified by column chromatography eluting with 1:4, Ethyl Acetate: Petroleum ether. Light yellow needle crystals were obtained (0.65 g, 1.65 mmol, yield 41.2%). Confirmed by ESI-MS and NMR. ESI-MS: m/z 396.2 (M+H+). $^1$H NMR (CDCl$_3$): d 8.809 (d, J=6.0, $^2$H), 8.335 (d, J=5.0, $^2$H), 8.090 (d, J=7.5, $^2$H), 7.750 (m, $^6$H), 6.543 (t, J=4.5, $^1$H), 3.868 (t, J=5.0, $^4$H), 3.404 (t, J=5.0, $^4$H).
Scheme 2

4,5-dihydro-6-phenyl-4-(pyridin-4-yl)pyridazin-3(2H)-one

To a 200 ml, three-necked, round-bottomed flask equipped with a magnetic stir bar, 150 ml pressure-equalizing addition funnel, reflux condenser and a glass stopper, was added 21 g (135 mmole) of 4-bromopyridine and 70 of anhydrous THF. The system was oven-dried and flushed with argon before use. 135 ml (135 mmole) of THF solution of phenylmagnesium bromide (1M) was placed in the pressure-equalizing addition funnel. Then, the grignard solution was added dropwise over a period of 10 minutes. After the addition, the reaction was stirred for 15 minutes for completion. The solution of Grignard reagent was then obtained. A solution of 4-pyridylmagnesium bromide obtained above was added to a hot suspension of 6-phenylpyridazinone compound 7.8 g (45 mmole) in dry toluene (50 ml). The mixture was refluxed for 8 h, left overnight at ambient temperature, then decomposed with a saturated solution of ammonium chloride. The organic layer was separated, and the aqueous layer was extracted with 100 ml of ethyl acetate. The solvent was removed and the residue was crystallized from ethanol. The crystals were collected by filtering and dried over a medium frit sintered glass funnel in vacuo to give 5.6 g of white crystals. Yield was 50%, confirmed by ESI-MS. ESI-MS: m/z 252.1 (M+H+).

6-phenyl-4-(pyridin-4-yl)pyridazin-3(2H)-one 4.4 g (17.5 mmole) of 6-pyridazinone obtained above was placed in a 50 ml single-necked round bottom flask followed by 4.7 g (35 mmole) of anhydrous copper (II) chloride and then 20 ml of acetonitrile to give a brown yellow suspension. A reflux condenser was connected to the flask and a dry tube filled with CaCl$_2$ was fitted to the top of the condenser. The reaction mixture was heated to reflux in an oil bath (110° C.) for 3 h. The color of the reaction suspension changed to dark yellow once the reflux started. After the completion of the reaction (monitored by HPLC), the flask was removed from the oil bath and cooled to ambient temperature. The mixture was poured on to 200 g of crushed ice and stirred vigorously for 10 minutes to give a gray precipitate and blue liquid. The precipitate was then collected by filtering (pH of the filtrate was 1.5-2.0), and washed with 50 ml of a 1N HCl solution to rid the solid of any remaining copper byproducts. This is followed by washing with 100 ml of Milli-Q water to get rid of the acid in the solid, and is monitored by checking the pH value of the filtrate. The solid was washed until the filtrate shows a pH of 7, after approximately 5 washes. The solid was dried over a medium frit sintered glass funnel in vacuo to give 3.9 g of a blue gray solid. Yield was 90%, confirmed by ESI-MS. ESI-MS: m/z 250.1 (M+H+).

3-chloro-6-phenyl-4-(pyridin-4-yl)pyridazine 2.0 g (8 mmole) of 6-phenylpyridazinone obtained above and 10 ml (54 mmole) of phosphorus oxychloride (reagent grade, Aldrich) were placed in a 50 ml single-necked round bottom flask. The flask was connected with a reflux condenser and a dry tube filled with CaCl$_2$ was fitted to the top of the condenser. (HCl gas is formed in the reaction so a basic solution such as NaOH may be needed to absorb HCl in a large-scale synthesis). The reaction mixture was stirred in an oil bath (90° C.) for 2 h, then cooled to ambient temperature and poured onto crushed ice. (phosphorus oxychloride can be decomposed by water to give HCl and H$_3$PO$_4$). The mixture was then stirred vigorously for 10 minutes to give a white suspension. The suspension was neutralized with a 2N NaOH solution until the pH of the suspension was pH=7. The precipitate was filtered, washed three times with 100 ml of water and dried over a medium frit sintered glass funnel in vacuo to provide 1.8 g of a light pink powder. Yield was 85%, confirmed by ESI-MS. ESI-MS: m/z 268.4 (M+H+).

4-pyridyl-6-phenyl-3-(4-pyrimidin-2-ylpiperazin-1-yl)pyridazine (MW01-6-189WH)

1.1 g (4.0 mmole) of 3-chloropyridazine obtained above was placed in a 30 ml pressure vessel followed by addition of 2.6 g (16.0 mmole) of 1-(2-pyrimidyl)piperazine and then 15 ml of 1-BuOH (reagent grade). The vessel was sealed tightly and placed into an oil bath and stirred at 130° C. (temperature of oil bath) for 3 days. The reaction mixture was then cooled to ambient temperature and transferred to a single-necked flask for evaporation under reduced pressure. Removal of solvent gave rise to a brown-red residue that was treated with 30 ml of water to give a brown suspension. The solid was collected by filtering and washed with 50 mL of water three times and dried over a filter funnel in vacuo to provide 0.96 g of light yellow solid. Yield was 90%, confirmed by ESI-MS and NMR. ESI-MS: m/z 396.2 (M+H+). $^1$H NMR (CDCl$_3$): d 8.809 (d, J=6.0, $^2$H), 8.335 (d, J=5.0, $^2$H), 8.090 (d, J=7.5, $^2$H), 7.750 (m, $^6$H), 6.543 (t, J=4.5, $^1$H), 3.868 (t, J=5.0, $^4$H), 3.404 (t, J=5.0, $^4$H).

E. Preparation of N-(cyclopropylmethyl)-6-phenyl-4-(pyridin-4-yl)pyridazin-3-amine (MW01-7-084WH)

Figure 10:
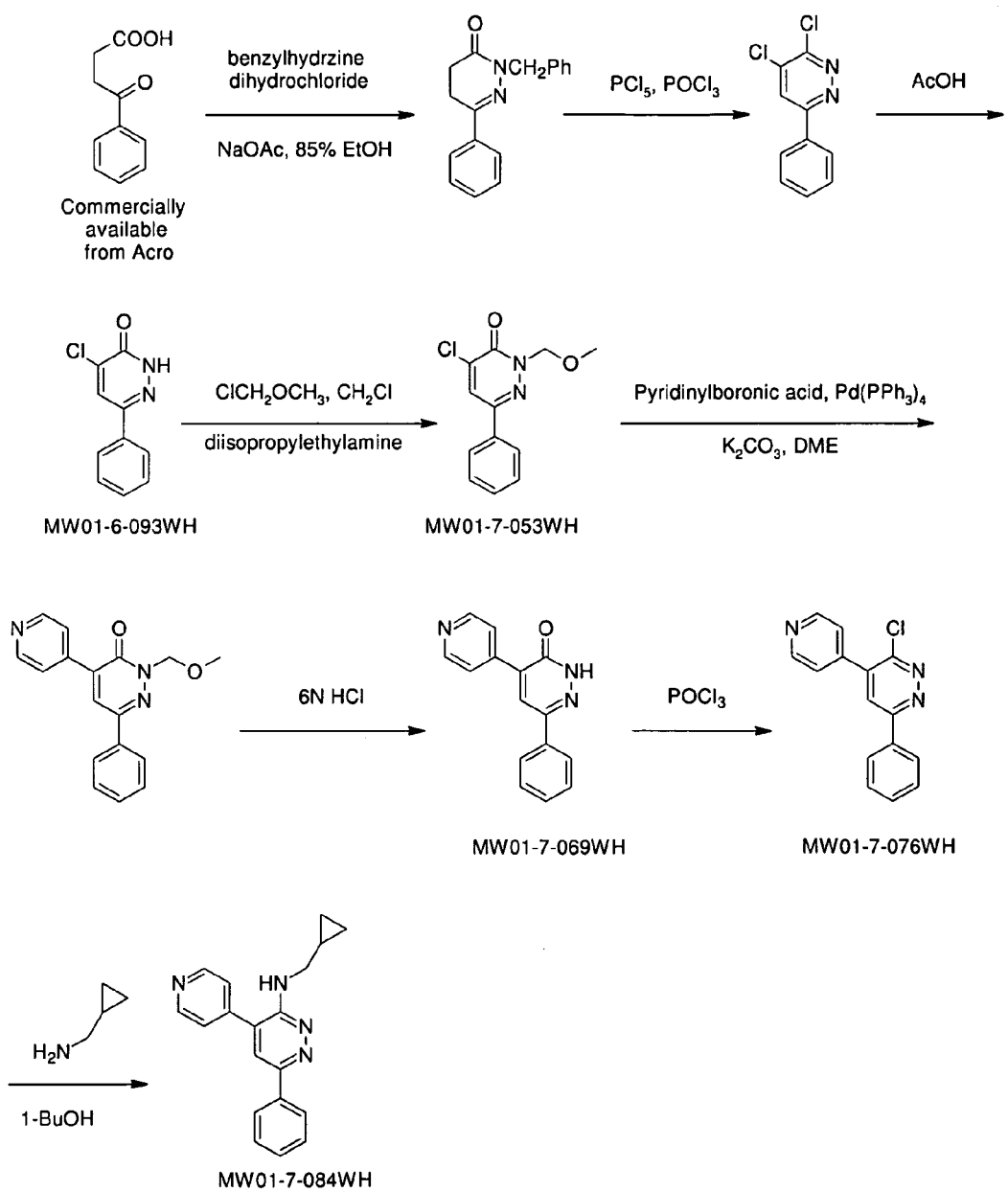
FIG. 10 depicts a synthetic scheme for MW01-7-084WH.

A synthetic scheme for the preparation of N-(cyclopropylmethyl)-6-phenyl-4-(pyridin-4-yl)pyridazin-3-amine (MW01-7-084WH) is depicted in FIG. 10, and synthesis was carried out as described herein.

4-chloro-6-phenylpyridazin-3(2H)-one (MW01-6-093WH)

4-chloro-6-phenylpyridazin-3(2H)-one was synthesized according to the procedure described by Coudert, P. supra.

4-chloro-2-(methoxymethyl)-6-phenylpyridazin-3(2H)-one (MW01-7-053WH)

A mixture of chloropyridazinone 1 (25.5 g, 0.12 mol), 4-N,N-dimethylaminopyridine (0.20 g) and i-Pr$_2$NEt (26.7 g, 0.21 mol) in anhydrous CH$_2$Cl$_2$ (300 mL) was stirred at 0° C. (ice bath) for 30 min. Methoxymethyl chloride (25 g, 0.31 mol) was added and the mixture was stirred at 0° C. for 1 h and then allowed to warm to room temperature. The reaction was stirred at room temperature till complete. The solvent was then removed in vacuo, the residue was treated with water, washed with dilute Na$_2$CO$_3$ solution and extracted with EtOAc. The organic layer was dried over anhydrous Na$_2$SO$_4$, filtered and evaporated. The residue was then purified by recrystallization from 95% ethanol to give 20.1 light yellow solid. Yield 66.9%.

6-phenyl-4-(pyridin-4-yl)pyridazin-3(2H)-one (MW01-7-069WH)

The protected pyridazinone MW01-7-053WH (1.0 equiv.) was mixed with arylboronic acid (1.37 equiv.), Pd(PPh$_3$)$_4$ (0.05 equiv.) and K$_2$CO$_3$ (3.1 equiv) and 200 mL of DME in a 350 ml of pressure vessel, flushed with argon for 3 min, and the mixture was then stirred and refluxed (oil bath, 120° C.) until the starting material had disappeared. After cooling, the solution was concentrated to dryness under reduced pressure, the residue was treated with water and filtered off. The filter cake was washed with water over filter funnel and then used for next step directly. The residue obtained above was dissolved in 200 ml of EtOH, 6 N HCl (200 mL) was added and the reaction mixture was refluxed (oil bath, 120° C.) for 6 h, then it was allowed to cool to room temperature, and concentrated to dryness under reduced pressure. The residue was neutralized with dilute NaOH solution. The suspension was then filtered off, washed with water and dried over a filter funnel. Recrystallization from 90% ethanol provided brown yellow solid. Yield 80.4%. ESI-MS: m/z 294.3 (M+H+)

3-chloro-6-phenyl-4-(pyridin-4-yl)pyridazine (MW01-7-076WH)

3-chloro-6-phenyl-4-(pyridin-4-yl)pyridazine (MW01-7-076WH) (66 mmol) was suspended in 75 ml phosphorus oxychloride and heated with stirring at 100° C. for 3 h. After cooling to room temperature the mixture was poured onto crushed ice. The mixture was then neutralized with NaOH solution to give white suspension. The precipitation was filtered off, washed with water, dried over filter funnel to yielding a light yellow solid. ESI-MS: m/z 268.4 (M+H+).

N-(cyclopropylmethyl)-6-phenyl-4-(pyridin-4-yl)pyridazin-3-amine (MW01-7-084WH)

A mixture of N-(cyclopropylmethyl)-6-phenyl-4-(pyridin-4-yl)pyridazin-3-amine (MW01-7-084WH) (0.5 mmol), C-Cyclopropyl-methylamine (2.0 mmol) in 3 ml of 1-BuOH was heated with stirring at 130° C. for 7 days. The solvent was removed by evaporation in vacuo, the residue was treated with water to give a suspension. The solid was then filtered off, washed with water, then 1:3, Ethyl Acetate: Petroleum ether, dried over filter funnel in vacuo yielding gray solid. ESI-MS: m/z 330.4 (M+H+).

F. Preparation of 3-(4-methylpiperazin-1-yl)-6-phenyl-4-(pyridin-4-yl)pyridazine (MW01-7-085WH)

Figure 11:
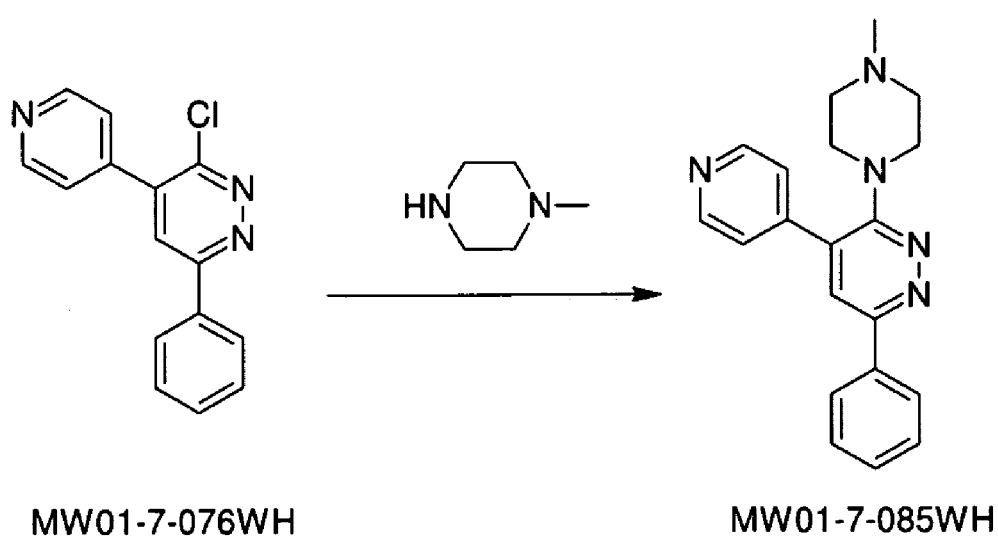
FIG. 11 depicts a synthetic scheme for MW01-7-085WH.

A mixture of 3-chloro-6-phenyl-4-(pyridin-4-yl)pyridazine (MW01-7-076WH) (0.5 mmol), 1-methyl-piperazine (2.0 mmol) in 3 ml of 1-BuOH was heated with stirring at 130° C. for about 7 days. The solvent was removed by evaporation in vacuo the residue was treated with water to give a suspension. The solid was then filtered off, washed with water, then 1:3, Ethyl Acetate: Petroleum ether, dried over a filter funnel in vacuo to yield a brown solid. ESI-MS: m/z 332.2 (M+H$^+$). A synthetic reaction scheme for the preparation of 3-(4-methylpiperazin-1-yl)-6-phenyl-4-(pyridin-4-yl)pyridazine (MW01-7-085WH) is depicted in FIG. 11.

G. Preparation of 6-methyl-4-phenyl-3-(4-pyrimidin-2-ylpiperazin-1-yl)pyridazine (MW01-7-057)

Figure 12:
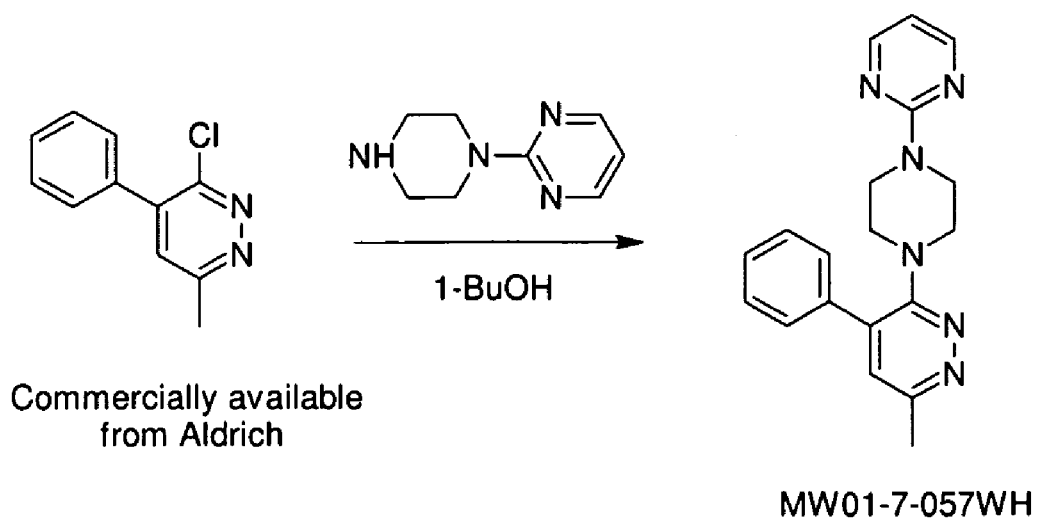
FIG. 12 depicts a synthetic scheme for MW01-7-057WH.

A synthetic reaction scheme for the preparation of 6-methyl-4-phenyl-3-(4-pyrimidin-2-ylpiperazin-1-yl)pyridazine (MW01-7-057) is depicted in FIG. 12, and synthesis was carried out as described herein. A mixture of 3-chloro-6-methyl-4-phenylpyridazine (100 mg, 0.5 mmol), 1-(2-pyrimidyl)piperazine (400 mg, 2.0 mmol) in 3 ml of 1-BuOH was heated with stirring at 130° C. for 7 days. The solvent was removed by evaporation in vacuo, the residue was treated with water to give a suspension. The solid was then filtered off, washed with water, then 1:3, Ethyl Acetate: Petroleum ether, dried over a filter funnel in vacuo to give light yellow solid (68 mg, 0.20 mmol, yield 41.7%). Purity >95%; ESI-MS: m/z 333.1 (M+H+). $^1$H NMR (CDCl$_3$): d 8.310 (d, J=5.0, $^2$H), 7.678 (d, J=7.5, $^2$H), 7.476 (m, $^3$H), 7.119 (s, H), 6.509 (t, J=4.5, $^1$H), 3.785 (t, J=4.5, J=5.0, $^4$H), 3.277 (t, J=4.5, J=5.0, $^4$H), 2.669 (s, $^3$H).

Example 2

Assays for Confirming Activity of Combinations of Pyridazine Compounds and Cholinesterase Inhibitors The six standard endpoint assays used as measures of neuroinflammation, synaptic damage and behavioral are IL-1α, TNFαα, synaptophysin, PSD-95, Y-maze, and the Morris water maze. They will be used to confirm the activity of combinations of pyridazine compounds and cholinesterase inhibitors, in particular combinations of MW01-2-151SRM, MW01-5-188WH, MW01-3-183WH, or MW01-6-189WH and Flurizant or LY450139. (The pyridazine compound and cholinesterase inhibitor are also referred to as "test compounds" below.)

Cell culture assays. Cell-based assays of the concentration-dependent activity of the test compounds will be conducted using methods previously described (Mirzoeva et al., J Med Chem 45:563-566, 2002). BV-2 mouse microglial cells ($1.25 \times 10^4$ cells/well in a 48-well plate) will be cultured for one day in αMEM media containing 10% fetal bovine serum (FBS), and then treated in serum-free media for 16 hrs with either control buffer or the standard glial activating stimulus lipopolysaccharide (LPS, from *Salmonella typhimurium;* 100 ng/ml final concentration) in the presence of diluent or compound. Stock solutions (20 mM) of compounds will be prepared in dimethylsulfoxide (DMSO). Solutions for cell treatments will be prepared by dilution of stock solutions into serum-free media immediately before adding to the cells. Control wells will contain the same final concentration of DMSO as the compound-containing wells. It has been previously determined that this concentration of DMSO is not toxic to the cells (Mirzoeva et al., Brain Res. 844:126-134, 1999). The accumulation of nitrite, the stable metabolite of nitric oxide (NO), will be measured in BV-2 conditioned media by the Griess assay as previously described (Mirzoeva et al., Brain Res. 844:126-134, 999; Mirzoeva et al., J Med Chem 45:563-566, 2002). Levels of IL-1β in cell lysates and TNFα in conditioned media will be measured by ELISA (Biosource International) as per the manufacturer's instructions. Cell lysates will be analyzed by Western blots as described (Mirzoeva et al., J Med Chem, 2002) to determine the levels of inducible nitric oxide synthase (iNOS), cyclooxygenase-2 (COX-2) and apolipoprotein E (apoE). For apoE measurements, rat primary mixed glia will be prepared and stimulated with human oligomeric $A\beta_{1-42}$ (10 μM) as previously described (Mirzoeva et al., 2002, supra). Antibodies and dilutions used for Western blots will be as follows: anti-COX-2 (1:1000, Santa Cruz), anti-iNOS (1:1000, Transduction Laboratories), anti-apoE (1:1000). Antibody against β-actin (1:500,000 dilution, Sigma) will be used to confirm equal protein loading among the samples.

In vivo efficacy studies in mice. The study design and treatment paradigm for intracerebroventricular (ICV) infusion of human oligomeric $A\beta_{1-42}$ into the mouse will be as described previously (Craft et al., Neurobiol Aging 25:1283-1292, 2004b), except that compounds administration will be by mouth. Female C57Bl/6 mice (Harlan) weighing 20-25 g (3-4 months old) will be housed in a pathogen free facility under an approximate 12 h/12 h dark and light cycle and they will have access ad libitum to food and water.

Mice will be administered by oral gavage either test compounds (2.5 mg/kg/day) or solvent control (10% DMSO) in a 0.5% (w/v) carboxymethylcellulose suspension. Once per day treatment will begin at day 21 after start of Aβ ICV infusion and continue for 14 days. Beginning at day 50 after start of Aβ ICV infusion, the Y maze test of spontaneous alternation will be used to evaluate hippocampus-dependent spatial learning as described previously (Craft et al., J Mol Neurosci 24:115-122, 2004a). Briefly, each mouse will be placed in the "start" arm and then released to choose one of the two other arms. The mouse will be blocked from exiting the chosen arm for 30s then they will be placed back in the start arm and released again to choose one of the two other arms. If the second choice is different from the first one, the mouse will be scored as alternating. Mice will be tested for 10 days with one trial per day, and a mean percent alternation will be calculated for each mouse. At day 60 after start of Aβ ICV infusion, mice will be anesthetized with pentobarbital (50 mg/kg) and perfused with a HEPES buffer (10 mM, pH 7.2) containing a protease inhibitor cocktail (1 g/ml leupeptin, 1 μM dithithreitol, 2 mM sodium vanadate, 1 μM phenylmethylsulphonylfluoride). The brain will be removed and longitudinally bisected as described previously (Craft et al., Neurobiolo Aging 25:1283-1292, 2004b). The right half of the brain will be fixed in 4% (v/v) paraformaldehyde and paraffin-embedded for histology. The hippocampus will be dissected from the left half of the brain and snap-frozen for subsequent biochemical evaluation. Hippocampal extract supernatants will be prepared by dounce and sonication in the HEPES buffer containing a protease inhibitor cocktail, followed by centrifugation as described (Craft et al., 2004b, supra).

Levels of IL-1β and TNFα in hippocampal supernatants will be measured by ELISA (Biosource International) per the manufacturer's instructions. S100B levels in hippocampal supernatants will be measured by a europium-based ELISA essentially as previously described (Van Eldik and Griffin, Biochem Biophys Acta 1223:398-403, 1994). Synaptophysin levels in hippocampal supernatants will be quantified by ELISA following the procedure described previously (Craft et al, 2004b, supra). PSD-95 levels will be determined by Western blots using anti-PSD-95 antibodies (1:100,000 dilution; Upstate Biotechnology) as described (Craft et al., 2004b).

Immunohistochemical detection of activated astrocytes and microglia will be performed on 10 μm sections as described previously (Craft et al, 2004b, supra), with anti-GFAP (1:1500; Sigma) and anti-F4/80 (1:100; Serotek) antibodies, respectively, using the mouse on mouse or Vectastain Universal Elite ABC immunodetection kits (Vector/Novocastra) and development with diaminobenzidine (DAB) substrate. Cell bodies will be manually counted in the hippocampus of three GFAP and F4/80 labeled sections positioned at −1.8, −2.1, and −2.3 mm from bregma. Aβ immunohistochemistry will be done with a rabbit anti-human Aβ antibody as previously described (Craft et al., 2004b, supra). Cell counts and amyloid plaque counts will be determined by two blinded observers and amyloid plaque area will be determined as previously described (Craft et al., 2004b, supra). Peroxynitrite-mediated neuronal damage will be measured with an anti-nitrotyrosine antibody (1:125; Chemicon), using the Vectastain Rabbit Elite ABC kit. For nitrotyrosine cell counts, all DAB-stained cell bodies in the neuronal layers of the hippocampus and subiculum will be counted on three sections roughly adjacent to those used for F4/80 and GFAP analysis, as described (Craft et al., 2004b, supra).

In vitro stability, oral bioavailability and brain uptake. The stability of test compounds (1 μM) in a standard incubation with rat liver microsomes (BD Biosciences) and an NADPH-regenerating system will be done at 37° C. for 30 and 120 min. Reactions will be stopped by acetonitrile, and the reaction mixture will be centrifuged at 16 000×g for 10 min. 10 μl of the supernatant will be analyzed by calibrated HPLC to quantify the percentage of the initial amount of compound remaining after the incubation. The HPLC system (Dionex Corp., Sunnyvale, Calif.) includes a Dionex P480 pump, a Phenomenex Luna C18 column (250×2.0 mm, 5 μm) with a guard column (Phenomenex, Torrance, Calif.) and a Dionex UVD340U Ultraviolet (UV) detector. The mobile phase will consist of 0.1% formic acid as reagent A and 0.08% formic acid/water in 80% acetonitrile as reagent B, at a flow rate of 0.2 ml per minute. The gradient will consist of the following linear and isocratic gradient elution changes in reagent B: isocratic at 60% from 0 to 5 min, 60% to 90% from 5 to 39 min, isocratic at 90% until 44 min. Peak quantification will be done based on absorption measured at 260 nm relative to a standard curve obtained by using serial dilutions of the compound.

To estimate oral bioavailability (concentration of compounds in the blood as a function of time after oral administration) and to gain insight into potential brain uptake, compounds (2.5 mg/kg) will be administered to mice by oral gavage in a 0.5% (w/v) carboxymethylcellulose suspension. At 5, 15, 60 and 120 min after compounds are administered the animals will be anesthetized with pentobarbital (50 mg/kg). Blood will be harvested by intracardiac puncture, collected in heparinized tubes, and plasma will be obtained by centrifugation. Mice will be perfused with a HEPES buffer (10 mM, pH 7.2) containing a protease inhibitor cocktail (1 µg/ml leupeptin, 1 µM dithithreitol, 2 mM sodium vanadate, 1 µM phenylmethylsulphonylfluoride), and brains will be removed and weighed. Brain homogenates will be prepared by dounce and sonication in the HEPES buffer containing a protease inhibitor cocktail. Brain homogenates will be centrifuged at 12000×g for 10 minutes and the supernatant acidified by diluting 1:3 with 0.1% formic acid (Fluka). Solid phase extraction followed by HPLC analysis will be used to quantify the amount of compound in brain supernatants. Briefly, cartridges (Sep-Pak® C18, Waters) will be conditioned with 1 ml of acetonitrile (HPLC grade, EMD Biosciences) and equilibrated with 1 ml of water. A structural analog of the compound will be used as an internal standard. The acidified brain supernatant will be added to the cartridge followed by a 1 ml wash with 30% acetonitrile. The compound will be eluted from the cartridge using 80% acetonitrile. The eluate will be evaporated to dryness, reconstituted in 0.08% formic acid/water in 80% acetonitrile and analyzed by HPLC using the following gradient in reagent B: 0% to 60% from 2 to 5 min, isocratic at 65% until 7 min, 65% to 80% from 7 to 12 min, isocratic at 80% until 15 min, 89% to 100% from 15 to 18 min and isocratic at 100% until 23 min. Plasma samples will be deproteinized in 0.1M perchloric acid and centrifuged at 12000×g for 10 min. The supernatant will be neutralized with 1M NaOH then extracted with dichloromethane, and the layers separated at 3000×g for 5 min. The organic phases from three successive extractions will be pooled and then evaporated to dryness under reduced pressure. The dried residue will be reconstituted in 50 µl of reagent B, and 10 µl of the reconstituted material will be analyzed by HPLC using the gradient described above for brain supernatants.

Suppression of CNS versus peripheral inflammation. Mice will be administered by oral gavage of compounds (2.5 mg/kg/day) or diluent (10% DMSO) in a 0.5% (w/v) carboxymethylcellulose suspension once daily for two weeks. After the last administration, mice will be injected intraperitoneally (i.p) with 10 mg/kg of LPS. Control mice will be injected with saline. Six hours after the LPS challenge, mice will be anesthetized with pentobarbital (50 mg/kg) and blood will be drawn by intracardiac puncture, allowed to clot, and centrifuged for serum preparation. Brains will be removed and processed as described above. Levels of IL-β and TNFα in brain supernatants and serum will be measured using a MSD multiplex assay per the manufacturer's instructions (Meso Scale Discovery, Gaithersburg, Md.).

Liver toxicity after chronic in vivo administration of Compound. Mice will be administered by oral gavage either test compounds (2.5 mg/kg/day) or diluent (10% DMSO) in a 0.5% (w/v) carboxymethylcellulose suspension once daily for two weeks. Mice will be anesthetized and sacrificed as described above. Livers will be removed, fixed in 4% (v/v) paraformaldehyde and paraffin-embedded for histology. To assess histological toxicity, 4 µm liver sections will be stained with haematoxylin and eosin. Two independent observers blinded to the treatment groups will perform microscopic assessment of the tissue for injury.

Morris Water Maze. This test is based on the swimming maze test for spatial memory (Morris Learn Mot 12:239-260, 1981; J Neurosci Methods 11:47-60, 1984) and takes advantage of the natural swimming ability of rodents and the ease of manipulating cues around the maze. In this task, a mouse is placed in a pool of liquid that is made opaque by the addition of non-toxic tempera powdered paint. The mouse then swims until as escape platform (hidden just under the surface of the water) is found. Finding the platform enables the mouse to escape from the water and therefore is positively reinforced. When the platform is kept in the same position, the animal quickly learns to use distal cues to locate the position of the platform, even if the mouse is placed in the pool at different starting positions. The experimental protocol for the Morris maze test is as described in Ohno et al, 2005, 2006. Briefly, the pool is 1.2 m in diameter and made of white metal. The water is maintained at 25±1° C. and is made opaque with nontoxic white paint to hide the square, white escape platform (10 cm×10 cm). During training, the platform is submerged (1 cm) below the water surface and remains in the same position to avoid quandrant biases. The mice receive six trialls per day for 4 days (3 blocks of two trials; 1 min intertrial intervals, 1-hour interblock intervals). The mouse is placed into the water facing the wall of the pool and is allowed to search for the platform. The starting position varies among four locations in a pseudorandom manner for each trial. The trial ends when an animal climbs onto the platform or when a maximum of 60 sec has elapsed. The mouse is placed on the platform for 60 sec before and after each trial. At the end of the training, all mice are given a probe test with the platform removed from the pool. The behaviour of the mouse is recorded by a video camera and analyzed computationally for several parameters such as latency to finding the platform, total distance traveled, and percent of time spent in the target quadrant.

At post-operative day 60 mice will be anesthetized and perfused with a Hepes buffer containing a protease inhibitor cocktail. The brains are then removed and longitudinally bisected. The right half of the brain is fixed in a paraformaldehyde/phosphate buffer solution and embedded in paraffin for histological examination, while the hippocampus is isolated from the left hemisphere and snap frozen for biochemical evaluation of endpoints.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the methods etc. which are reported therein which might be used in connection with the invention. Nothing herein is to be construed as an admission that the invention is not entitled to antedate such disclosure by virtue of prior invention.

TABLE 1

| Compound Number | Compound Structure | Synthetic Code |
|---|---|---|
| 1 | (structure) | MW01-ES1 |
| 4 | (structure) | MW01-ES112 |
| 10 | (structure) | MW01-ES159 |
| 11 | (structure) | MW01-ES21 |
| 12 | (structure) | MW01-ES31 |

TABLE 1-continued

| Compound Number | Compound Structure | Synthetic Code |
| --- | --- | --- |
| 13 | 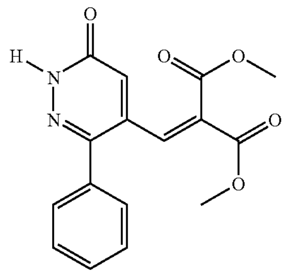 | MW01-ES60 |
| 14 | 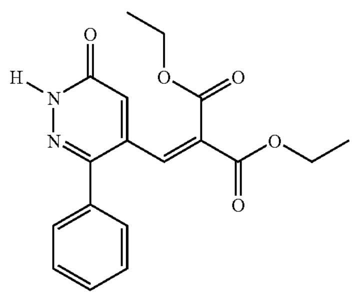 | MW01-ES61 |
| 16 | 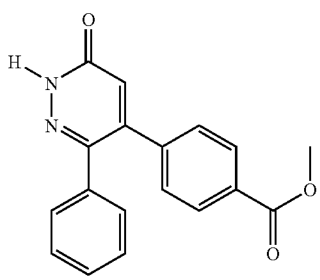 | MW01-ES75 |
| 17 | 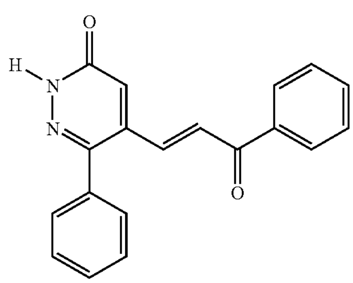 | MW01-ES81 |
| 18 | 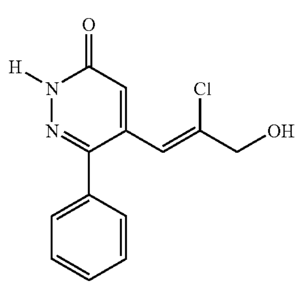 | MW01-ES91 |

TABLE 1-continued

| Compound Number | Compound Structure | Synthetic Code |
|---|---|---|
| 20 | 5-methyl-3-chloro benzo[h]cinnoline | MW01-1-04-L-D04 |
| 23 | N-((1-benzylpiperidin-4-yl)methyl)-6-phenylpyridazin-3-amine | MW01-1-15-L-H07 |
| 24 | 3-methoxy-6-phenylpyridazine | MW01-1-16-L-F05 |
| 25 | N-(3-morpholinopropyl)-6-phenylpyridazin-3-amine | MW01-1-18-L-B09 |
| 31 | 3,5-dibromo-4-phenylpyridazine | MW01-1-035LKM |
| 40 | 3-amino-4-(4-methoxyphenethyl)-6-phenyl-1-(3-carboxypropyl)pyridazinium | MW01-1-09-L-G07 |

TABLE 1-continued

| Compound Number | Compound Structure | Synthetic Code |
|---|---|---|
| 41 | ethyl 3-((2-morpholinoethyl)amino)-6-phenylpyridazine-4-carboxylate | MW01-2-03-L-C02 |
| 43 | 6-hydrazinyl-3,4-diphenylpyridazine | MW01-1-15-L-E09 |
| 44 | 6-hydrazinyl-4-methyl-3-phenylpyridazine | MW01-1-16-L-B11 |
| 47 | 6-(4-chlorophenyl)pyridazin-3-amine | MW01-4-198B-Z |
| 48 | 6-(3,4-dimethoxyphenyl)pyridazin-3-amine | MW01-5-144A-Z |
| 49 | 4-methyl-6-phenylpyridazin-3-amine | MW01-4-198C-Z |
| 50 | 4-(4-chlorophenyl)-6-phenylpyridazin-3-amine | MW01-5-144C-Z |
| 51 | 4-(4-methoxyphenyl)-6-phenylpyridazin-3-amine | MW01-5-144D-Z |

TABLE 1-continued

| Compound Number | Compound Structure | Synthetic Code |
|---|---|---|
| 52 | 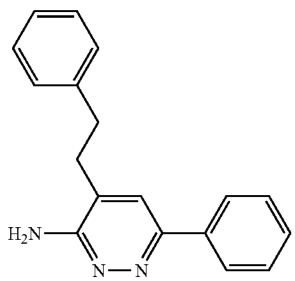 | MW01-5-145A-Z |
| 54 | 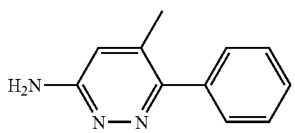 | MW01-5-189Z |
| 55 | 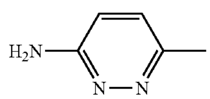 | MW01-5-202B-Z |
| 61 | 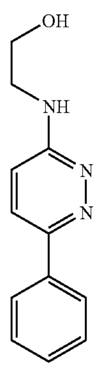 | MW01-1-01-L-D06 |
| 65 | 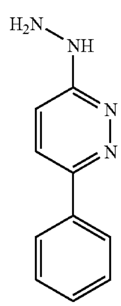 | MW01-1-01-L-E10 |
| 66 | 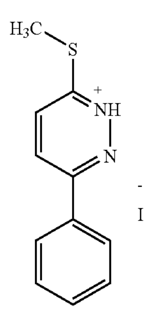 | MW01-1-02-L-E08 |

TABLE 1-continued
| Compound Number | Compound Structure | Synthetic Code |
|---|---|---|
| 70 | 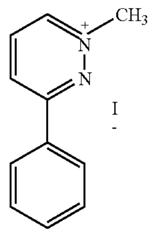 | MW01-1-03-L-D03 |
| 71 | 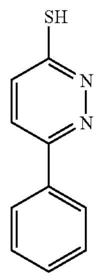 | MW01-1-03-L-F03 |
| 73 | 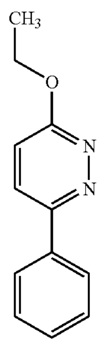 | MW01-1-03-L-G10 |
| 74 | 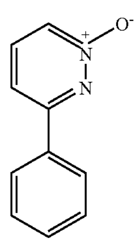 | MW01-1-03-L-H06 |
| 75 | 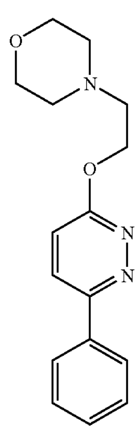 | MW01-1-04-L-C03 |
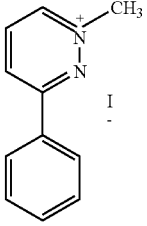

TABLE 1-continued
| Compound Number | Compound Structure | Synthetic Code |
|---|---|---|
| 76 | 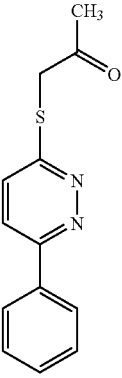 | MW01-1-07-L-H04 |
| 88 | 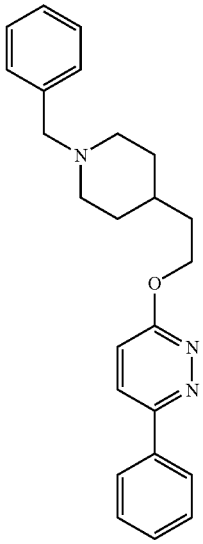 | MW01-1-100-L-A04 |
| 89 | 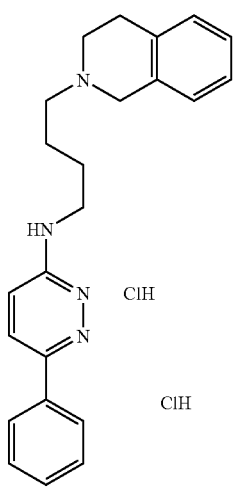 | MW01-1-100-L-A05 |

TABLE 1-continued
| Compound Number | Compound Structure | Synthetic Code |
|---|---|---|
| 90 | 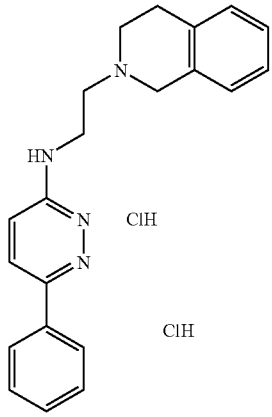 | MW01-1-100-L-A08 |
| 91 | 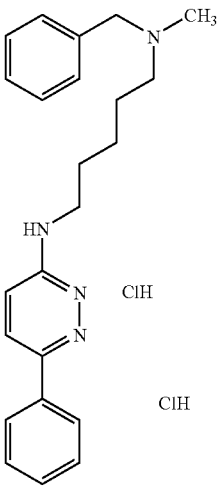 | MW01-1-100-L-A09 |
| 92 | 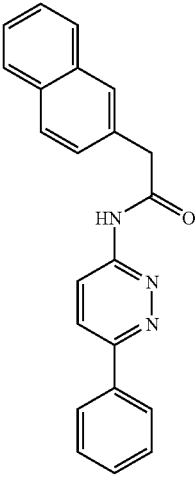 | MW01-1-11-L-E08 |

TABLE 1-continued
| Compound Number | Compound Structure | Synthetic Code |
|---|---|---|
| 94 | 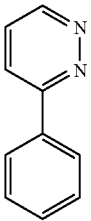 | MW01-1-15-L-G09 |
| 97 | 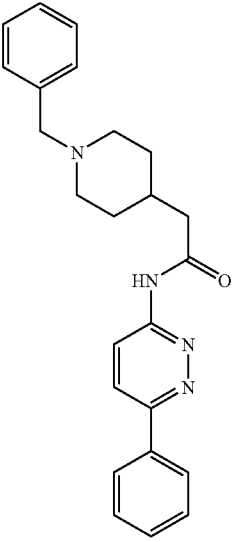 | MW01-1-16-L-G03 |
| 106 | 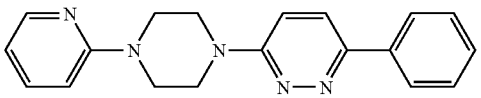 | MW01-9-039Z |
| 107 | 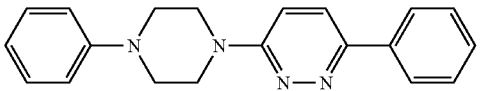 | MW01-9-040Z |
| 108 | 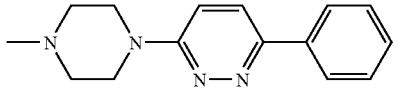 | MW01-9-041Z |
| 109 | 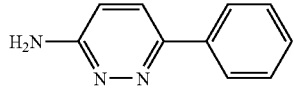 | MW01-9-104A-Z |
| 110 | 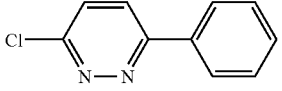 | MW01-9-105A-Z |
| 111 | 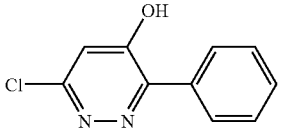 | MW01-9-110A-Z |

TABLE 1-continued

| Compound Number | Compound Structure | Synthetic Code |
|---|---|---|
| 112 | 3,6-diamino-3-phenylpyridazine structure | MW01-9-133A-Z |
| 113 | 3-chloro-4,6-diphenylpyridazine structure | MW01-9-149A-Z |
| 114 | 3,4-dichloro-6-phenylpyridazine structure | MW01-9-159A-Z |
| 115 | 3-chloro-4-methyl-6-phenylpyridazine structure | MW01-9-171Z |
| 116 | 3-chloro-6-methylpyridazine structure | MW01-9-172Z |
| 118 | 1-phenyl-4-(3-chlorophenylamino)phthalazine structure | MW01-9-204Z |
| 120 | N-(2-piperidin-1-ylethyl)-6-phenylpyridazin-3-amine structure | MW01-1-16-L-G08 |

TABLE 1-continued
| Compound Number | Compound Structure | Synthetic Code |
|---|---|---|
| 122 | 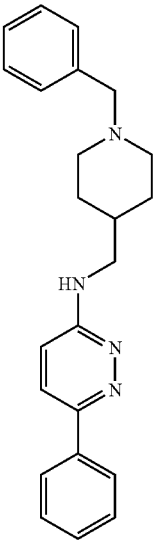 | MW01-1-17-L-G05 |
| 123 | 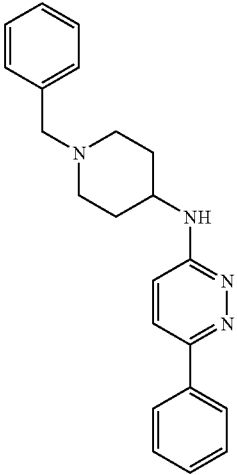 | MW01-1-17-L-G11 |
| 125 | 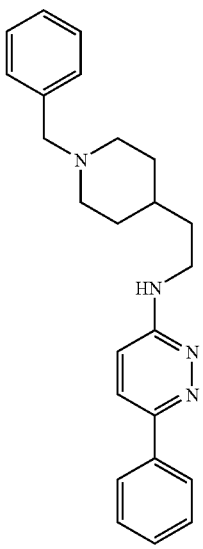 | MW01-1-17-L-H03 |

TABLE 1-continued

| Compound Number | Compound Structure | Synthetic Code |
|---|---|---|
| 127 | 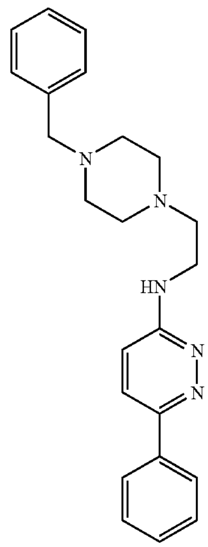 | MW01-1-17-L-H11 |
| 130 | 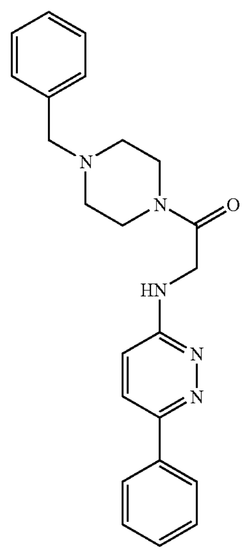 | MW01-1-18-L-A08 |
| 137 | 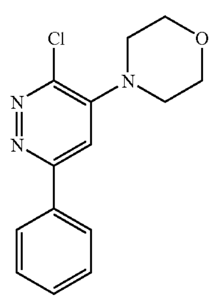 | MW01-2-020SRM |
| 143 | 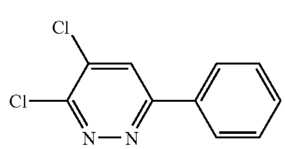 | MW01-2-056WH |

TABLE 1-continued

| Compound Number | Compound Structure | Synthetic Code |
|---|---|---|
| 149 | 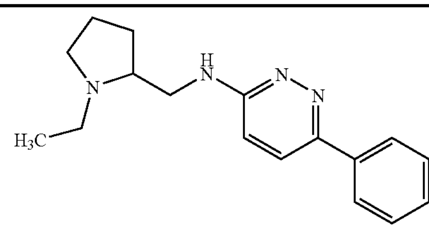 | MW01-1-18-L-A11 |
| 150 | 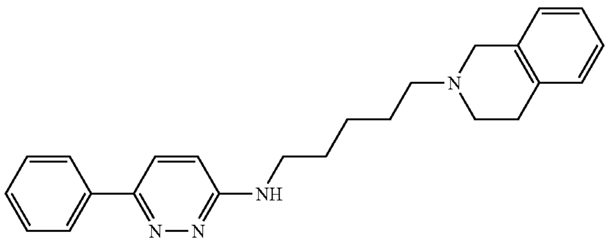 | MW01-1-18-L-B03 |
| 151 | 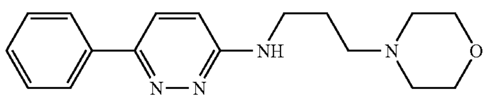 | MW01-1-18-L-B09 |
| 158 | 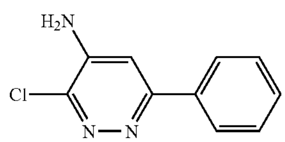 | MW01-3-033WH |
| 159 | 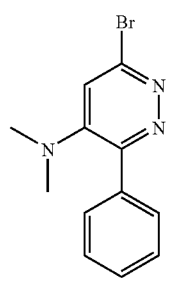 | MW01-3-009WH |
| 173 | 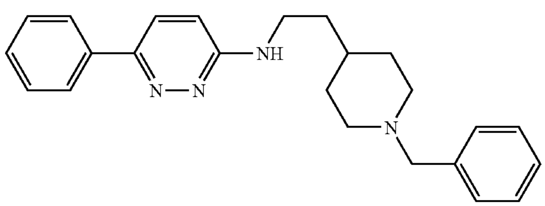 | MW01-2-03-L-D02 |
| 175 | 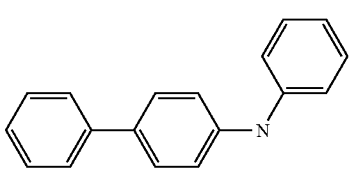 | MW01-2-06-L-F04 |
| 175A | 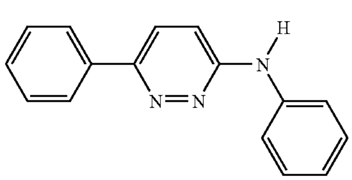 | |

TABLE 1-continued
| Compound Number | Compound Structure | Synthetic Code |
|---|---|---|
| 179 | 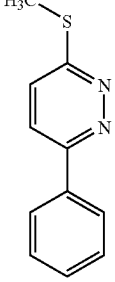 | MW01-2-33-L-B02 |
| 180 | 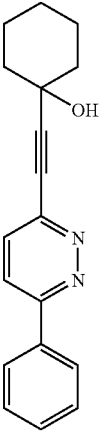 | MW01-3-01-L-G07 |
| 183 | 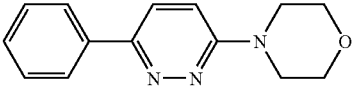 | MW01-5-160WH |
| 184 | 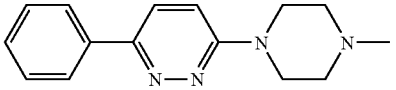 | MW01-5-161WH |
| 189 | 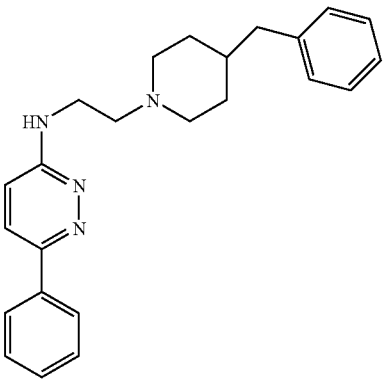 | MW01-6-041WH |

TABLE 1-continued

| Compound Number | Compound Structure | Synthetic Code |
|---|---|---|
| 190 | 6-phenyl-N-(2-aminoethyl)pyridazin-3-amine | MW01-6-044WH |
| 192 | 6-methyl-N-(2-aminoethyl)pyridazin-3-amine | MW01-6-050WH |
| 197 | N-(2-hydroxyethyl)-4,6-diphenylpyridazin-3-amine | MW01-1-01-L-A10 |
| 198 | N-(2-methoxyethyl)-4,6-diphenylpyridazin-3-amine | MW01-1-01-L-B03 |

TABLE 1-continued
| Compound Number | Compound Structure | Synthetic Code |
|---|---|---|
| 199 | 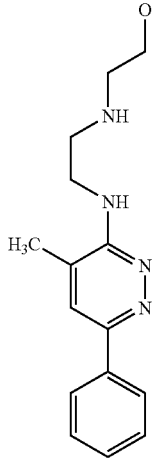 | MW01-1-01-L-B09 |
| 201 | 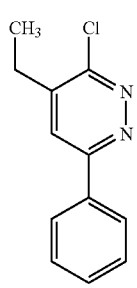 | MW01-1-01-L-E03 |
| 202 | 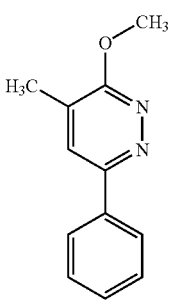 | MW01-1-01-L-E04 |
| 205 | 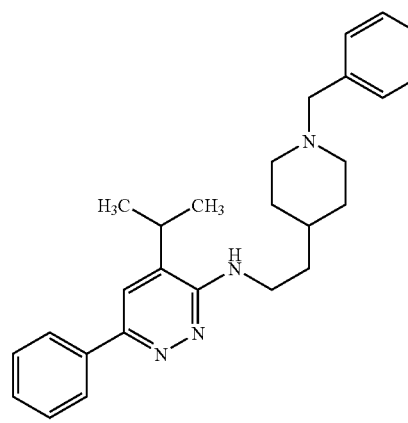 | MW01-1-18-L-B07 |

TABLE 1-continued
| Compound Number | Compound Structure | Synthetic Code |
|---|---|---|
| 208 | 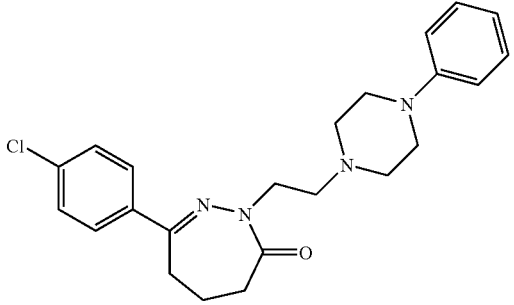 | MW01-1-03-L-G03 |
| 210 | 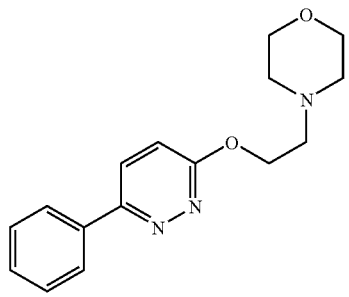 | MW01-1-04-L-C03 |
| 217 | 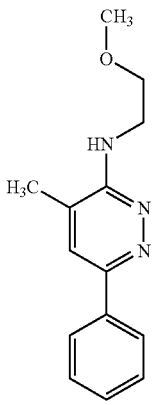 | MW01-1-02-L-E03 |
| 218 | 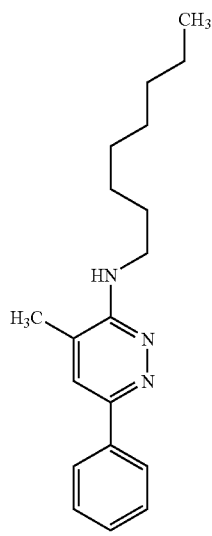 | MW01-1-02-L-E06 |

TABLE 1-continued

| Compound Number | Compound Structure | Synthetic Code |
|---|---|---|
| 221 | 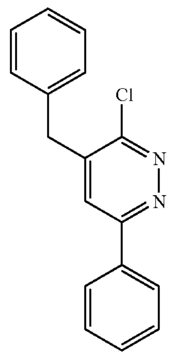 | MW01-1-02-L-F02 |
| 223 | 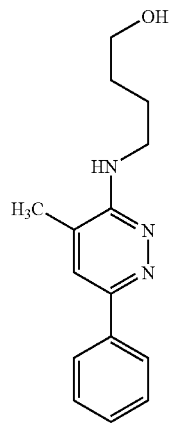 | MW01-1-02-L-F08 |
| 225 | 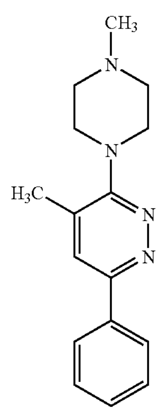 | MW01-1-02-L-G05 |
| 226 | 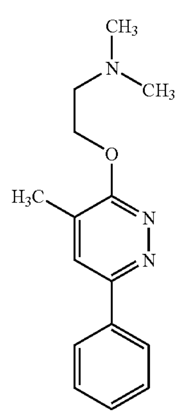 | MW01-1-02-L-G06 |

TABLE 1-continued

| Compound Number | Compound Structure | Synthetic Code |
|---|---|---|
| 227 | 3-((2-methoxyethyl)amino)-4,6-diphenylpyridazine | MW01-1-03-L-A02 |
| 229 | 3-chloro-4-methyl-6-phenylpyridazine | MW01-1-03-L-B09 |
| 230 | 2-((4-methyl-6-phenylpyridazin-3-yl)amino)ethanol | MW01-1-03-L-B10 |
| 231 | 3-bromo-4-methyl-6-phenylpyridazine | MW01-1-03-L-C03 |

TABLE 1-continued

| Compound Number | Compound Structure | Synthetic Code |
|---|---|---|
| 233 | 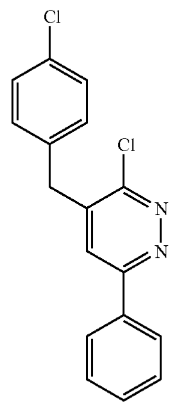 | MW01-1-03-L-C08 |
| 235 | 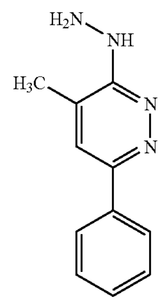 | MW01-1-03-L-E08 |
| 236 | 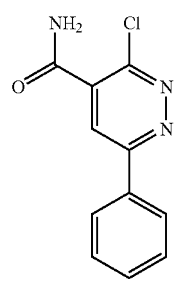 | MW01-1-03-L-E09 |
| 240 | 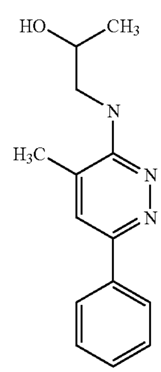 | MW01-1-04-L-A06 |
| 242 | 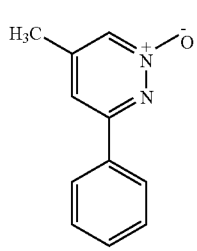 | MW01-1-04-L-D10 |

TABLE 1-continued
| Compound Number | Compound Structure | Synthetic Code |
|---|---|---|
| 250 | 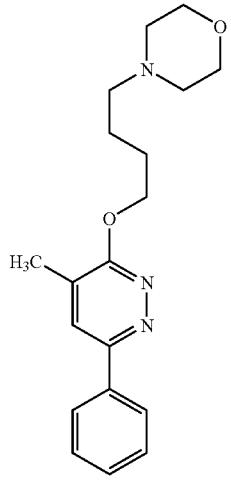 | MW01-1-05-L-B11 |
| 251 | 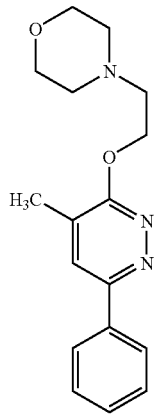 | MW01-1-05-L-C02 |
| 254 | 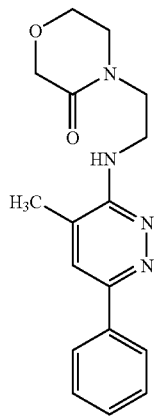 | MW01-1-05-L-G11 |

TABLE 1-continued

| Compound Number | Compound Structure | Synthetic Code |
| --- | --- | --- |
| 255 | 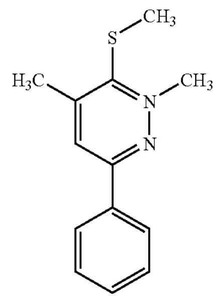 | MW01-1-05-L-H05 |
| 266 | 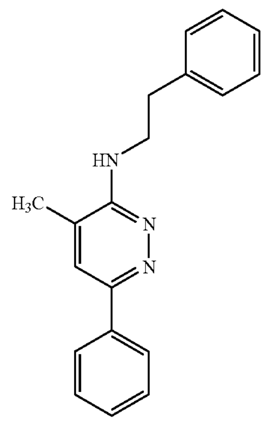 | MW01-1-08-L-D09 |
| 268 | 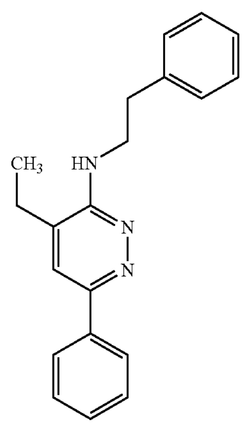 | MW01-1-09-L-C06 |
| 270 | 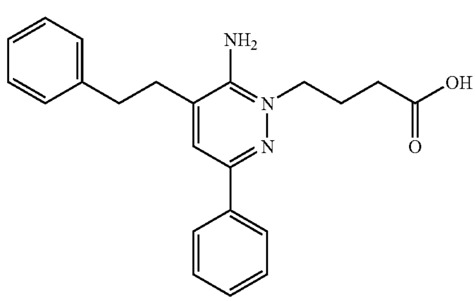 | MW01-1-09-L-G05 |

TABLE 1-continued

| Compound Number | Compound Structure | Synthetic Code |
|---|---|---|
| 271 | 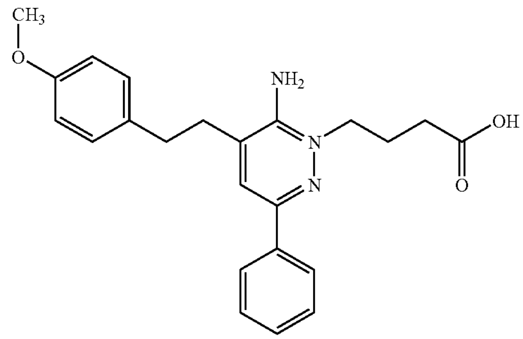 | MW01-1-09-L-G07 |
| 272 | 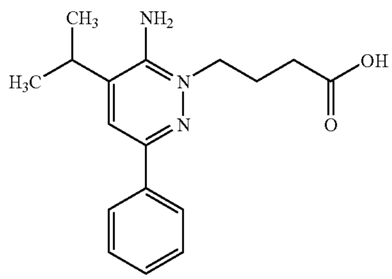 | MW01-1-09-L-G09 |
| 274 | 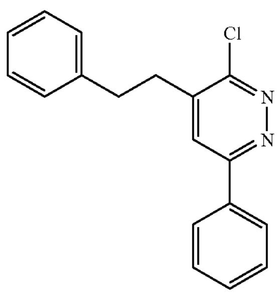 | MW01-1-09-L-H07 |
| 275 | 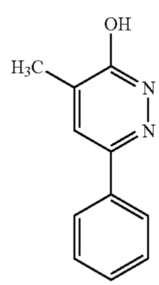 | MW01-1-15-L-A04 |
| 276 | 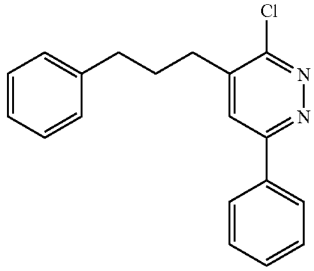 | MW01-1-15-L-B02 |

TABLE 1-continued

| Compound Number | Compound Structure | Synthetic Code |
|---|---|---|
| 278 | 3-chloro-4-isobutyl-6-phenylpyridazine | MW01-1-15-L-B10 |
| 280 | 4-butyl-6-phenylpyridazin-3-ol | MW01-1-15-L-C04 |
| 282 | 3-chloro-4-isopropyl-6-phenylpyridazine | MW01-1-15-L-D03 |
| 284 | 5-methyl-3-phenylpyridazine | MW01-1-15-L-G10 |
| 292 | 3-(3-morpholinopropoxy)-4-methyl-6-phenylpyridazine | MW01-1-17-L-A09 |

TABLE 1-continued
| Compound Number | Compound Structure | Synthetic Code |
|---|---|---|
| 293 | 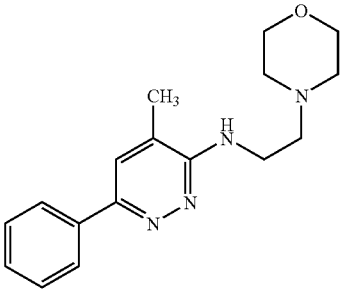 | MW01-1-17-L-A11 |
| 294 | 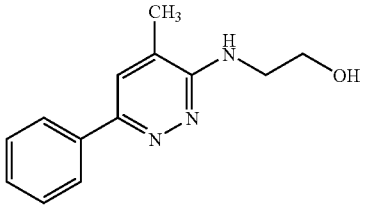 | MW01-1-17-L-B02 |
| 295 | 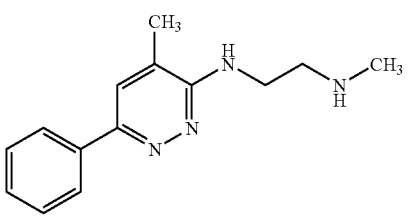 | MW01-1-17-L-B10 |
| 296 | 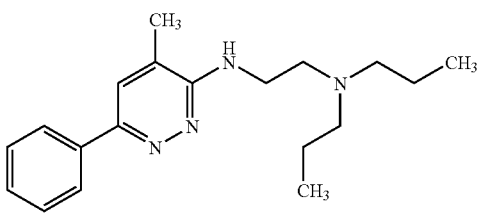 | MW01-1-17-L-E11 |
| 297 | 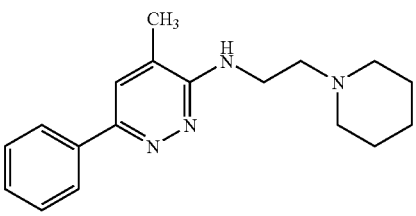 | MW01-1-17-L-F03 |
| 298 | 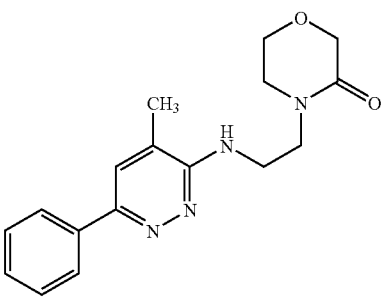 | MW01-1-17-L-H05 |

TABLE 1-continued
| Compound Number | Compound Structure | Synthetic Code |
|---|---|---|
| 299 | 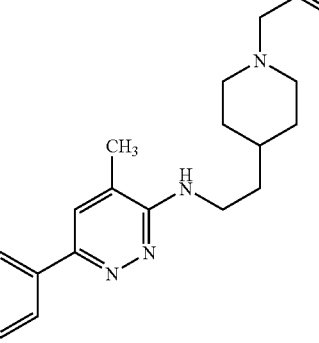 | MW01-1-18-L-A09 |
| 308 | 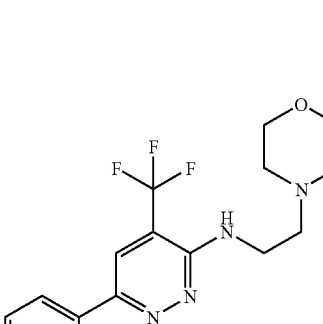 | MW01-2-03-L-B08 |
| 310 | 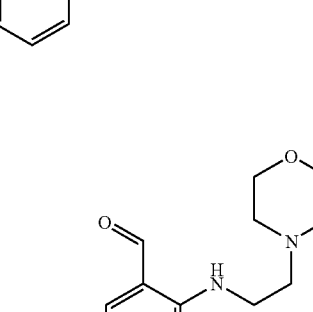 | MW01-2-03-L-C05 |
| 313 | 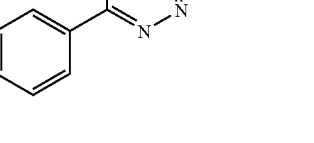 | MW01-2-03-L-G07 |

TABLE 1-continued

| Compound Number | Compound Structure | Synthetic Code |
|---|---|---|
| 318 | 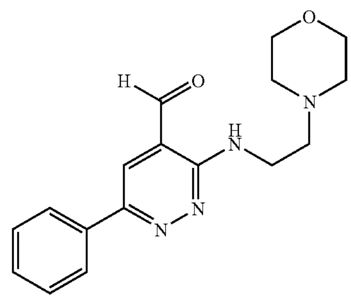 | MW01-2-101-L-H08 |
| 319 | 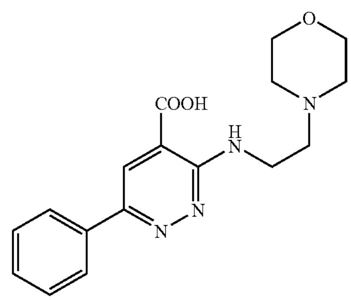 | MW01-2-10-L-E05 |
| 320 | 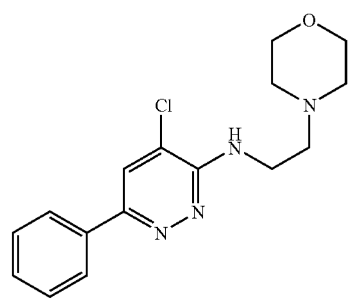 | MW01-2-10-L-E06 |
| 321 | 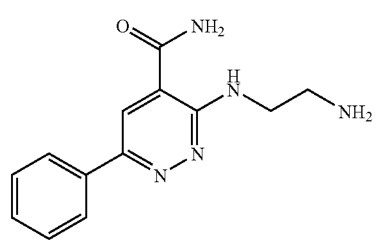 | MW01-2-20-L-B02 |
| 323 | 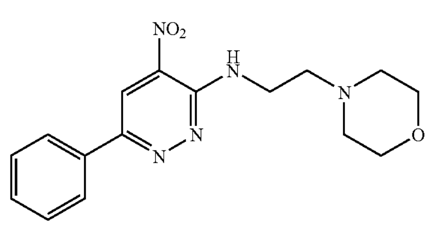 | MW01-2-20-L-D05 |

TABLE 1-continued

| Compound Number | Compound Structure | Synthetic Code |
|---|---|---|
| 324 | 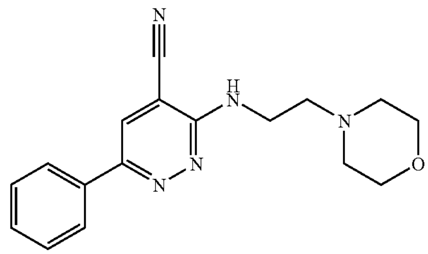 | MW01-2-20-L-E09 |
| 326 | 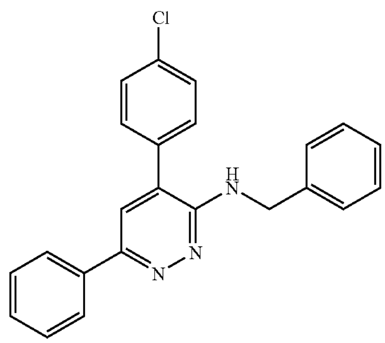 | MW01-2-25-L-H06 |
| 328 | 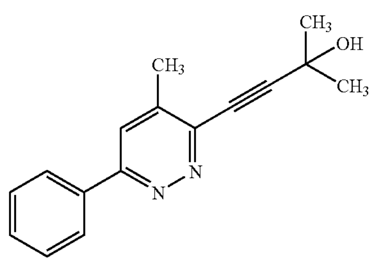 | MW01-3-01-L-G03 |
| 329 | 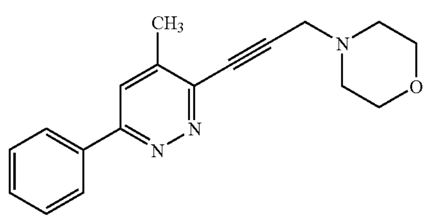 | MW01-3-01-L-G04 |
| 331 | 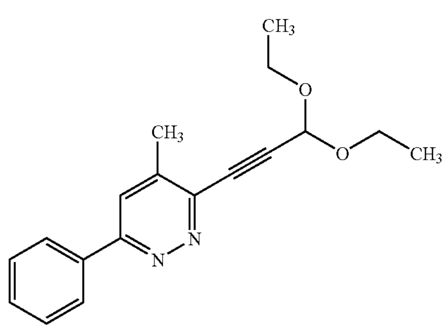 | MW01-3-01-L-G08 |

TABLE 1-continued

| Compound Number | Compound Structure | Synthetic Code |
|---|---|---|
| 332 | 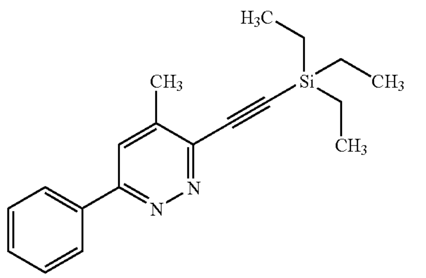 | MW01-3-01-L-G09 |
| 335 | 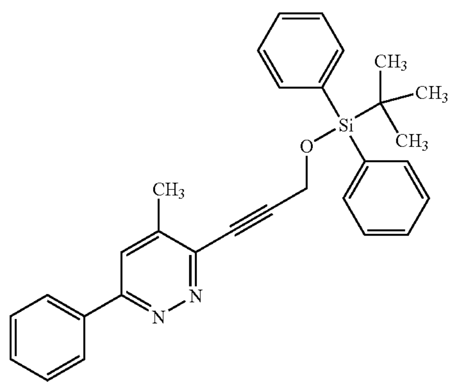 | MW01-3-06-L-E09 |
| 337 | 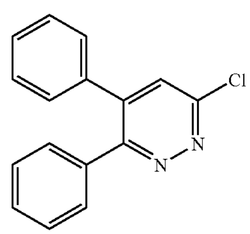 | MW01-1-07-L-G07 |
| 339 | 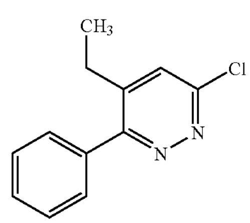 | MW01-1-15-L-C11 |
| 340 | 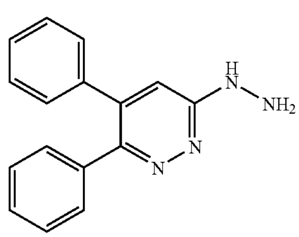 | MW01-1-15-L-E09 |
| 341 | 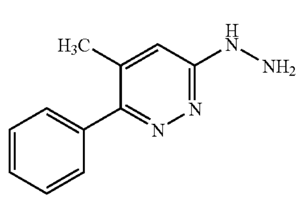 | MW01-1-16-L-B11 |

TABLE 1-continued

| Compound Number | Compound Structure | Synthetic Code |
| --- | --- | --- |
| 346 | (5-ethyl-6-phenylpyridazin-3-yl)-NH-CH₂CH₂-N(CH₂CH₃)₂ | MW01-1-17-L-F10 |
| 347 | (5-ethyl-6-phenylpyridazin-3-yl)-NH-CH₂CH₂-morpholine | MW01-1-17-L-F11 |
| 350 | (5-methyl-6-phenylpyridazin-3-yl)-NH-CH₂-pyrrolizidine | MW01-2-20-L-B11 |
| 352 | methyl 5-methyl-6-phenylpyridazine-3-carboxylate | MW01-3-01-L-F09 |
| 359 | 3-chloro-6-(2,4-dichlorophenyl)-4-cyanopyridazine | MW01-1-03-L-E05 |

TABLE 1-continued
| Compound Number | Compound Structure | Synthetic Code |
|---|---|---|
| 360 | 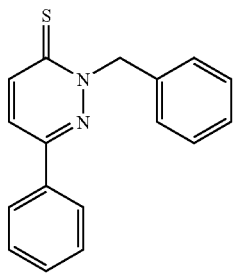 | MW01-1-03-L-A08 |
| 361 | 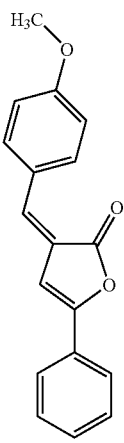 | MW01-1-03-L-H08 |
| 362 | 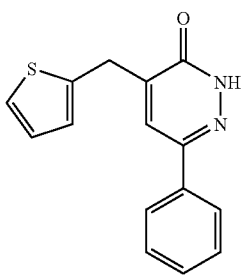 | MW01-1-01-L-H04 |
| 363 | 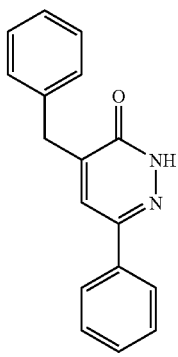 | MW01-1-01-L-H06 |

TABLE 1-continued

| Compound Number | Compound Structure | Synthetic Code |
|---|---|---|
| 366 | 4-methyl-6-(4-chlorophenyl)-2H-pyridazine-3-thione | MW01-1-03-L-E07 |
| 367 | 2-((4-nitrobenzyl)thio)-4,5-dihydro-1H-imidazole | MW01-1-05-L-E05 |
| 368 | 4-methyl-6-(naphthalen-1-yl)-2H-pyridazin-3(2H)-one | MW01-1-03-L-B03 |
| 371 | 2-amino-4-(4-nitrophenyl)thiazole | MW01-1-05-L-E07 |
| 372 | 4-methyl-6-(4-chlorophenyl)-2H-pyridazin-3(2H)-one | MW01-1-03-L-A03 |

TABLE 1-continued
| Compound Number | Compound Structure | Synthetic Code |
| --- | --- | --- |
| 373 | 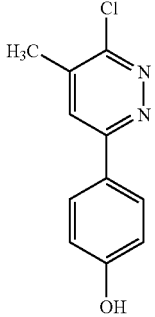 | MW01-1-03-L-E03 |
| 374 | 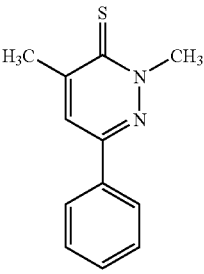 | MW01-1-01-L-H10 |
| 375 | 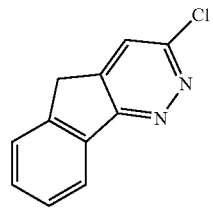 | MW01-1-04-L-H08 |
| 376 | 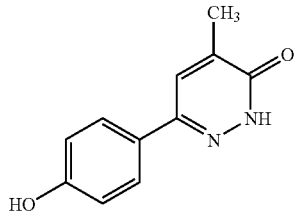 | MW01-1-01-L-G10 |
| 377 | 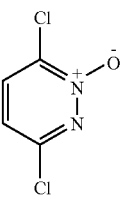 | MW01-1-03-L-G11 |
| 380 | 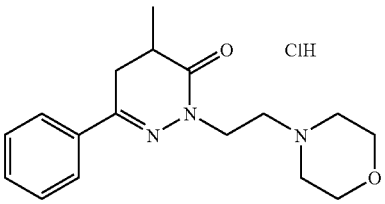 | MW01-1-04-L-B07 |

TABLE 1-continued
| Compound Number | Compound Structure | Synthetic Code |
|---|---|---|
| 381 | 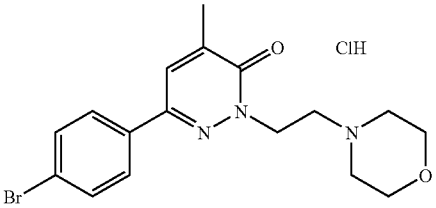 | MW01-1-04-L-C09 |
| 382 | 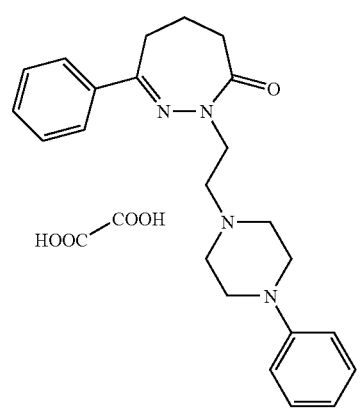 | MW01-1-10-L-G05 |
TABLE 2
| Compound Number | Compound Structure | Synthetic Code |
|---|---|---|
| 22 | 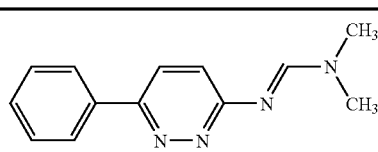 | MW01-1-15-L-E08 |
| 26 | 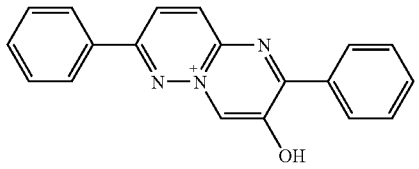 | MW01-2-02-L-H09 |
| 29 | 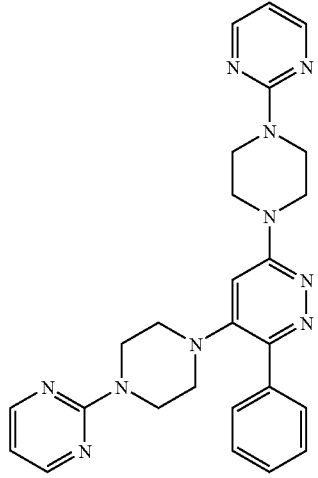 | MW01-1-030A-LKM |

TABLE 2-continued

| Compound Number | Compound Structure | Synthetic Code |
|---|---|---|
| 30 | 6-bromo-5-[4-(pyrimidin-2-yl)piperazin-1-yl]-3-phenylpyridazine | MW01-1-030B-LKM |
| 32 | tert-butyl N-[2-[(6-bromo-3-phenylpyridazin-4-yl)amino]ethyl]carbamate | MW01-1-048AB-LKM |
| 33 | 6-[4-(pyrimidin-2-yl)piperazin-1-yl]-4-(4-fluorophenyl)-3-phenylpyridazine | MW01-2-065LKM |
| 34 | 6-[4-(pyrimidin-2-yl)piperazin-1-yl]-5-[(4-chlorophenyl)amino]-3-phenylpyridazine | MW01-2-127LKM |

TABLE 2-continued

| Compound Number | Compound Structure | Synthetic Code |
|---|---|---|
| 35 | 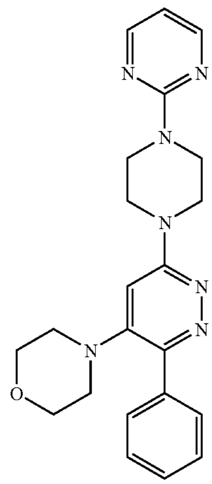 | MW01-2-134LKM |
| 36 | 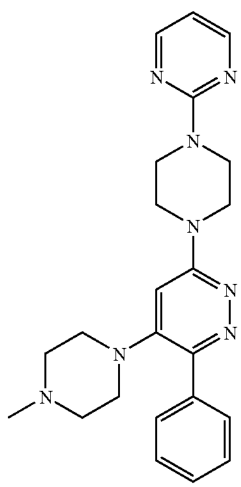 | MW01-2-146LKM |
| 37 | 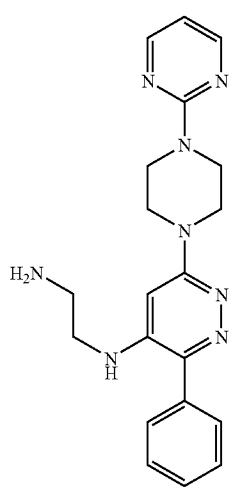 | MW01-2-147LKM |
| 38 | 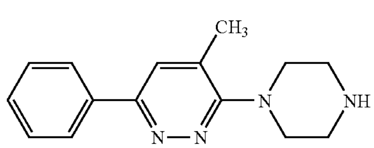 | MW01-1-02-L-B11 |

TABLE 2-continued
| Compound Number | Compound Structure | Synthetic Code |
|---|---|---|
| 39 | 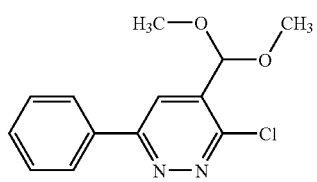 | MW01-1-04-L-F10 |
| 42 | 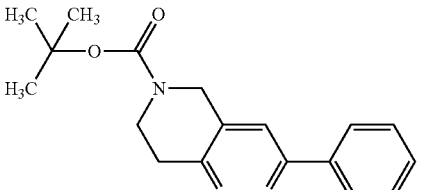 | MW01-2-33-L-A11 |
| 45 | 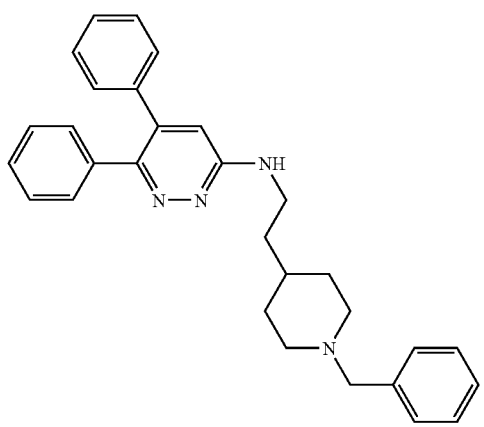 | MW01-1-17-L-E06 |
| 46 | 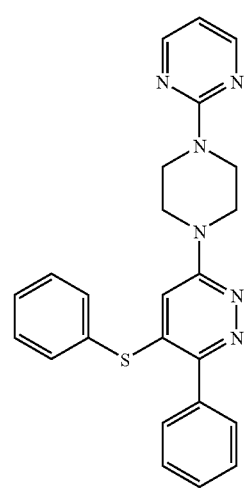 | MW01-1-045MAS |

TABLE 2-continued

| Compound Number | Compound Structure | Synthetic Code |
|---|---|---|
| 53 | 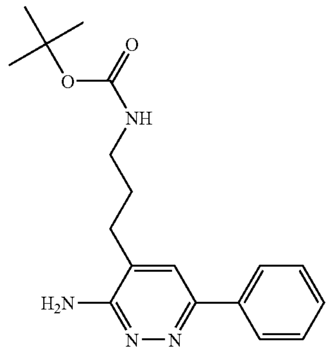 | MW01-5-145B-Z |
| 56 | 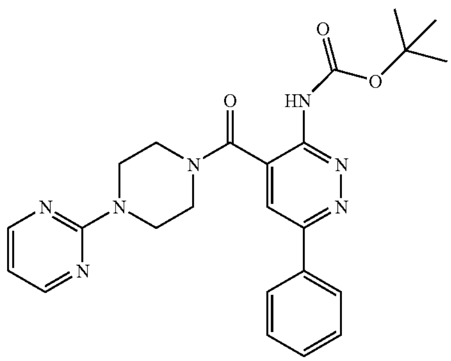 | MW01-7-127AB-Z |
| 60 | 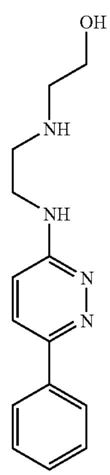 | MW01-1-01-L-B04 |
| 62 | 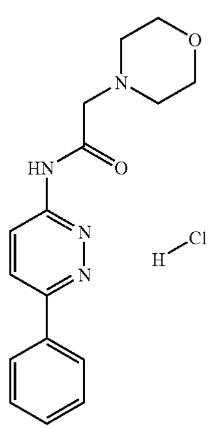 | MW01-1-01-L-D10 |

TABLE 2-continued
| Compound Number | Compound Structure | Synthetic Code |
|---|---|---|
| 63 | 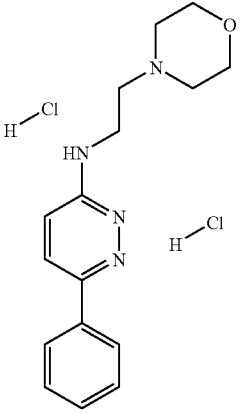 | MW01-1-01-L-E02 |
| 64 | 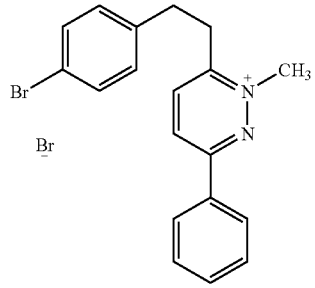 | MW01-1-01-L-E08 |
| 67 | 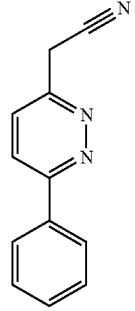 | MW01-1-02-L-H10 |
| 68 | 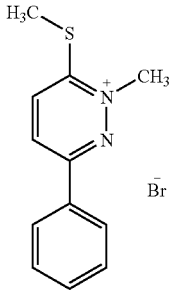 | MW01-1-03-L-A05 |

TABLE 2-continued
| Compound Number | Compound Structure | Synthetic Code |
|---|---|---|
| 69 | 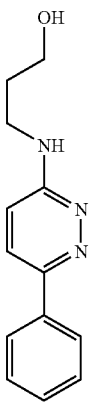 | MW01-1-03-L-B08 |
| 72 | 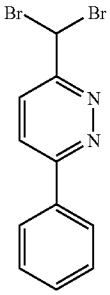 | MW01-1-03-L-G09 |
| 87 | 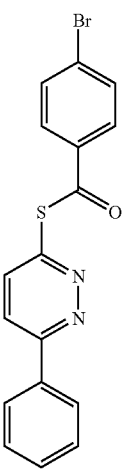 | MW01-1-08-L-E11 |

TABLE 2-continued

| Compound Number | Compound Structure | Synthetic Code |
|---|---|---|
| 93 | 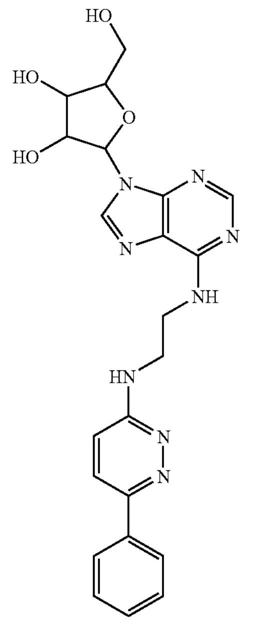 | MW01-1-13-L-G06 |
| 95 | 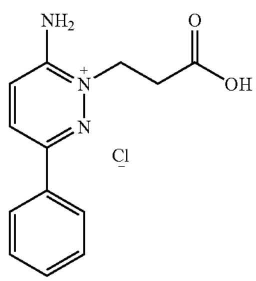 | MW01-1-16-L-D09 |
| 96 | 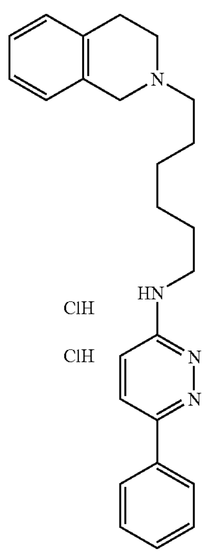 | MW01-1-16-L-E02 |
| 105 | 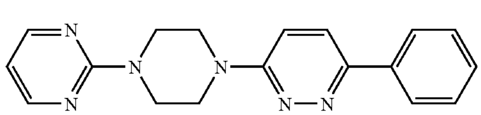 | MW01-9-038Z |

TABLE 2-continued
| Compound Number | Compound Structure | Synthetic Code |
|---|---|---|
| 121 | 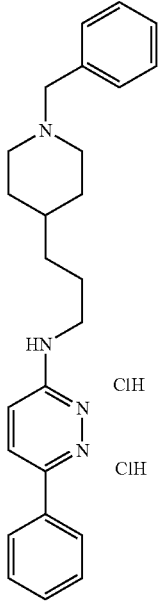 ClH ClH | MW01-1-17-L-G04 |
| 124 | 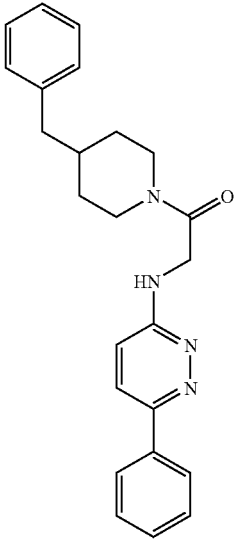 | MW01-1-17-L-H02 |
| 126 | 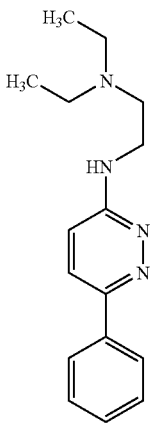 | MW01-1-17-L-H07 |

TABLE 2-continued
| Compound Number | Compound Structure | Synthetic Code |
|---|---|---|
| 128 | 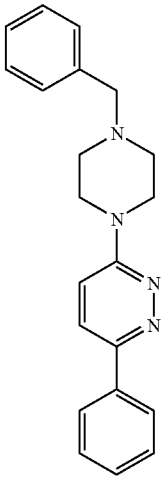 | MW01-1-18-L-A02 |
| 129 | 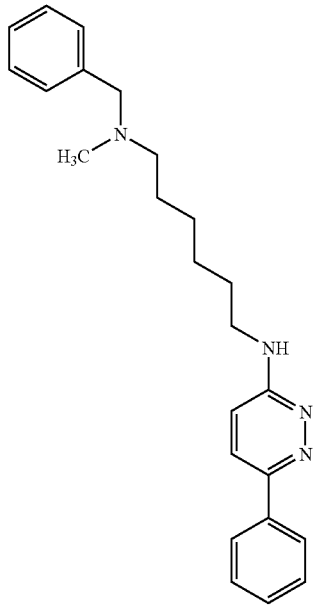 | MW01-1-18-L-A03 |
| 136 | 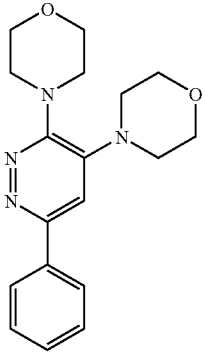 | MW01-2-018SRM |

TABLE 2-continued
| Compound Number | Compound Structure | Synthetic Code |
|---|---|---|
| 138 | 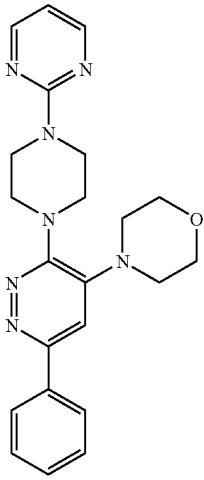 | MW01-2-023SRM |
| 147 | 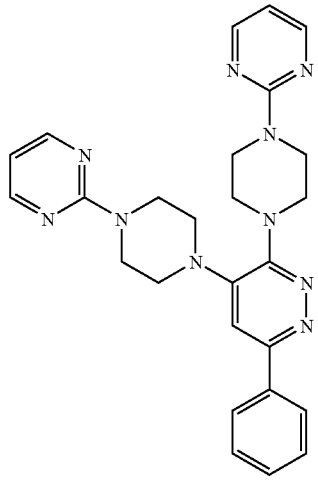 | MW01-2-177A-WH |
| 148 | 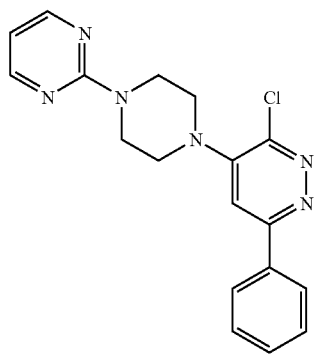 | MW01-2-177B-WH |

TABLE 2-continued
| Compound Number | Compound Structure | Synthetic Code |
|---|---|---|
| 153 | 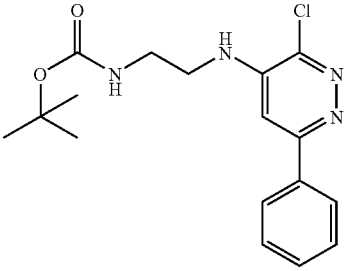 | MW01-2-184WH |
| 155 | 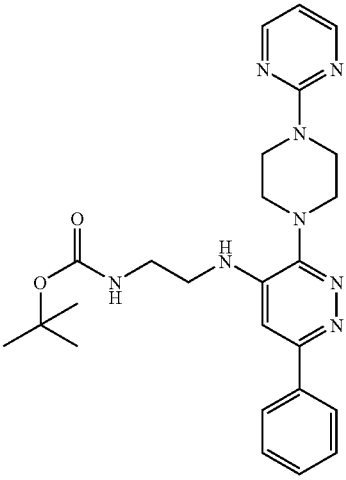 | MW01-2-191A-WH |
| 156 | 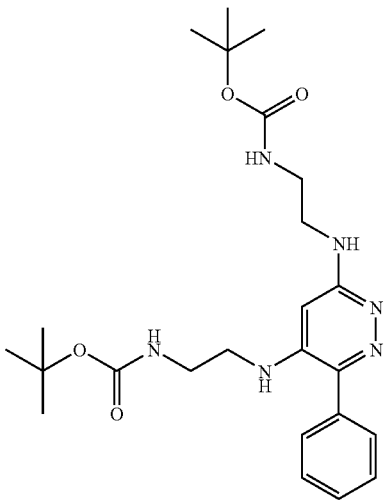 | MW01-2-193B-WH |
| 157 | 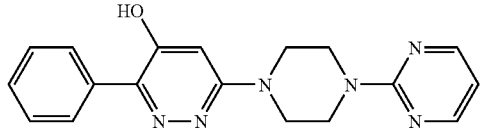 | MW01-3-003WH |
| 160 | 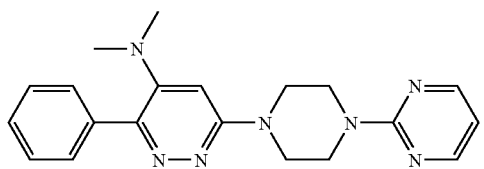 | MW01-3-019A-WH |

TABLE 2-continued

| Compound Number | Compound Structure | Synthetic Code |
|---|---|---|
| 161 | 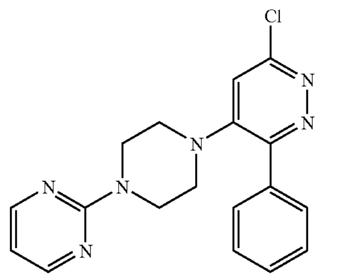 | MW01-3-060A-WH |
| 162 | 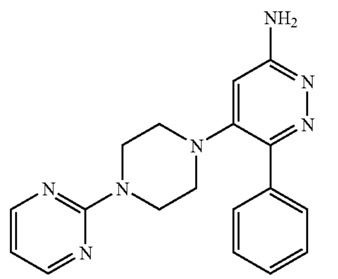 | MW01-3-072WH |
| 163 | 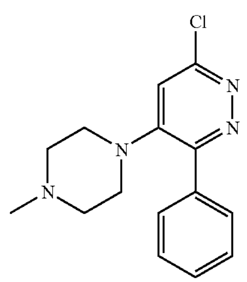 | MW01-3-117WH |
| 164 | 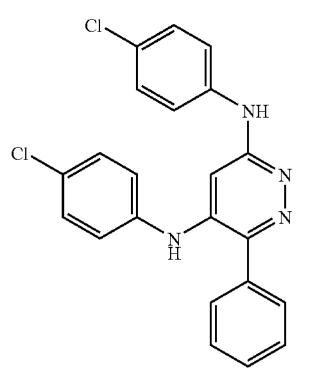 | MW01-3-118WH |
| 166 | 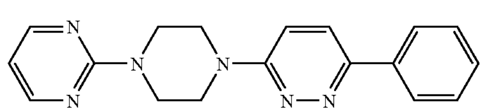 | MW01-3-183WH |
| 171 | 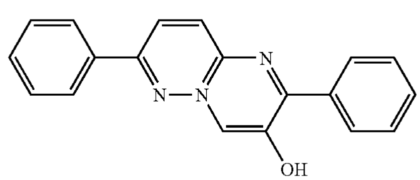 | MW01-2-03-L-G03 |

TABLE 2-continued

| Compound Number | Compound Structure | Synthetic Code |
| --- | --- | --- |
| 172 | [Structure: 6-phenylpyridazin-3-yl-NH-C(=O)-CH2-morpholine] | MW01-2-03-L-C04 |
| 174 | [Structure: 6-phenylpyridazin-3-yl-N(phenyl)-C(=O)-CH2-morpholine] | MW01-2-03-L-G03 |
| 176 | [Structure: 6-phenylpyridazin-3-yl-NH-C(=O)-O-CH2-CH3] | MW01-2-102-L-C11 |
| 177 | [Structure: 3-amino-1-benzyl-6-phenylpyridazinium] | MW01-2-21-L-F04 |
| 178 | [Structure: 1-(6-phenylpyridazin-3-yl)pyrrolidine-2-carboxylic acid] | MW01-2-24-L-G09 |

TABLE 2-continued

| Compound Number | Compound Structure | Synthetic Code |
|---|---|---|
| 181A | 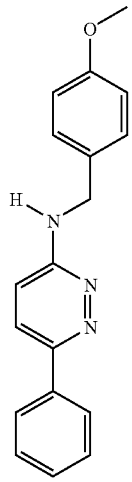 | |
| 186 | 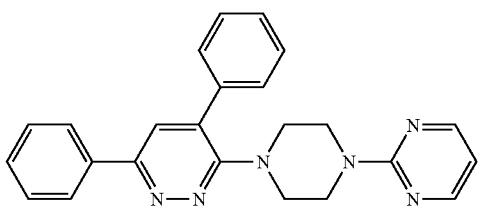 | MW01-5-188WH |
| 188 | 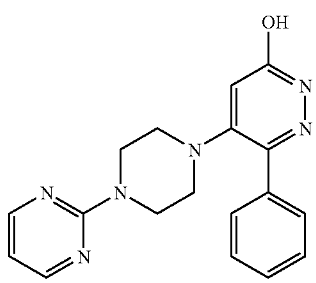 | MW01-6-003WH |
| 191 | 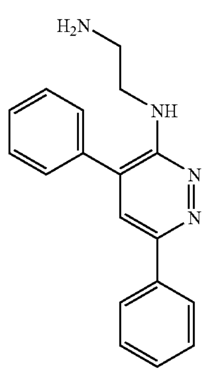 | MW01-6-046WH |

TABLE 2-continued
| Compound Number | Compound Structure | Synthetic Code |
|---|---|---|
| 200 | 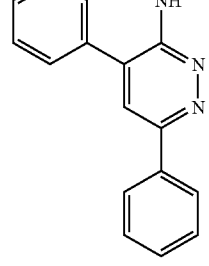 | MW01-1-01-L-C06 |
| 203 | 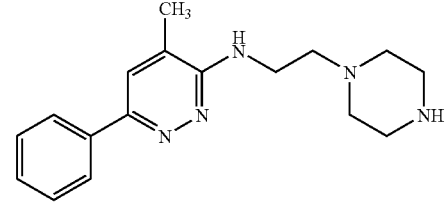 | MW01-2-03-L-D09 |
| 204 | 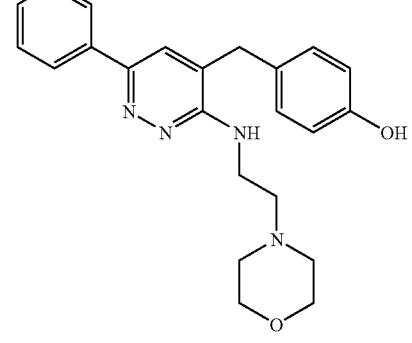 | MW01-1-01-L-B02 |
| 206 | 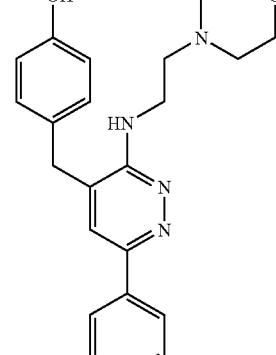 | MW01-2-03-L-D09 |

TABLE 2-continued
| Compound Number | Compound Structure | Synthetic Code |
|---|---|---|
| 207 | 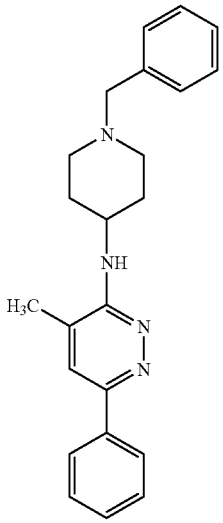 | MW01-2-03-L-G04 |
| 209 | 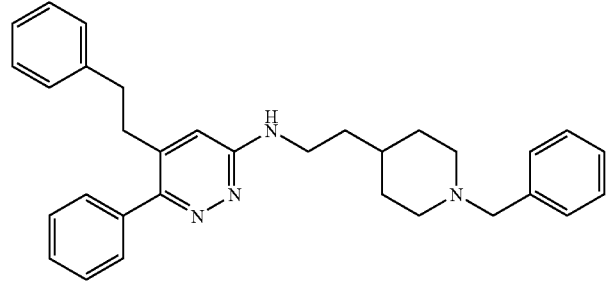 | MW01-1-17-L-E05 |
| 211 | 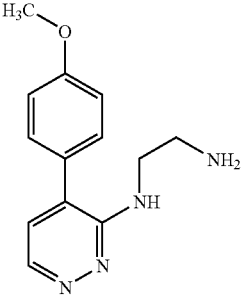 | MW01-1-04-L-C03 |
| 212 | 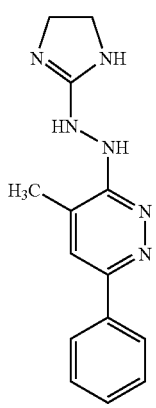 | MW01-1-01-L-E11 |

TABLE 2-continued
| Compound Number | Compound Structure | Synthetic Code |
|---|---|---|
| 213 | 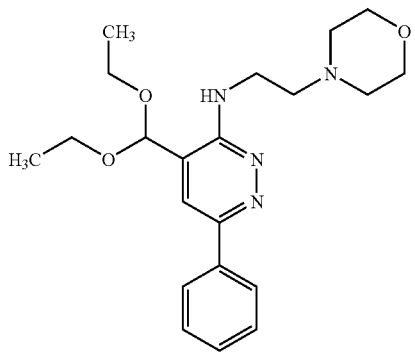 | MW01-1-01-L-F02 |
| 214 | 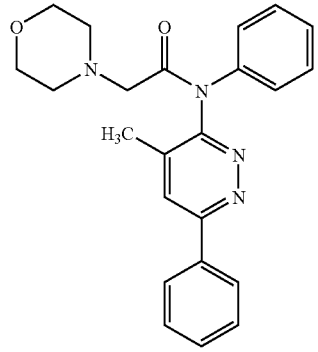 | MW01-1-01-L-F03 |
| 215 | 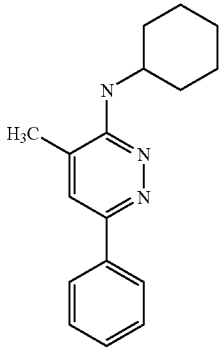 | MW01-1-01-L-G08 |

TABLE 2-continued
| Compound Number | Compound Structure | Synthetic Code |
|---|---|---|
| 216 | 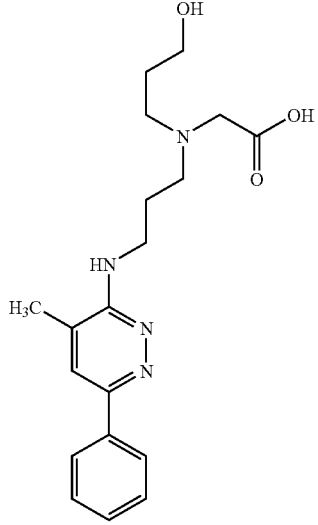 | MW01-1-02-L-D11 |
| 219 | 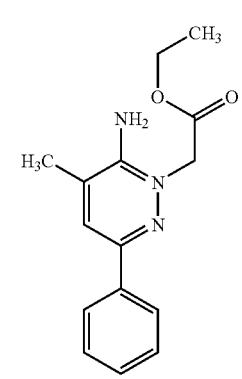 | MW01-1-02-L-E04 |
| 220 | 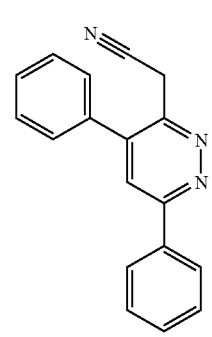 | MW01-1-02-L-E11 |
| 222 | 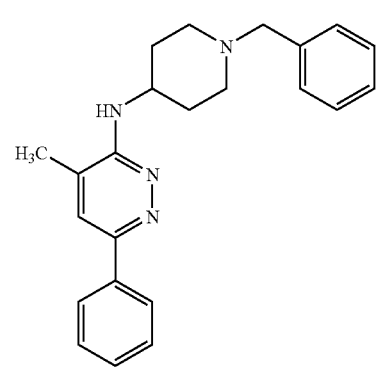 | MW01-1-02-L-F04 |

TABLE 2-continued
| Compound Number | Compound Structure | Synthetic Code |
|---|---|---|
| 224 | 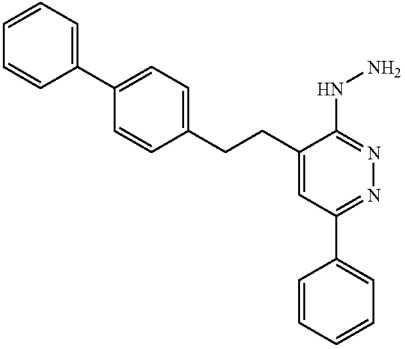 | MW01-1-02-L-F09 |
| 228 | 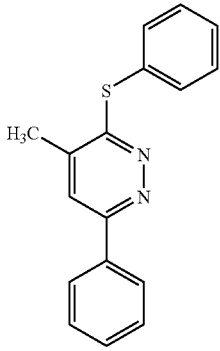 | MW01-1-03-L-A04 |
| 232 | 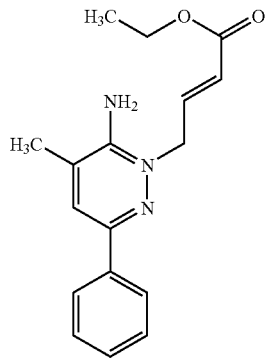 | MW01-1-03-L-C04 |
| 234 | 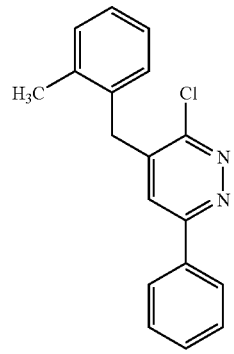 | MW01-1-03-L-E04 |

TABLE 2-continued
| Compound Number | Compound Structure | Synthetic Code |
|---|---|---|
| 237 | 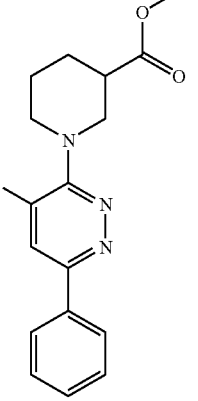 | MW01-1-03-L-E10 |
| 238 | 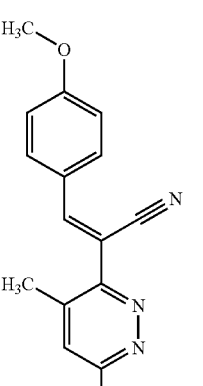 | MW01-1-03-L-G02 |
| 239 | 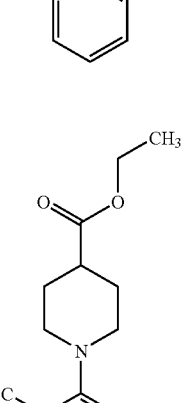 | MW01-1-03-L-H04 |

TABLE 2-continued
| Compound Number | Compound Structure | Synthetic Code |
|---|---|---|
| 241 | 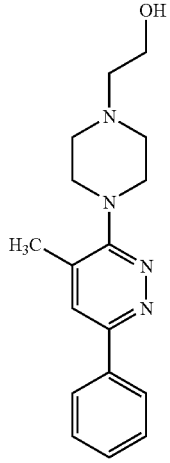 | MW01-1-04-L-D08 |
| 243 | 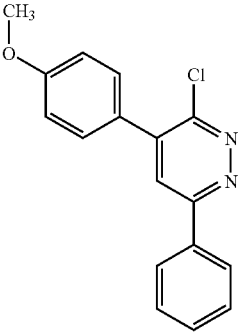 | MW01-1-04-L-E03 |
| 244 | 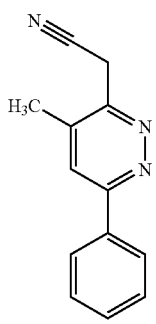 | MW01-1-04-L-E04 |
| 245 | 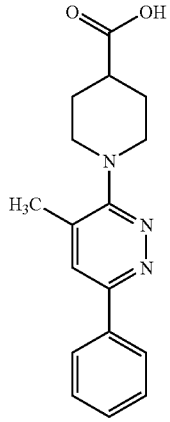 | MW01-1-04-L-E09 |

TABLE 2-continued
| Compound Number | Compound Structure | Synthetic Code |
|---|---|---|
| 246 | 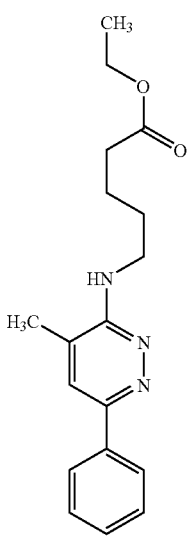 | MW01-1-04-L-F06 |
| 247 | 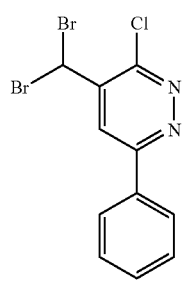 | MW01-1-04-L-G06 |
| 248 | 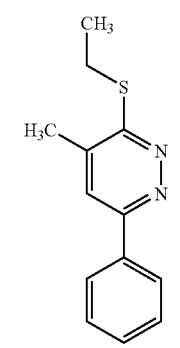 | MW01-1-04-L-H06 |
| 249 | 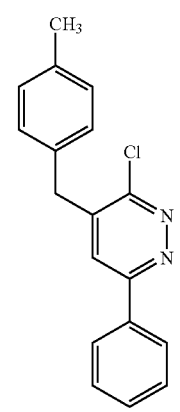 | MW01-1-04-L-H07 |

TABLE 2-continued

| Compound Number | Compound Structure | Synthetic Code |
|---|---|---|
| 252 | 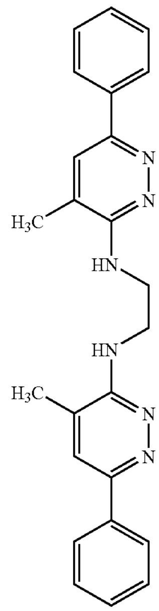 | MW01-1-05-L-F05 |
| 253 | 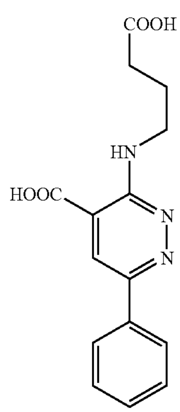 | MW01-1-05-L-G10 |
| 256 | 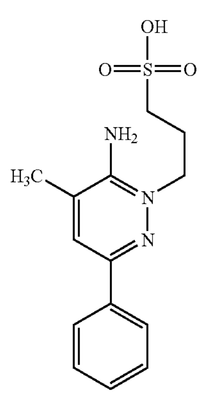 | MW01-1-05-L-H07 |

TABLE 2-continued

| Compound Number | Compound Structure | Synthetic Code |
|---|---|---|
| 257 | 3-hydrazinyl-6-phenylpyridazine-4-carbonitrile | MW01-1-05-L-H09 |
| 258 | 4-methyl-1-methyl-6-phenylpyridazin-3-amine | MW01-1-05-L-H11 |
| 259 | 4-methyl-6-phenyl-3-(pyrrolidin-1-yl)pyridazine | MW01-1-07-L-E07 |
| 260 | 3-((4-chlorophenyl)thio)-4-methyl-6-phenylpyridazine | MW01-1-07-L-G09 |

TABLE 2-continued

| Compound Number | Compound Structure | Synthetic Code |
|---|---|---|
| 261 | 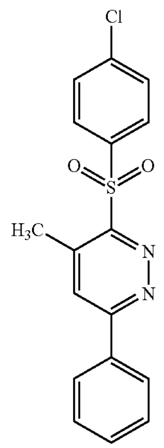 | MW01-1-07-L-H03 |
| 262 | 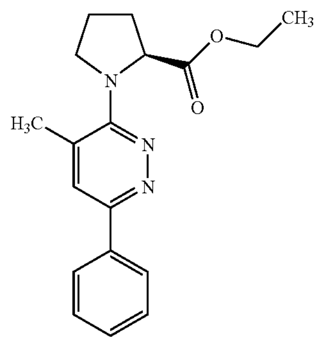 | MW01-1-07-L-H05 |
| 263 | 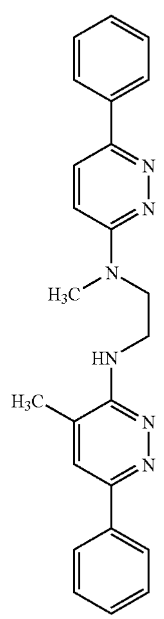 | MW01-1-07-L-H06 |

TABLE 2-continued

| Compound Number | Compound Structure | Synthetic Code |
|---|---|---|
| 264 | 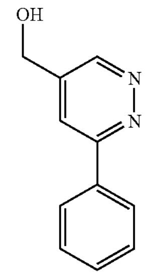 | MW01-1-08-L-C07 |
| 265 | 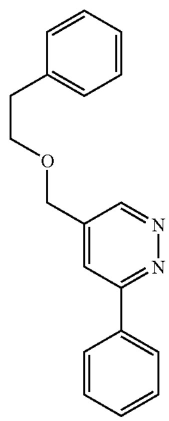 | MW01-1-08-L-C09 |
| 267 | 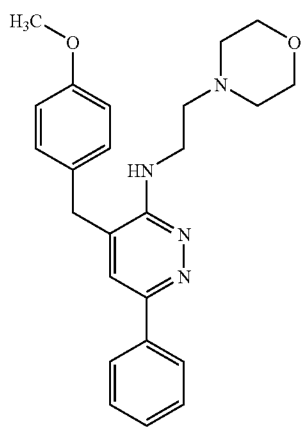 | MW01-1-08-L-E04 |
| 269 | 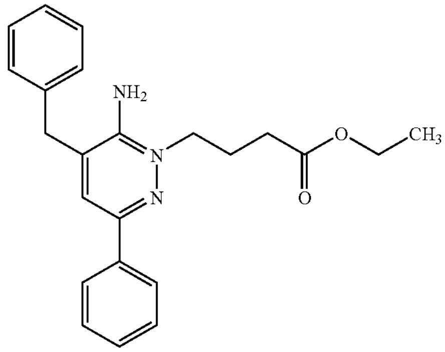 | MW01-1-09-L-G04 |

TABLE 2-continued
| Compound Number | Compound Structure | Synthetic Code |
|---|---|---|
| 273 | 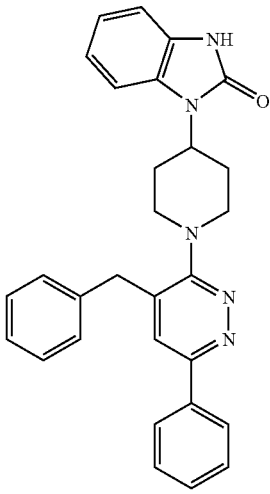 | MW01-1-09-L-G11 |
| 277 | 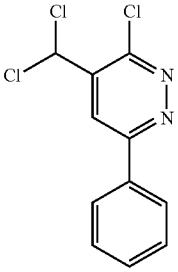 | MW01-1-15-L-B07 |
| 279 | 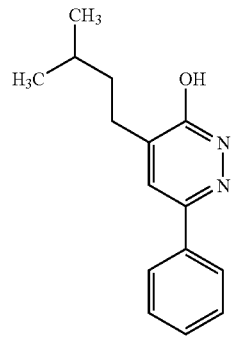 | MW01-1-15-L-B11 |
| 281 | 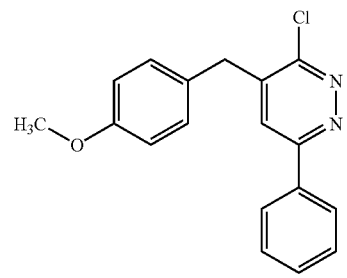 | MW01-1-15-L-D02 |

TABLE 2-continued
| Compound Number | Compound Structure | Synthetic Code |
|---|---|---|
| 282 | 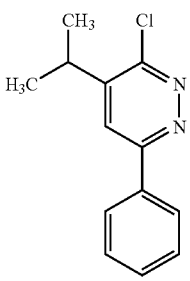 | MW01-1-15-L-D03 |
| 283 | 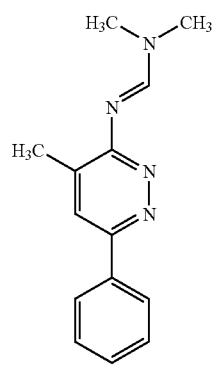 | MW01-1-15-L-E10 |
| 285 | 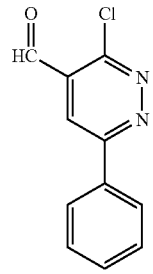 | MW01-1-15-L-H09 |
| 286 | 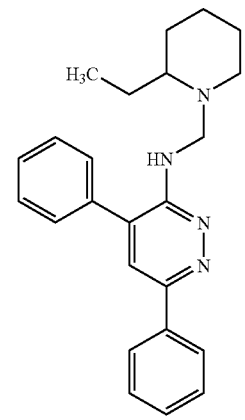 | MW01-1-16-L-E05 |
| 287 | 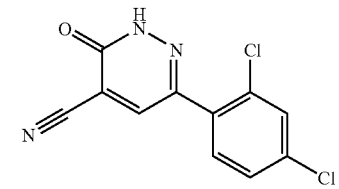 | MW01-1-01-L-F11 |

TABLE 2-continued

| Compound Number | Compound Structure | Synthetic Code |
|---|---|---|
| 288 | 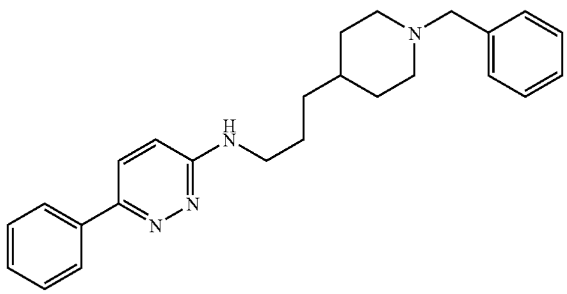 | MW01-1-17-L-B05 |
| 290 | 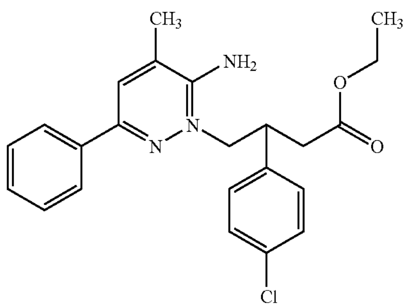 | MW01-1-16-L-E08 |
| 291 | 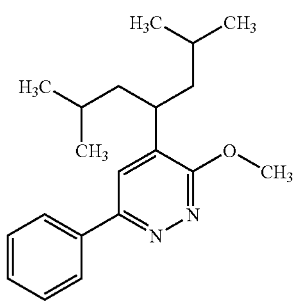 | MW01-1-16-L-G07 |
| 297 | 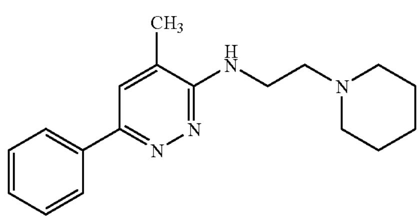 | MW01-1-17-L-F03 |
| 300 | 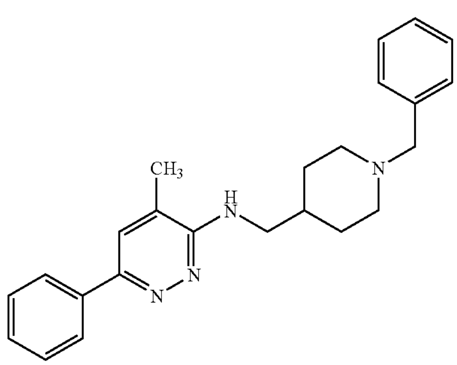 | MW01-1-18-L-B04 |

TABLE 2-continued

| Compound Number | Compound Structure | Synthetic Code |
|---|---|---|
| 301 | 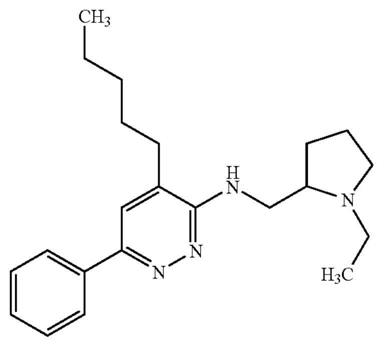 | MW01-1-18-L-B10 |
| 302 | 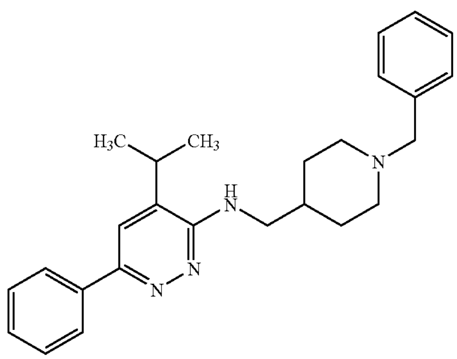 | MW01-1-18-L-B11 |
| 303 | 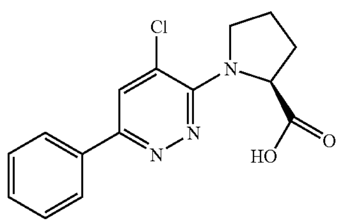 | MW01-1-18-L-C05 |
| 304 | 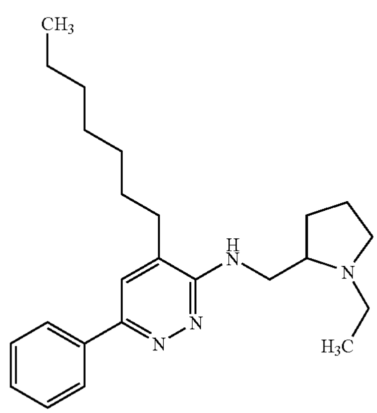 | MW01-1-18-L-C06 |
| 305 | 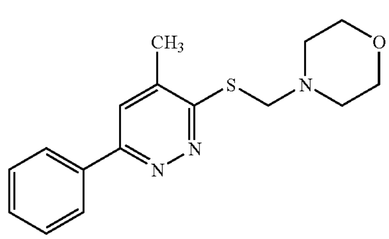 | MW01-1-18-L-C08 |

TABLE 2-continued

| Compound Number | Compound Structure | Synthetic Code |
|---|---|---|
| 306 | 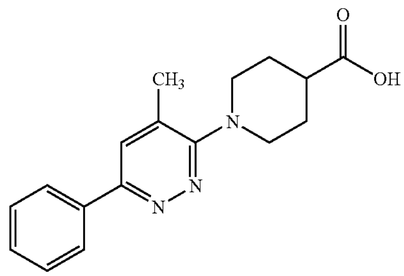 | MW01-1-18-L-C10 |
| 307 | 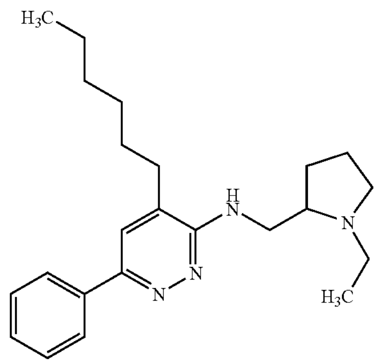 | MW01-1-18-L-D04 |
| 309 | 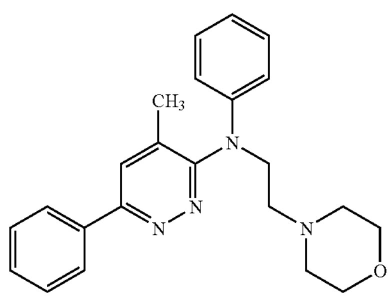 | MW01-2-03-L-C03 |
| 311 | 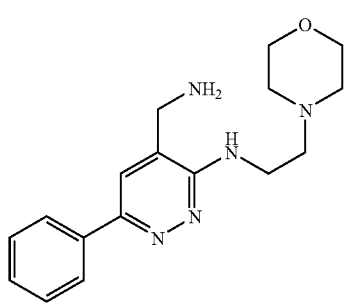 | MW01-2-03-L-D07 |
| 312 | 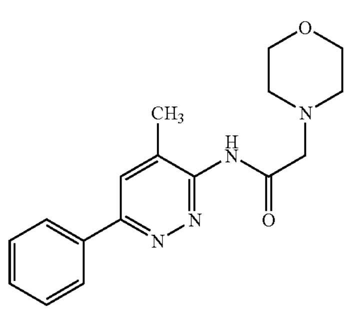 | MW01-2-03-L-D08 |

TABLE 2-continued

| Compound Number | Compound Structure | Synthetic Code |
|---|---|---|
| 314 | 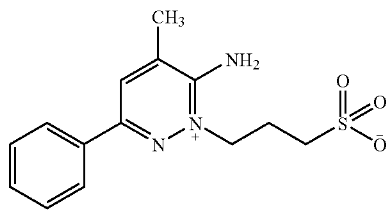 | MW01-2-03-L-G10 |
| 315 | 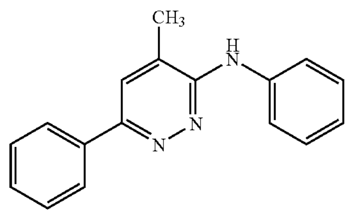 | MW01-2-06-L-F06 |
| 316 | 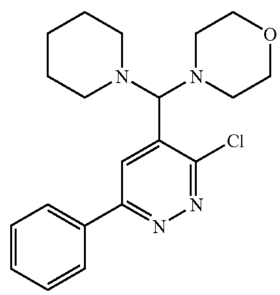 | MW01-2-09-L-B08 |
| 317 | 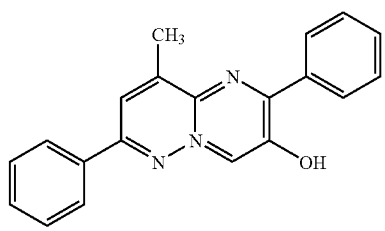 | MW01-2-09-L-E10 |
| 322 | 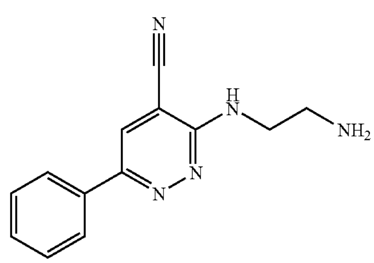 | MW01-2-20-L-B10 |
| 325 | 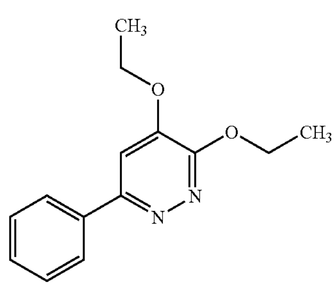 | MW01-2-24-L-A05 |

TABLE 2-continued
| Compound Number | Compound Structure | Synthetic Code |
|---|---|---|
| 327 | 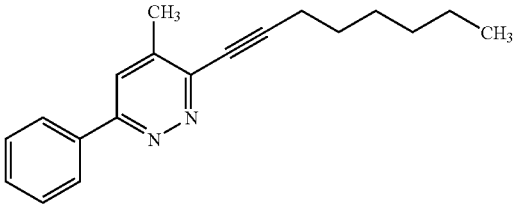 | MW01-3-01-L-G02 |
| 330 | 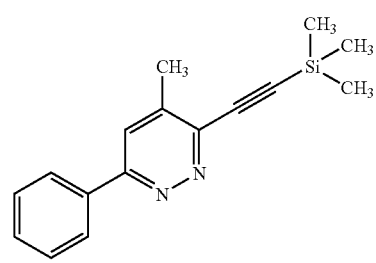 | MW01-3-01-L-G05 |
| 333 | 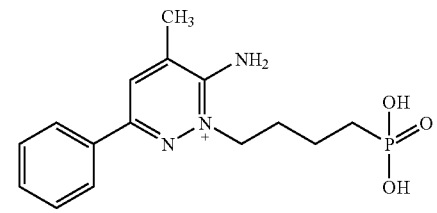 | MW01-3-06-L-B07 |
| 334 | 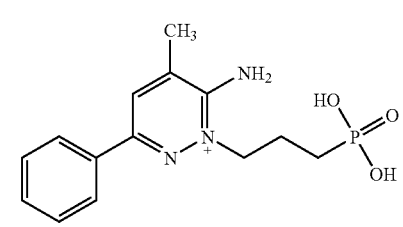 | MW01-3-06-L-B08 |
| 336 | 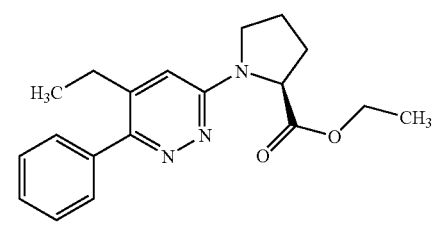 | MW01-1-07-L-G07 |
| 338 | 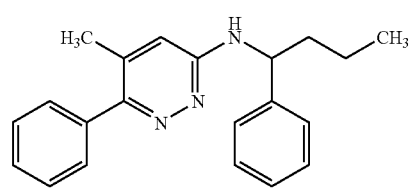 | MW01-1-08-L-D03 |

TABLE 2-continued

| Compound Number | Compound Structure | Synthetic Code |
|---|---|---|
| 342 | 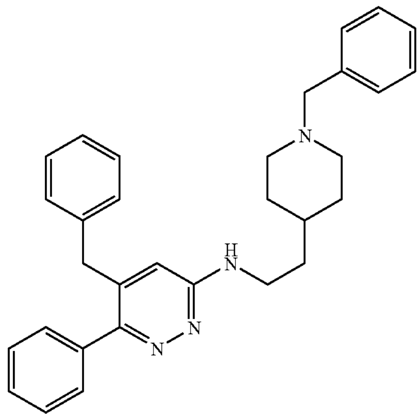 | MW01-1-16-L-E09 |
| 343 | 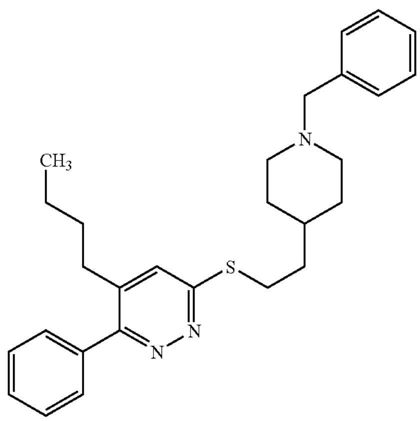 | MW01-1-17-L-C09 |
| 344 | 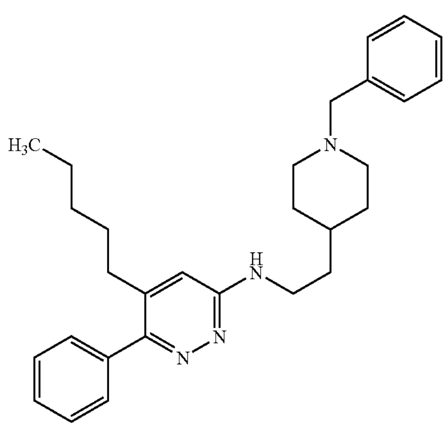 | MW01-1-17-L-E07 |

TABLE 2-continued

| Compound Number | Compound Structure | Synthetic Code |
|---|---|---|
| 345 | (structure) | MW01-1-17-L-E08 |
| 348 | (structure) | MW01-1-18-L-A04 |
| 349 | (structure) | MW01-1-18-L-B05 |
| 351 | (structure) | MW01-2-33-L-A10 |

TABLE 2-continued

| Compound Number | Compound Structure | Synthetic Code |
|---|---|---|
| 356 | 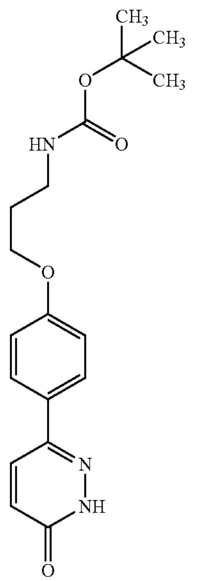 | MW01-1-01-L-E06 |
| 357 | 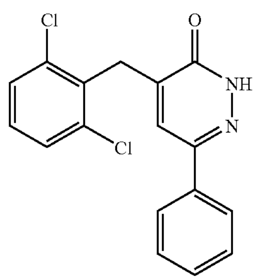 | MW01-1-01-L-H09 |
| 358 | 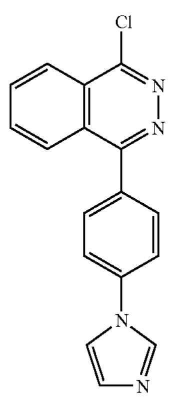 | MW01-1-05-L-D07 |
| 365 | 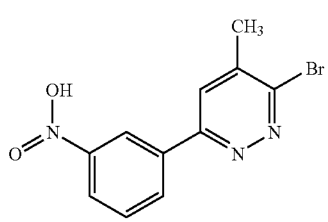 | MW01-1-03-L-D04 |

TABLE 2-continued
| Compound Number | Compound Structure | Synthetic Code |
|---|---|---|
| 369 | 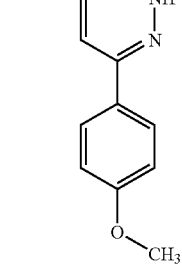 | MW01-1-04-L-G02 |
| 379 | 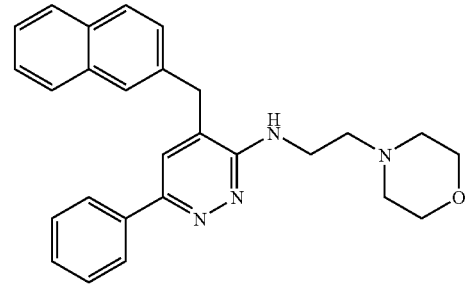 | MW01-2-24-L-E07 |
| | 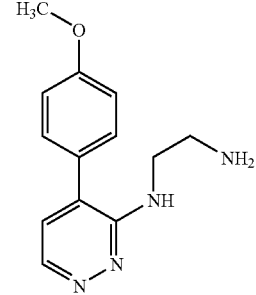 | MW01-01-01-L-B07 |
| | 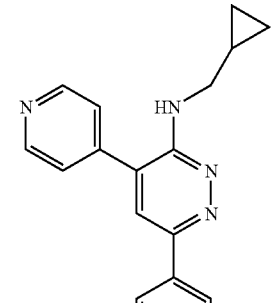 | MW01-7-084WH |

TABLE 2-continued
| Compound Number | Compound Structure | Synthetic Code |
|---|---|---|
| | 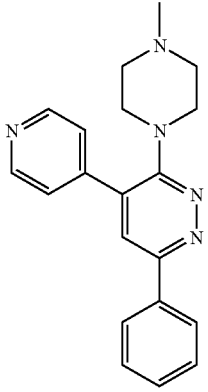 | MW01-7-085WH |
| | 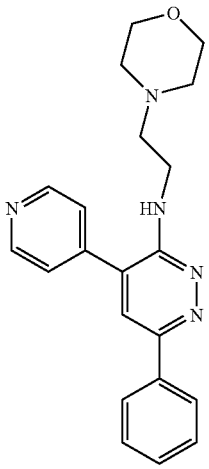 | MW01-7-091WH |
| | 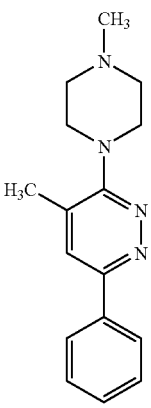 | MW01-10-12-L-G05 |

TABLE 2-continued
| Compound Number | Compound Structure | Synthetic Code |
|---|---|---|
|  | 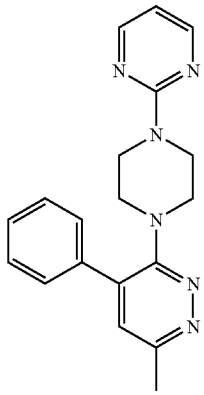 | MW01-7-057WH |
TABLE 3
Compounds of the Formula II
2-(4-(6-phenylpyridazin-3-yl)piperazine-1-yl) pyrimidine and Derivatives
| Structure | Code |
|---|---|
| 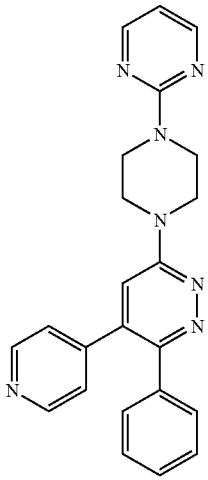 | MWo1-2-069A-SRM |
| 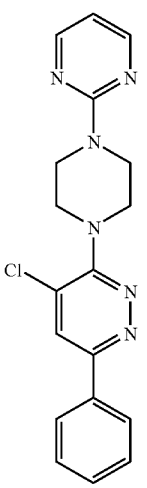 | MW01-6-127WH |

TABLE 3-continued

Compounds of the Formula II
2-(4-(6-phenylpyridazin-3-yl)piperazine-1-yl) pyrimidine and Derivatives

| Structure | Code |
|---|---|
| 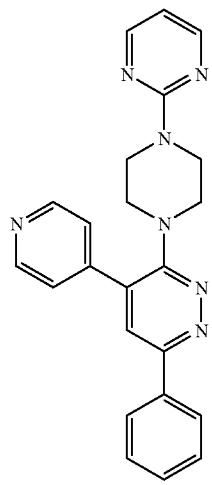 | MW01-6-189WH |
| 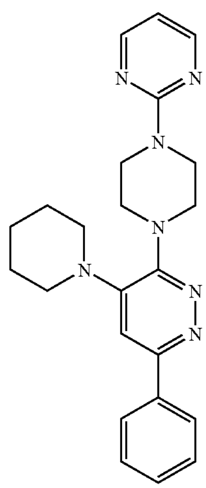 | MW01-7-107WH |
| 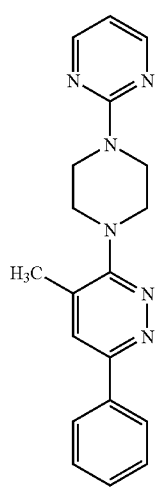 | WH 151SRM |

TABLE 3-continued

Compounds of the Formula II
2-(4-(6-phenylpyridazin-3-yl)piperazine-1-yl) pyrimidine and Derivatives

| | Structure | Code |
|---|---|---|
| | | MW01-2-069A-SRM |
| 29 | 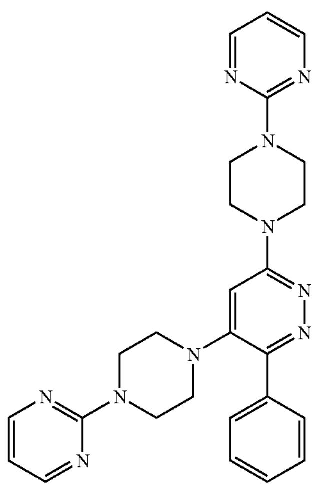 | MW01-1-030A-LKM |
| 33 | 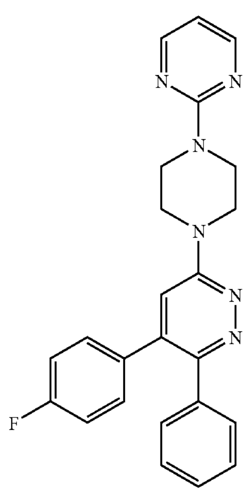 | MW01-2-065LKM |

TABLE 3-continued

Compounds of the Formula II
2-(4-(6-phenylpyridazin-3-yl)piperazine-1-yl) pyrimidine and Derivatives

| | Structure | Code |
|---|---|---|
| 34 | 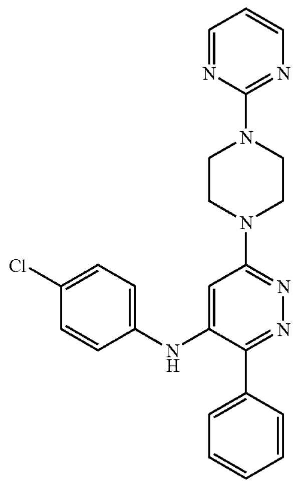 | MW01-2-127LKM |
| 35 | 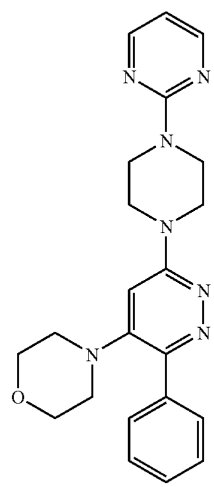 | MW01-2-134LKM |
| 36 | 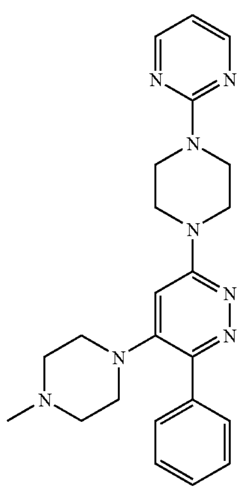 | MW01-2-146LKM |

TABLE 3-continued

Compounds of the Formula II
2-(4-(6-phenylpyridazin-3-yl)piperazine-1-yl) pyrimidine and Derivatives

| | Structure | Code |
|---|---|---|
| 37 | 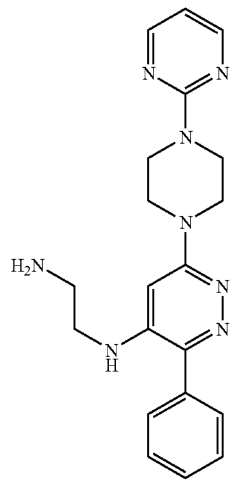 | MW01-2-147LKM |
| 46 | 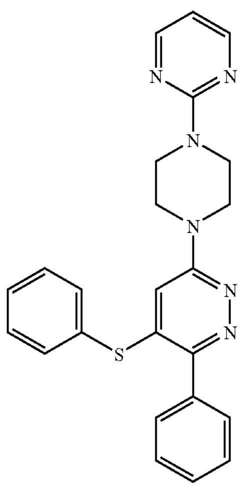 | MW01-1-045MAS |
| 105 | 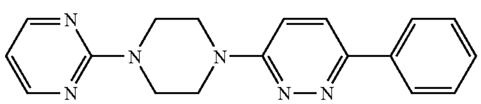 | MW01-9-038Z |
| 138 | 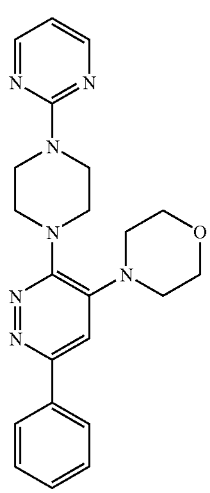 | MW01-2-023SRM |

TABLE 3-continued

Compounds of the Formula II
2-(4-(6-phenylpyridazin-3-yl)piperazine-1-yl) pyrimidine and Derivatives

| | Structure | Code |
|---|---|---|
| 147 | 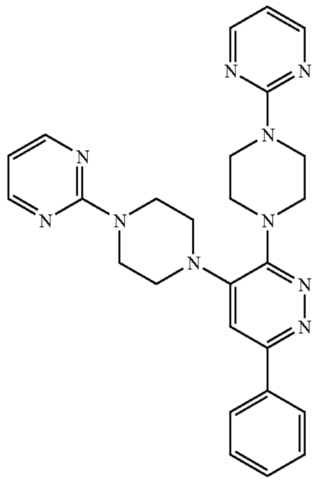 | MW01-2-177A-WH |
| 155 | 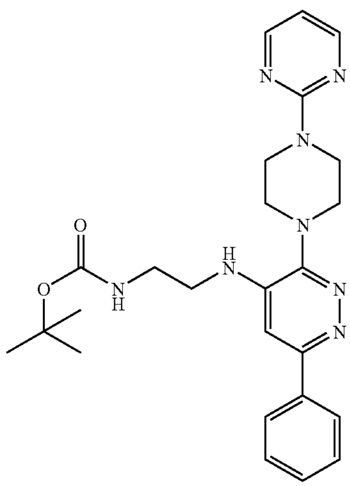 | MW01-2-191A-WH |
| 157 | 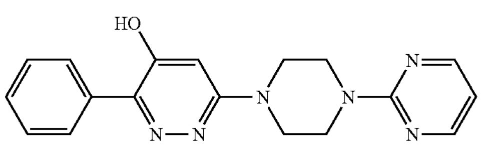 | MW01-3-003WH |
| 160 | 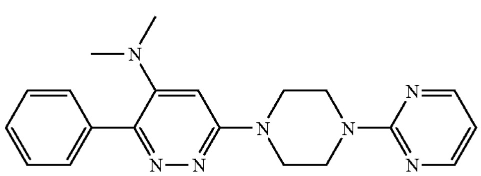 | MW01-3-019A-WH |
| 186 | 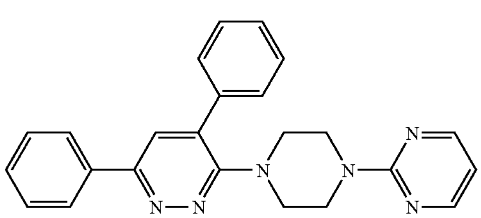 | MW01-5-188WH |

TABLE 3-continued
Compounds of the Formula II
2-(4-(6-phenylpyridazin-3-yl)piperazine-1-yl) pyrimidine and Derivatives
| | Structure | Code |
|---|---|---|
| 252 | 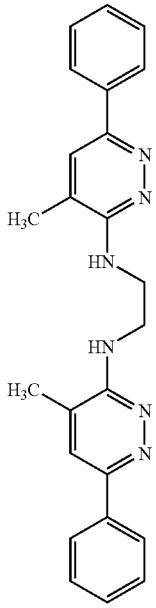 | MW01-1-05-L-F05 |
| 263 | 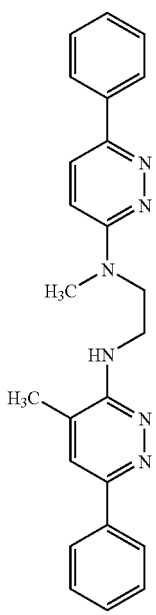 | MW01-1-07-L-H06 |

TABLE 4
| Compound | Code |
|---|---|
| 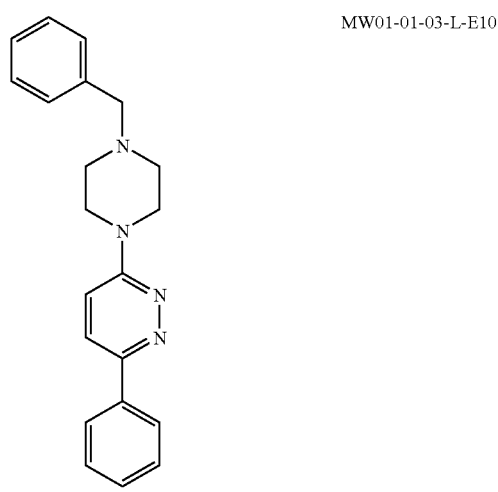 | MW01-01-02-L-G05 |
| 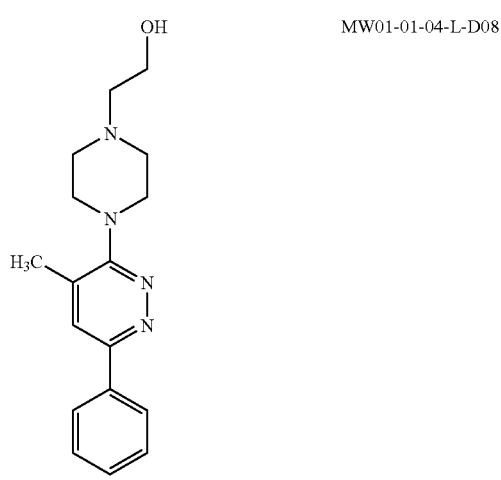 | MW01-01-03-L-E10 |
| | MW01-01-04-L-D08 |

TABLE 4-continued

| Compound | Code |
|---|---|
| (structure) | MW01-01-18-L-A02 |
| (structure) | MW01-01-18-L-C02 |
| (structure) | MW01-02-03-L-G04 |
| (structure) | MW01-2-18SRM |

TABLE 4-continued
| Compound | Code |
|---|---|
| 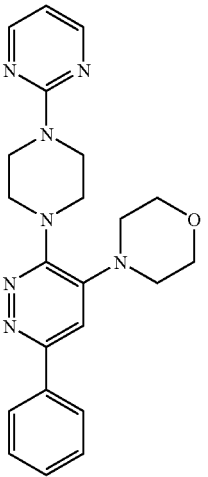 | MW01-2-023SRM |
| 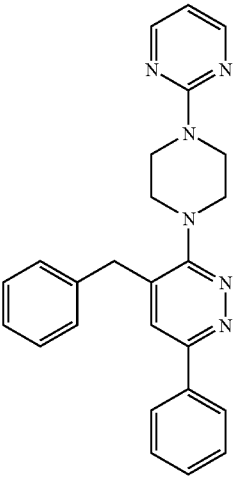 | MW01-2-141SRM |
| 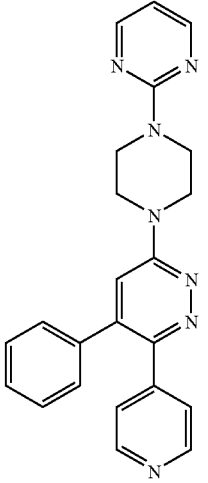 | MW01-2-163MAS |

TABLE 4-continued
| Compound | Code |
|---|---|
| 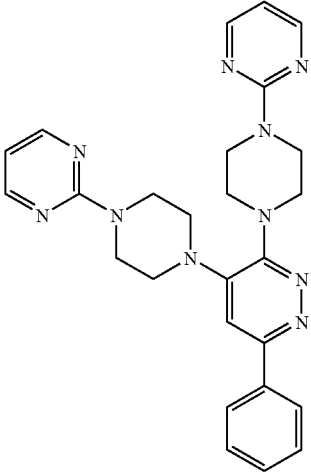 | MW01-2-177A-WH |
| 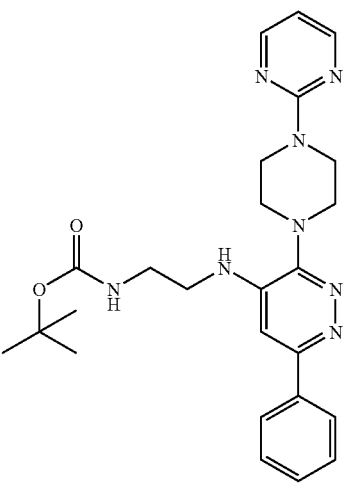 | MW01-2-191A-WH |
| 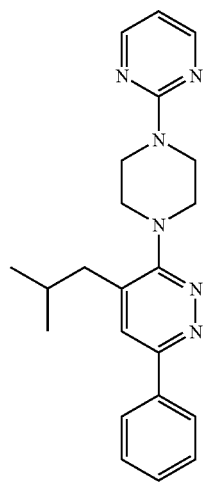 | MW01-3-024SRM |

TABLE 4-continued

| Compound | Code |
|---|---|
| (structure) | MW01-3-027SRM |
| (structure) | MW01-3-057SRM |
| (structure) | MW01-3-065SRM |
| (structure) | MW01-3-066SRM |
| (structure) | MS01-3-183-WH |

| Compound | Code |
|---|---|
| | MW01-4-179LKM |
| | MW01-4-188LKM |
| | MW01-7-027B-WH |
| | MW01-7-029WH |

TABLE 4-continued
| Compound | Code |
|---|---|
| 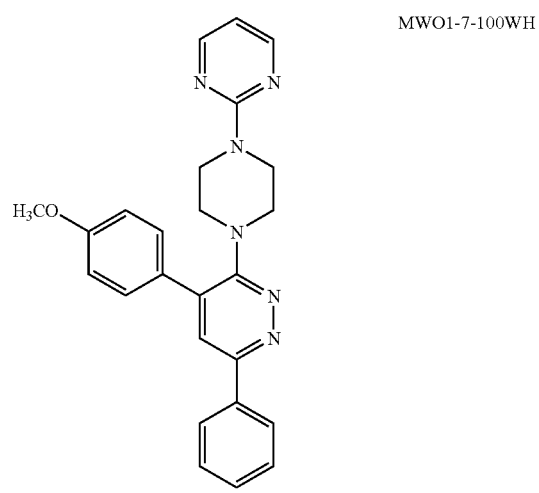 | MW01-7-031WH |
| 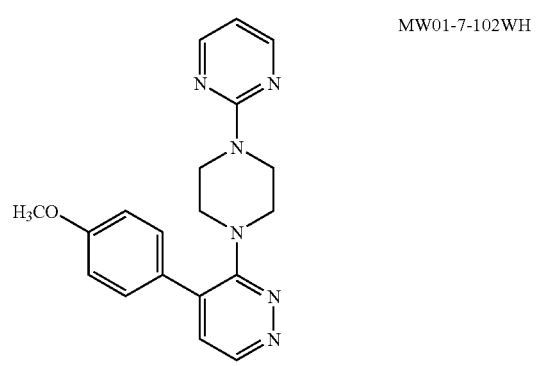 | MW01-7-100WH |
| | MW01-7-102WH |

TABLE 4-continued
| Compound | Code |
|---|---|
| 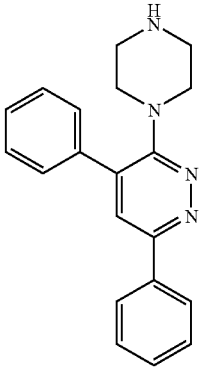 | MW01-7-133WH |
| 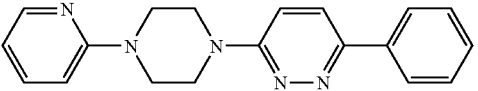 | MW01-9-039MZ |
| 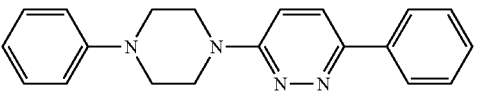 | MW01-9-040MZ |
| 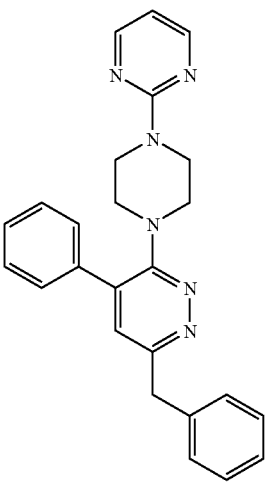 | MW01-210LPI |
| 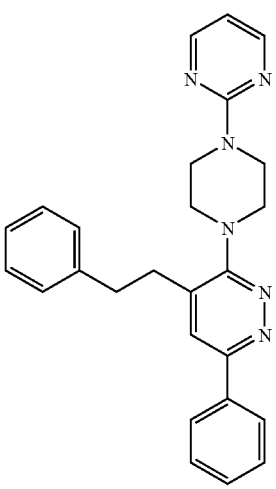 | MW01-2103LPI |

TABLE 5
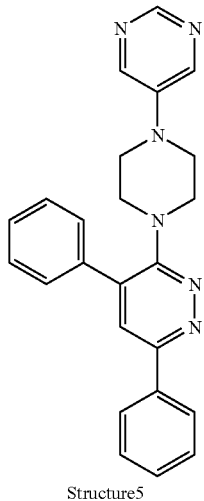
Structure5
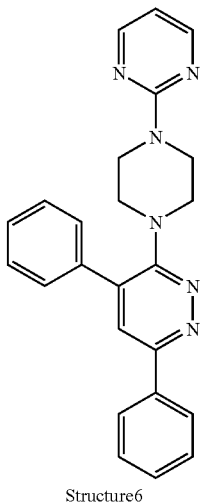
Structure6
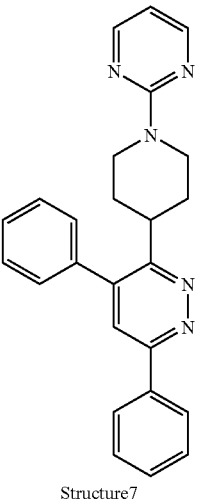
Structure7
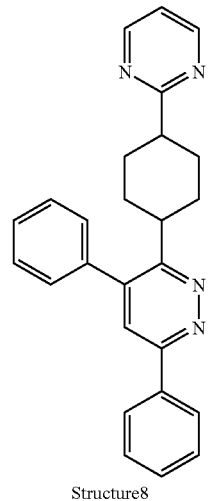
Structure8
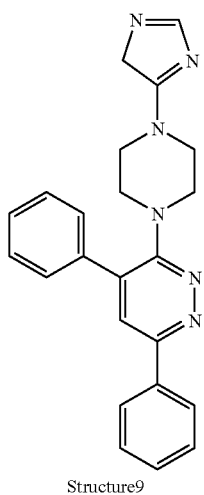
Structure9
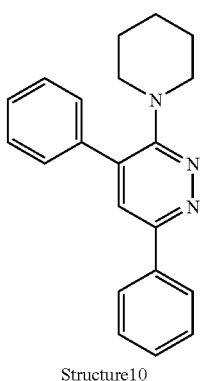
Structure10
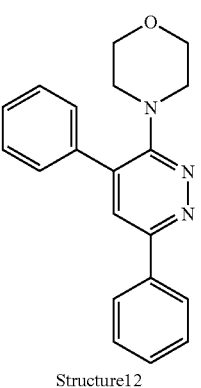
Structure12
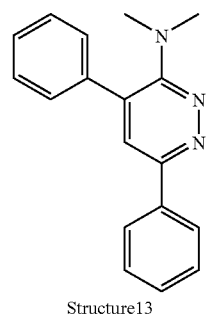
Structure13
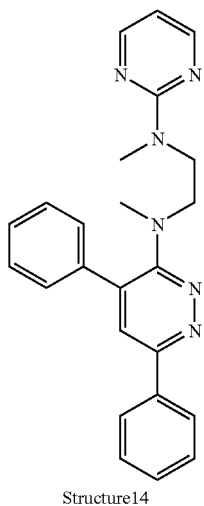
Structure14
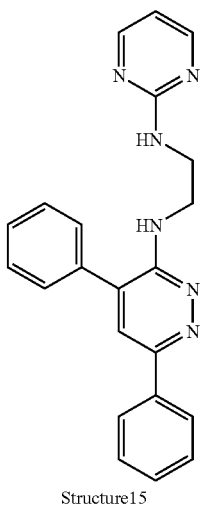
Structure15
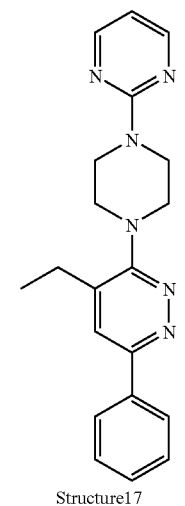
Structure17
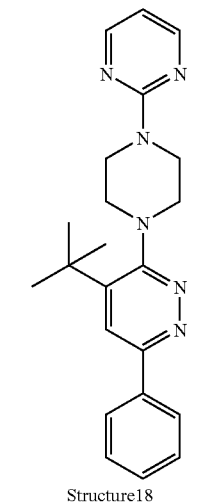
Structure18

TABLE 5-continued
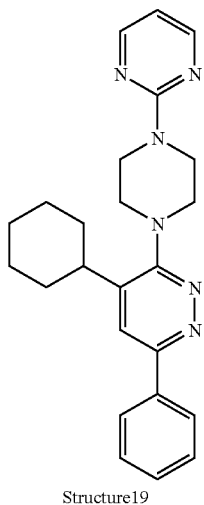
Structure19
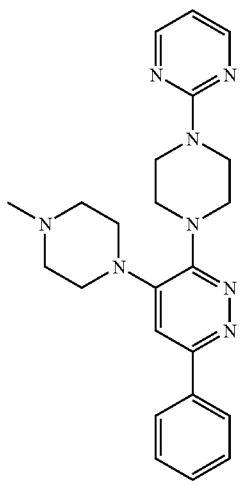
Structure21
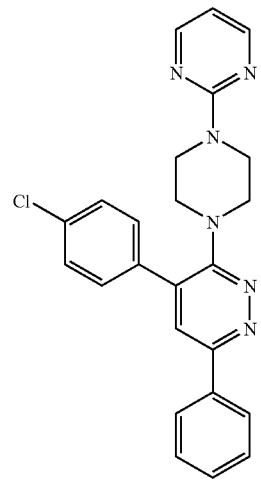
Structure22
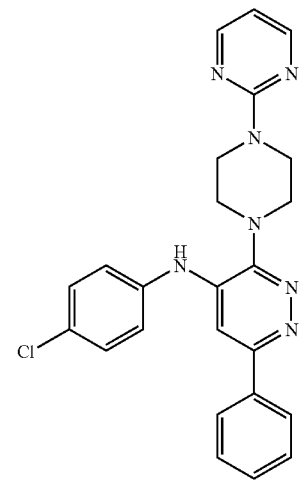
Structure23
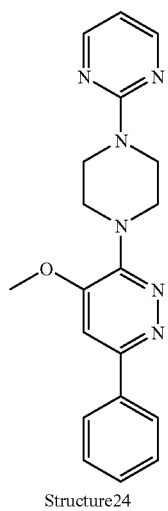
Structure24
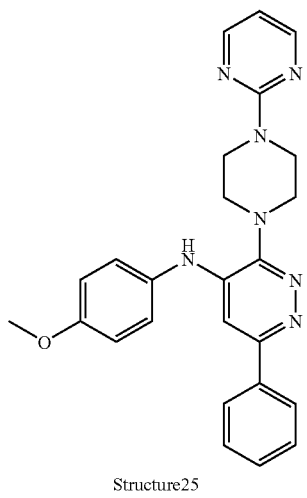
Structure25    Structure26
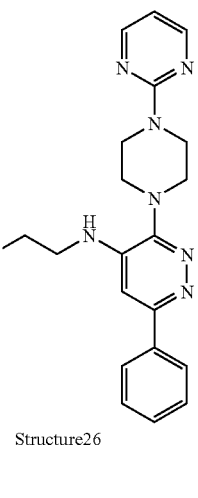
Structure27 (left of this label)
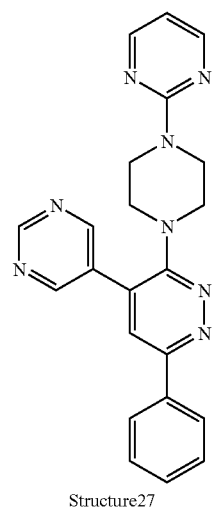
Structure27
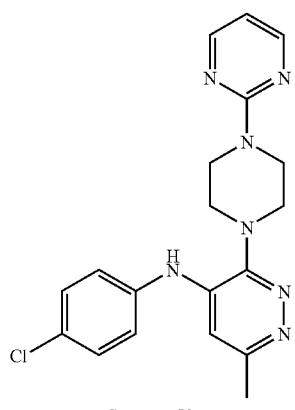
Structure50
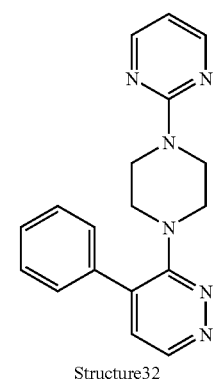
Structure32
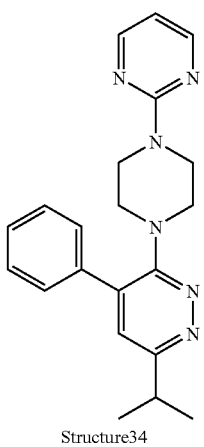
Structure34
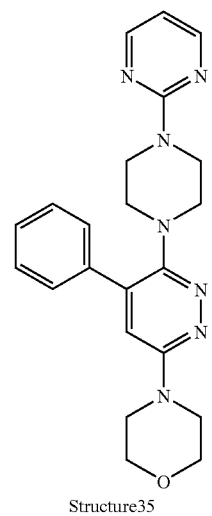
Structure35

TABLE 5-continued
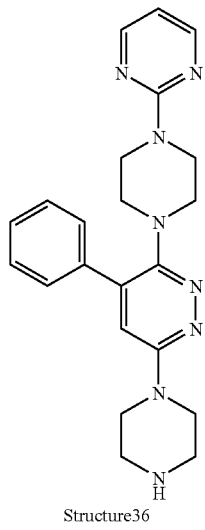
Structure36
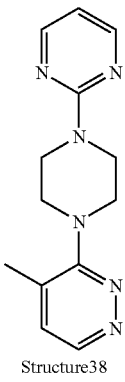
Structure38
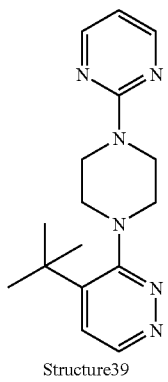
Structure39
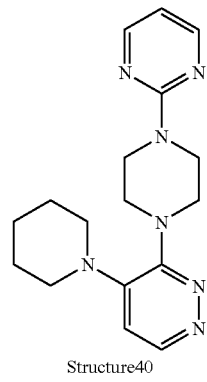
Structure40
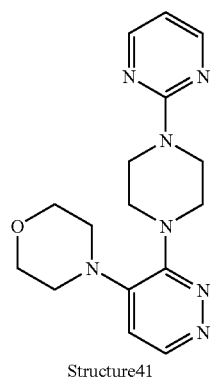
Structure41
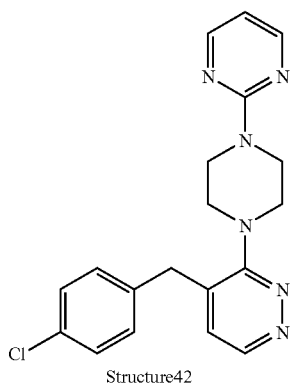
Structure42
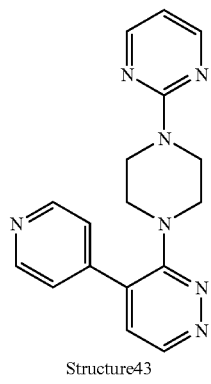
Structure43
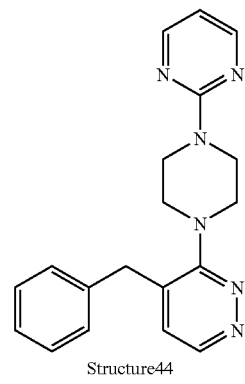
Structure44
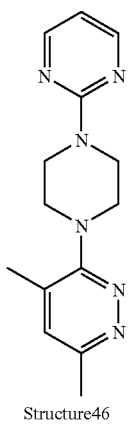
Structure46
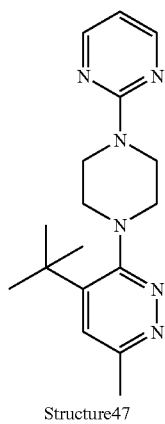
Structure47
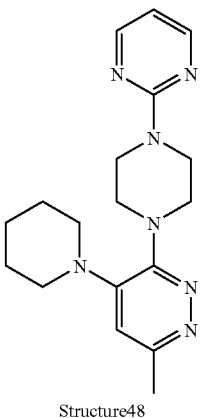
Structure48
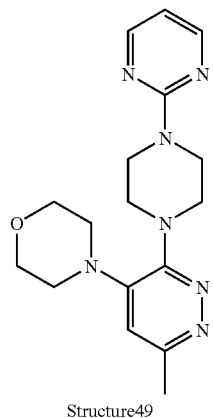
Structure49

TABLE 5-continued
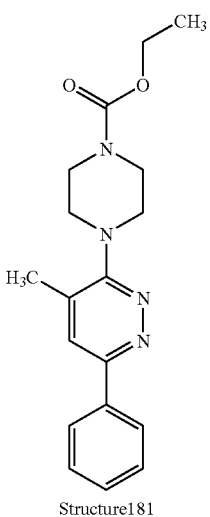
Structure181
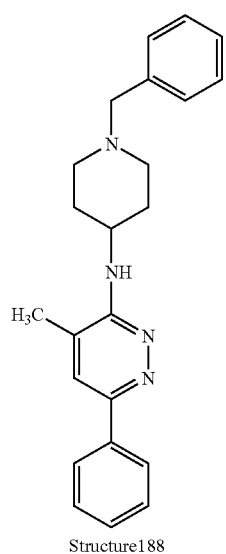
Structure188
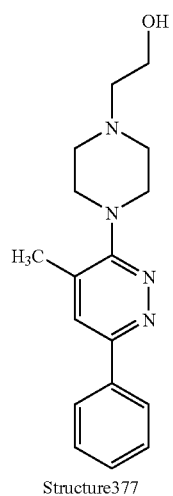
Structure377
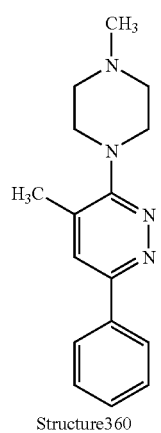
Structure360
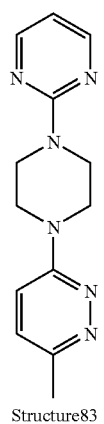
Structure83
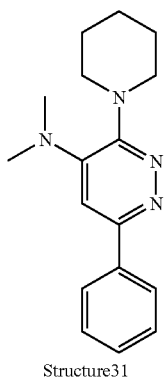
Structure31
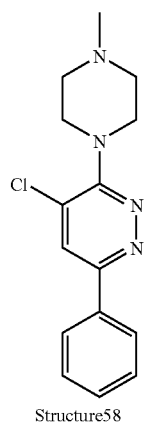
Structure58
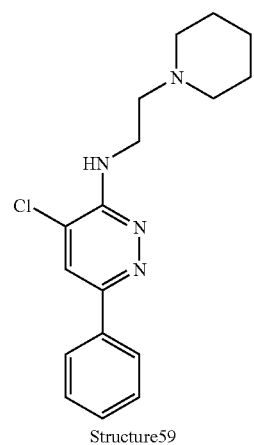
Structure59
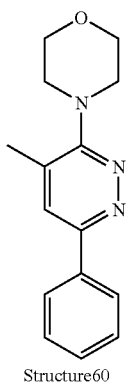
Structure60
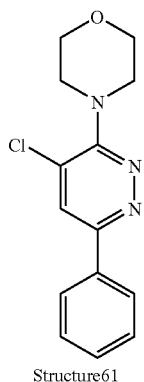
Structure61
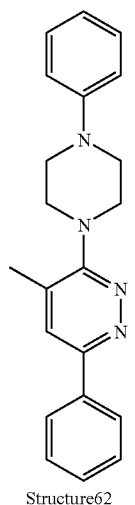
Structure62
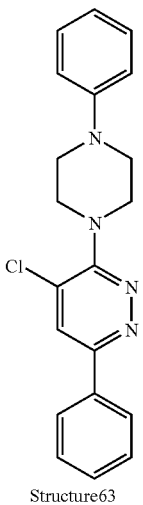
Structure63

TABLE 5-continued
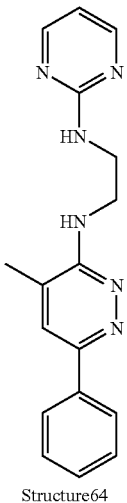
Structure64
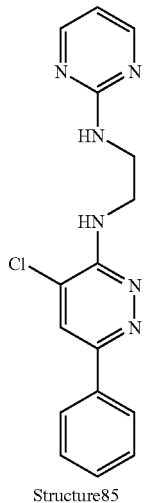
Structure85
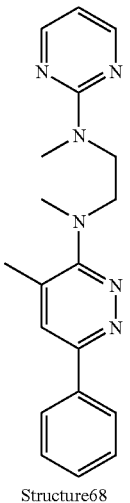
Structure68
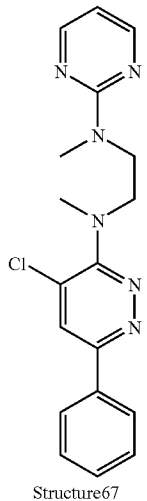
Structure67
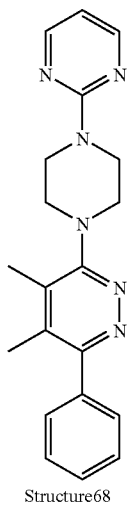
Structure68
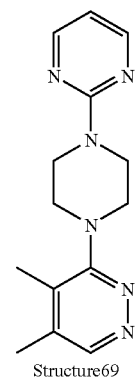
Structure69
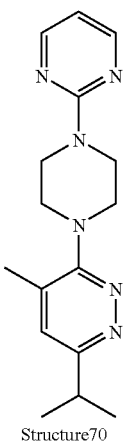
Structure70
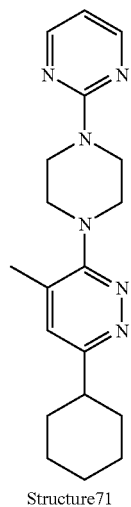
Structure71
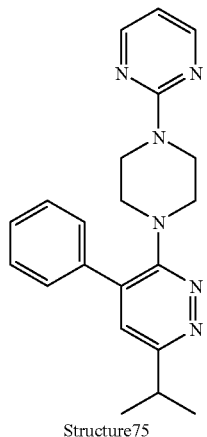
Structure75
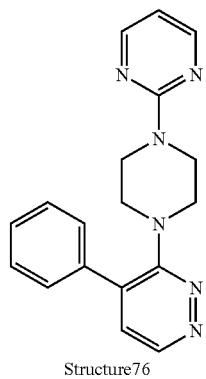
Structure76
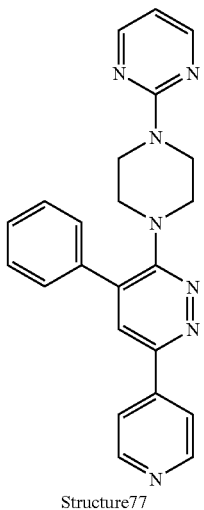
Structure77
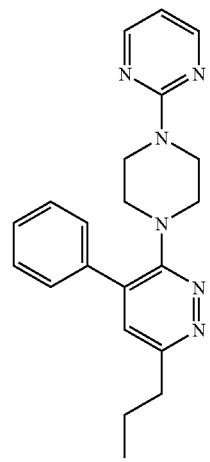
Structure78

TABLE 5-continued
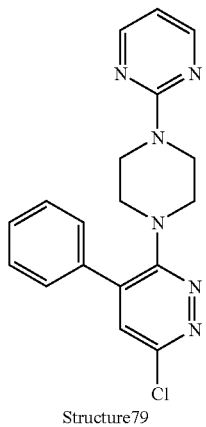
Structure79
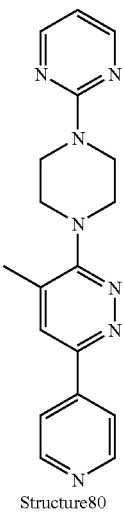
Structure80
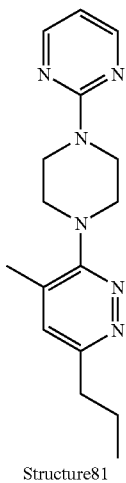
Structure81
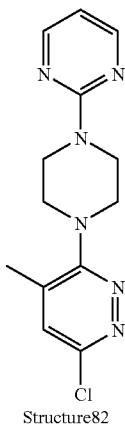
Structure82
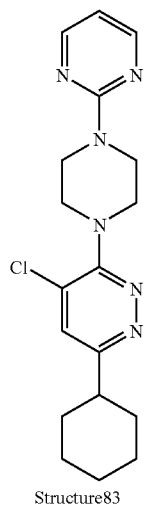
Structure83
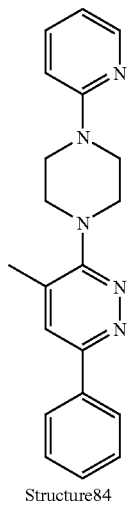
Structure84
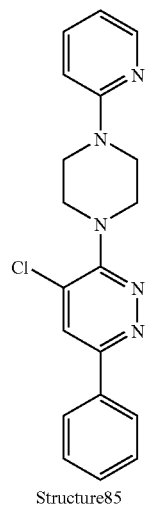
Structure85
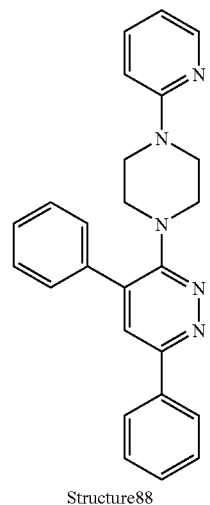
Structure88
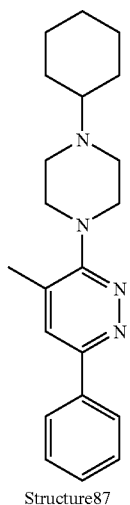
Structure87
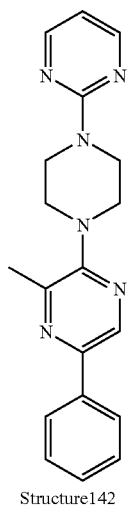
Structure142
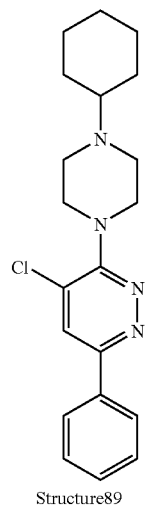
Structure89
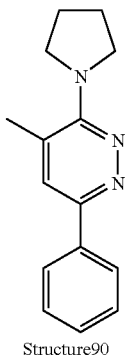
Structure90

TABLE 5-continued
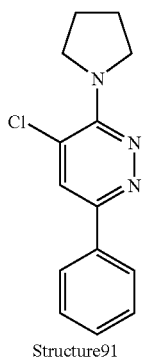
Structure91
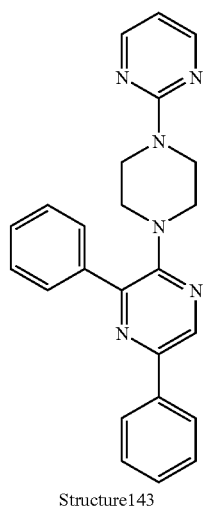
Structure143
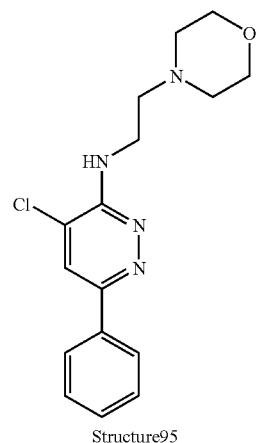
Structure95
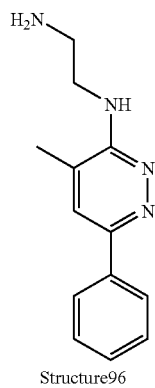
Structure96
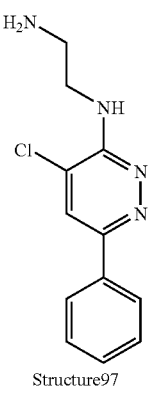
Structure97
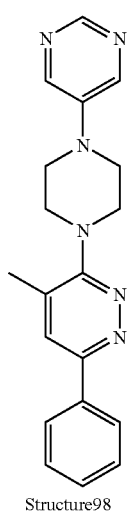
Structure98
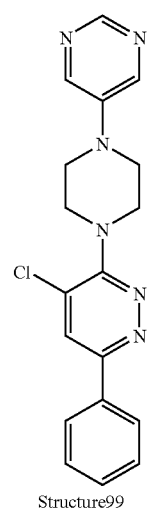
Structure99
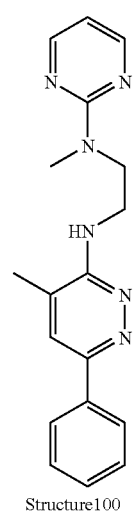
Structure100
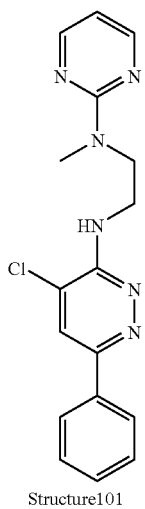
Structure101
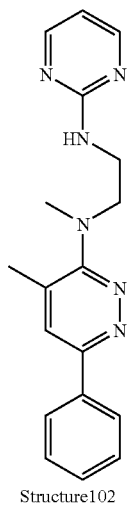
Structure102
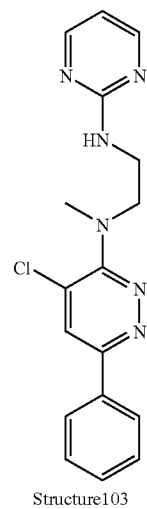
Structure103
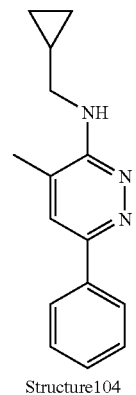
Structure104

TABLE 5-continued
Structure105
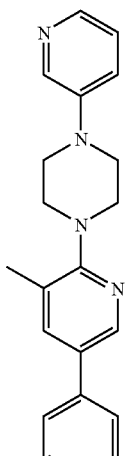
Structure106
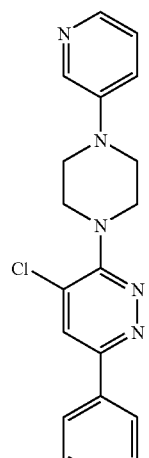
Structure107
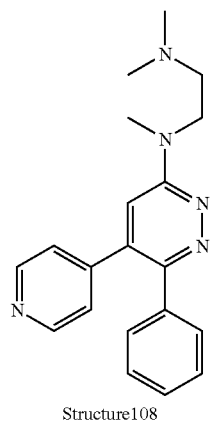
Structure108
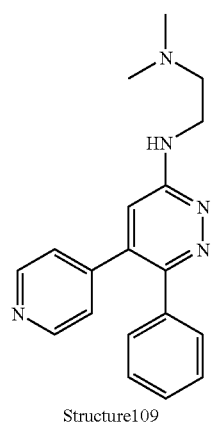
Structure109
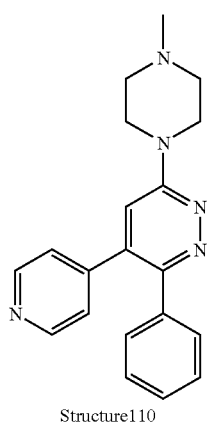
Structure110
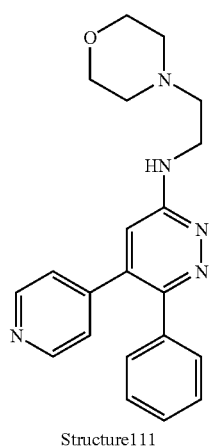
Structure111
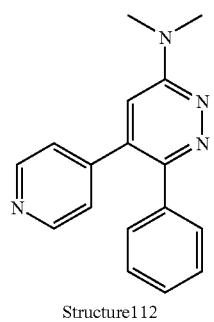
Structure112
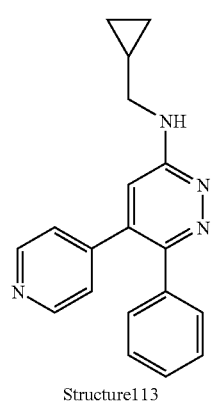
Structure113
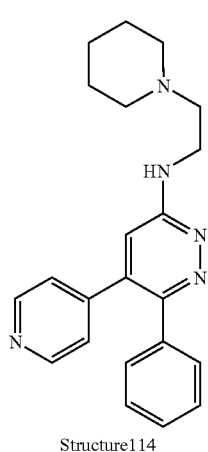
Structure114
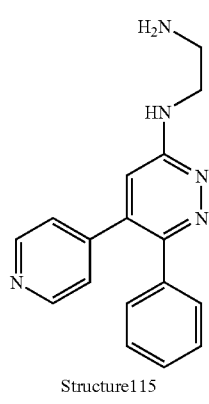
Structure115
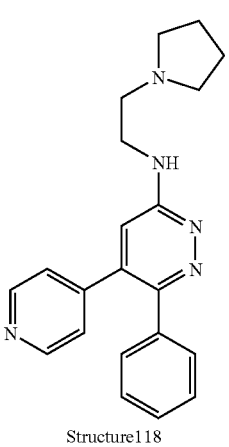
Structure118

TABLE 5-continued
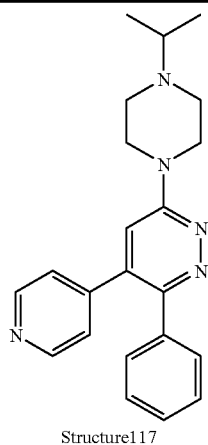
Structure117
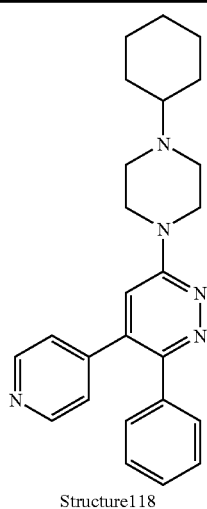
Structure118
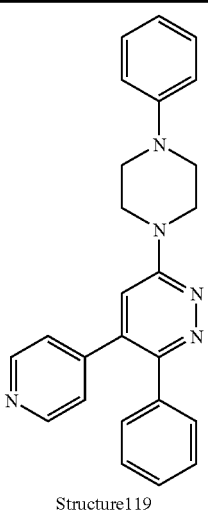
Structure119
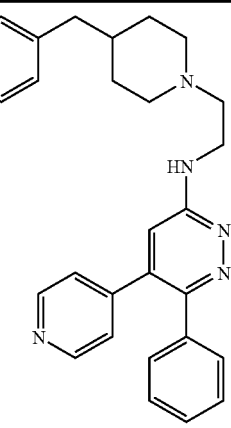
Structure120
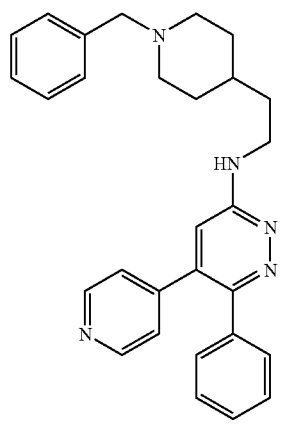
Structure121
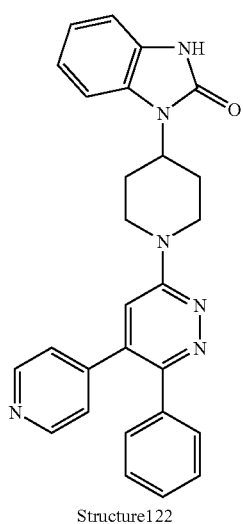
Structure122
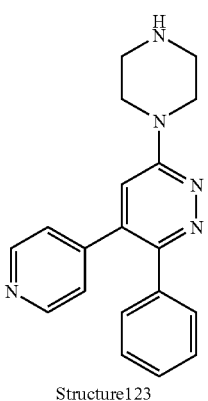
Structure123
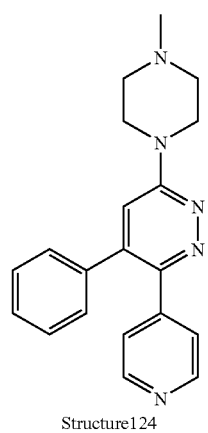
Structure124
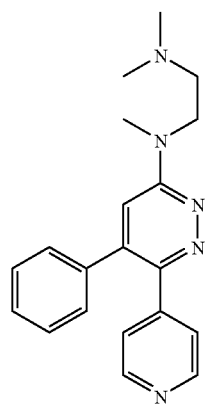
Structure125
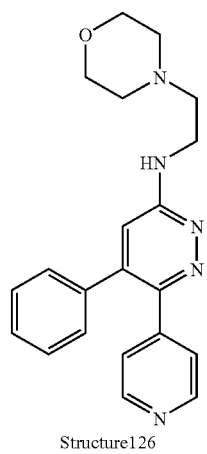
Structure126
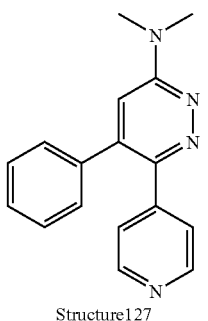
Structure127
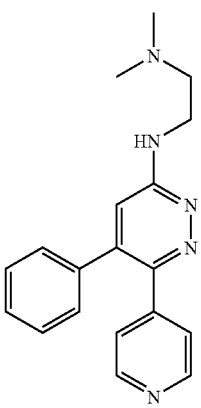
Structure128

TABLE 5-continued
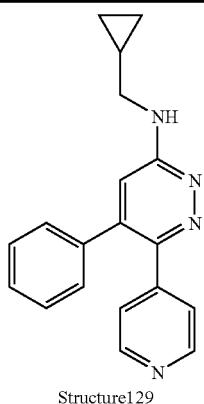
Structure129
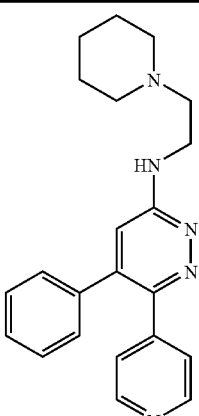
Structure130
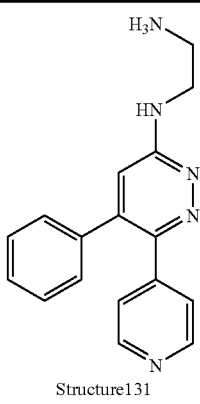
Structure131
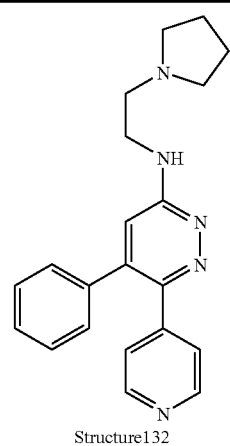
Structure132
-continued
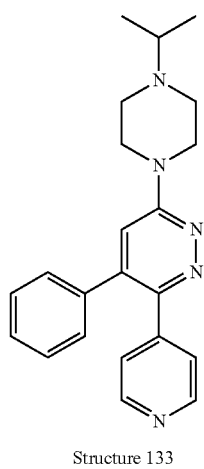
Structure 133
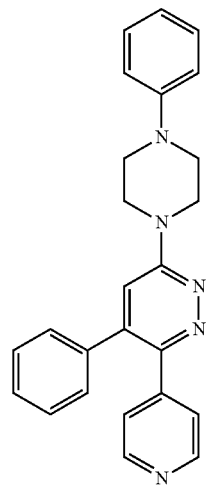
Structure 135
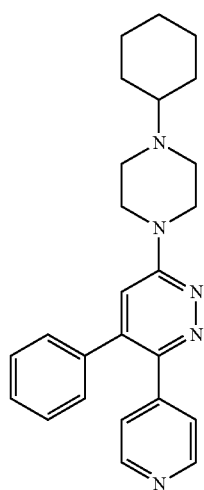
Structure 134
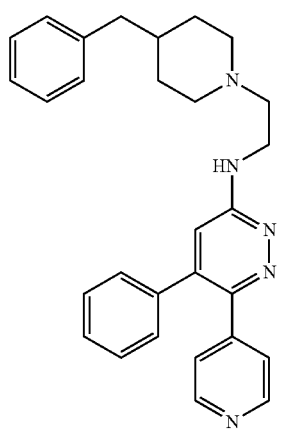
Structure 136

| 267 -continued | 268 -continued |
|---|---|
| 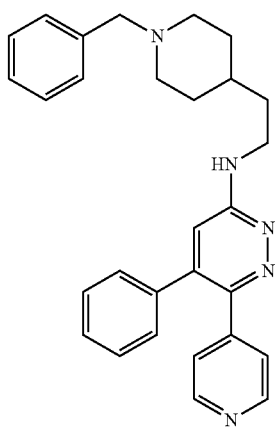<br>Structue 137 | 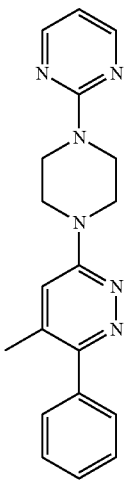<br>Structure 140 |
| 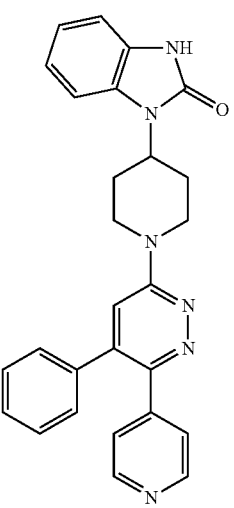<br>Structure 138 | 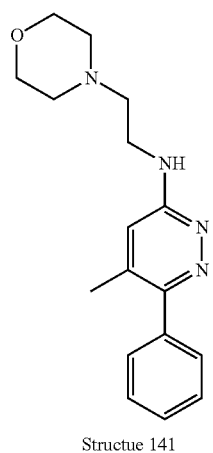<br>Structue 141 |
| 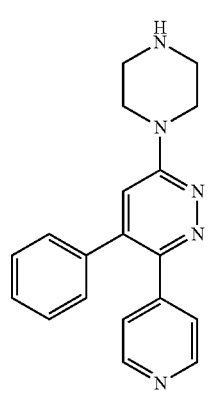<br>Structure 139 | 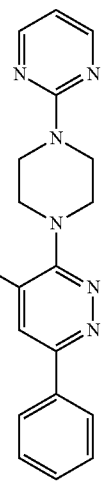<br>Structure 144 |

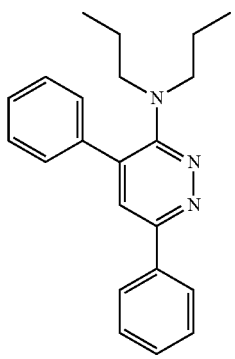

Structure 145

What is claimed is:

1. A pharmaceutical composition comprising therapeutically effective amounts of a pyridazine compound and at least one cholinesterase inhibitor, and a pharmaceutically acceptable carrier, excipient, or vehicle, wherein the pyridazine compound has the following formula:

2. A pharmaceutical composition according to claim 1 wherein the therapeutically effective amounts are suboptimal relative to the amount of each compound administered alone for treatment of an inflammatory disease.

3. A pharmaceutical composition according to claim 1 wherein the pyridazine compound is in combination with the cholinesterase inhibitor at a therapeutically effective weight ratio of between about 1:1.5 to 1:150.

4. A pharmaceutical composition according to claim 1 wherein the cholinesterase inhibitor is one or more of tacrine or tacrine analogues, huperzine A or its analogues, galantamine or its analogues, rivastigmine or its analogues, donepezil or its analogues, zifrosilone or its analogues, or pharmaceutically acceptable salts thereof.

* * * * *